US007297341B1

(12) United States Patent
Murdin et al.

(10) Patent No.: US 7,297,341 B1
(45) Date of Patent: Nov. 20, 2007

(54) CHLAMYDIA ANTIGENS AND CORRESPONDING DNA FRAGMENTS AND USES THEREOF

(75) Inventors: Andrew D. Murdin, Richmond Hill (CA); Raymond P. Oomen, Aurora (CA); Joe Wang, Toronto (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 09/868,987

(22) PCT Filed: Dec. 23, 1999

(86) PCT No.: PCT/CA99/01230

§ 371 (c)(1),
(2), (4) Date: Oct. 1, 2001

(87) PCT Pub. No.: WO00/39158

PCT Pub. Date: Jul. 6, 2000

Related U.S. Application Data

(60) Provisional application No. 60/114,050, filed on Dec. 28, 1998, provisional application No. 60/114,056, filed on Dec. 28, 1998, provisional application No. 60/114,057, filed on Dec. 28, 1998, provisional application No. 60/114,058, filed on Dec. 28, 1998, provisional application No. 60/114,059, filed on Dec. 28, 1998, provisional application No. 60/114,061, filed on Dec. 28, 1998, provisional application No. 60/113,280, filed on Dec. 23, 1998, provisional application No. 60/113,281, filed on Dec. 23, 1998, provisional application No. 60/113,282, filed on Dec. 23, 1998, provisional application No. 60/113,283, filed on Dec. 23, 1998, provisional application No. 60/113,284, filed on Dec. 23, 1998, provisional application No. 60/113,285, filed on Dec. 23, 1998, provisional application No. 60/113,385, filed on Dec. 23, 1998.

(51) Int. Cl.
*A61K 39/11* (2006.01)
*A61K 39/02* (2006.01)
*C12N 1/20* (2006.01)
*C12P 21/04* (2006.01)
*C07H 21/04* (2006.01)

(52) U.S. Cl. .................. 424/263.1; 424/184.1; 424/190.1; 424/192.1; 514/44; 435/69.1; 435/69.7; 435/70.1; 435/71.1; 435/71.2; 435/254.11; 536/23.7

(58) Field of Classification Search ............. 424/184.1, 424/190.1, 192.1, 263.1; 435/69.1, 69.7, 435/70.1, 71.1, 71.2, 254.11; 514/44; 536/23.7
See application file for complete search history.

(56) References Cited

U.S. PATENT DOCUMENTS

| 6,521,745 | B1 | 2/2003 | Murdin et al. |
| 6,559,294 | B1* | 5/2003 | Griffais et al. |
| 6,693,087 | B1 | 2/2004 | Murdin et al. |
| 6,808,713 | B1 | 10/2004 | Murdin et al. |
| 6,822,071 | B1 | 11/2004 | Stephens et al. |
| 7,019,125 | B2 | 3/2006 | Murdin et al. |
| 7,070,792 | B2 | 7/2006 | Murdin et al. |
| 7,081,245 | B2 | 7/2006 | Murdin et al. |
| 2002/0082402 | A1 | 6/2002 | Murdin et al. |
| 2002/0094340 | A1 | 7/2002 | Murdin et al. |
| 2002/0094965 | A1 | 7/2002 | Murdin et al. |
| 2002/0099188 | A1 | 7/2002 | Murdin et al. |
| 2002/0132994 | A1 | 9/2002 | Murdin et al. |
| 2003/0100706 | A1 | 5/2003 | Murdin et al. |
| 2004/0254130 | A1 | 12/2004 | Murdin et al. |

FOREIGN PATENT DOCUMENTS

| EP | 0784059 A | 7/1997 |
| WO | WO 99/28475 | 6/1999 |
| WO | WO9927105 A | 6/1999 |
| WO | WO 00/24765 | 5/2000 |
| WO | WO00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 A1 | 3/2001 |

(Continued)

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129-2138, 1990.*
Lazar et al., Molecular and Cellular Biology, 8(3): 1247-1252, 1988.*
Jobling et al. (Mol. Microbiol. 1991, 5(7): 1755-67.*

(Continued)

*Primary Examiner*—Susan Ungar

(57) ABSTRACT

The present invention provides purified and isolated polynucleotide molecules that encode *Chlamydia* polypeptides which can be used in methods to prevent, treat, and diagnose *Chlamydia* infection. In one form of the invention, the polynucleotide molecules are selected from DNA that encode polypeptides CPN100686 RY 54 (SEQ ID Nos: 1 and 14), CPN100696 RY-55 (SEQ ID Nos: 2 and 15), CPN100709 RY-57 (SEQ ID Nos: 3 and 16), CPN100710 RY-58 (SEQ ID Nos: 4 and 17), CPN100711 RY-59 (SEQ ID Nos: 5 and 18), CPN100877 RY-61 (SEQ ID Nos: 6 and 19), CPN100325 RY-62 (SEQ ID Nos: 7 and 20), CPN100368 RY-63 (SEQ ID Nos: 8 and 21), CPN100624 RY-64 (SEQ ID Nos:9 and 22), CPN100633 RY-65 (SEQ ID Nos:10 and 23), CPN100985 RY-66 (SEQ ID Nos:11 and 24), CPN100987 RY-67 (SEQ ID Nos:12 and 25) and CPN100988 RY-68 (SEQ ID Nos:13 and 26).

18 Claims, 96 Drawing Sheets

FOREIGN PATENT DOCUMENTS

Figure 1B:
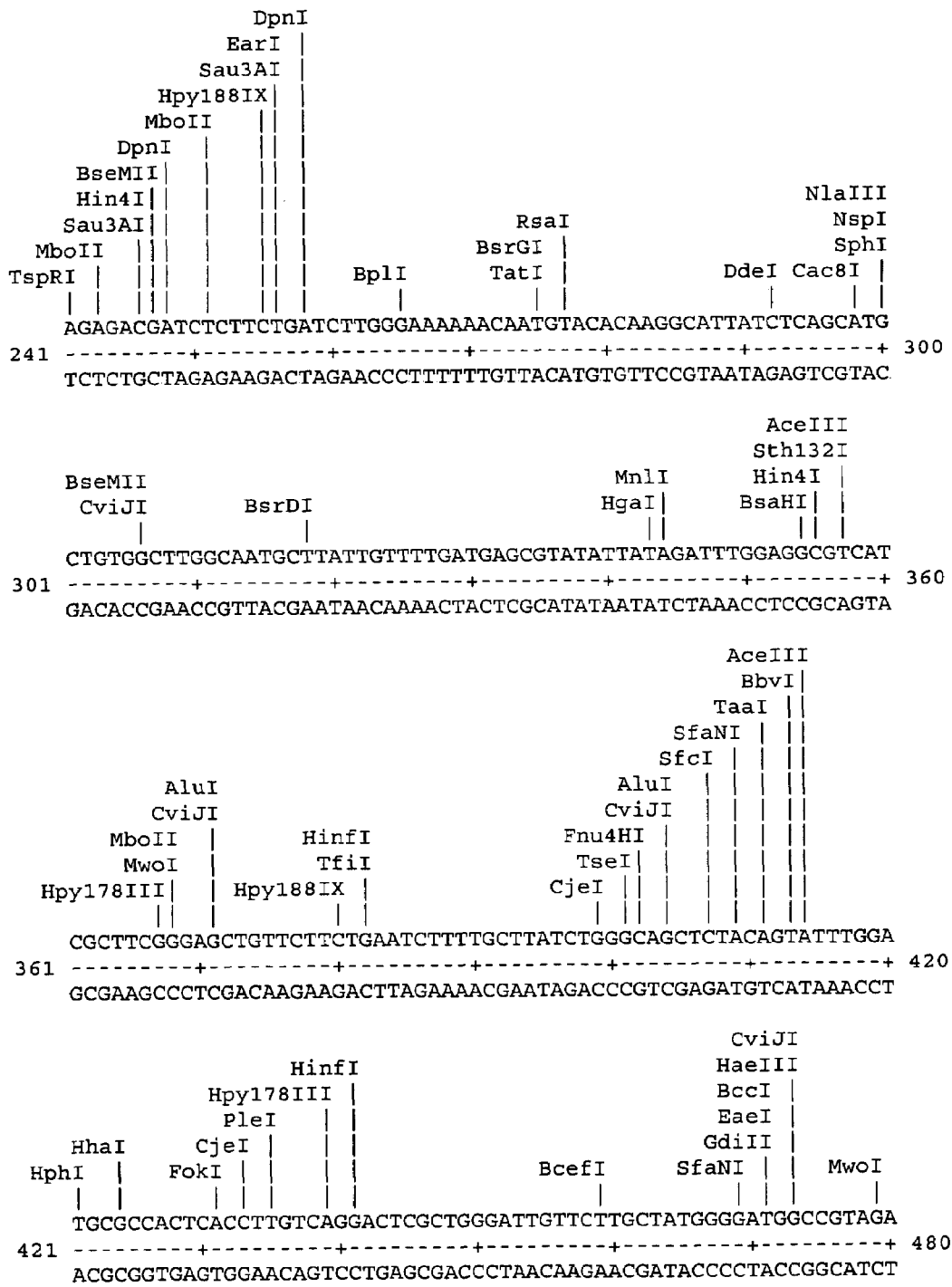
Figure 1C:
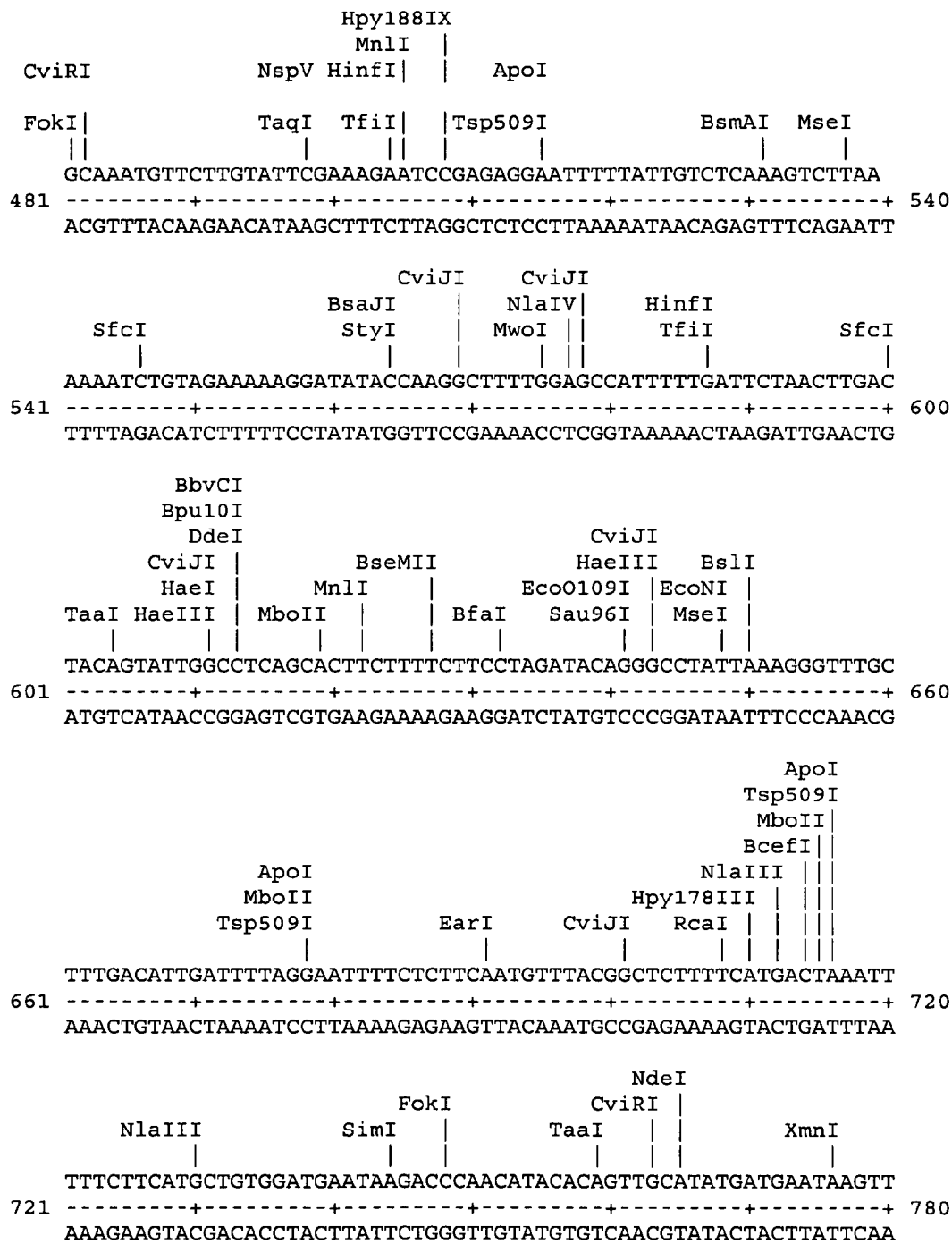
Figure 1D:
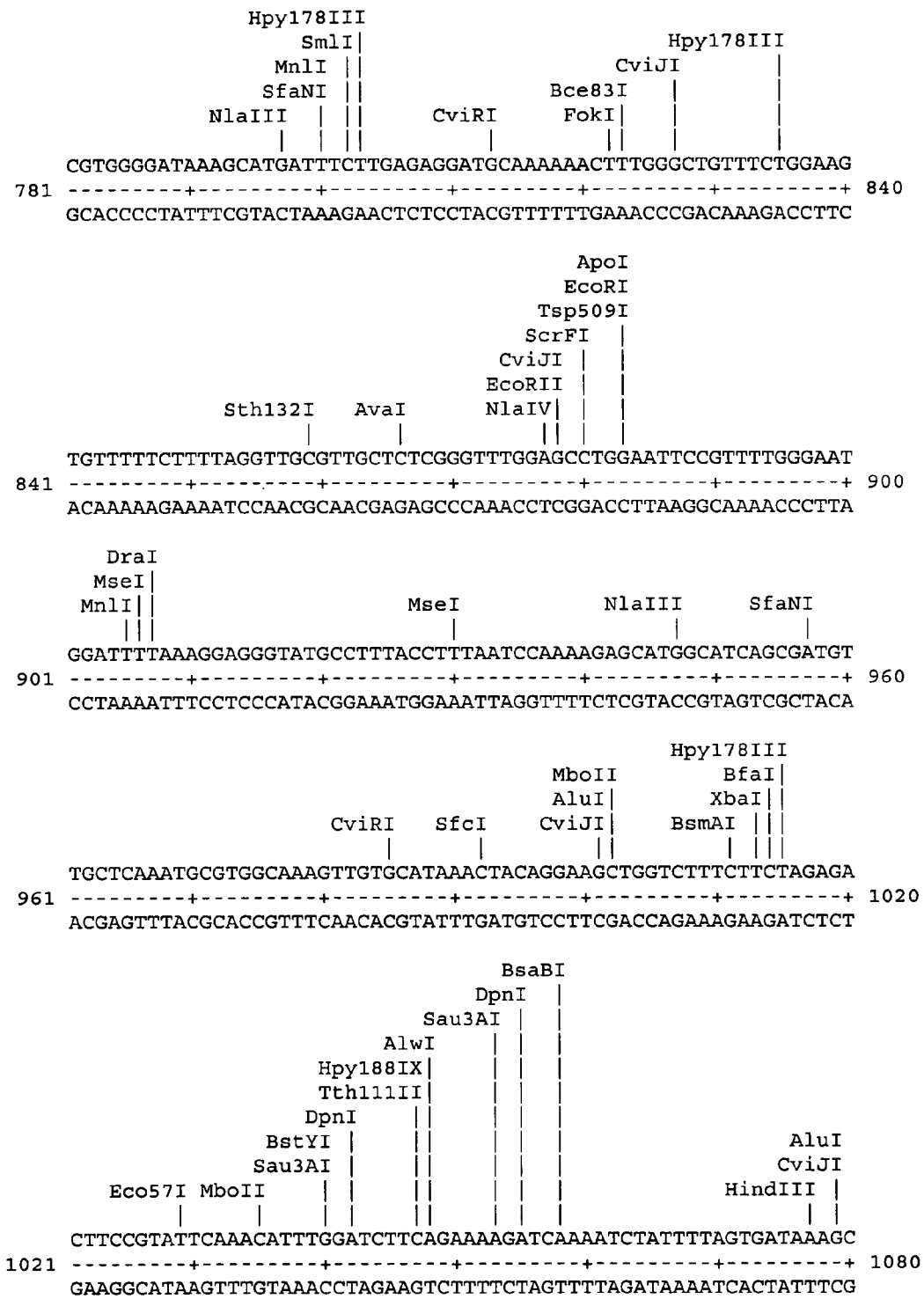
Figure 1E:
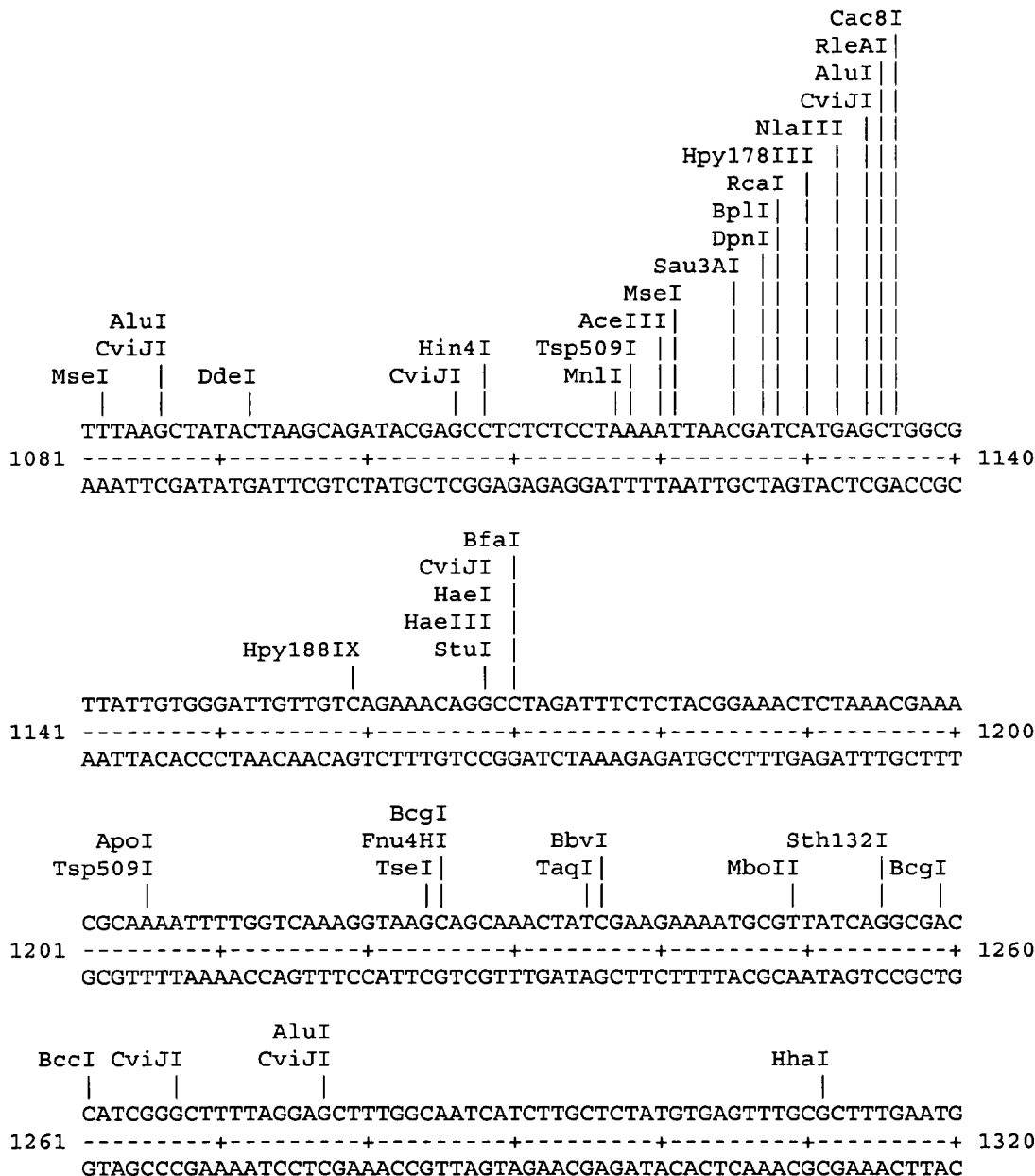
Figure 1F:
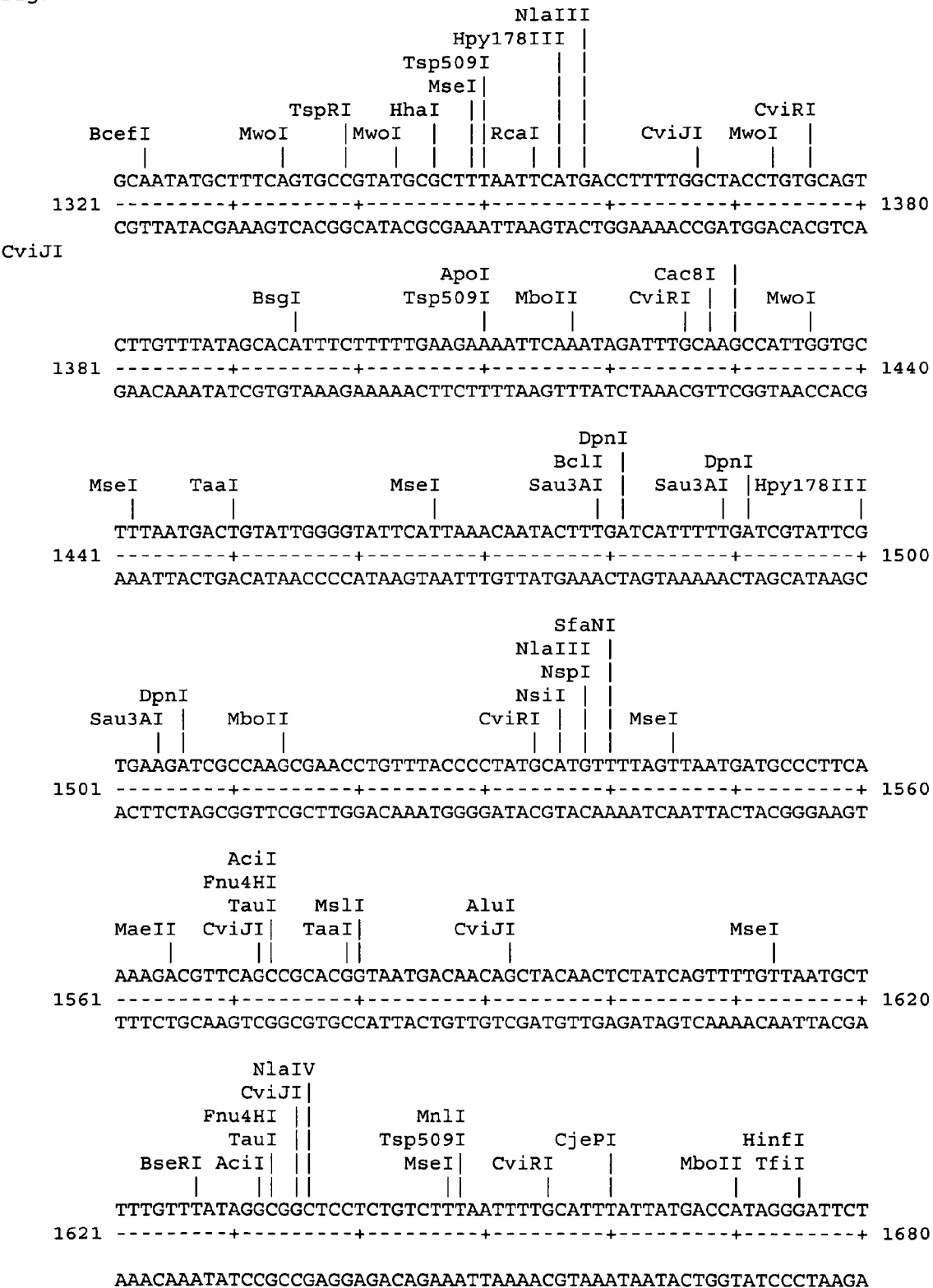
Figure 2A:
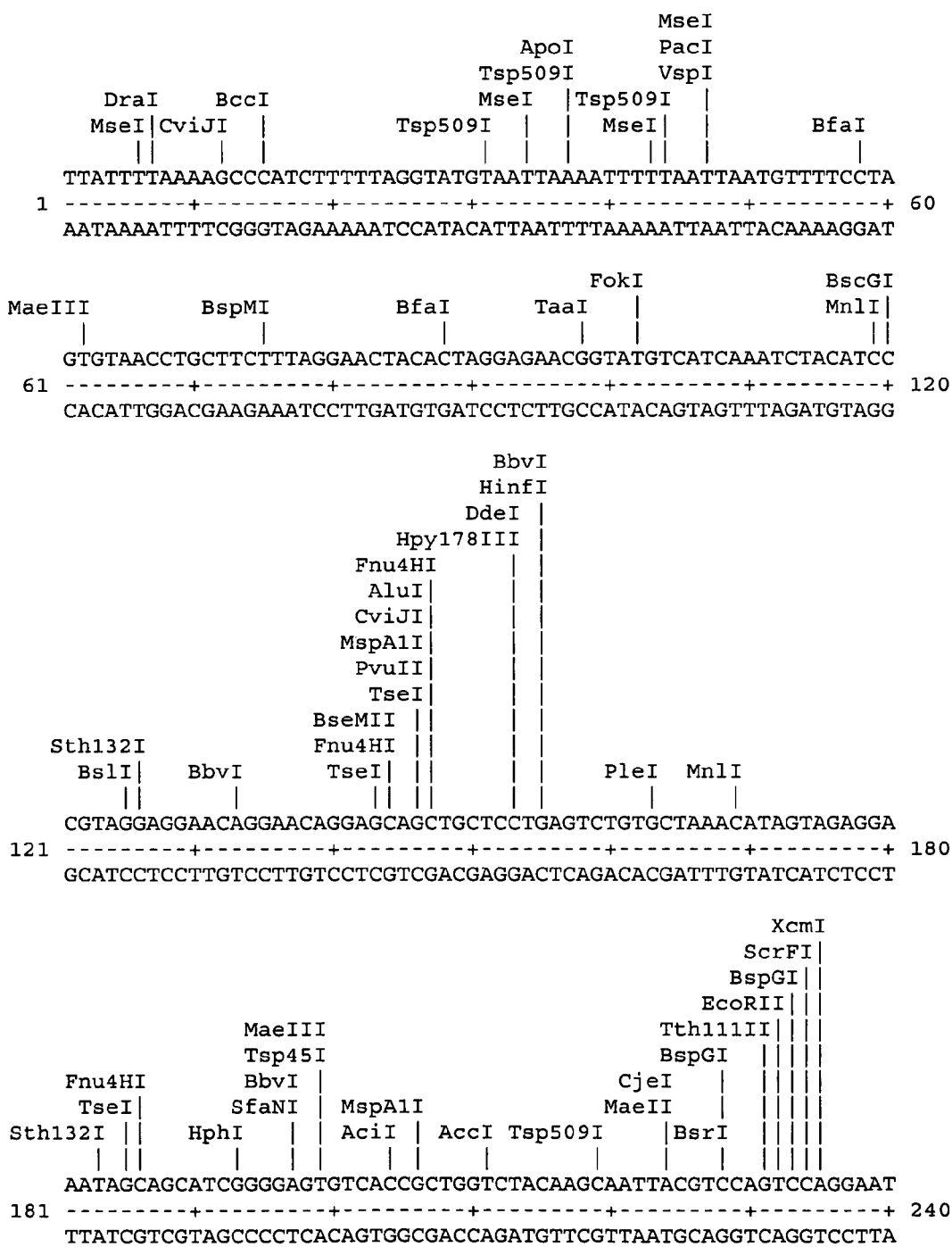
Figure 2C:
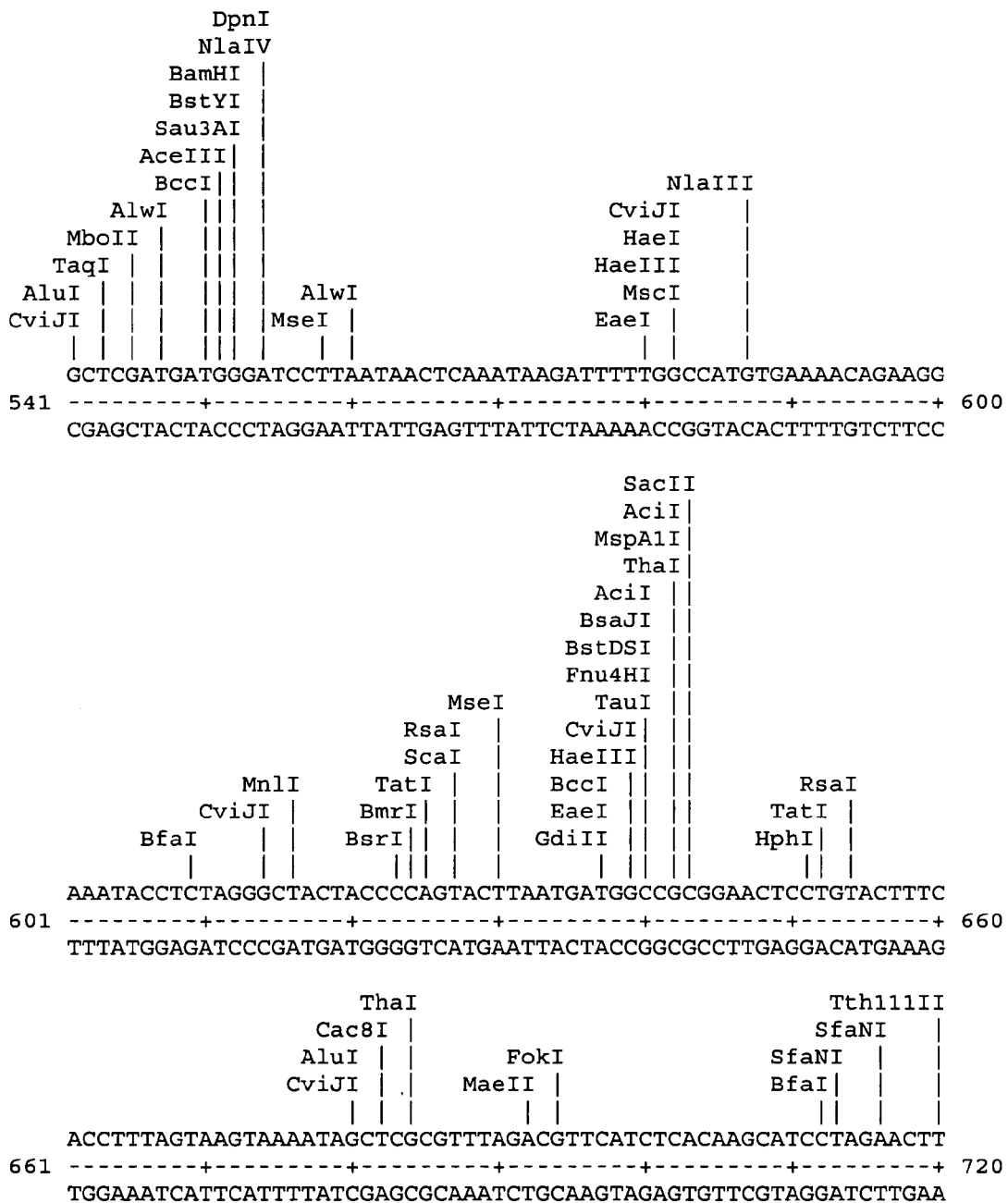
Figure 3A:
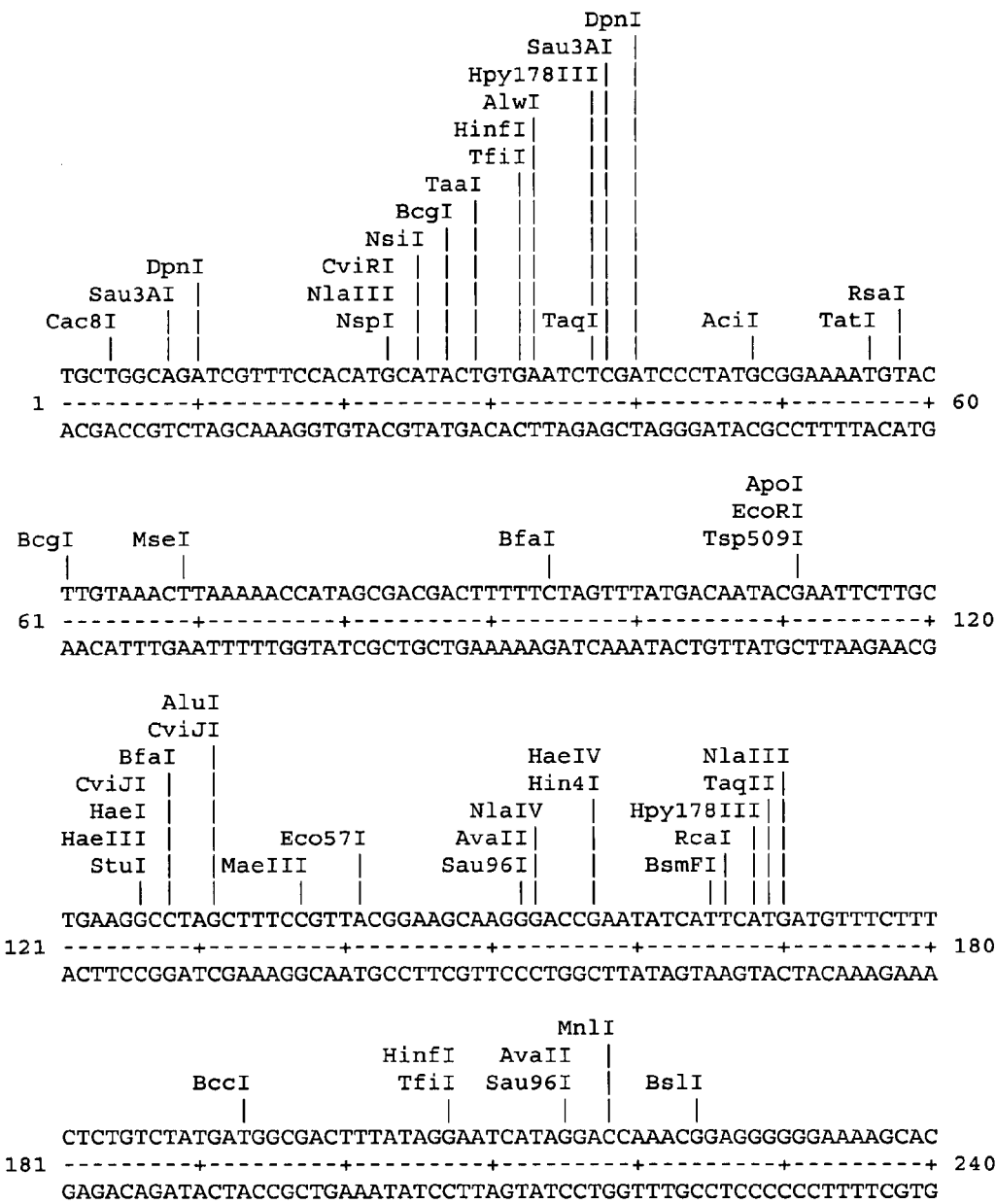
Figure 3B:
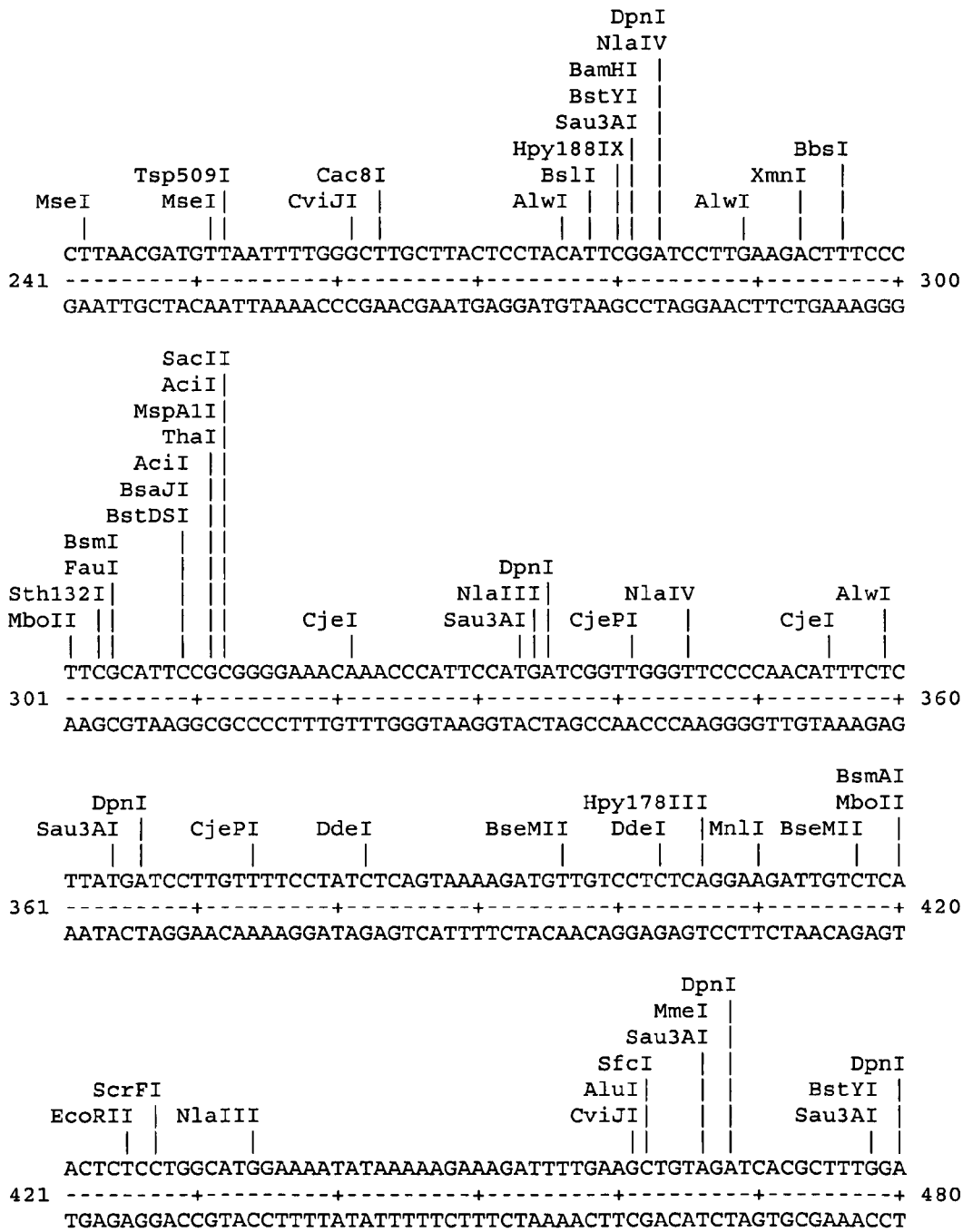
Figure 3C:
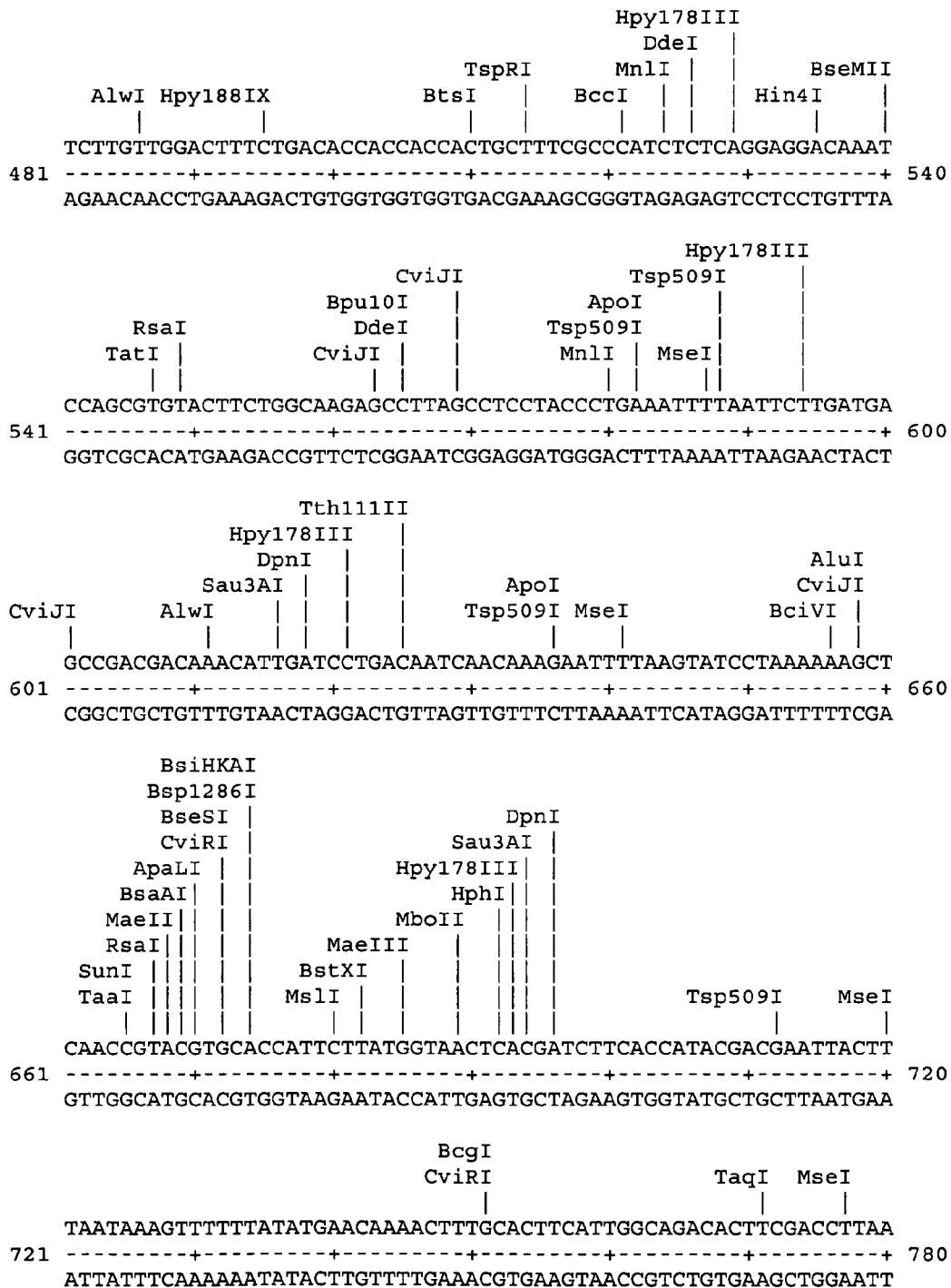
Figure 3D:
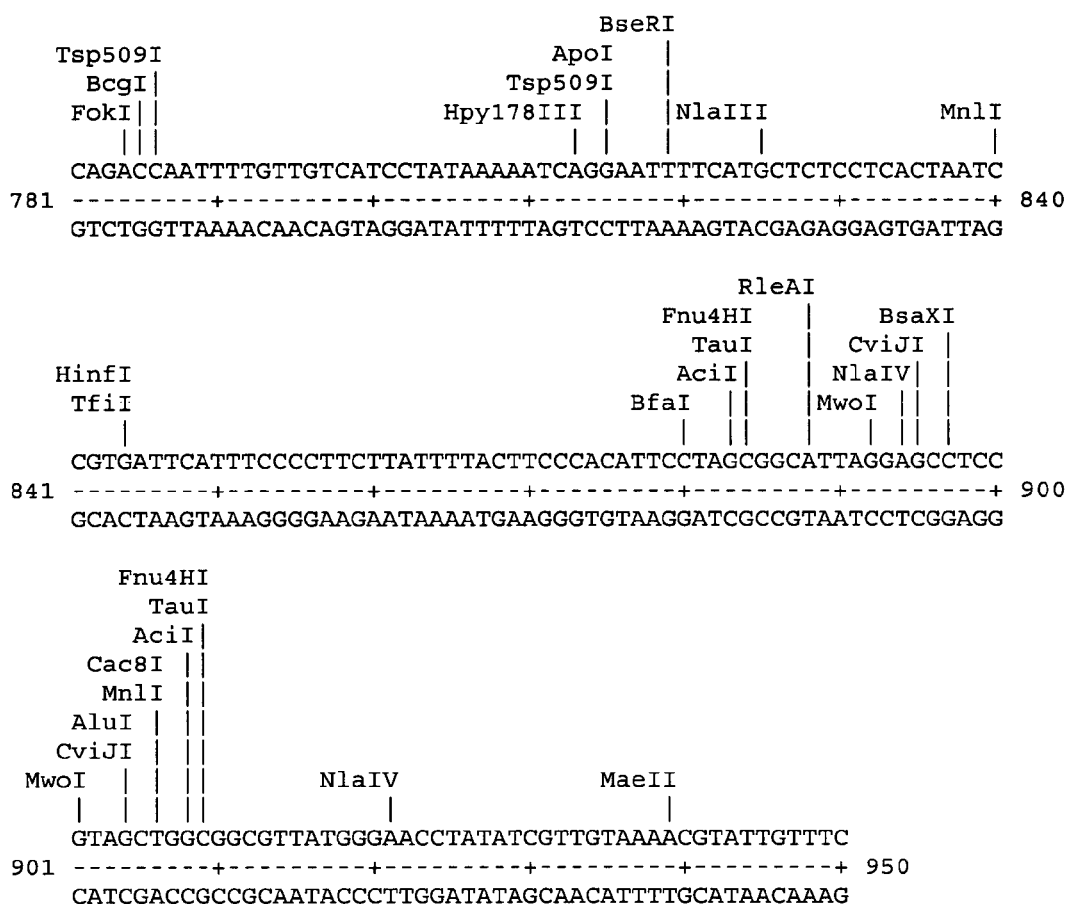
Figure 4C:
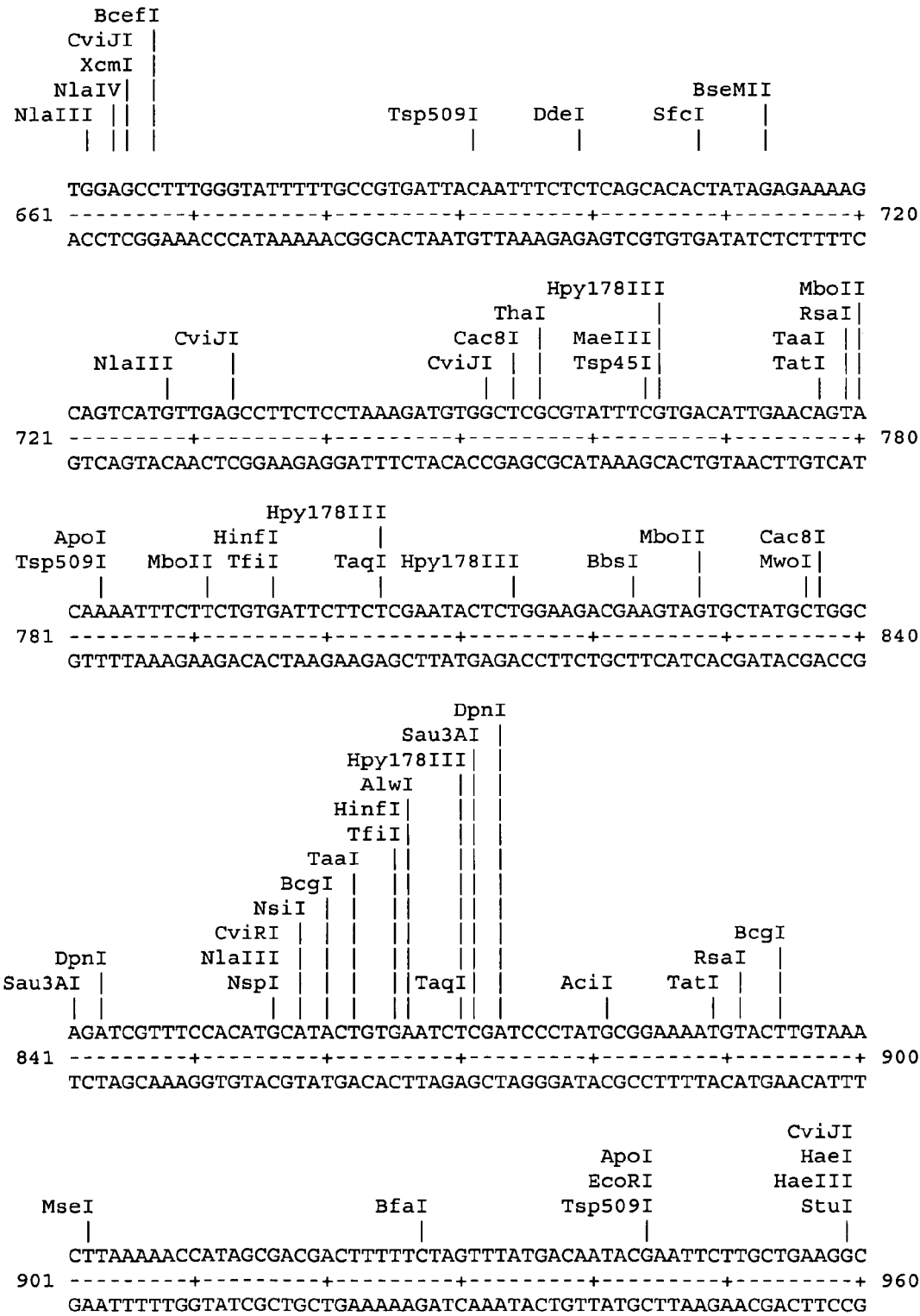
Figure 5A:
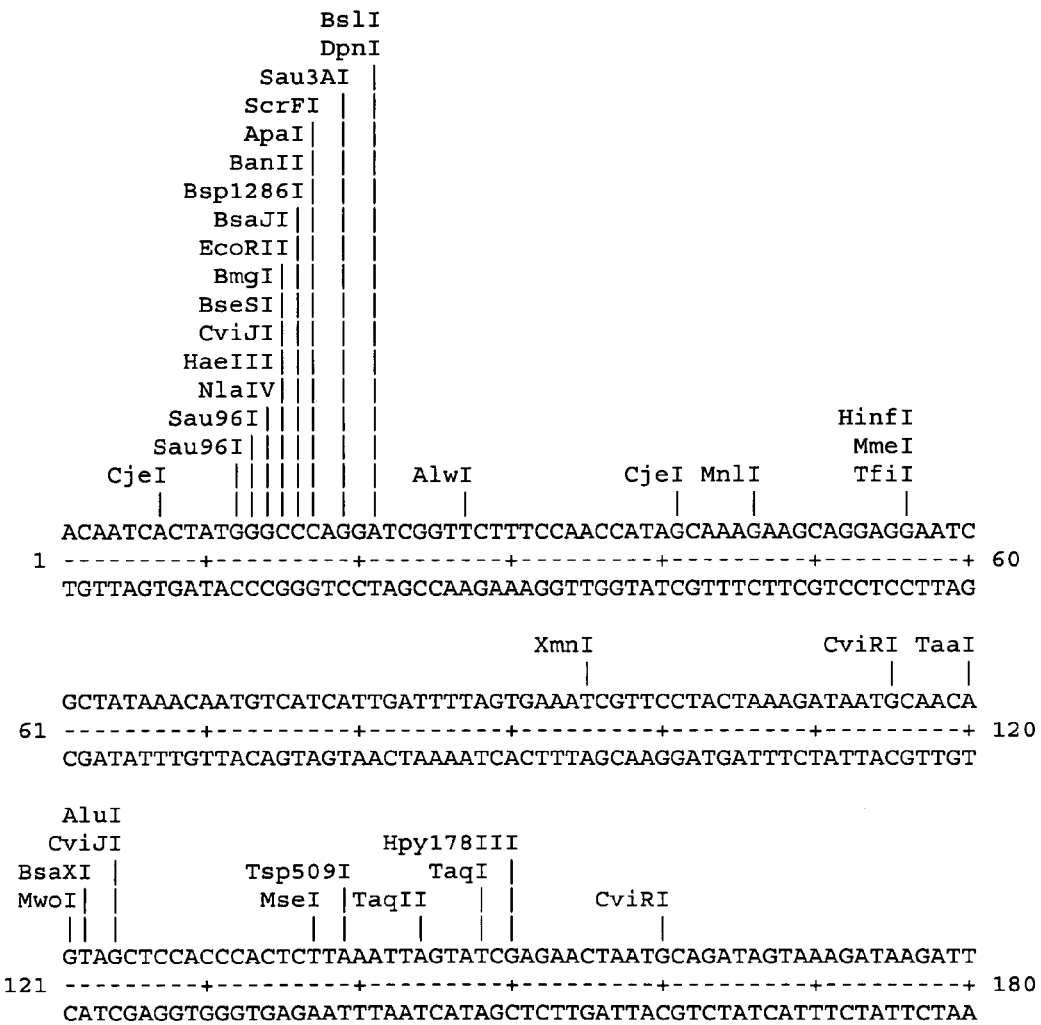
Figure 5D:
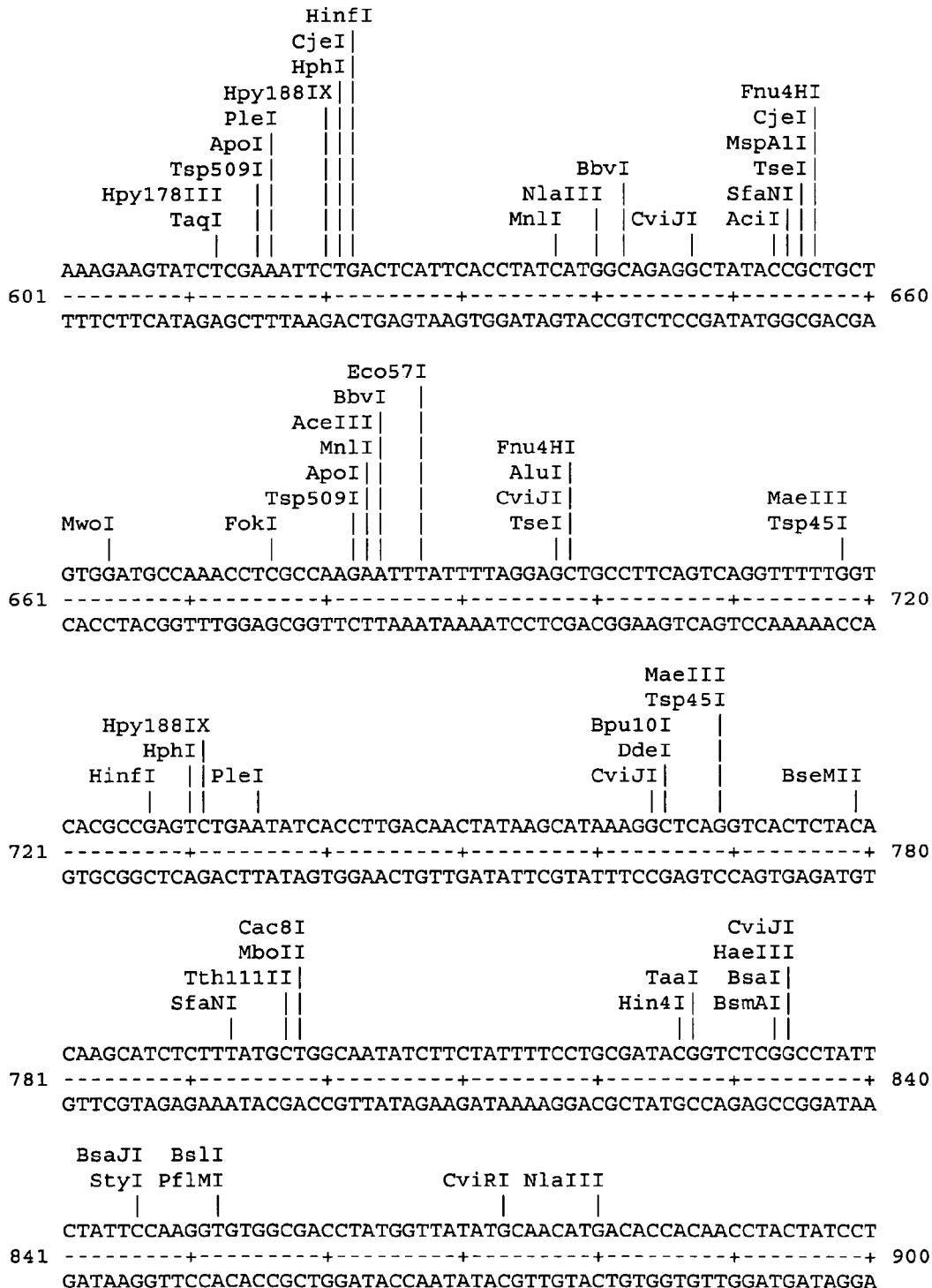
Figure 5E:
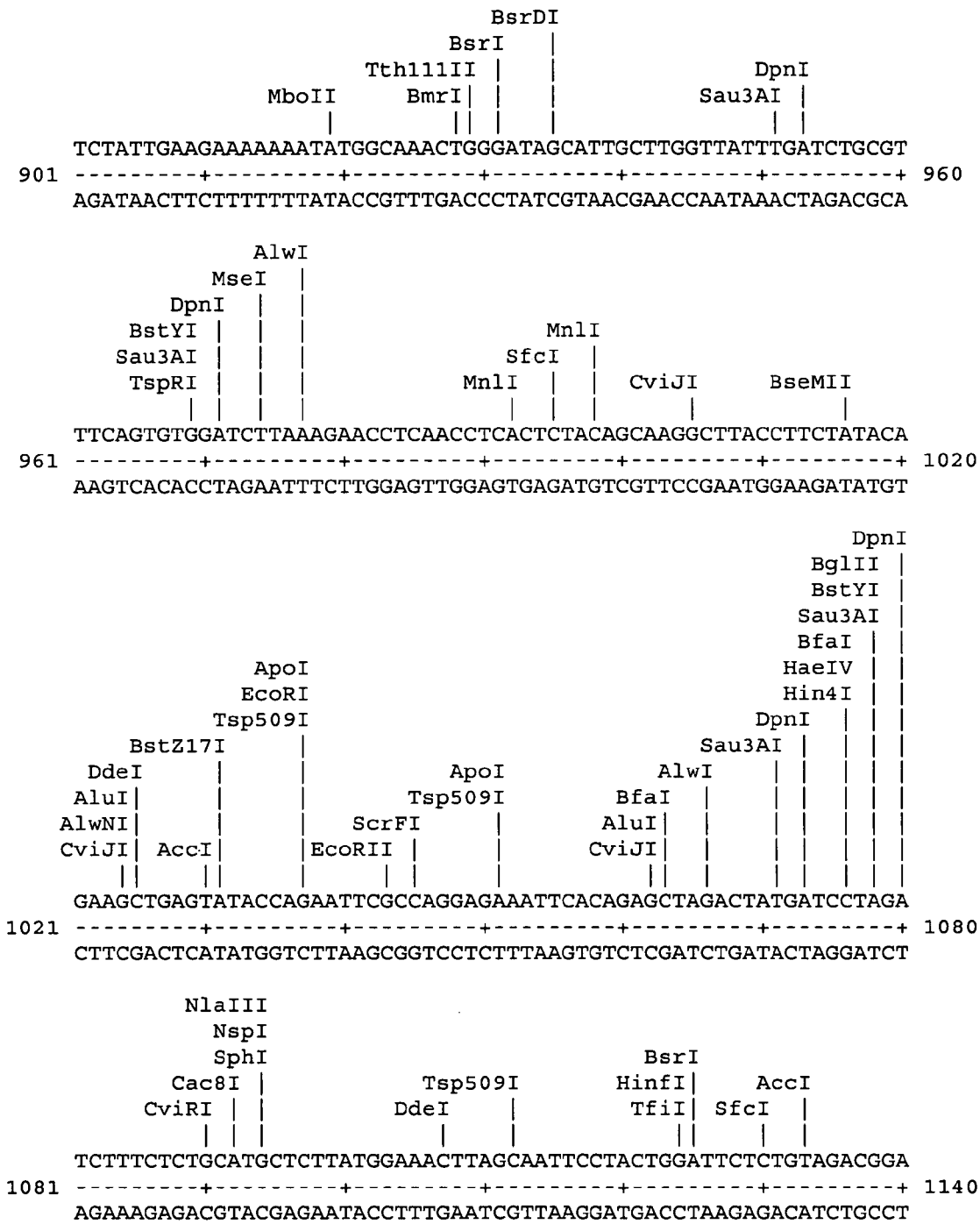
Figure 5F:
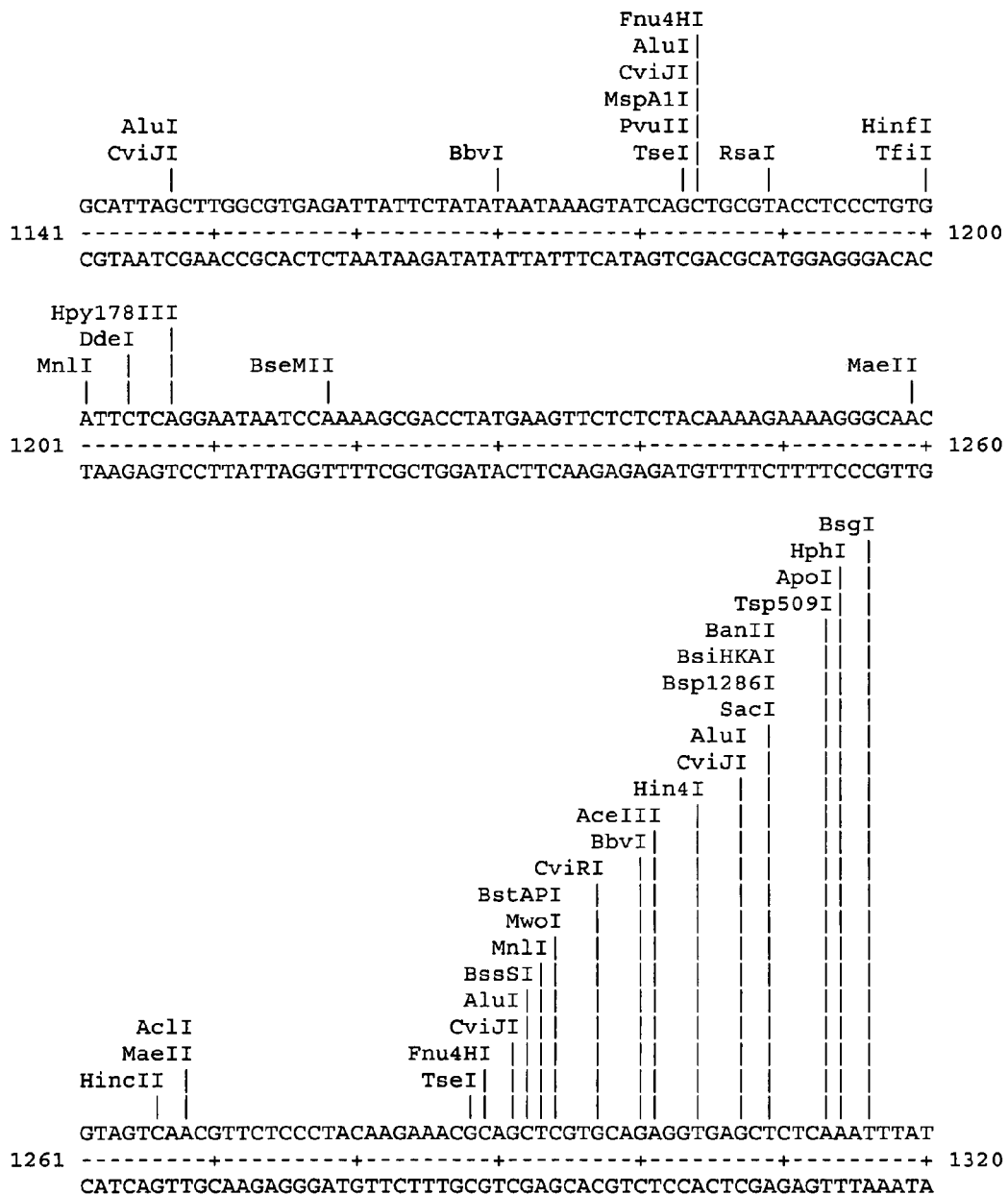
Figure 5G:
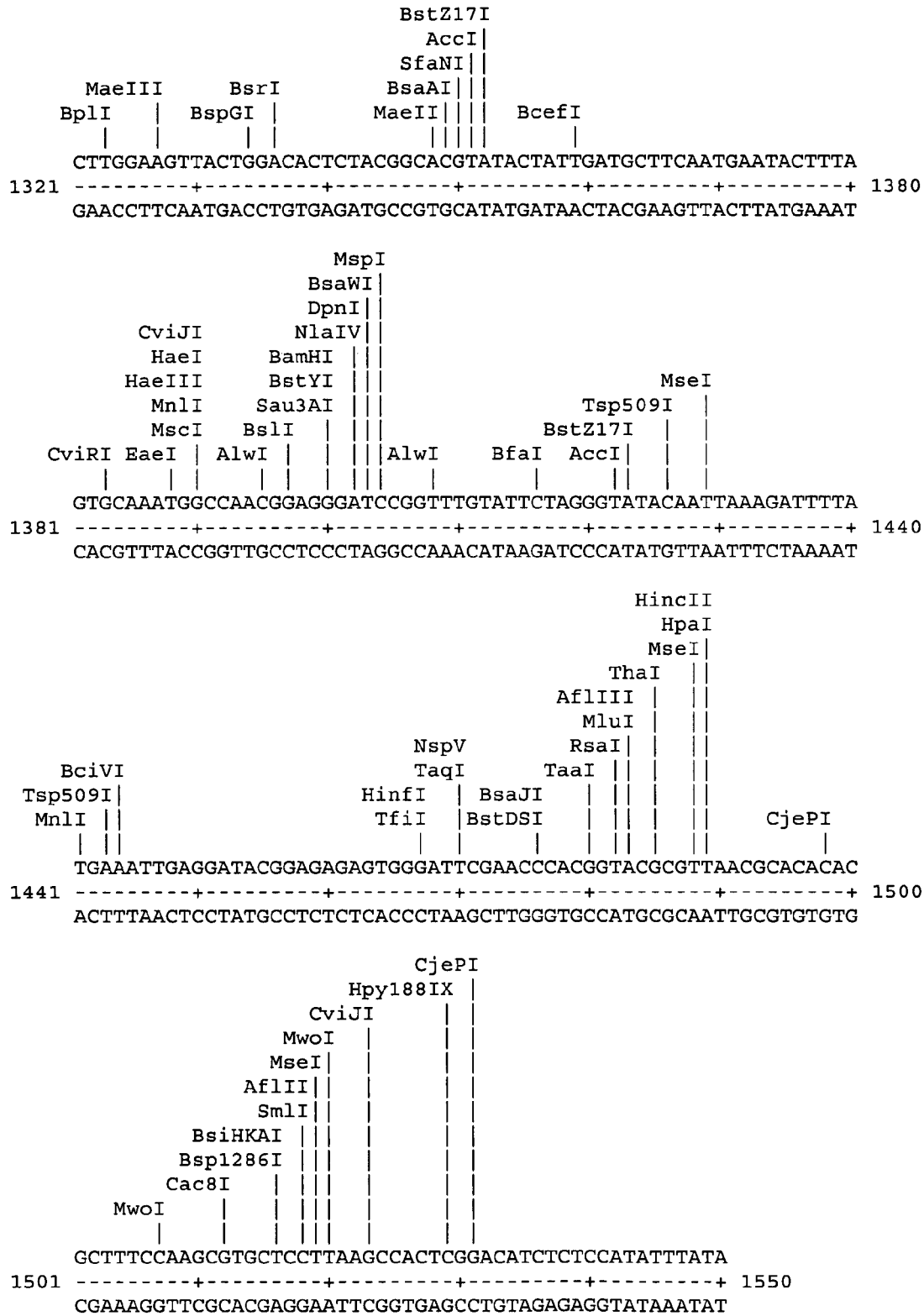
Figure 6C:
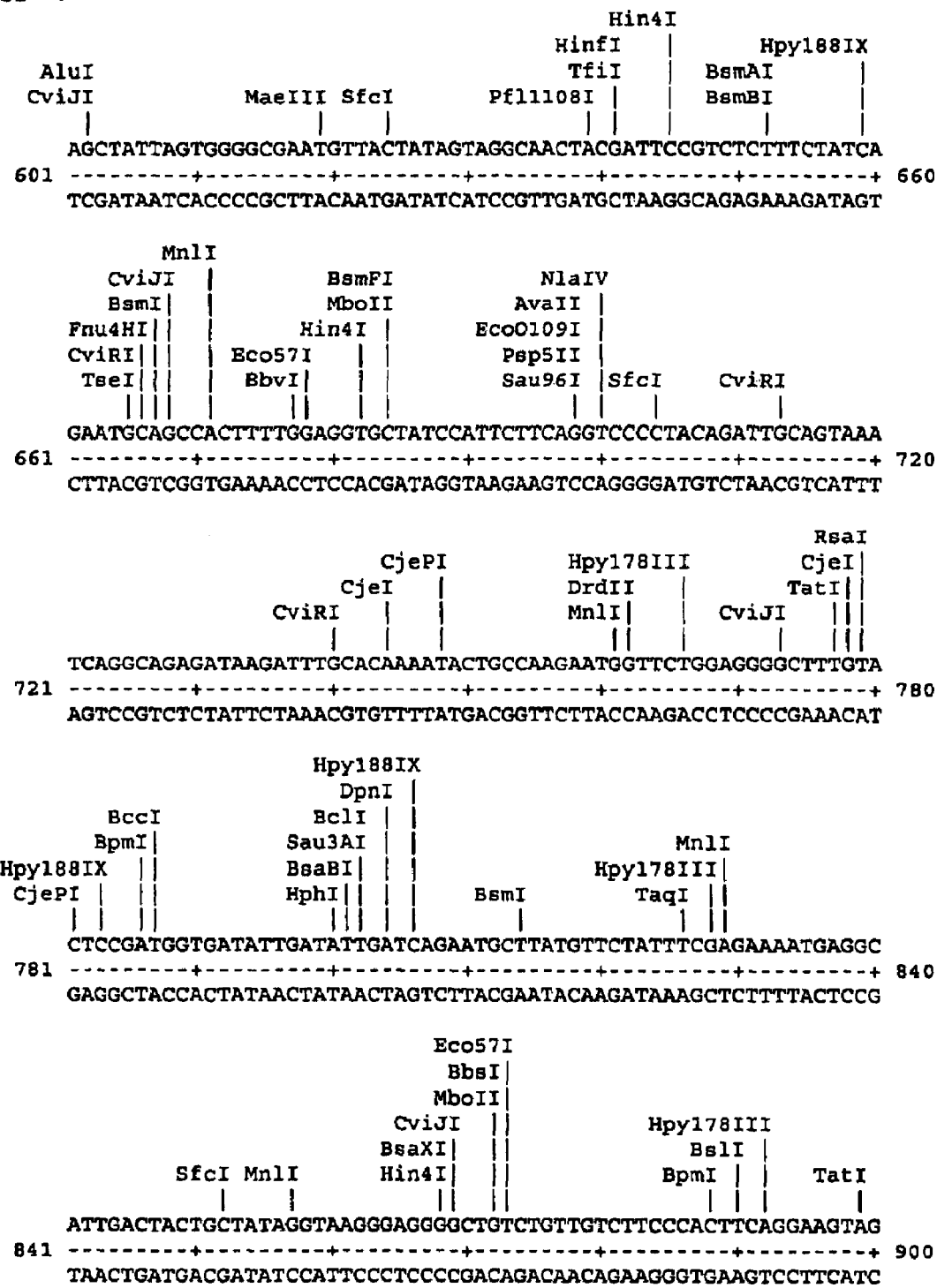
Figure 6E:
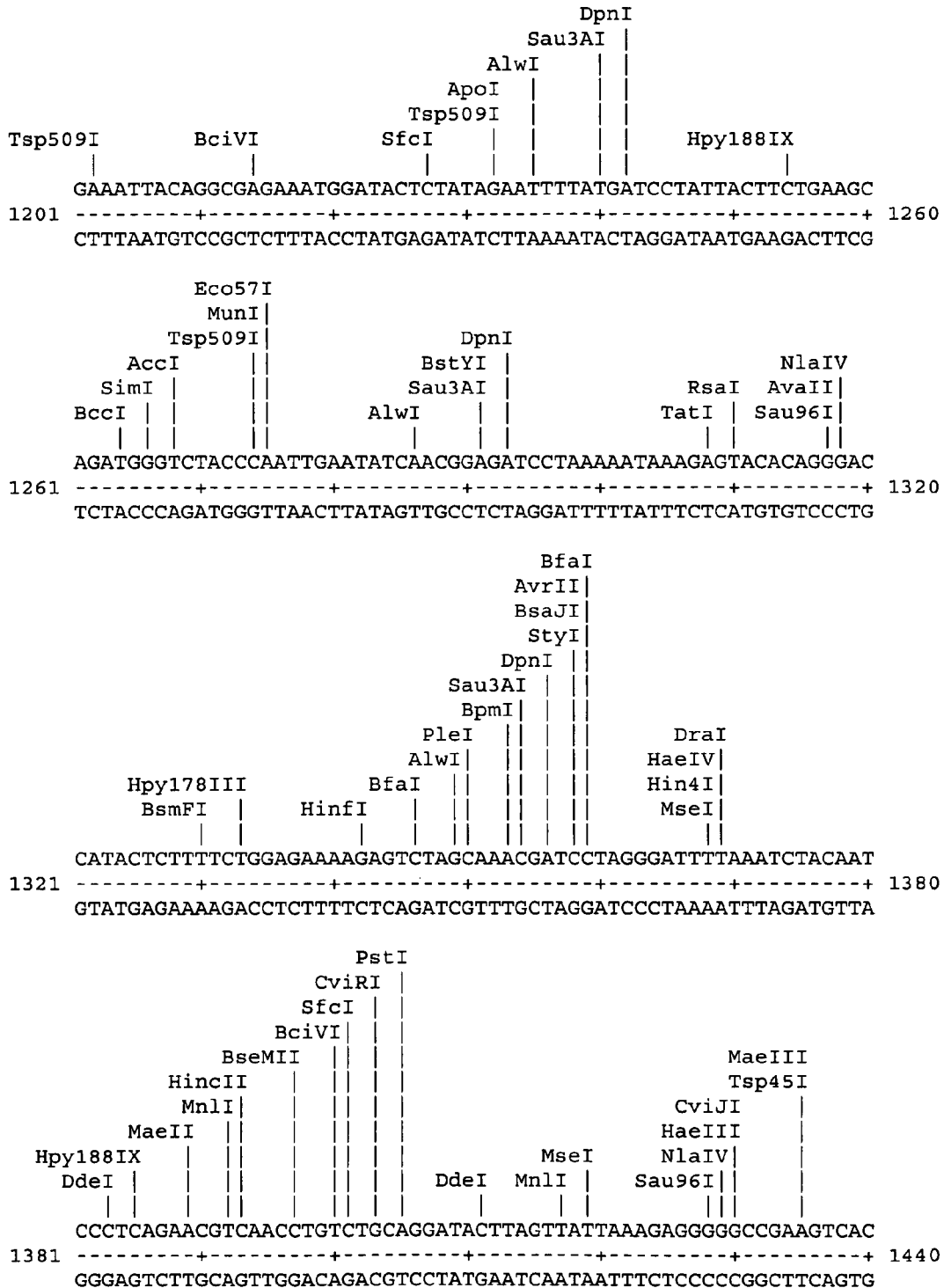
Figure 6F:
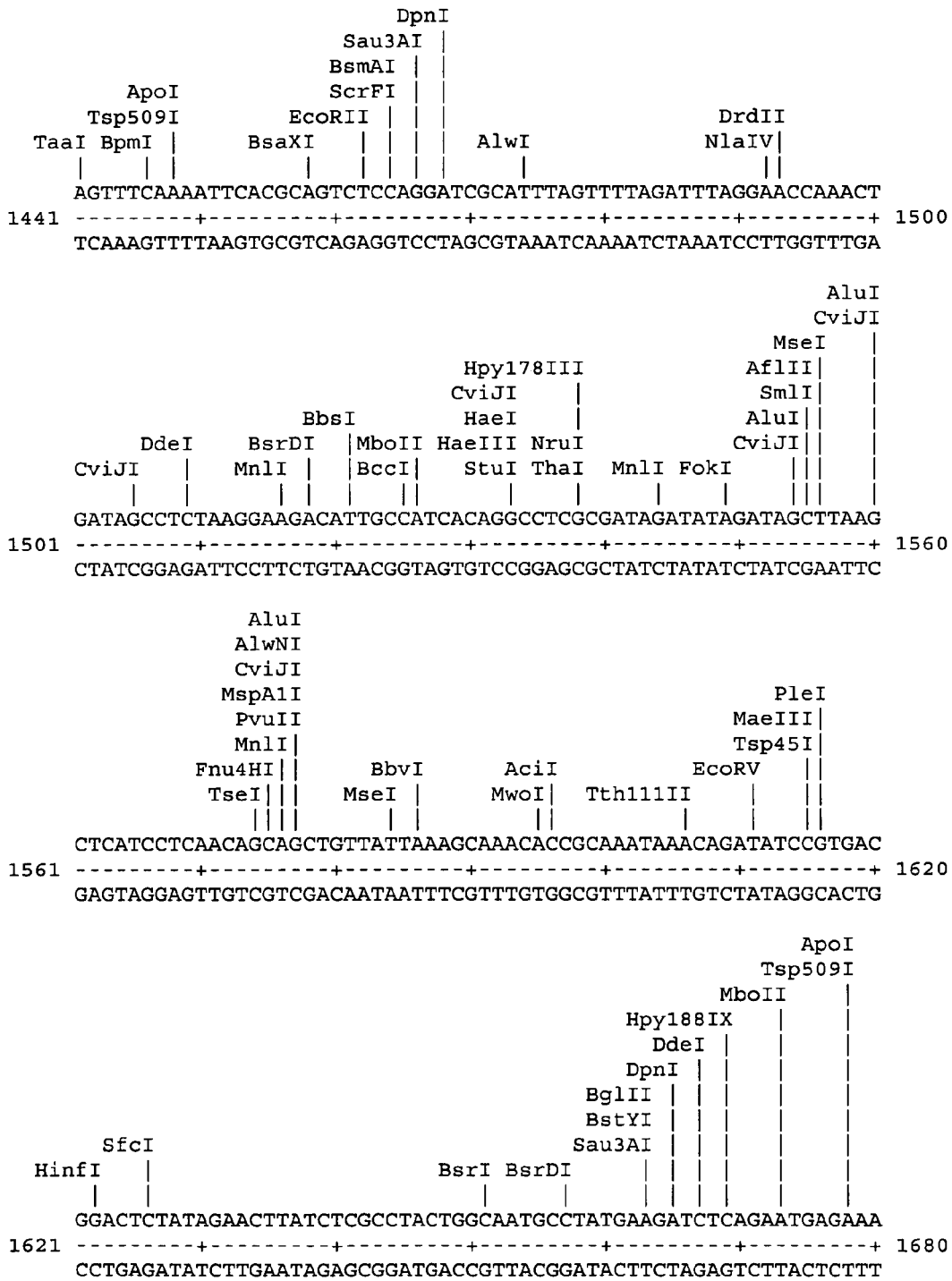
Figure 6G:
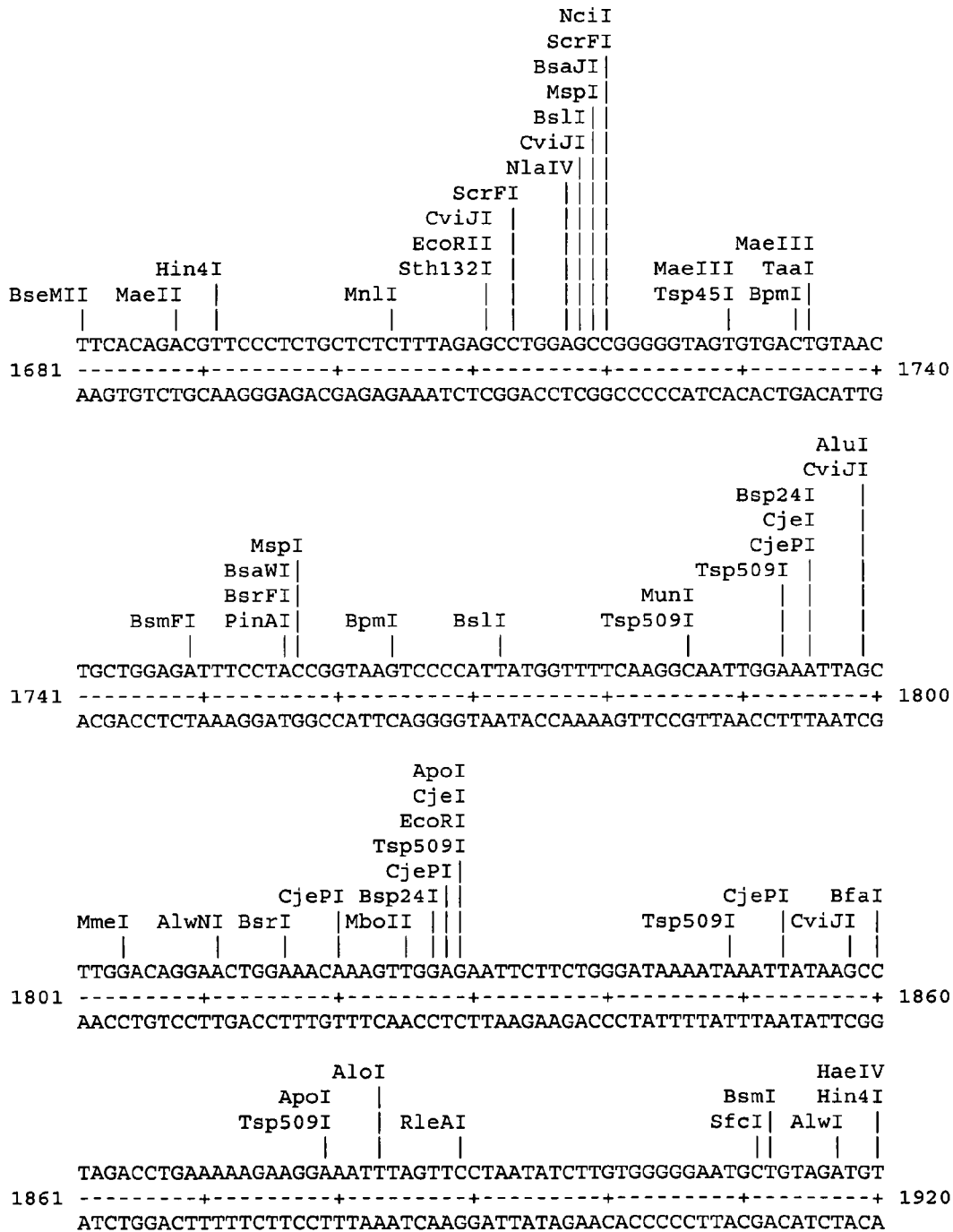
Figure 6H:
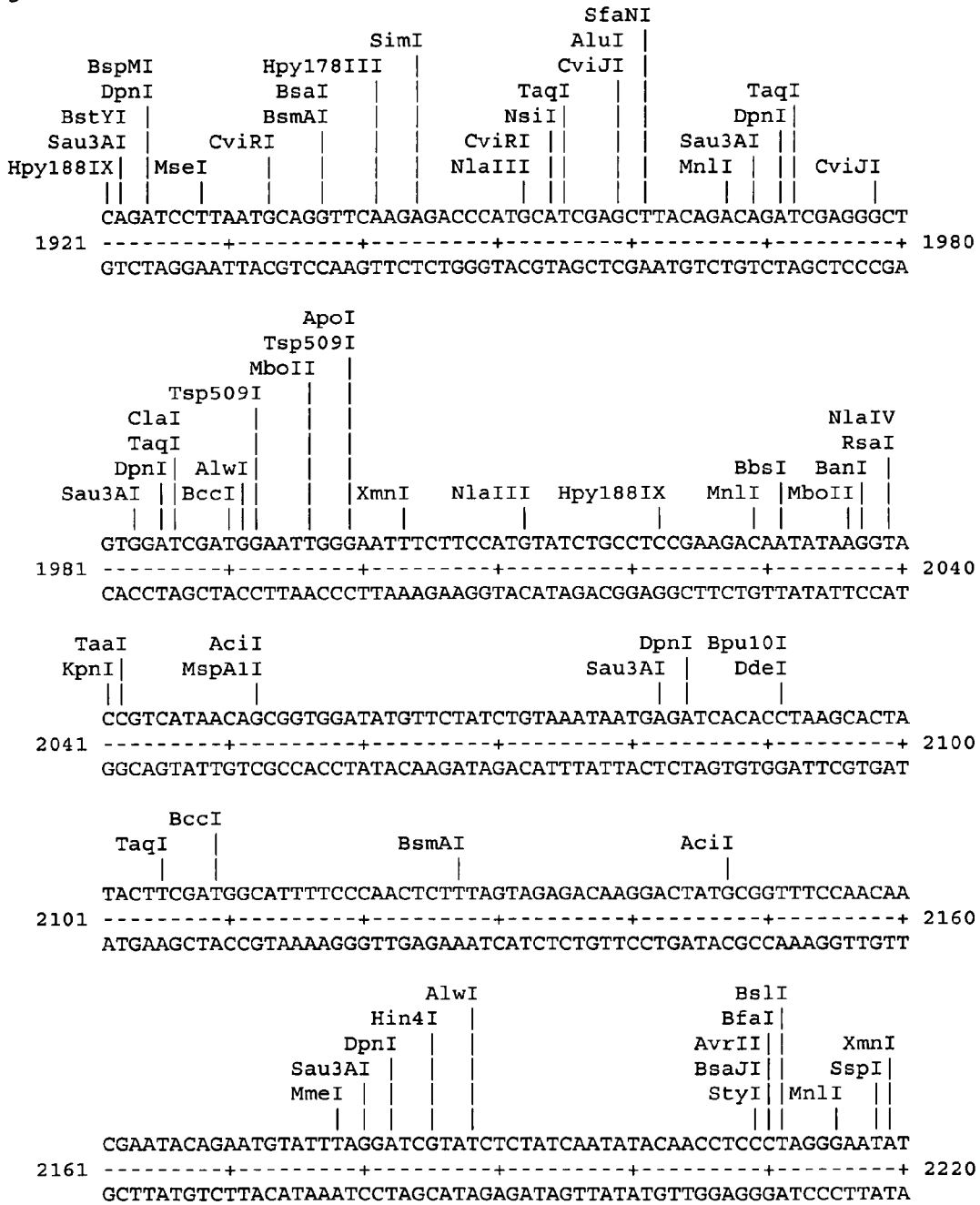
Figure 6I:
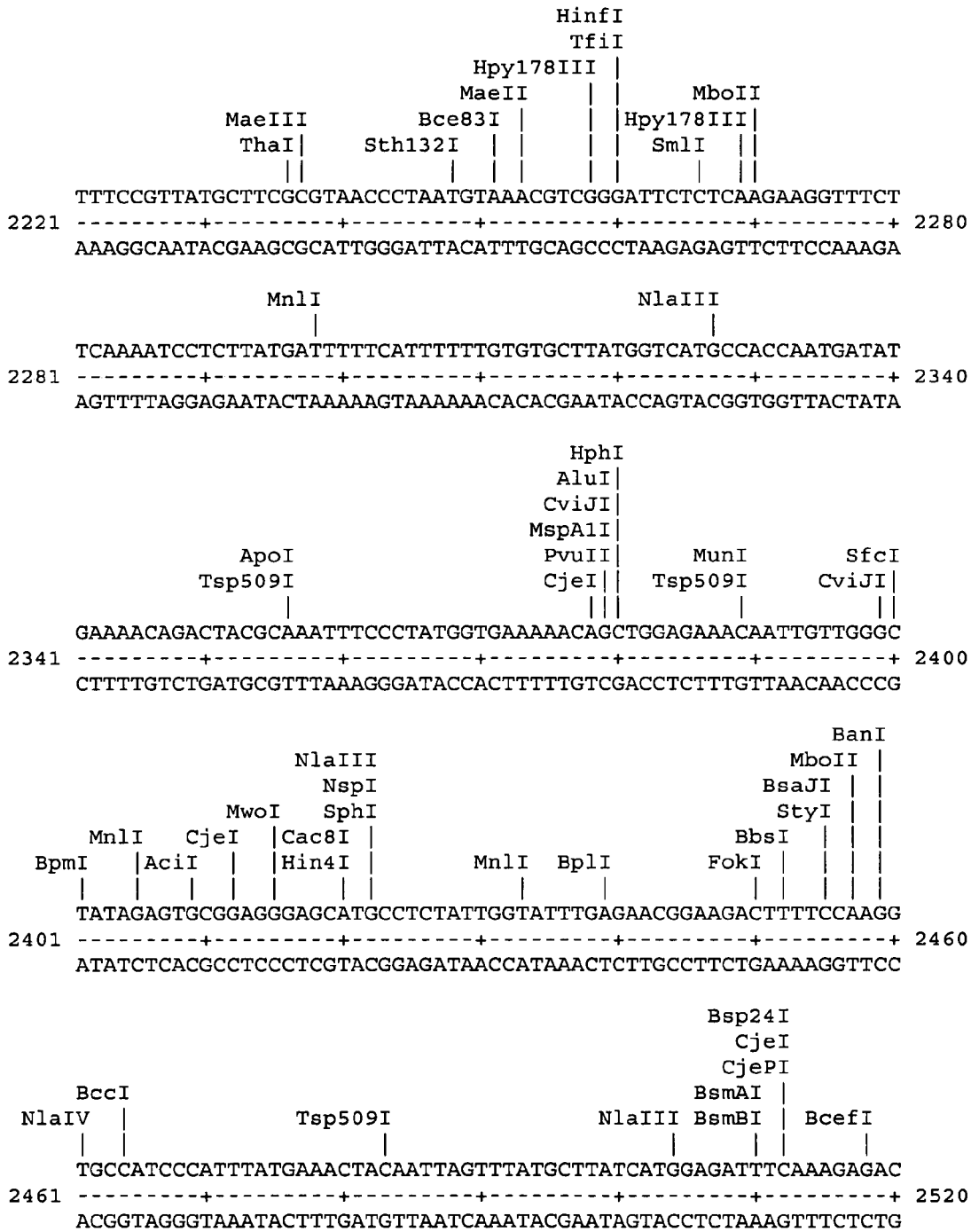
Figure 6J:
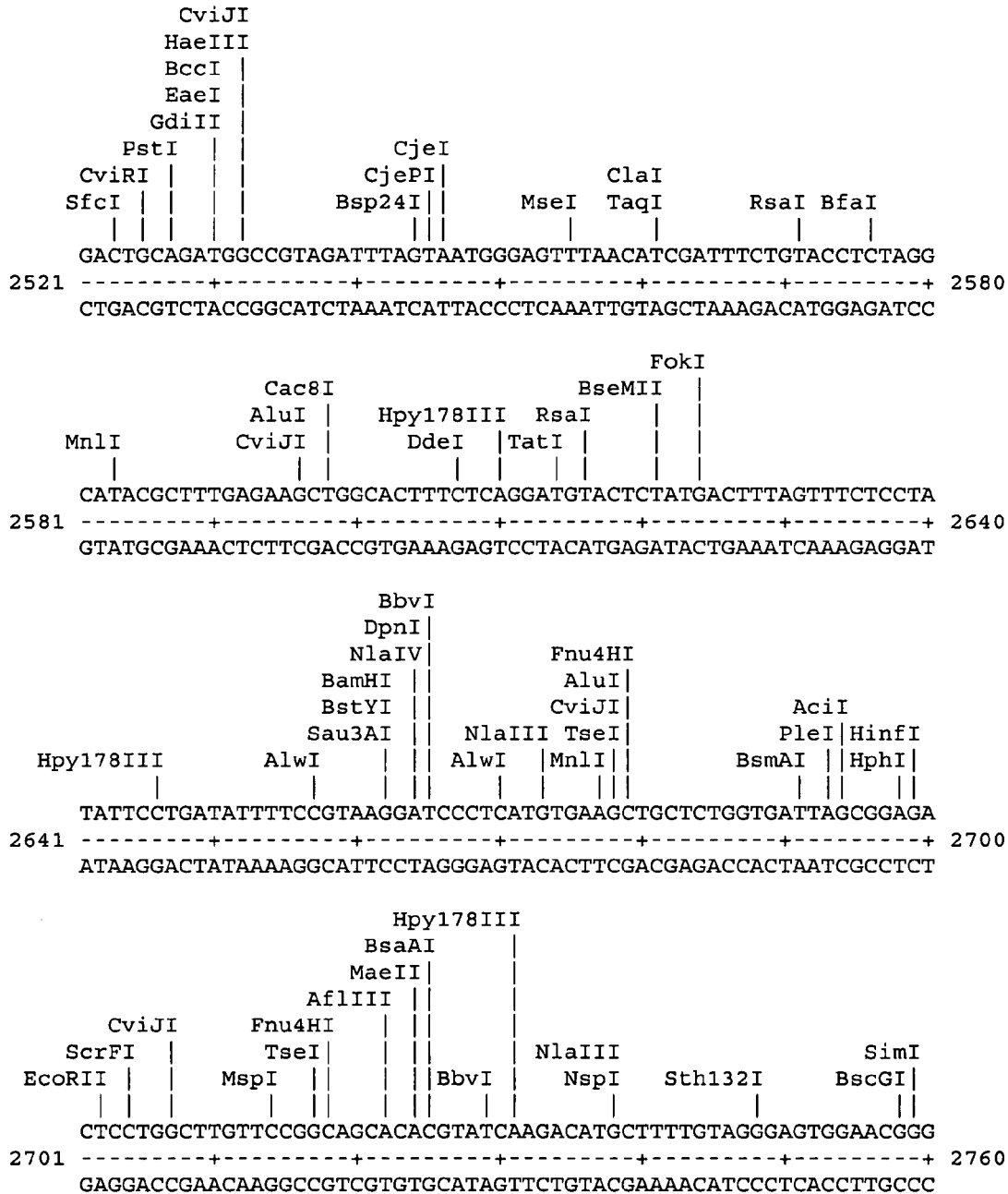
Figure 6K:
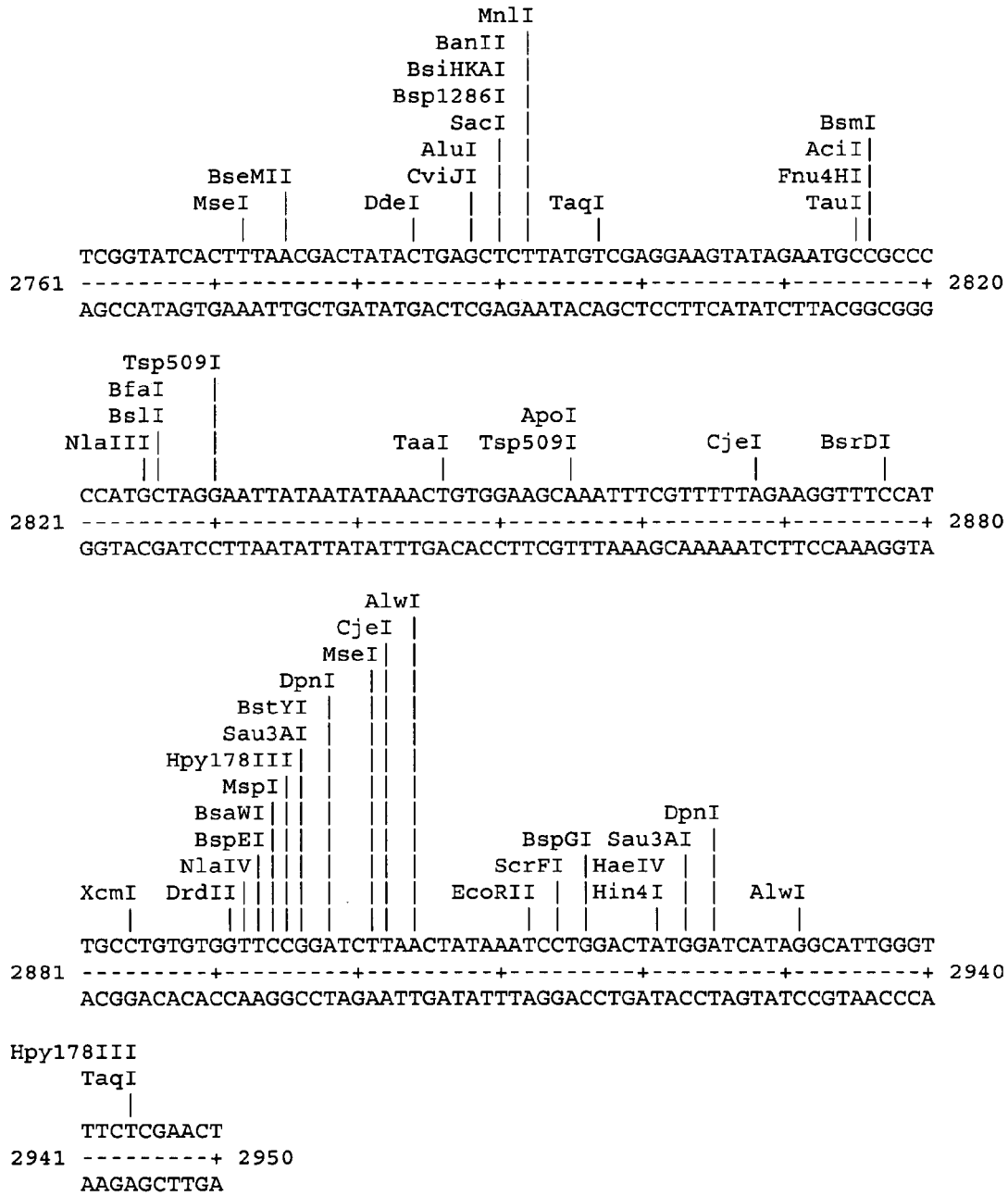
Figure 7A:
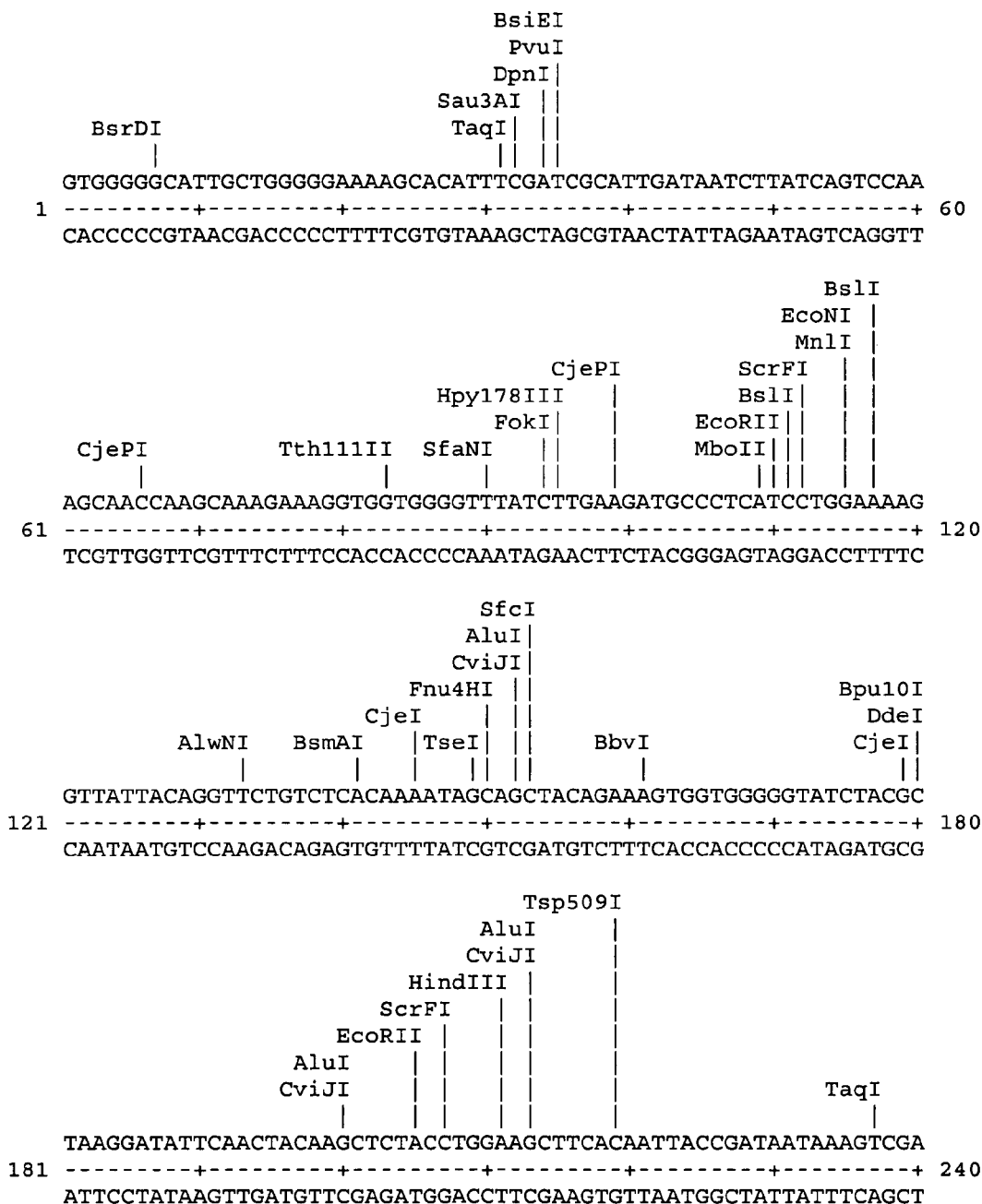
Figure 7B:
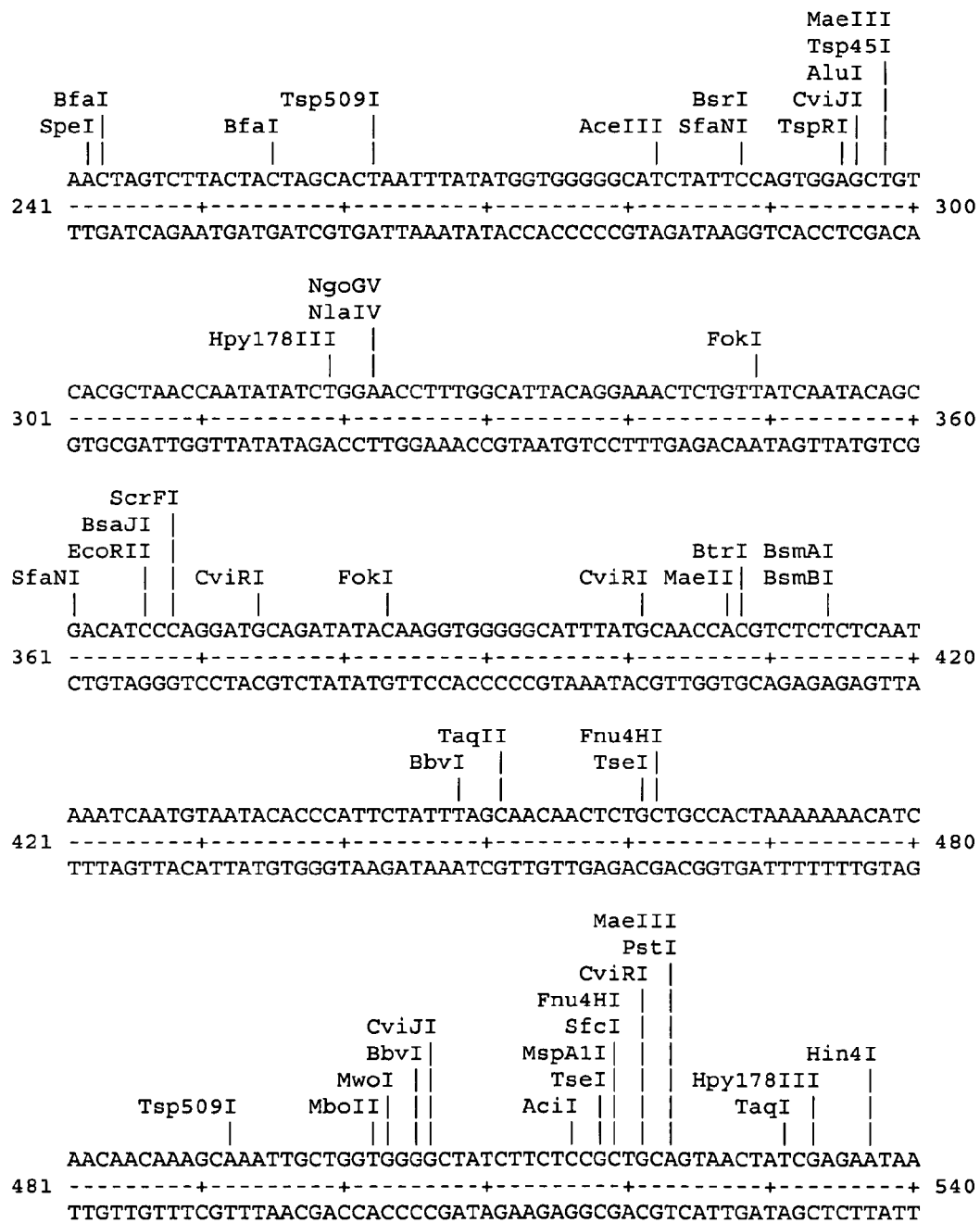
Figure 7C:
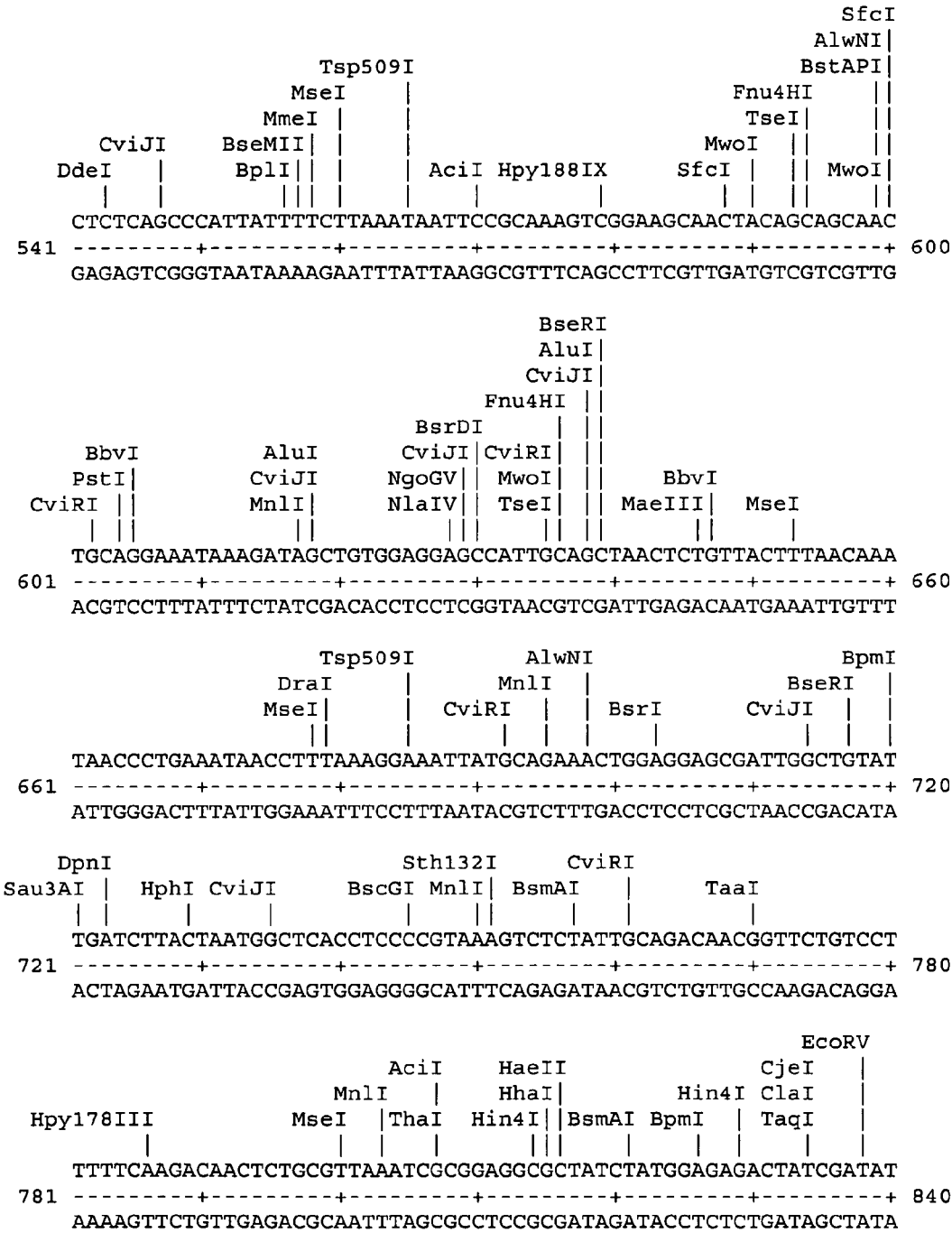
Figure 7D:
Figure 7E:
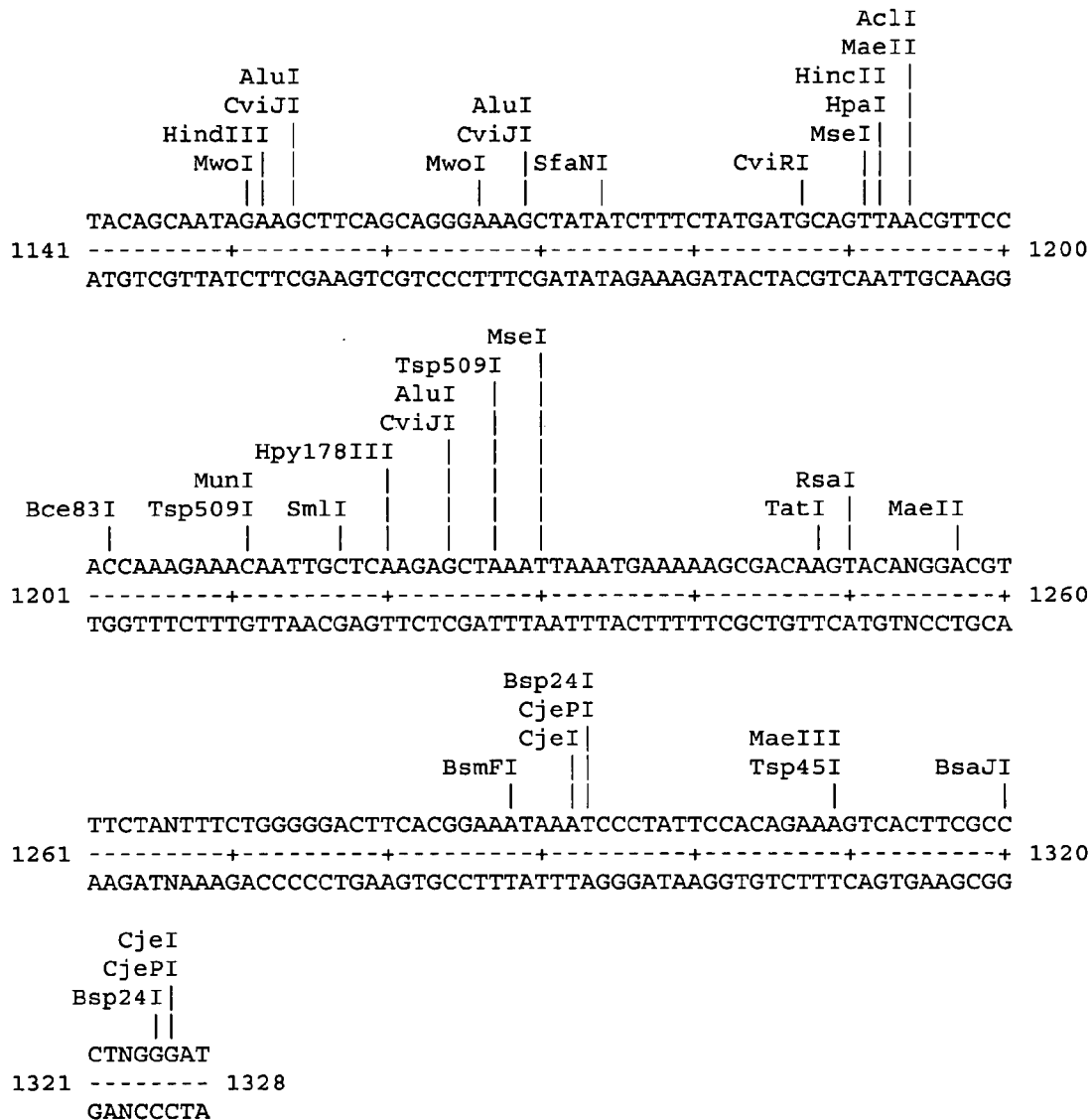
Figure 8B:
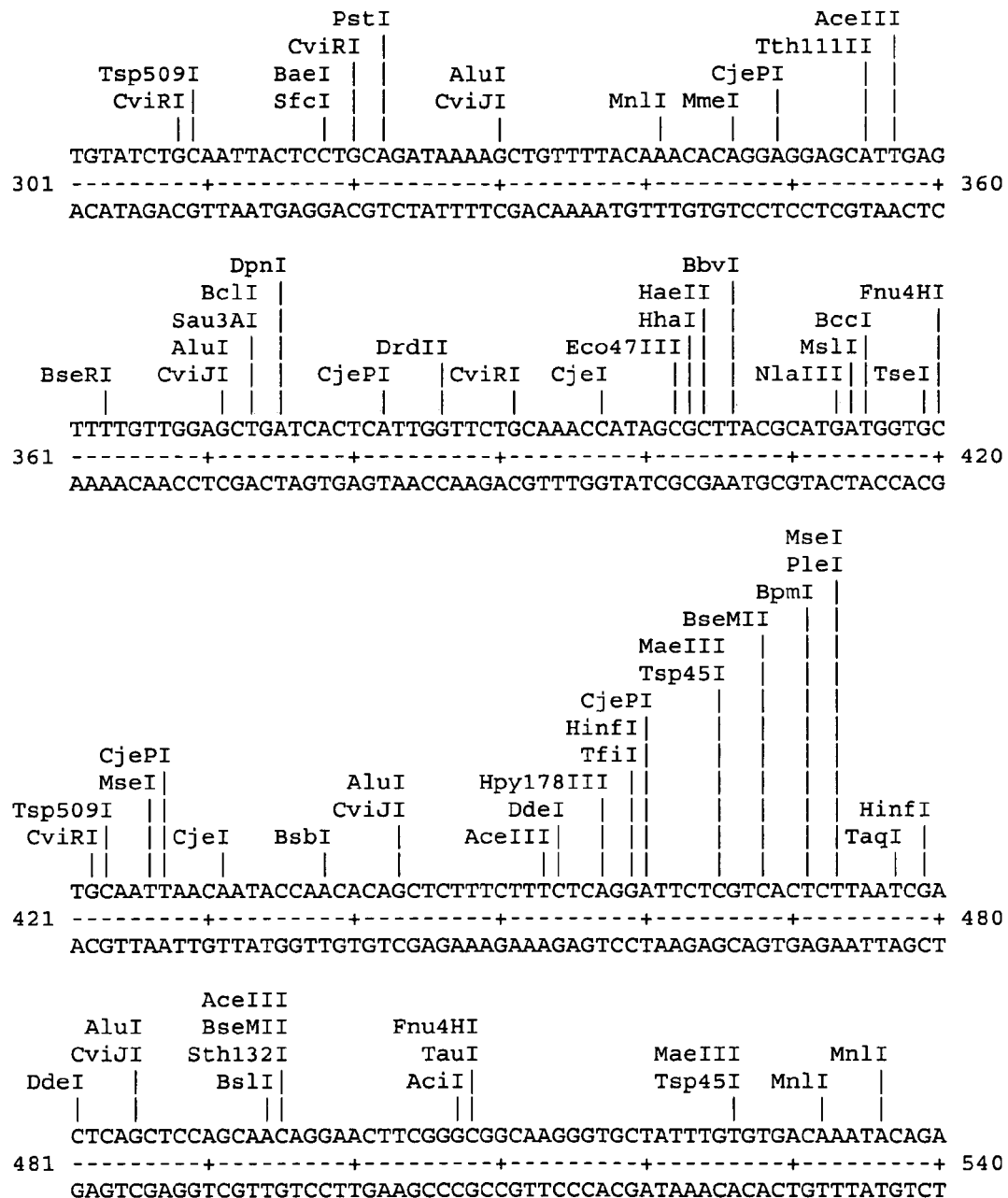
Figure 8C:
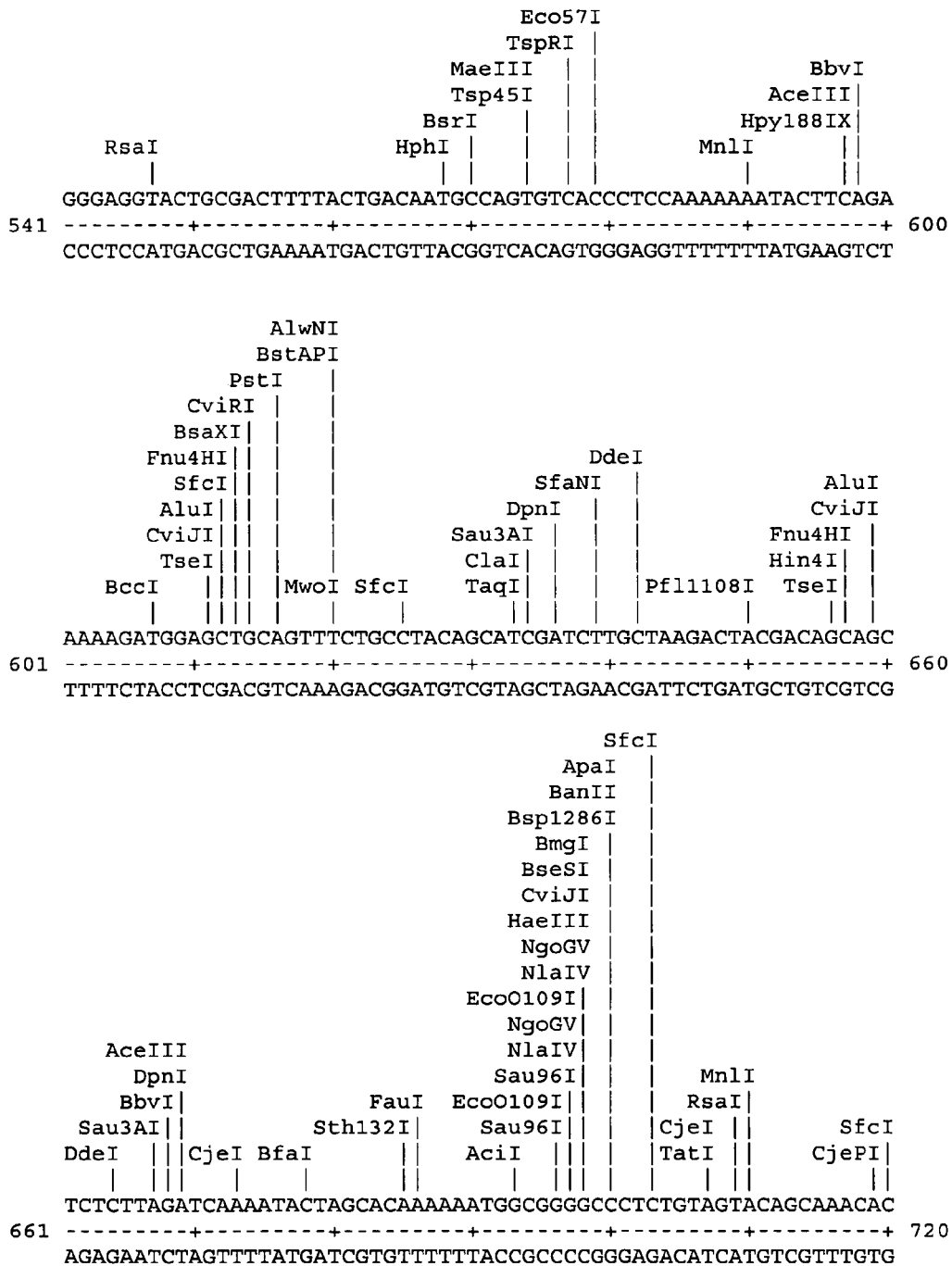
Figure 8D:
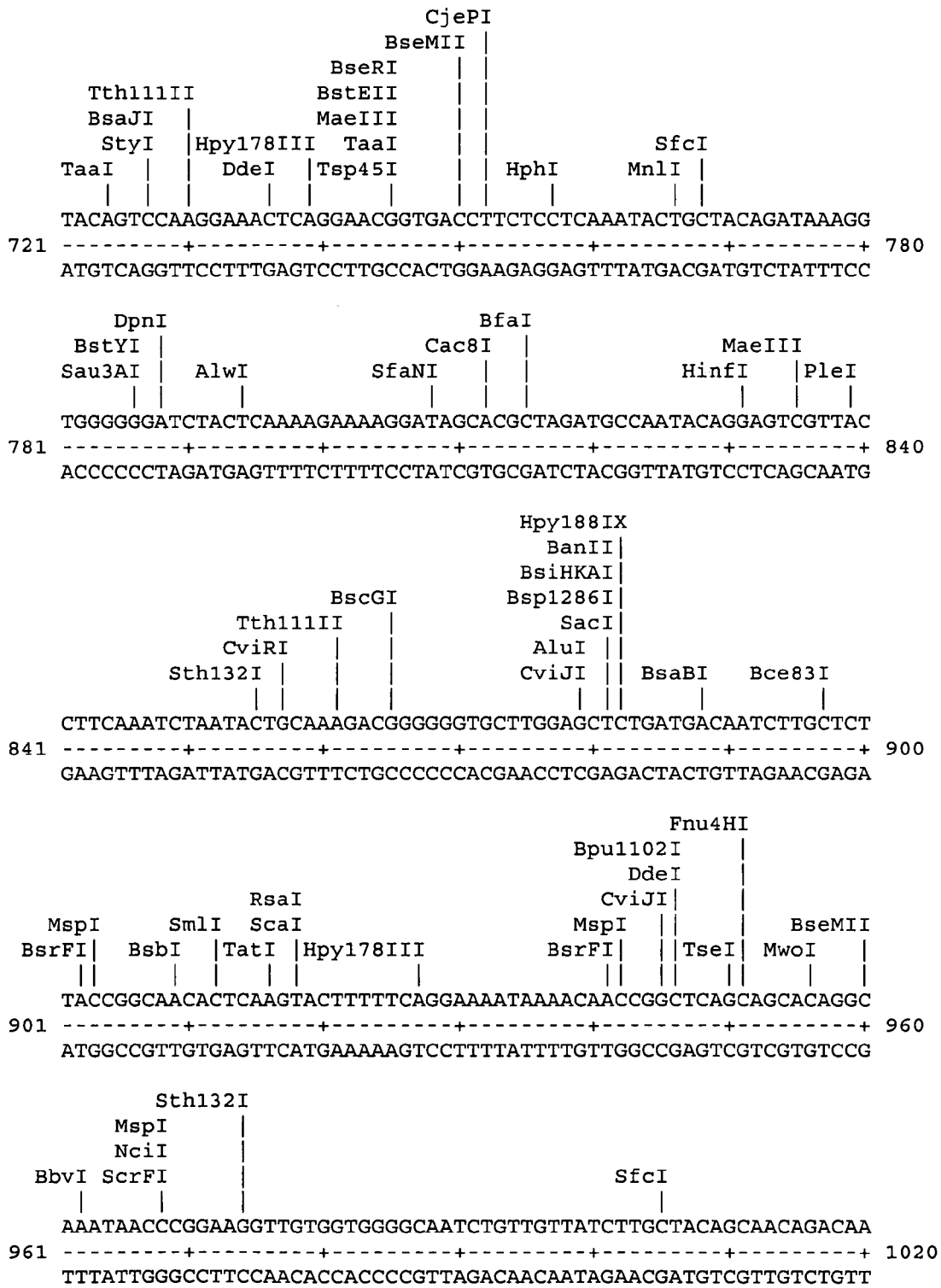
Figure 8E:
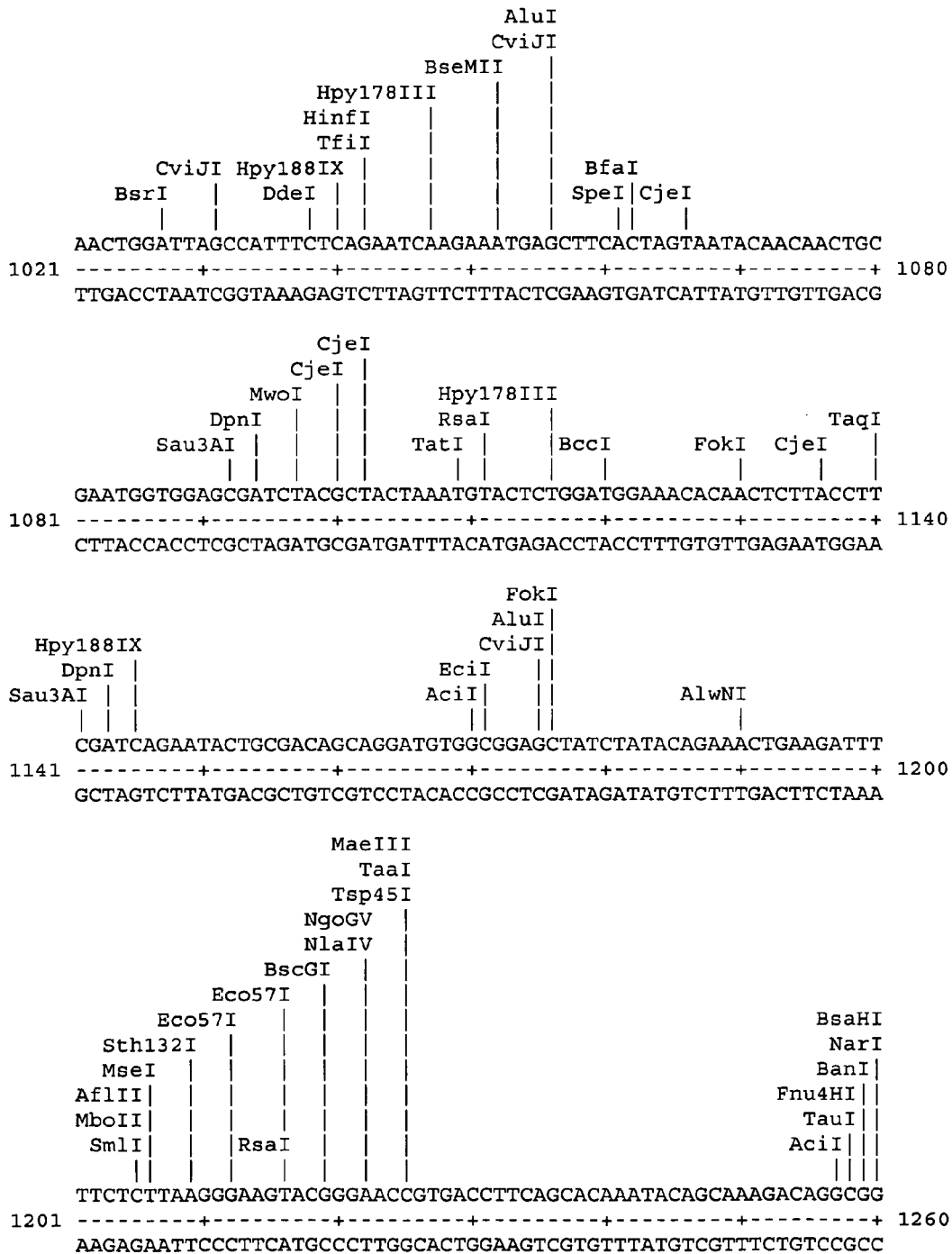
Figure 8G:
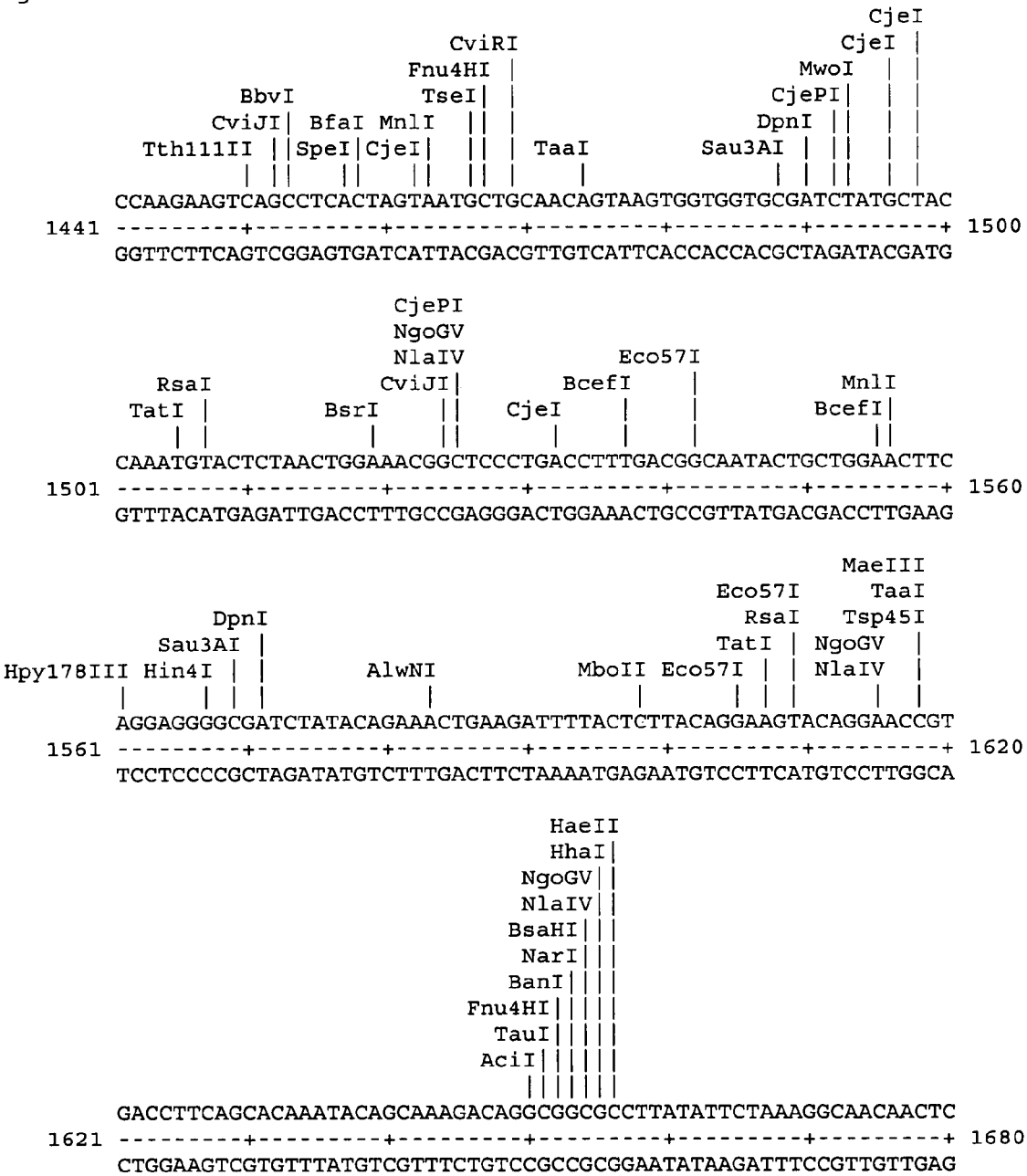
Figure 8H:
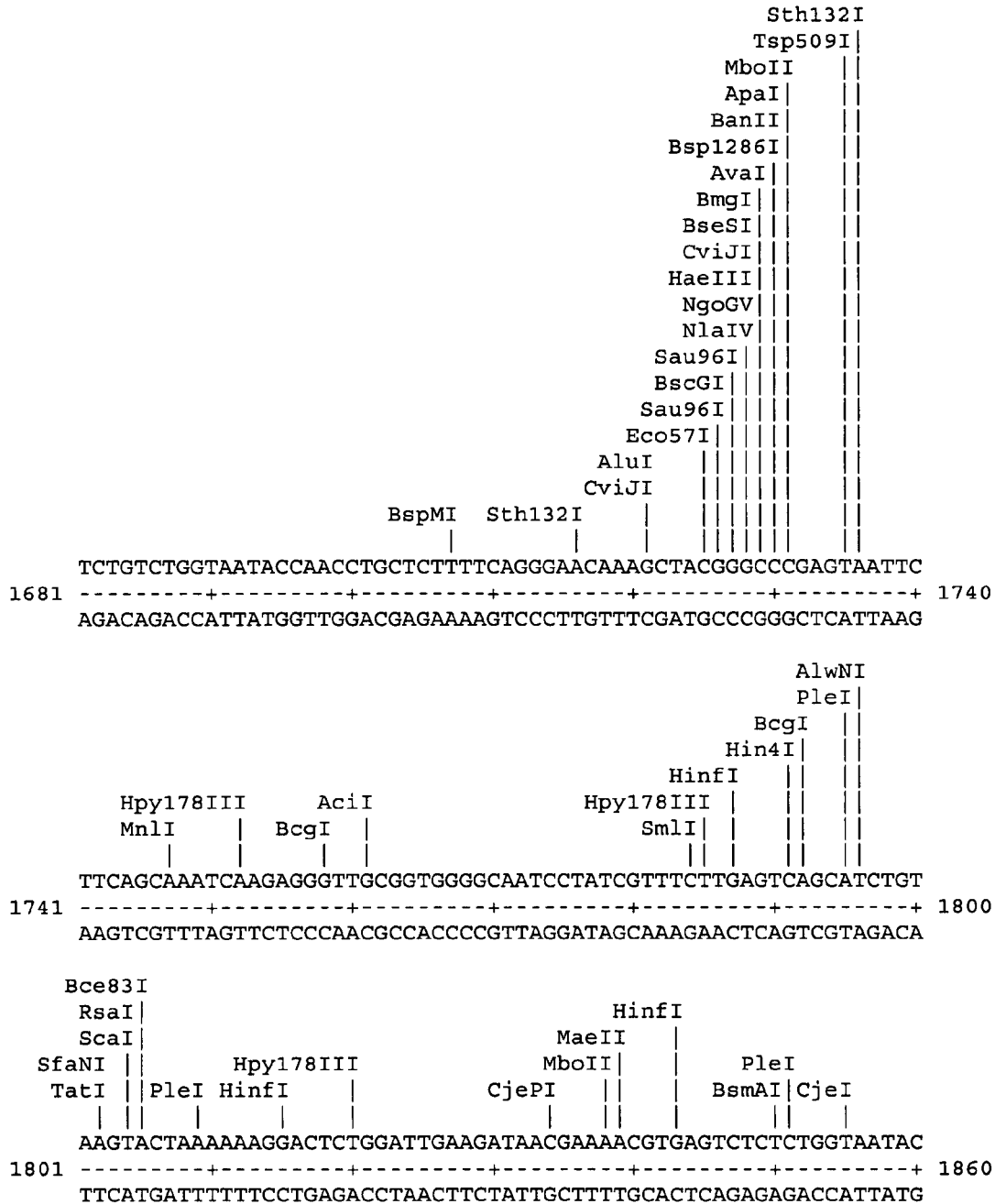
Figure 8I:
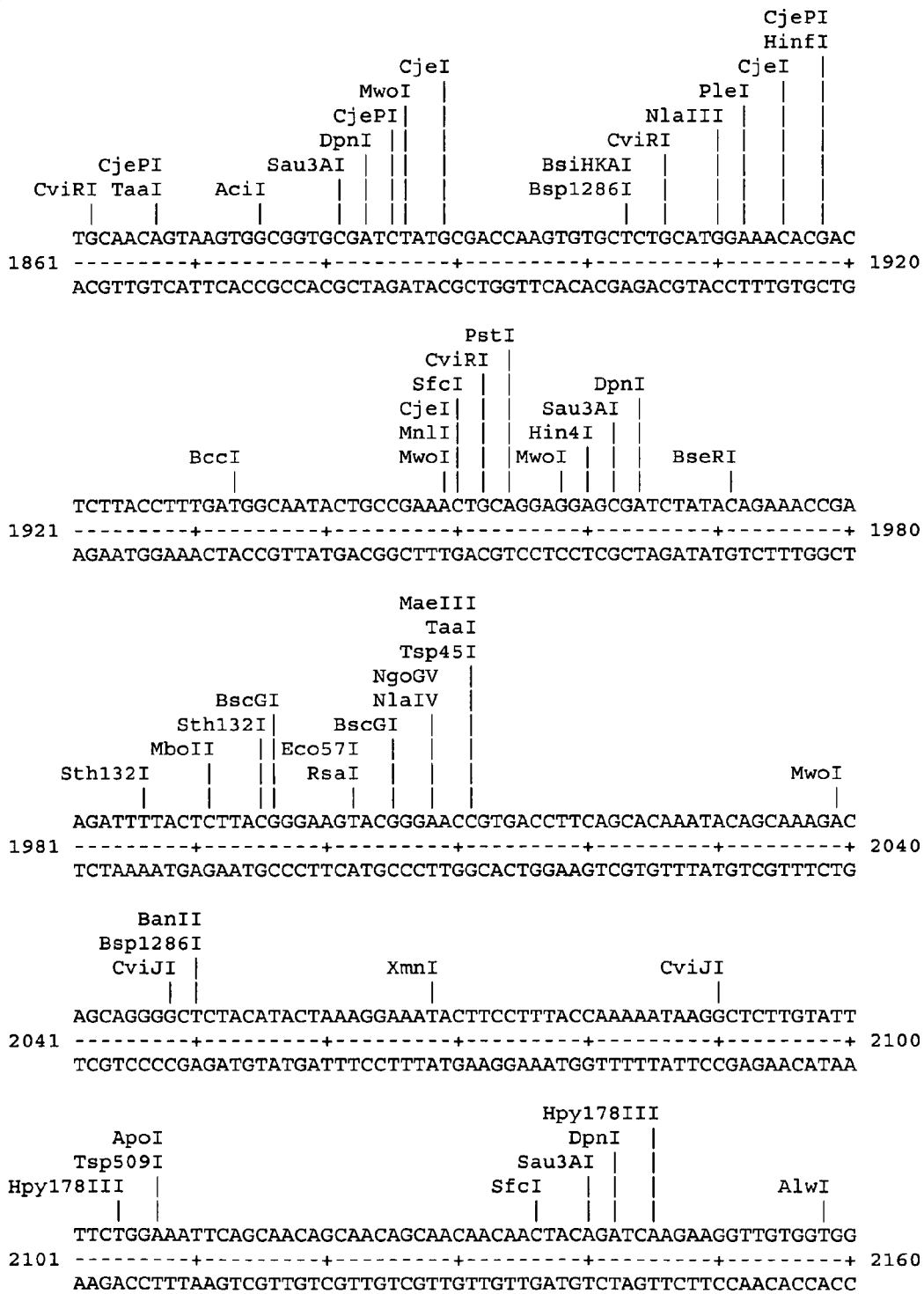
Figure 8J:
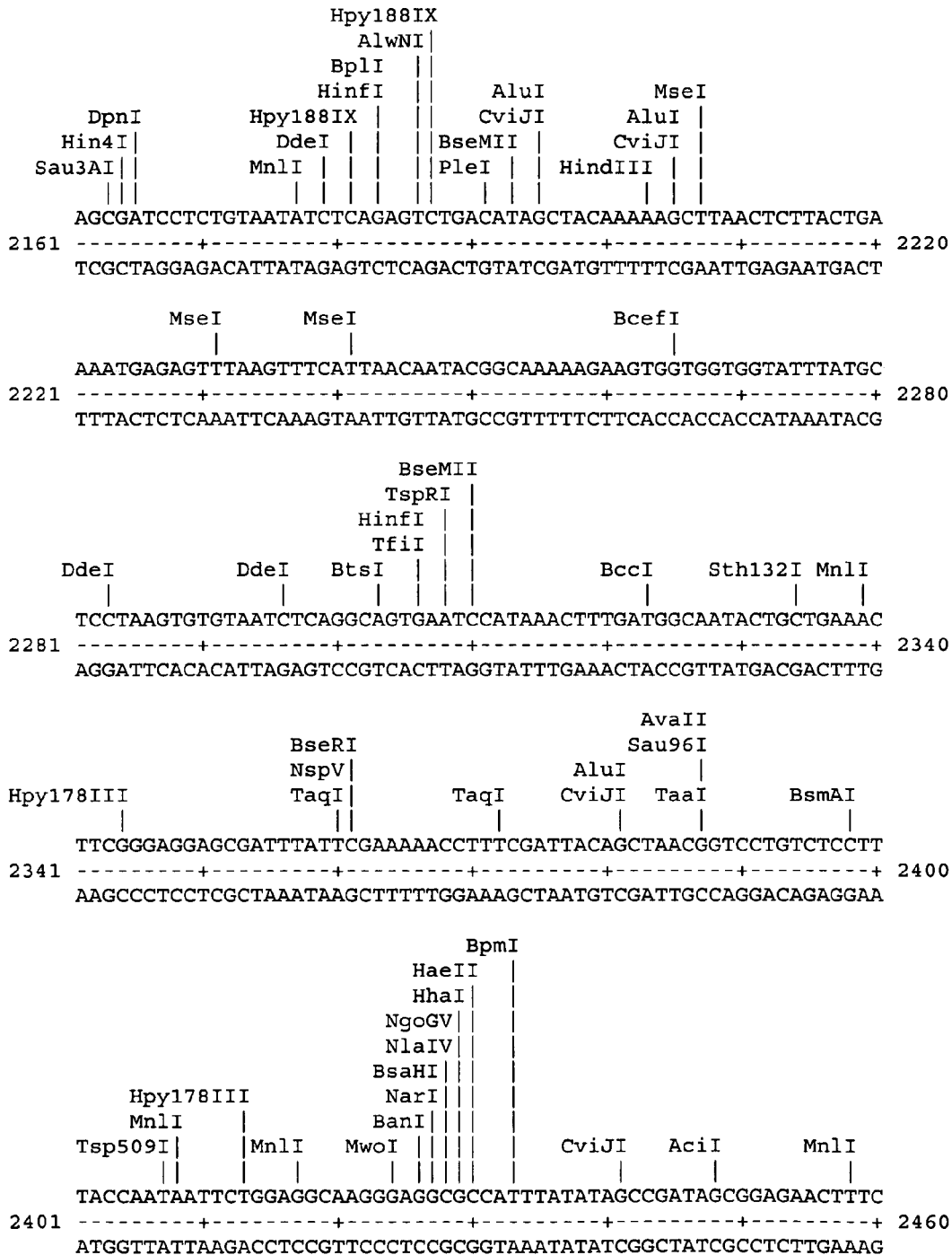

| | | |
|---|---|---|
| WO | WO 01/21811 A1 | 3/2001 |
| WO | WO 01/40474 A2 | 6/2001 |
| WO | WO 01/46224 A2 | 6/2001 |
| WO | WO 01/81379 A2 | 11/2001 |
| WO | WO 01/85972 A2 | 11/2001 |
| WO | WO 02/02606 A2 | 1/2002 |
| WO | WO 02/08267 A2 | 1/2002 |

OTHER PUBLICATIONS

Boehringer Mannheim Biochemicals (1991 Catalog p. 557).*
Stratagene (1991 Product Catalog, p. 66).*
Promega (1993/1994 Catalog, pp. 90-91) or.*
New England BioLabs (Catalog 1986/1987, pp. 60-62).*
Gibco BRL (Catalogue & Reference Guide 1992, p. 292).*
Hillier et al (Genome Research. vol. 6, No. 9, pp. 807-828. 1996.*
Allen et al, Journal of Immunology 1991, 147; 674-679.*
Batteiger et al 1996, Infection and Immunity , 64; 2839-2841.*
Murdin et al (J. Infectious Diseases, 2000, 181, Suppl. 3:S552-S557.*
Verma et al. (1997) Nature, vol. 389, p. 239.*
Miller et al , The FASEB Journal 1995, 9: 190-199).*
Niman et al, PNAS, USA1983, vol. 80:4949-4953.*
Current Protocols in Immunology, 1997 unit 9.7.1-9.7.5, 9.7.16-9.7.19.*
Reece et al, 1994, J. Immunol, vol. 172 , 241.*
Grayston et al. (1995) *Journal of Infectious Diseases* 168:1231.
Campos et al. (1995) *Investigation of Ophthalmology and Visual Science* 36:1477.
Grayston et al (1990) *Journal of Infectious Diseases* 161:618.
Marrie (1993) *Clinical Infectious Diseases*. 18:501.
Wang et al (1986) Chlamydial infectious. Cambridge University Press, Cambridge. p. 329.
Saikku et al. (1988) *Lancet*;ii:983.
Thom et al. (1992) *JAMA* 268:68.
Linnanmaki et al. (1993), *Circulation* 87:1130.
Saikku et al. (1992) *Annals Internal Medicine* 116:273.
Melnick et al (1993) *American Journal of Medicine* 95:499.
Shor et al. (1992) *South African. Medical Journal* 82:158.
Kuo et al. (1993) *Journal of Infectious Diseases* 167:841.
Kuo et al. (1993) *Arteriosclerosis and Thrombosis* 13:1501.
Campbell et al (1995) *Journal of Infectious Diseases* 172:585.
Chiu et al (1997) *Circulation*. 96 (7) :2144-2148.
Ramirez et al (1996) *Annals of Internal Medicine* 125:979.
Jackson et al. Abst. K121, p272, 36th *ICAAC*, Sep. 15-18, 1996, New Orleans.
Fong et al (1997) *Journal of Clinical Microbiology* 35:48.
Hahn DL, et al. "Evidence for *Chlamydia pneumoniae* infection in steroid-dependent asthma". *Ann Allergy Asthma Immunol.* Jan. 1998; 80(1): 45-49.
Hahn DL, et al. "Association of *Chlamydia pneumoniae* IgA antibodies with recently symptomatic asthma". *Epidemiol Infect.* Dec. 1996; 117(3): 513-517.
Bjornsson E, et al. "Serology of chlamydia in relation to asthma and bronchial hyperresponsiveness". *Scand J Infect Dis*. 1996; 28(1): 63-69.
Hahn DL. "Treatment of *Chlamydia pneumoniae* infection in adult asthma: a before-after trial". J Fam Pract. Oct. 1995; 41(4): 345-351.
Allegra L, et al. "Acute exacerbations of asthma in adults": *role of Chlamydia pneumoniae infection.* Eur Respir J. Dec. 1994; 7(12): 2165-2168.
Hahn DL, et al. "Association of *Chlamydia pneumoniae* (strain TWAR) infection with wheezing, asthmatic bronchitis, and adult-onset asthma". *JAMA*. Jul. 10, 1991; 266(2): 225-230.
Pal et al. (1996) *Infection and Immunity*. 64:5341.
Jones et al. (1995) *Vaccine* 13:715.
Igietseme et al (1993) *Regional Immunology* 5:317.
Magee et al (1993) *Regional Immunology* 5: 305.
Landers et al (1991) *Infection & Immunity* 59:3774.
Magee et al (1995) *Infection & Immunity* 63:516.
Cotter et al. (1995) *Infection and Immunity* 63:4704.
Campbell et al (1990) *Infection and Immunity* 58:93.
McCafferty et al (1995) *Infection and Immunity* 63:2387-9.
Gaydos et al.; "Similarity of *Chlamydia pneumoniae* strains in the Variable Domain IV Region of the Major Outer Membrane Protein Gene"; Infection and Immunity; 60(12):5319-5323. Dec. 1992.
Wiedmann-Al-Ahmad M, et al. "Reactions of polyclonal and neutralizing anti-p54 monoclonal antibodies with an isolated, species-specific 54-kilodalton protein of *Chlamydia pneumoniae*". *Clin Diagn Lab Immunol*. Nov. 1997; 4(6:700-704).
Hughes et al., 1992. *Infect. Immun.* 60(9): 3497.
Dion et al., 1990. *Virology* 179:474-477.
Snijders et al., 1991. *J. Gen. Virol*. 72:557-565.
Langeveld et al., *Vaccine* 12(15):1473-1480, 1994.
Kunkel et al. *Proc. Natl. Acad. Sci. USA* (1985) 82:488.
Casey & Davidson, *Nucl. Acid Res*. (1977) 4:1539.
Cagnon et al., *Protein Engineering* (1991) 4(7):843.
Takase et al., *J. Bact*. (1987) 169:5692.
Perez Melgosa et al., *Infect Immun* (1994) 62:880.
Watson et al., Nucleic Acids Res (1990) 18:5299.
Watson et al., *Microbiology* (1995) 141:2489.
Melgosa et al., "Outer membrane complex proteins of *Chlamydia pneumoniae*" FEMS Microbiol Lett., NL, Amsterdam, Sep. 1993; 112(2:199-204).
Campbell et al., *J Clin Microbiol* (1990) 28 :1261.
Iijima et al., "Characterization of *Chlamydia pneumoniae* species-specific proteins immunodominant in humans" *J Clin Microbiol*. Mar. 1994; 32(3:583-588).
Http://chlamydia-www.berkeley.edu:4231/.
Bachmaier et al., Science (1999) 283:1335.
Ausubel et al.; "Current Protocols in Molecular Biology"; John Wiley & Sons Inc., vol. 1; 1993; 15 sheets.
Silhavy et al.; "Experiments with Gene Fusions"; Cold Spring Harbor Laboratory Press; 1984; pp. 191-195.
Davis et al., "A Manual for Genetic Engineering: Advanced Bacterial Genetics" Cold Spring Harbor Laboratory Press; 1980; pp. 174-176.
Database GENEMBL [Online], Jul. 22, 1998, Stephens et al., "*Chlamydia trachomatis* section 45 of 87 of the complete genome", XP002133142, Accession AE001318.
Stephens et al., "Genome Sequence of an Obligate Intracellular Pathogen of Humans: *Chlamydia trachomatis*", Science, vol. 282, Oct. 23, 1998, pp. 754-759, XP002104802.
Database GENEMBL [Online], Mar. 15, 1999, Kalman et al., "*Chlamydia pneumoniae* section 57 of 103 of the complete genome", XP002133143, Accession AE001641.
Kalman et al., "Comparative Genomes of *Chlamydia pneumoniae* and *C. trachomatis*", Nature Genetics, vol. 21, Apr. 1999, pp. 385-389, XP000853883.
Gu L et al., "Cloning and characterization of a secY homolog from *Chlamydia trachomatis*", Molecular and General Genetics, vol. 243, No. 4, May 25, 1994, pp. 482-487, XP000864462.
Melgosa M P et al., "Isolation and Characterization of a Gene Encoding a Chlamydia Pneumoniae 76-Kilodalton Protein Containing a Species-Specific Epitope", Infection and Immunity, US, American Society for Microbiology. Washington, vol. 62, No. 3, Mar. 1, 1994, pp. 880-886, XP002059939.
Watson M W et al., The nucleotide sequence of the 60kDa cysteine rich outer membrane protein of *Chlamydia pneumoniae* strain IOL-207, *Nucleic Acids Research* (1990), vol. 18, No. 17, 1990 , p. 5299, XP000891318.
Melgosa M P et al., "Sequence Analysis of the Major Outer Membrane Protein Gene of *Chlamydia pneumoniae*", Infection and Immunity (1991), vol. 59, No. 6, 1991, pp. 2195-2199, XP000891319.
U.S. Appl. No. 09/857,128, filed Sep. 20, 2001, Murdin et al.
U.S. Appl. No. 09/471,194, filed Dec. 23, 1999, Murdin et al.
U.S. Appl. No. 09/523,647, filed Mar. 10, 2000, Murdin et al.
U.S. Appl. No. 09/522,606, filed Mar. 10, 2000, Murdin et al.
U.S. Appl. No. 09/609,243, filed Jun. 30, 2000, Murdin et al.
U.S. Appl. No. 09/662,813, filed Sep. 15, 2000, Murdin et al.
U.S. Appl. No. 09/663,362, filed Sep. 15, 2000, Murdin et al.
U.S. Appl. No. 09/663,360, filed Sep. 15, 2000, Murdin et al.

U.S. Appl. No. 09/663,361, filed Sep. 15, 2000, Murdin et al.
U.S. Appl. No. 09/662,814, filed Sep. 15, 2000, Murdin et al.
U.S. Appl. No. 09/662,812, filed Sep. 15, 2000, Murdin et al.
U.S. Appl. No. 09/709,473, filed Nov. 13, 2000, Murdin et al.
U.S. Appl. No. 09/709,474, filed Nov. 13, 2000, Murdin et al.
U.S. Appl. No. 09/709,384, filed Nov. 13, 2000, Murdin et al.
U.S. Appl. No. 09/747,349, filed Dec. 22, 2000, Murdin et al.
Howard RF, Jacobson KC, Rickel E, Thurman. Analysis of inhibitory epitopes in the Plasmodium falciparum rhoptry protein RAP-1 including identification of a second inhibitory epitope. J. Infect Immun. Jan. 1998; 66(1):380-6. [Abstract].
AbD Serotec Excerpt from technical brochure from www.ab-direct.com.
Ayyildiz. Technical Approach to Generate Polyclonal Antibodies Against Bacterially Expressed GST-PYK-C. Tr. J. Medical Sciences. 29 (1999) 355-360 [Abstract].
Cassill JA, Whitney M, Joazeiro CA, Becker A, Zuker CS. Isolation of Drosophila genes encoding G protein-coupled receptor kinases. Proc Natl Acad Sci U S A. Dec. 15, 1991;88(24):11067-70. [pp. 11067 & 11068].
Lutzelschwab R, Klambt C, Rossa R, Schmidt O. A protein of the Drosophila recessive tumor gene, 1 (2) giant gl, potentially has cell adhesion properties. EMBO J. Jun. 1987;6(6):1791-1797. [pp. 1791 & 1792].

Schoneck R, Plumas-Marty B, Taibi A, Billaut-Mulot O, Loyens M, Gras-Masse H, Capron A, Ouaissi A. Trypanosoma cruzi cDNA encodes a tandemly repeated domain structure characteristic of small stress proteins and glutathione S-transferases. Biol Cell. 1994;80(1):1-10. [pp. 1 & 2].
Philippe B, Brion JP, Coppens E, Octave JN. Generation of a monclonal antibody to the carboxy-terminal domain of tau by immunization with the amino-terminal domain of the amyloid precursor protein. J Neurosci Res. Dec. 15, 1996; 46(6):709-19. [Abstract].
Yu H, Nakano Y, Yamashita Y, Oho T and Koga T. Effects of antibodies against cell surface protein antigen PAc-glucosyltransferase fusion proteins on glucan synthesis and cell adhesion of Streptococcus mutans. Infect. Immun., Jun. 1997, 2292-2298, vol. 65, No. 6 [Abstract].
Zhou FC, Xu Y. Bledsoe S, Lin R, Kelley MR. Serotonin transporter antibodies: production, characterization, and localization in the brain. Brain Res Mol Brain Res. Dec. 31, 1996;43(1-2):267-78. [Abstract].

* cited by examiner

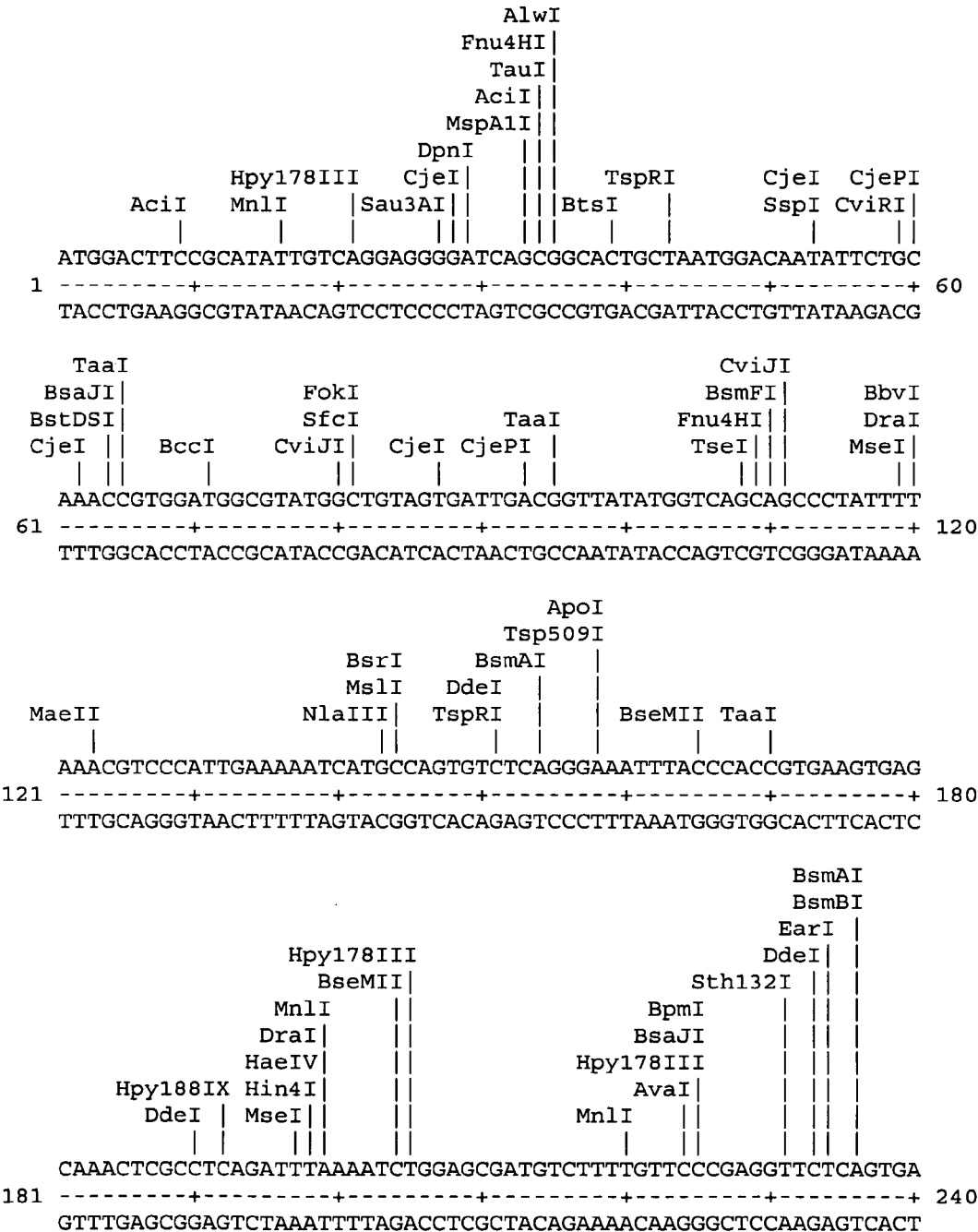

Figure 1G

```
                    BsmAI                                AvaII
    BfaI   CjePI   BsmBI    CviRI              MnlI    Sau96I
     |      |       |         |                  |       |
        TCTAGGAACTTTATCGTCTCTTTATATTGCACCACCTCTGTTGTTGTTTATGGTCCGTAA
1681 ---------+---------+---------+---------+---------+---------+ 1740
        AGATCCTTGAAATAGCAGAGAAATATAACGTGGTGGAGACAACAACAAATACCAGGCATT
                          MseI
                   TaaI   |              AflIII
                  RsaI |  |    MseI     MaeII
                    |  |  |      |        |
        AGAAAATCGCTCAAAATAAGTACCGTTAAACTTAATCTAACGTGTAGCAATATAAAAATC
1741 ---------+---------+---------+---------+---------+---------+ 1800
        TCTTTTAGCGAGTTTTATTCATGGCAATTTGAATTAGATTGCACATCGTTATATTTTTAG

NlaIV
                            CviJI|
                            HaeIII|
                            EcoO109I||      ApoI        Hpy188IX
                            Sau96I||      Tsp509I        ApoI   |
    BsmFI       PshAI    BsmFI |||       MseI  |      Tsp509I   |
     |           |         |   |||        | |            |      |
        TCCTTTGGGACTTTAGTCCCAAAGGCCCCTGTGGTATTAAATTTATGACAAATTCAGATA
1801 ---------+---------+---------+---------+---------+---------+ 1860
        AGGAAACCCTGAAATCAGGGTTTCCGGGGACACCATAATTTAAATACTGTTTAAGTCTAT

ATGC
1861 ---- 1864
        TACG
```

Restriction enzyme analysis of CPN100696 (RY 55 - SEQ ID NO. 2)

Figure 2B

```
                                                              HinfI
                                    ApoI                       TfiI
         HinfI          BccI       Tsp509I          BsaAI       |
         TfiI    HphI CjeI  |       FokI |          MaeII|      |
          |      |    | |   |       |    |           | | |      |
          GGTGAATCTACTCATAGGATGGGCAAAGACAAAATTTATTCAACCTATACGTGAATCAAA
    241   ---------+---------+---------+---------+---------+---------+ 300
          CCACTTAGATGAGTATCCTACCCGTTTCTGTTTTAAATAAGTTGGATATGCACTTAGTTT Tsp509I
                     Cac8I     |
                     AluI |    |                       ApoI
         AluI        CviJI|    |                       EcoRI
         CviJI  Hpy178III |    |           CjePI      Tsp509I
          |       |      ||    |             |          |
          GCTCTTTCAATCCAGAGCTTGCCAAATTACCCTGCTCGTTTTAGGAATTCTTTTGGTTGT
    301   ---------+---------+---------+---------+---------+---------+ 360
          CGAGAAAGTTAGGTCTCGAACGGTTTAATGGGACGAGCAAAATCCTTAAGAAAACCAACA CjeI
                 MboII   |
                 NlaIII| |                                    CjeI
         CjePI    |  | |                          BsrI         NsiI|
         MwoI|  NspI| |            CviJI|  BslI   CviRI  | |   BbvI
          ||    ||  |                ||    |       |     | |    |
          TGCTGGATTAGCATGTATGTTTATCTTCCATAGCCAGTTAGGGGCAAATGCATTTTGGTT
    361   ---------+---------+---------+---------+---------+---------+ 420
          ACGACCTAATCGTACATACAAATAGAAGGTATCGGTCAATCCCCGTTTACGTAAAACCAA MaeIII
                 Fnu4HI     MaeIII BfaI |
                 TseI|      MseI  |SpeI| |    MsII        HindIII
                 ||          |    | ||  |      |            |
          GATTATTCCTGCTGCCATAGGATTGATTAAGTTACTAGTTACATCATTATGTTTTGATGA
    421   ---------+---------+---------+---------+---------+---------+ 480
          CTAATAAGGACGACGGTATCCTAACTAATTCAATGATCAATGTAGTAATACAAAACTACT Hpy188IX
            RsaI    |
         BsrGI |    |
            TatI|   |
         AluI | |   |                                      DpnI
         CviJI| |   |      NlaIII BspMI BslI  AarI         Sau3AI |
          | | | |   |         |    |    |     |             |    ||
          AGCTTGTACATCTGAAAAACTCATGGTTTTCCAAAAATGGGCAGGTGTTTTAGAAGATCA
    481   ---------+---------+---------+---------+---------+---------+ 540
          TCGAACATGTAGACTTTTTGAGTACCAAAAGGTTTTTACCCGTCCACAAAATCTTCTAGT
```

Figure 2D

```
                        Hpy188IX
                   DpnI |
              Sau3AI | |
          RsaI   | | |
        BsaAI |  | | |
         SunI |  | | |
        MaeII|  | | |            Tsp509I
        FokI||  | | |            TaaI  |

||| |  | | |              | |
     GGGATGCTACTTTCCACGTACGAGATCAGATGTAAAGAGCAACAGTAATTATTTTCTACA
721  ---------+---------+---------+---------+---------+---------+ 780
     CCCTACGATGAAAGGTGCATGCTCTAGTCTACATTTCTCGTTGTCATTAATAAAAGATGT

TspRI
     TaaI |        NlaIII
      | |           |
     CTGTTGTAATAAAATCATGT
781  ---------+---------+ 800
     GACAACATTATTTTAGTACA
```

Restriction enzyme analysis of CPN100709 (RY 57 - SEQ ID NO. 3)

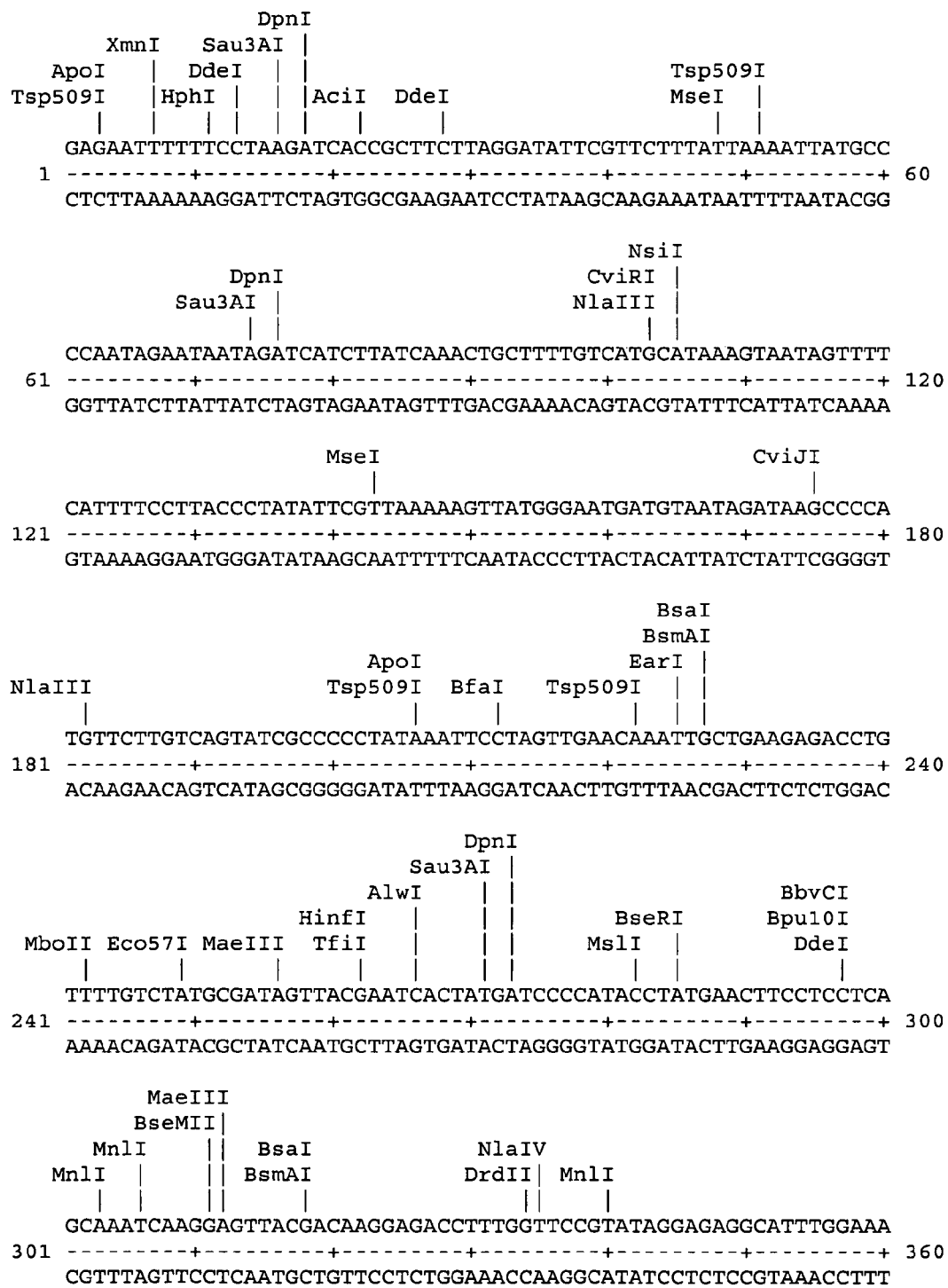

Figure 4B

```
                              DpnI
                    CviRI     CjePI|                   HinfI
                    NlaIII    Sau3AI||                 TfiI
                    NspI      TaqI|||                  BsmAI      |
                      |          ||||                    |        | |
        AAACTTGTTAGAGAAACCTTACATGCAACAAGTCGATCTTTCCCAAAATGTCTCGCTGAT
    361 ---------+---------+---------+---------+---------+---------+ 420
        TTTGAACAATCTCTTTGGAATGTACGTTGTTCAGCTAGAAAGGGTTTTACAGAGCGACTA CviJI
              CviJI                     Pfl1108I            TaqII|
              CjePI  |                  CjeI  |        BslI MseI ||
                | |                        | |           |    |  ||
        TCAAGGAAAGCCTTGCTGTAATCAACATACCACGAACTACGACACCCACACTTGGTTAAG
    421 ---------+---------+---------+---------+---------+---------+ 480
        AGTTCCTTTCGGAACGACATTAGTTGTATGGTGCTTGATGCTGTGGGTGTGAACCAATTC MseI                 MaeIII
        RleAI    CjeI|    BsmAI       CjeI    |      MseI
          |       ||       |             |    |        |
        CCCTAAAAACCTTAAAGTCCAAGTGGAGACTATCGTTACCACTTTAAGTAAAAAATATCC
    481 ---------+---------+---------+---------+---------+---------+ 540
        GGGATTTTTGGAATTTCAGGTTCACCTCTGATAGCAATGGTGAAATTCATTTTTTATAGG HaeIV
                       Hin4I
               HinfI       |
               MnlI|       |
               ThaI||      |
        BsbI   ||||        |                        AvaII
        CjeI   ||||        |                        Sau96I
        PleI   ||||        |                        AluI        |
          |     ||||       |         BsrDI          CviJI       |      MnlI
          |     ||||       |            |              |        |        |
        TCAACACGCGACTCTATATCAAAGCAATGGAGAGAAACTTCTGTTAGCTTTGGACCAACT
    541 ---------+---------+---------+---------+---------+---------+ 600
        AGTTGTGCGCTGAGATATAGTTTCGTTACCTCTCTTTGAAGACAATCGAAACCTGGTTGA BsaJI
                                                           BstDSI
                 ApoI                                      NcoI
                 Tsp509I              MnlI                 StyI
                    |                    |                   |
        CAATGAGGAAATTCTTACGATTACCTCCAAAGCGAAACAACGCCATATTTTAGTTTCCCA
    601 ---------+---------+---------+---------+---------+---------+ 660
        GTTACTCCTTTAAGAATGCTAATGGAGGTTTCGCTTTGTTGCGGTATAAAATCAAAGGGT
```

Figure 4D

```
                                HaeIV           NlaIII
                                Hin4I           TaqII |
            AluI                NlaIV   | Hpy178III| |
            CviJI    Eco57I     AvaII|  |   RcaI   | | |
        BfaI |  MaeIII    |     Sau96I| |   BsmFI  | | |
          | |     |       |        | | |      |   | | | |
          CTAGCTTTCCGTTACGGAAGCAAGGGACCGAATATCATTCATGATGTTTCTTTCTCTGTC
     961  ---------+---------+---------+---------+---------+---------+ 1020
          GATCGAAAGGCAATGCCTTCGTTCCCTGGCTTATAGTAAGTACTACAAAGAAAGAGACAG

MnlI
                         HinfI  AvaII   |
              BccI       TfiI   Sau96I  |    BslI              MseI
                |          |      | |   |      |                 |
          TATGATGGCGACTTTATAGGAATCATAGGACCAAACGGAGGGGGGAAAAGCACCTTAACG
    1021  ---------+---------+---------+---------+---------+---------+ 1080
          ATACTACCGCTGAAATATCCTTAGTATCCTGGTTTGCCTCCCCCCTTTTCGTGGAATTGC DpnI
                                    NlaIV
                                    BamHI |
                                    BstYI |
                                    Sau3AI |                      BsmI
                                    Hpy188IX|  |        BbsI     FauI
           Tsp509I      Cac8I       BslI | | |   XmnI   |Sth132I|
           MseI|        CviJI       AlwI | | |   AlwI   | |MboII| |
              | |         | |          | | | |      |   |    |  | | |
          ATGTTAATTTTGGGCTTGCTTACTCCTACATTCGGATCCTTGAAGACTTTCCCTTCGCAT
    1081  ---------+---------+---------+---------+---------+---------+ 1140
          TACAATTAAAACCCGAACGAATGAGGATGTAAGCCTAGGAACTTCTGAAAGGGAAGCGTA SacII
          AciI|
          MspA1I|
          ThaI|
          AciI | |
          BsaJI| |
          BstDSI| |
              | | |
          TCCGCGGGGAAACAAACCCATT
    1141  ---------+---------+-- 1162
          AGGCGCCCCTTTGTTTGGGTAA
```

Restriction enzyme analysis of CPN100711 (RY 59 - SEQ ID NO. 5)

Figure 5B

```
                                          DpnI
                                    BstYI |
                                   Sau3AI |
                                    EarI| |
                               Hpy178III| |
                 HinfI                 || |
                 PpiI |                || |
              MaeIII|  |               || |
                TaaI|  |               || |
              Tsp45I|  |               || |
             AlwNI |   |     BfaI      || |
             MboII |   |     XbaI|     || |
              PleI|    |  |AlwI |      || |                       ApoI
                 |||   |  |  ||||      || |                    Tsp509I
                 |||   |  |  ||||      || |                         |
         GATATTACAGGAACTGTGACTCTTCTAGATCCTAATGGCAACTTATATCAAAATTCTTAT
    181  ---------+---------+---------+---------+---------+---------+ 240
         CTATAATGTCCTTGACACTGAGAAGATCTAGGATTACCGTTGAATATAGTTTTAAGAATA MboII
                      EcoRV|
                      HphI ||
                    BbsI | ||
                    ThaI | ||                                MaeIII
                    AciI | ||       Tsp509I   CviRI   MwoI        |
                    ||| |||            |        |       |         |
         CTTGGTGAAGACCGCGATATCACTCTTTTCAATATAGACAATTCTGCAAGTGGGGCAGTT
    241  ---------+---------+---------+---------+---------+---------+ 300
         GAACCACTTCTGGCGCTATAGTGAGAAAAGTTATATCTGTTAAGACGTTCACCCCGTCAA HphI            ApoI                           ScrFI
         CviJI  |MaeIII       Tsp509I    AluI                EcoRII |
         MwoI   |Tsp45I         BslI    CviJI                NlaIV| |
           | |  |  |              |       |                      |||
         ACAGCCACGAATGTCACCCTTCAAGGGAATTTAGGAGCTAAAAAAGGATATTTAGGAACC
    301  ---------+---------+---------+---------+---------+---------+ 360
         TGTCGGTGCTTACAGTGGGAAGTTCCCTTAAATCCTCGATTTTTTCCTATAAATCCTTGG
```

Figure 5C

```
                        AvaI
                        BsaJI|
               AlwI     | |
               ApoI   | | |
              Tsp509I | | |
              Sth132I|| | |
               DpnI  || | |
               NlaIV || | |
             BamHI   || | |
             BstYI   || | |
             Sau3AI  || | |
     AlwI            || | |
     ApoI|           || | |   Tsp509I          AvaII
    Tsp509I|         || | |   MnlI |          Sau96I  CjeI
       | |           || | |      | |             |      |
       TGGAATTTGGATCCAAATTCCTCGGGTTCAAAAATTATTCTAAAATGGACCTTTGACAAA
  361  ---------+---------+---------+---------+---------+---------+ 420
       ACCTTAAACCTAGGTTTAAGGAGCCCAAGTTTTTAATAAGATTTTACCTGGAAACTGTTT

CviJI
                 HaeIII
                 BspMI|
                 Sau96I|
                 Cac8I||           CjeI
                 HhaI |||     BfaI  |
        FokI     | |||   BsmAI |    |      CjeI
         |       | |||     | | |    |        |
         TACCTGCGCTGGCCCTACATCCCTAGAGACAACCACTTCTACATCAACTCTATTTGGGGA
  421    ---------+---------+---------+---------+---------+---------+ 480
         ATGGACGCGACCGGGATGTAGGGATCTCTGTTGGTGAAGATGTAGTTGAGATAAACCCCT

DdeI
                                   DpnI  |
                                   BstYI | |
                                   Sau3AI| |
                              BsaJI | |  | |        NlaIII
                MaeIII        StyI  | |  | |   AflIII   |
      BsiHKAI   Tsp45I        DrdII|| |  | |  |BspLU11I |
      Bsp1286I  CjeI     TaaI  | | || |  | |  |AlwI  |NspI     CviRI
         |        |        |   | | || |  | |  | |   |  |        |
         GCACAAAACTCTTTAGTGACTGTGAACCAAGGGATCTTAGGGAACATGTTGAACAATGCA
  481    ---------+---------+---------+---------+---------+---------+ 540
         CGTGTTTTGAGAAATCACTGACACTTGGTTCCCTAGAATCCCTTGTACAACTTGTTACGT

DpnI
                    CjeI                                CjeI|
                    DpnI |                              BstYI|  |
                    BstYI|  |                          Sau3AI||   Bsu36I
                   Sau3AI|  |                     SfcI      ||| DdeI
           AlwI     | |  | MboII         CviJI CviJI|       ||| AlwI|
              |     | |  |   |             |     ||         |||    ||
              AGGTTTGAAGATCCTGCTTTCAACAACTTCTGGGCTTCGGCTATAGGATCTTTCCTTAGG
       541    ---------+---------+---------+---------+---------+---------+ 600
              TCCAAACTTCTAGGACGAAAGTTGTTGAAGACCCGAAGCCGATATCCTAGAAAGGAATCC
```

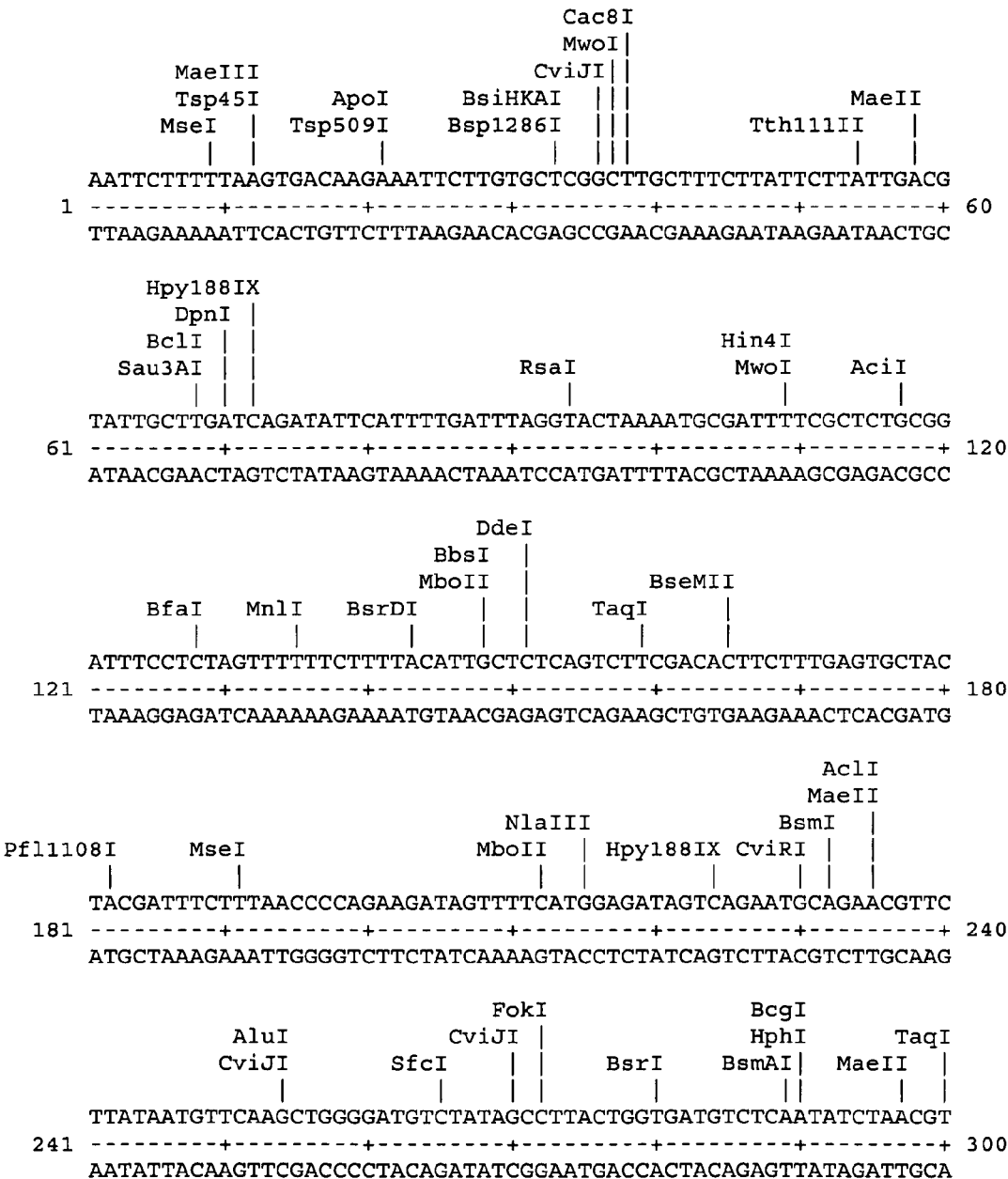

Figure 6B

```
                                                              BseMII
                                            Hpy178III         MaeII|
                          Cac8I             Bsu36I   |MaeIII  ||
            MseI          BcgI|    MaeIII    |       | MnlI   ||
     CviRI   |            CviJI|| Tsp45I DdeI |      |Tsp45I  ||
       | |    |            |||     |     |   |      |    |    ||
        CGATAACTCTGCATTAAATAAAGCCTGCTTCAATGTGACCTCAGGAAGTGTGACGTTCGC
301     ---------+---------+---------+---------+---------+---------+ 360
        GCTATTGAGACGTAATTTATTTCGGACGAAGTTACACTGGAGTCCTTCACACTGCAAGCG

Hpy178III
                                 Bsu36I      BseMII
            NlaIII     MseI  SspI DdeI   |    MnlI    |    CviJI
             |          |     |    |     |    |       |     |
        AGGAAATCATCATGGGTTATATTTTAATAATATTTCCTCAGGAACTACAAAGGAAGGGGC
361     ---------+---------+---------+---------+---------+---------+ 420
        TCCTTTAGTAGTACCCAATATAAAATTATTATAAAGGAGTCCTTGATGTTTCCTTCCCCG

SmlI
                    DpnI  |
        Bce83I      BstYI |         Tth111II
        RsaI   |    Sau3AI|         MaeII     |
        TatI   |    AlwI  |         MnlI      |    BcefI
         |  |  |     | |  |  |       |        |     |
        TGTACTTTGTTGCCAAGATCCTCAAGCAACGGCACGTTTTTCTGGGTTCTCCACGCTCTC
421     ---------+---------+---------+---------+---------+---------+ 480
        ACATGAAACAACGGTTCTAGGAGTTCGTTGCCGTGCAAAAAGACCCAAGAGGTGCGAGAG MseI
                    Sth132I      |
              MspI               |
              NciI               |
              ScrFI              |
              BanII|             |
              Bsp1286I|          |
              BsaJI||            |
              CviJI|||           |              FokI
        Hpy188IX ||||            |        BsmAI  |     CviRI
           |    ||||             |           |   |       |
        TTTTATTCAGAGCCCCGGAGATATTAAAGAACAGGGATGTCTCTATTCAAAAAATGCACT
481     ---------+---------+---------+---------+---------+---------+ 540
        AAAATAAGTCTCGGGGCCTCTATAATTTCTTGTCCCTACAGAGATAAGTTTTTTACGTGA Tsp509I                                              EciI
        MseI  |                                                  AciI|
         |    |                                                   ||
        TATGCTCTTAAACAATTATGTAGTGCGTTTTGAACAAAACCAAAGTAAGACTAAAGGCGG
541     ---------+---------+---------+---------+---------+---------+ 600
        ATACGAGAATTTGTTAATACATCACGCAAAACTTGTTTTGGTTTCATTCTGATTTCCGCC
```

Figure 6D

```
            BsrI                                                      TaqII
   RsaI      |      MaeIII                                    XmnI|
   ScaI      |      Tsp45I    Hpy188IX         TaaI           CjeI    ||
    |   |    |        |          |              |              |      ||
         TACTCCAGTTCCTATTGTGACTTTCTCTGACAATAAACAGTTAGTCTTTGAAAGAAACCA
901      ---------+---------+---------+---------+---------+---------+   960
         ATGAGGTCAAGGATAACACTGAAAGAGACTGTTATTTGTCAATCAGAAACTTTCTTTGGT

AvaII
                                                              EcoO109I
                                                              Psp5II
                                                              Sau96I
                                                              Sse8647I
                     CviJI           Eco57I                    EarI       |
                      NlaIV|          BfaI  |                  Hpy178III  |
                      EciI  | |       CjeI  |     MboII        SfaNI|     |
                      AciI| | |       MwoI  | |   DdeI|        MnlI    || |
                        | | | |         | | |     | |           |      || |
         TTCCATAATGGGTGGCGGAGCCATTTATGCTAGGAAACTTAGCATCTCTTCAGGAGGTCC
961      ---------+---------+---------+---------+---------+---------+  1020
         AAGGTATTACCCACCGCCTCGGTAAATACGATCCTTTGAATCGTAGAGAAGTCCTCCAGG

ApoI
                              Tsp509I
                              CviRI  |       ApoI              AluI
                      NdeI     |  |           Tsp509I          CviJI
                       |       | ||              |               |
         TACTCTATTTATCAATAATATATCATATGCAAATTCGCAAAATTTAGGTGGAGCTATTGC
1021     ---------+---------+---------+---------+---------+---------+  1080
         ATGAGATAAATAGTTATTATATAGTATACGTTTAAGCGTTTTAAATCCACCTCGATAACG

DpnI
                    Sau3AI  |
                     Hin4I | |                                BsaJI
           MnlI      BsrI  | |        BpmI         Tsp509I    StyI
            |         |    | ||         |             |        |
         CATTGATACTGGAGGGGAGATCAGTTTATCAGCAGAGAAAGGAACAATTACATTCCAAGG
1081     ---------+---------+---------+---------+---------+---------+  1140
         GTAACTATGACCTCCCCTCTAGTCAAATAGTCGTCTCTTTCCTTGTTAATGTAAGGTTCC

Hpy178III
           MspI    AluI   TaaI            SfaNI          ApoI        |
           BsaWI|  CviJI FokI|            BccI           Tsp509I     |
            ||    |    ||                  |              |          |
         AAACCGGACGAGCTTACCGTTTTTGAATGGCATCCATCTTTTACAAAATGCTAAATTCCT
1141     ---------+---------+---------+---------+---------+---------+  1200
         TTTGGCCTGCTCGAATGGCAAAAACTTACCGTAGGTAGAAAATGTTTTACGATTTAAGGA
```

Restriction enzyme analysis of CPN100325 (RY 62 - SEQ ID NO. 7)

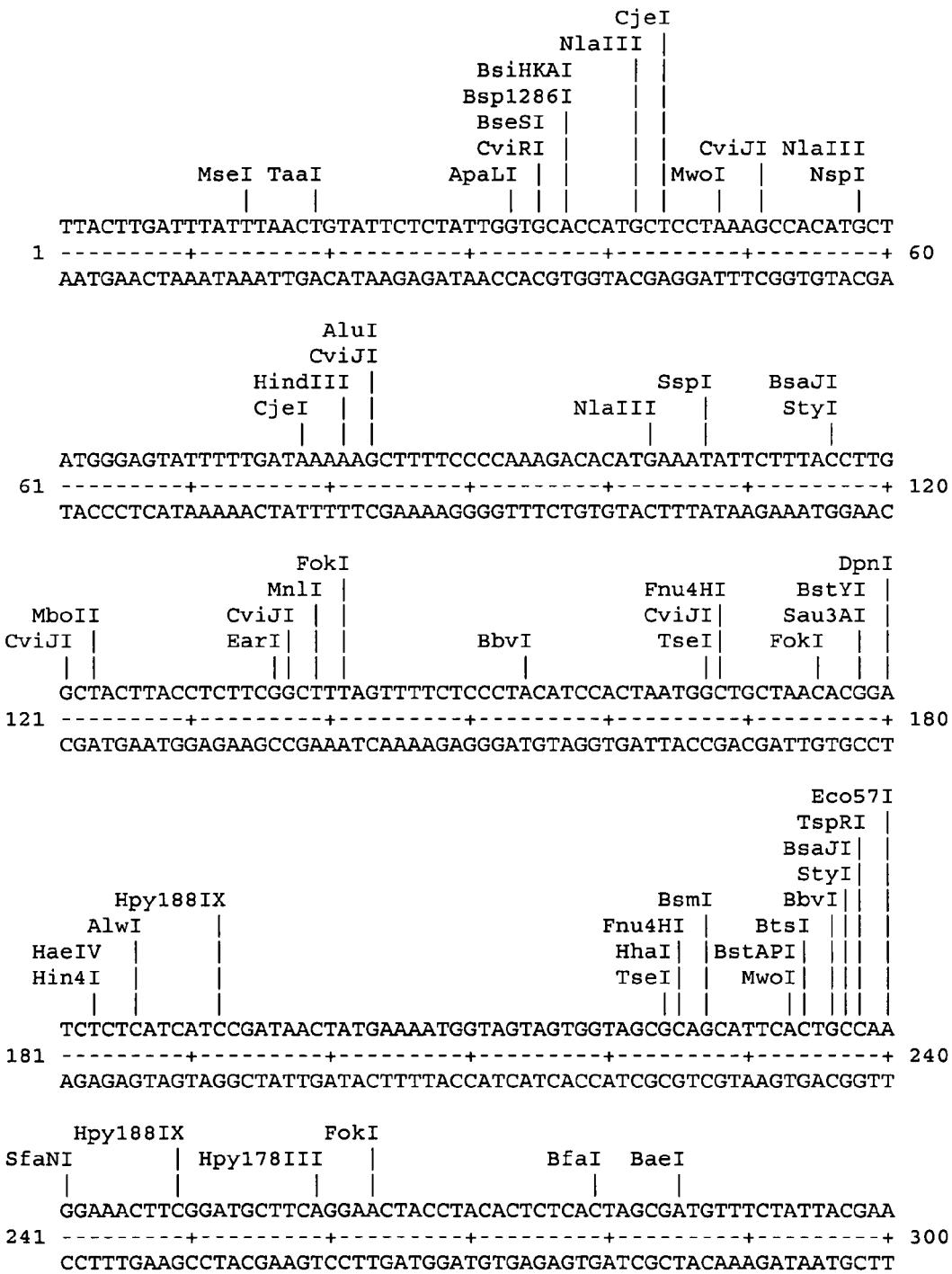

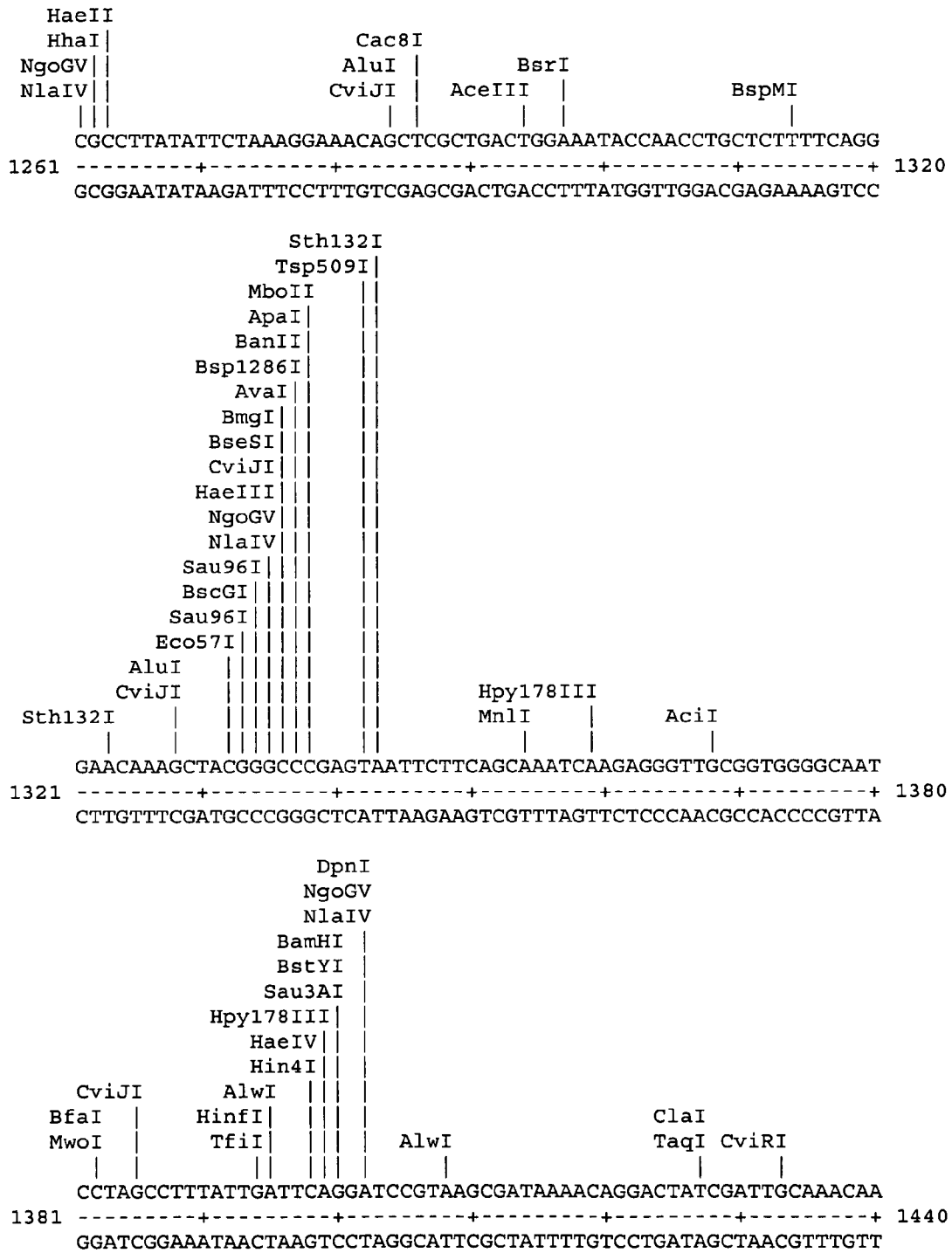

Figure 8K

```
                                            BseMII      DdeI          BsaXI
                                            NgoGV|BseMII  |           AloI|
     DdeI    CviJI     BccI        DdeI     NlaIV|MnlI |  |           PpiI|
      |       |         |           |        || |  | |  |              ||
      CTTAGAGGCTATTGATGGGGATATTACTTTCTCAGGGAACCGAGCGACTGAGGGAACTTC
2461  ---------+---------+---------+---------+---------+---------+ 2520
      GAATCTCCGATAACTACCCCTATAATGAAAGAGTCCCTTGGCTCGCTGACTCCCTTGAAG

ScrFI
                                                              AlwNI|
                                                              EcoRII||
                                                              AluI  |||
                                                              CviJI |||
                                                              Fnu4HI |||
                                                              TseI|  |||
                                                              Fnu4HI|| |||
                                                              CviRI|  |||
                                   ScrFI          TseI|         |||
                                   BsaJI|         Cac8I||        |||
                                   EcoRII|        AluI  |         |||
                          DpnI     NgoGV||        CviJI |         |||
               Sau3AI      |       NlaIV||        HindIII         |||
                  TaqI|    |       BanI |||        DpnI           |||
            AlwI  |   |    |       MslI ||||      Sau3AI |DdeI    |||
              |   ||  |    |        |  ||||        |  |   |      |||
      AACTCCCAACTCGATCCATTTAGGTGCCAGGGGCAAGATCACTAAGCTTGCAGCAGCTCC
2521  ---------+---------+---------+---------+---------+---------+ 2580
      TTGAGGGTTGAGCTAGGTAAATCCACGGTCCCCGTTCTAGTGATTCGAACGTCGTCGAGG MnlI
                                                              SfaNI |
                                         AluI    Hpy178III      | |
        AceIII              DpnI         CviJI    BsII          | |
          BbvI|            Sau3AI        Hin4I    CviRI         | |
        BbvI ||      AlwI   |   |        BccI |   MnlI          | |
          |  ||       |     |   |         |   |    |            | |
      TGGTCATACGATTTATTTTTATGATCCTATTACGATGGAAGCTCCTGCATCTGGAGGAAC
2581  ---------+---------+---------+---------+---------+---------+ 2640
      ACCAGTATGCTAAATAAAAATACTAGGATAATGCTACCTTCGAGGACGTAGACCTCCTTG BseRI                    XcmI
                             AluI|                    MnlI |
              BpmI    BseRI  CviJI|          MnlI      | |
               |       |      ||                |      | |
      AATAGAGGAGTTAGTCATCAATCCTGTTGTCAAAGCTATTGTTCCTCCTCCCCAACCAAA
2641  ---------+---------+---------+---------+---------+---------+ 2700
      TTATCTCCTCAATCAGTAGTTAGGACAACAGTTTCGATAACAAGGAGGAGGGGTTGGTTT
```

Figure 8L

```
            AvaII
         Sau96I                        BsmI      Hpy178III
       BslI     |              Bce83I    |         SmlI    |   ApoI
     PflMI      |                MboII   |         CviJI   |   Tsp509I
         | |                        | |             || |         |
         AAATGGTCCTATATAGAAGAAAAACGAATGCTCTTTGTAAGGCTCAAGAGTAAAAAATTC
    2701 ---------+---------+---------+---------+---------+---------+ 2760
         TTTACCAGGATATATCTTCTTTTTGCTTACGAGAAACATTCCGAGTTCTCATTTTTTAAG

Eco57I
                     Hpy188IX              ApoI        |
                BcefI    |    Fnu4HI     EcoRI         |
              BbvI |     |     TseI|    Tsp509I        |
                 | |     |       ||       |           |
         TAAAGGTATTCTCTCAATAGGTTCTGAAGTGCTGCCGTAGAATTCATAAATATCTC
    2761 ---------+---------+---------+---------+---------+------ 2816
         ATTTCCATAAGAGAGTTATCCAAGACTTCACGACGGCATCTTAAGTATTTATAGAG
```

Figure 9C:
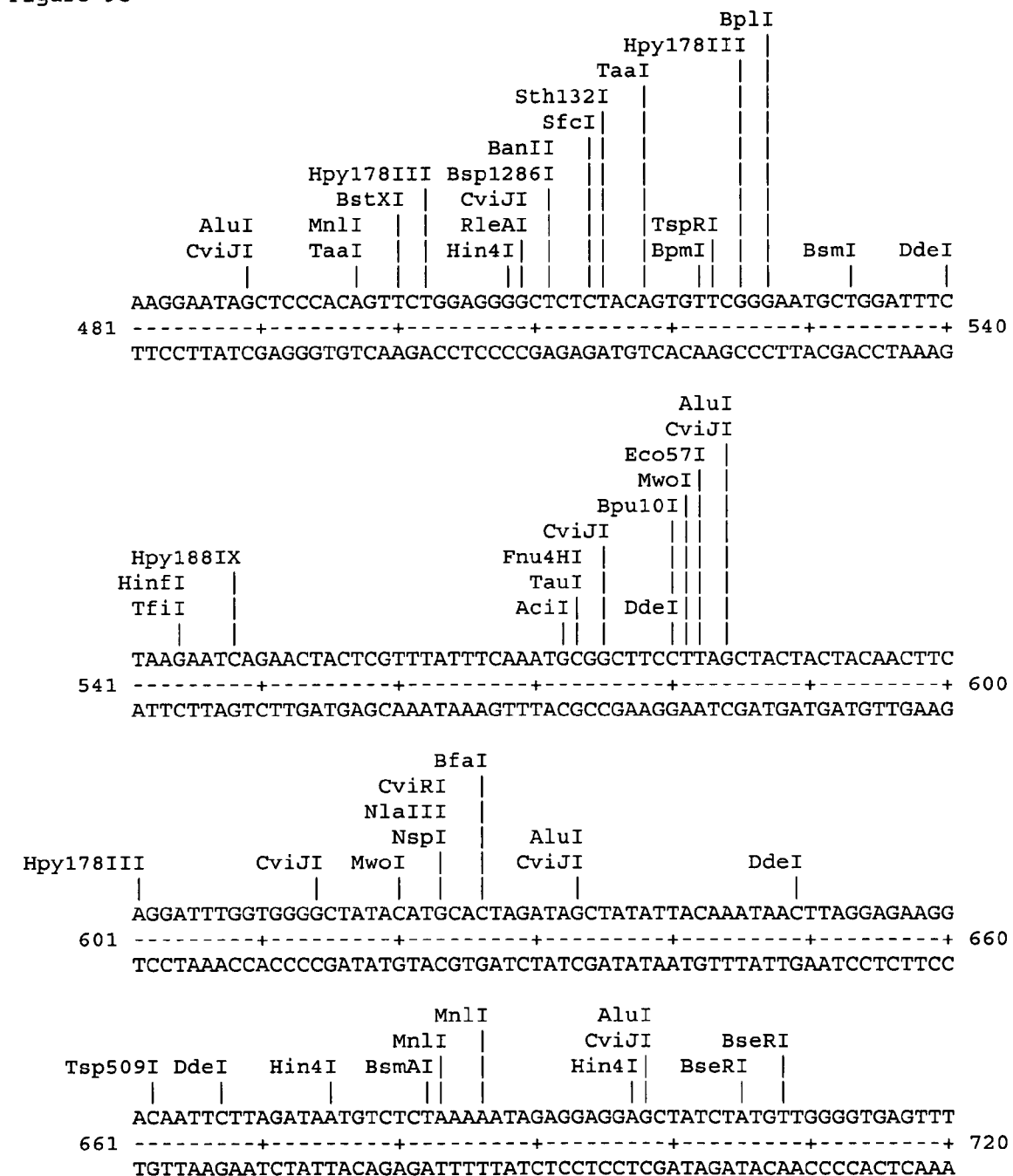
Figure 9E:
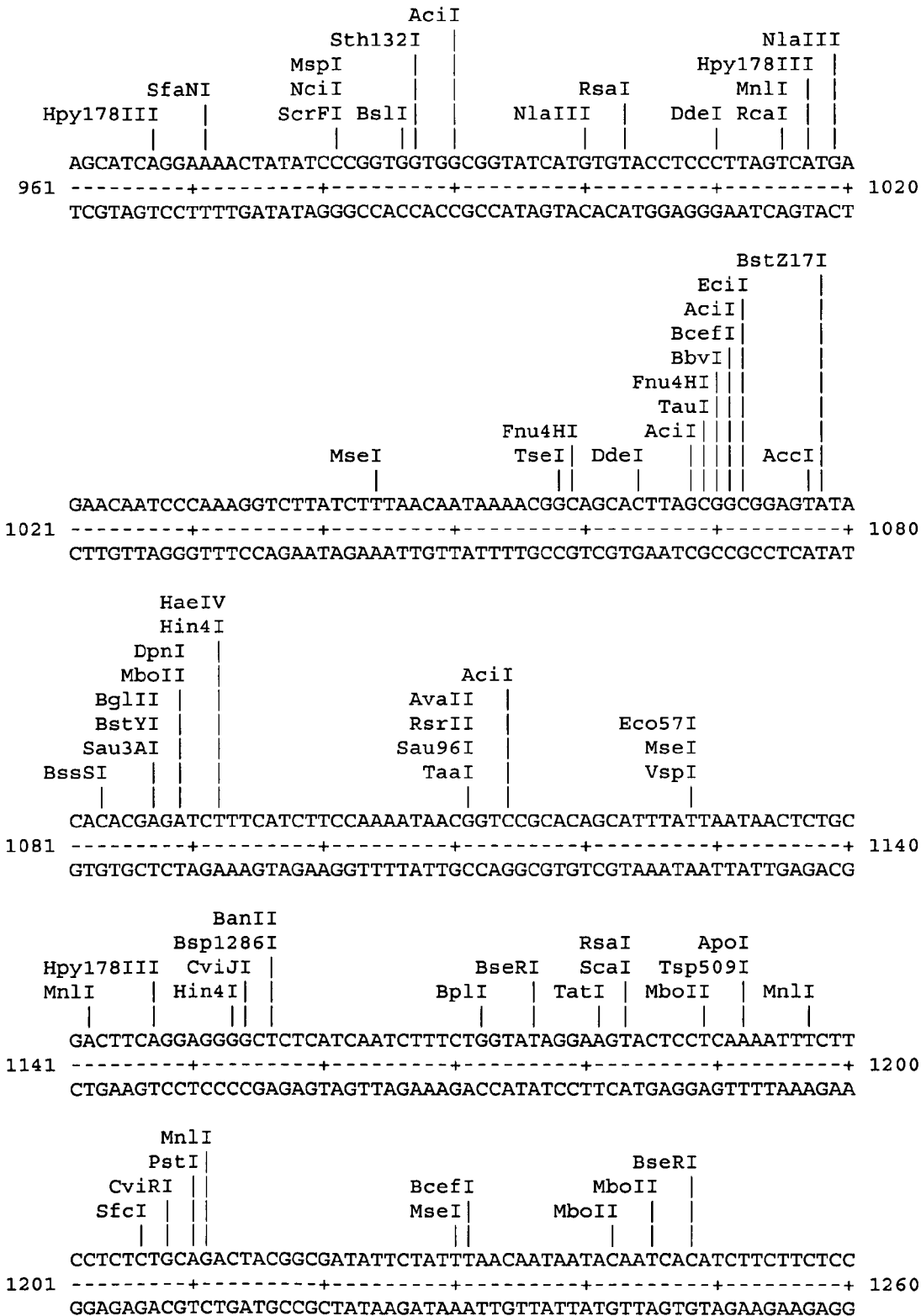
Figure 9F:
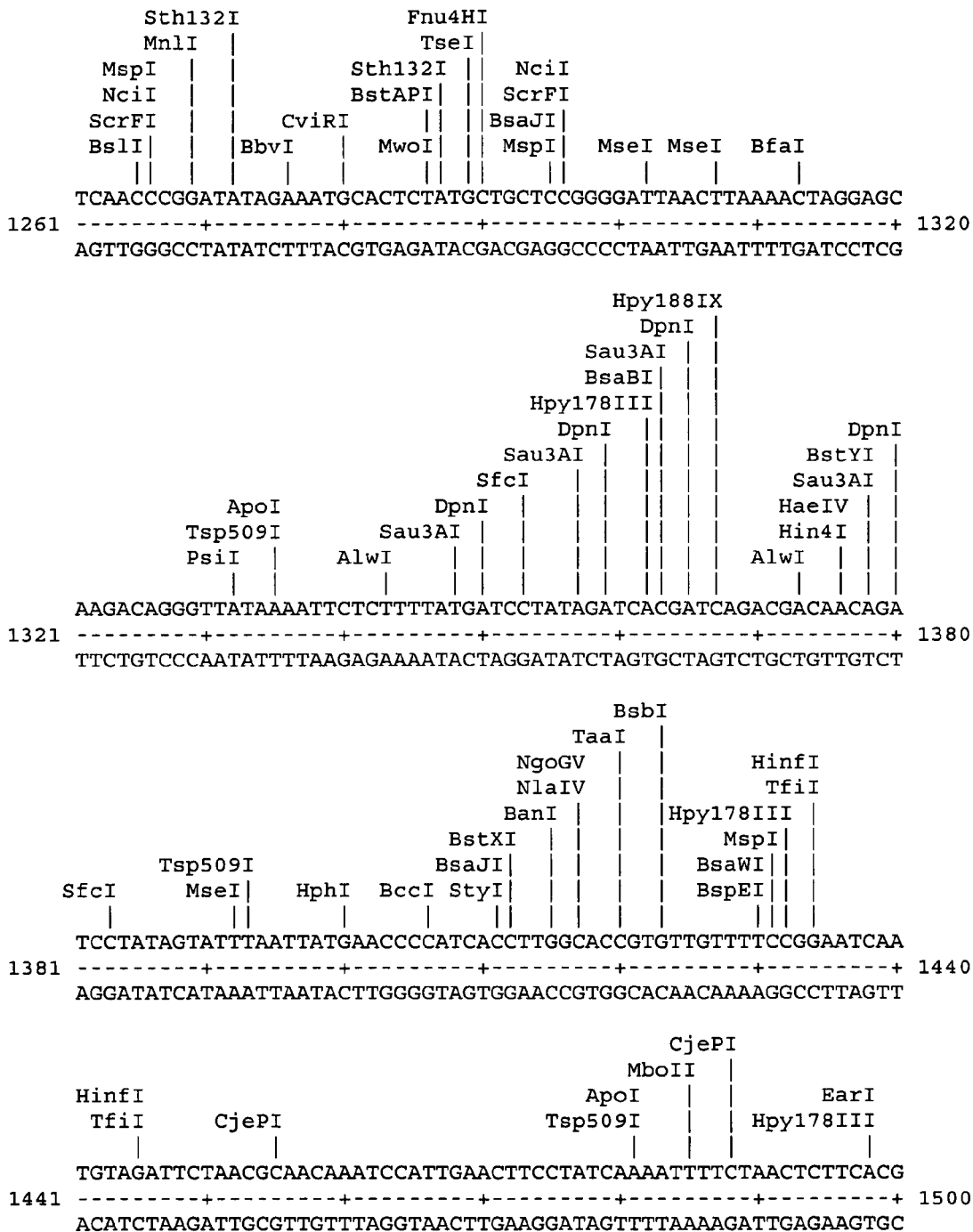
Figure 9G:
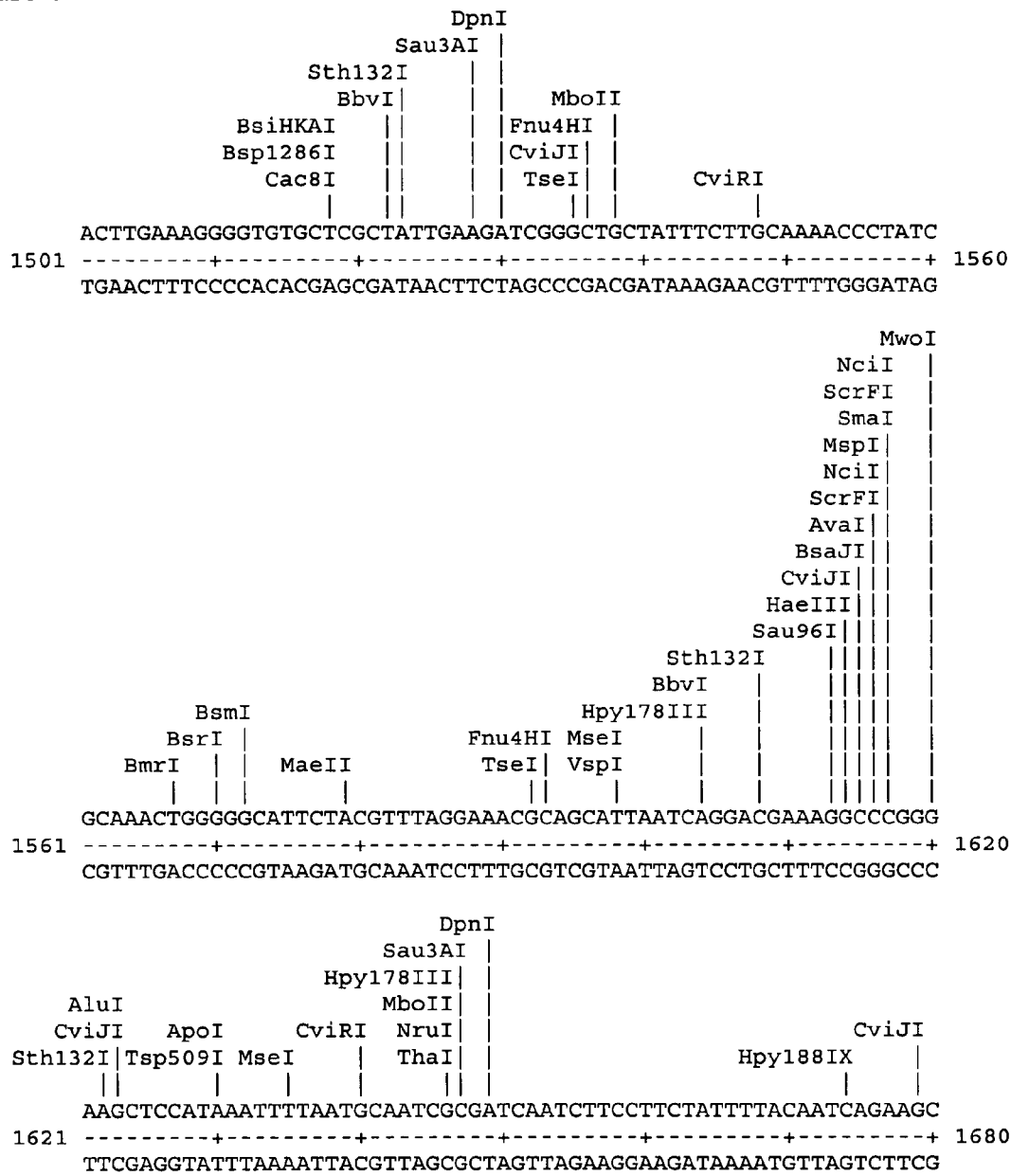
Figure 9H:
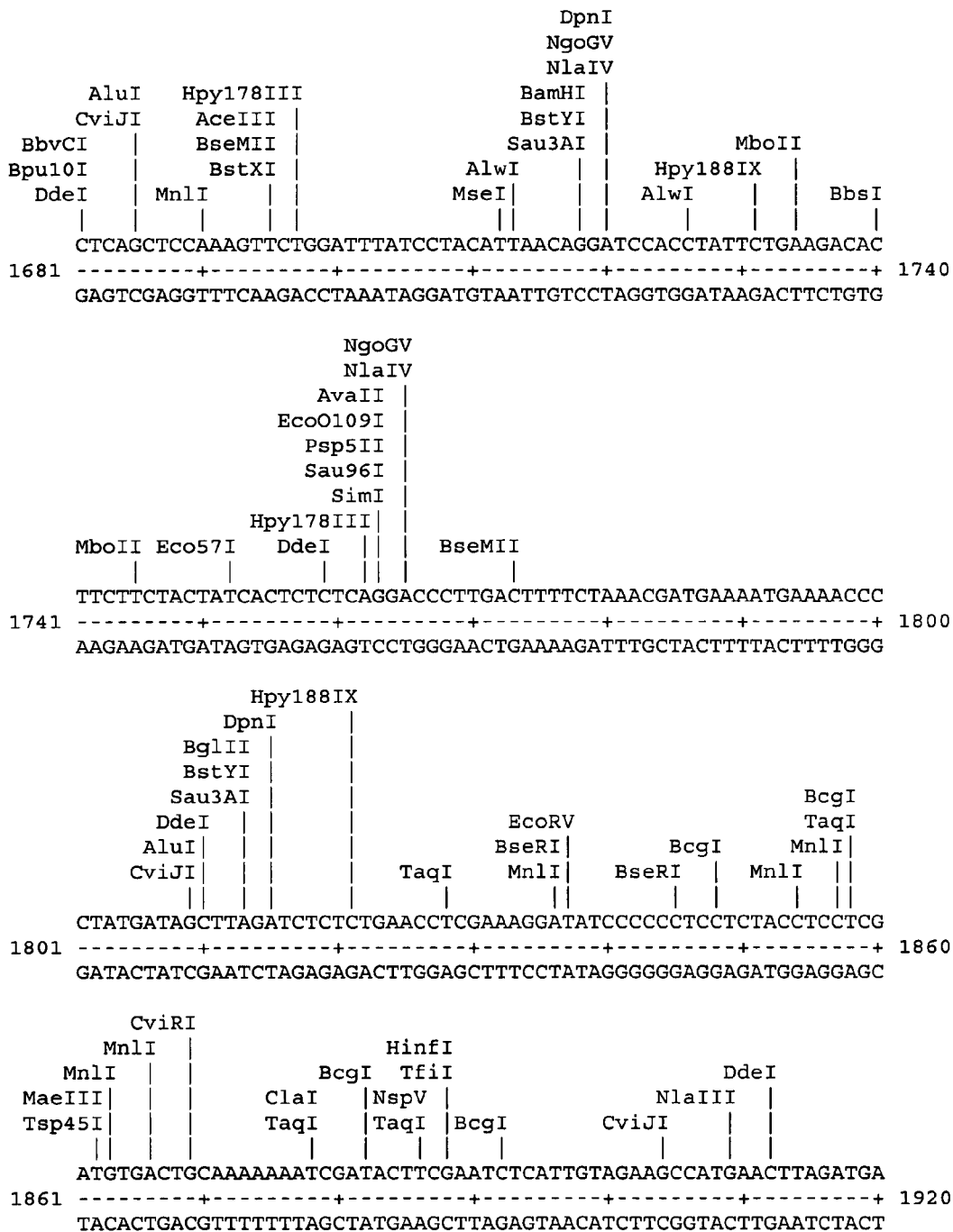
Figure 9I:
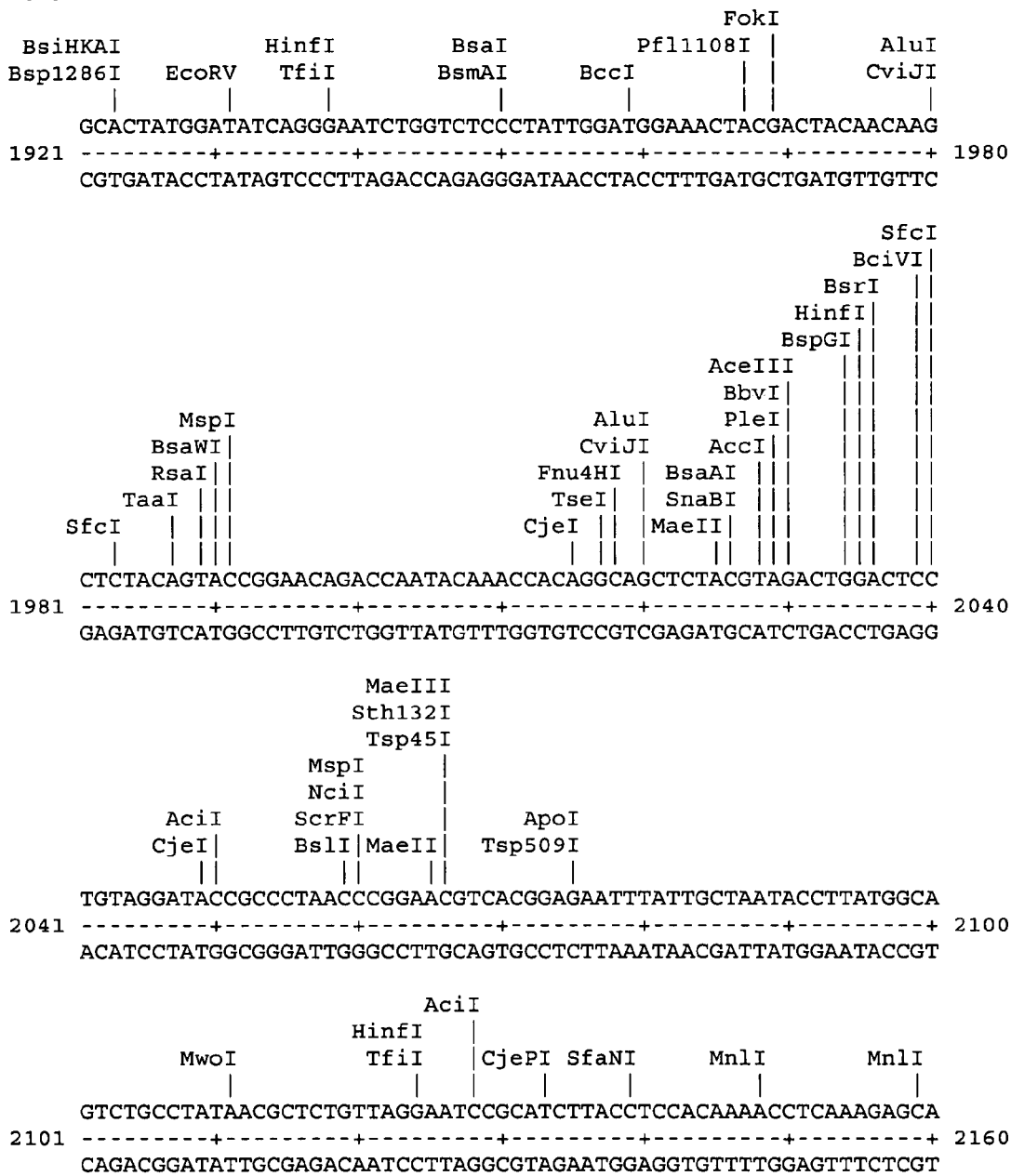
Figure 9J:
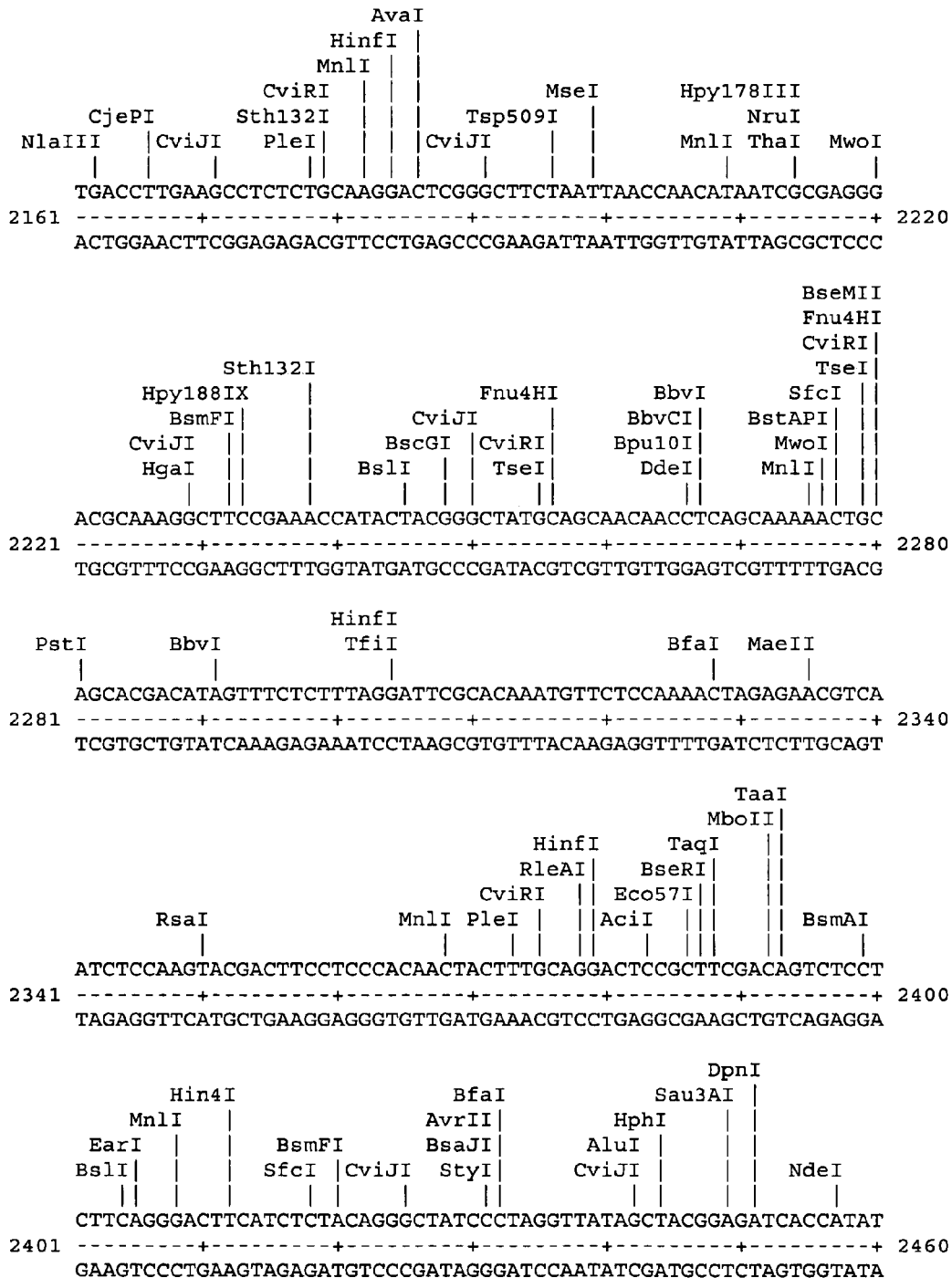
Figure 9L:
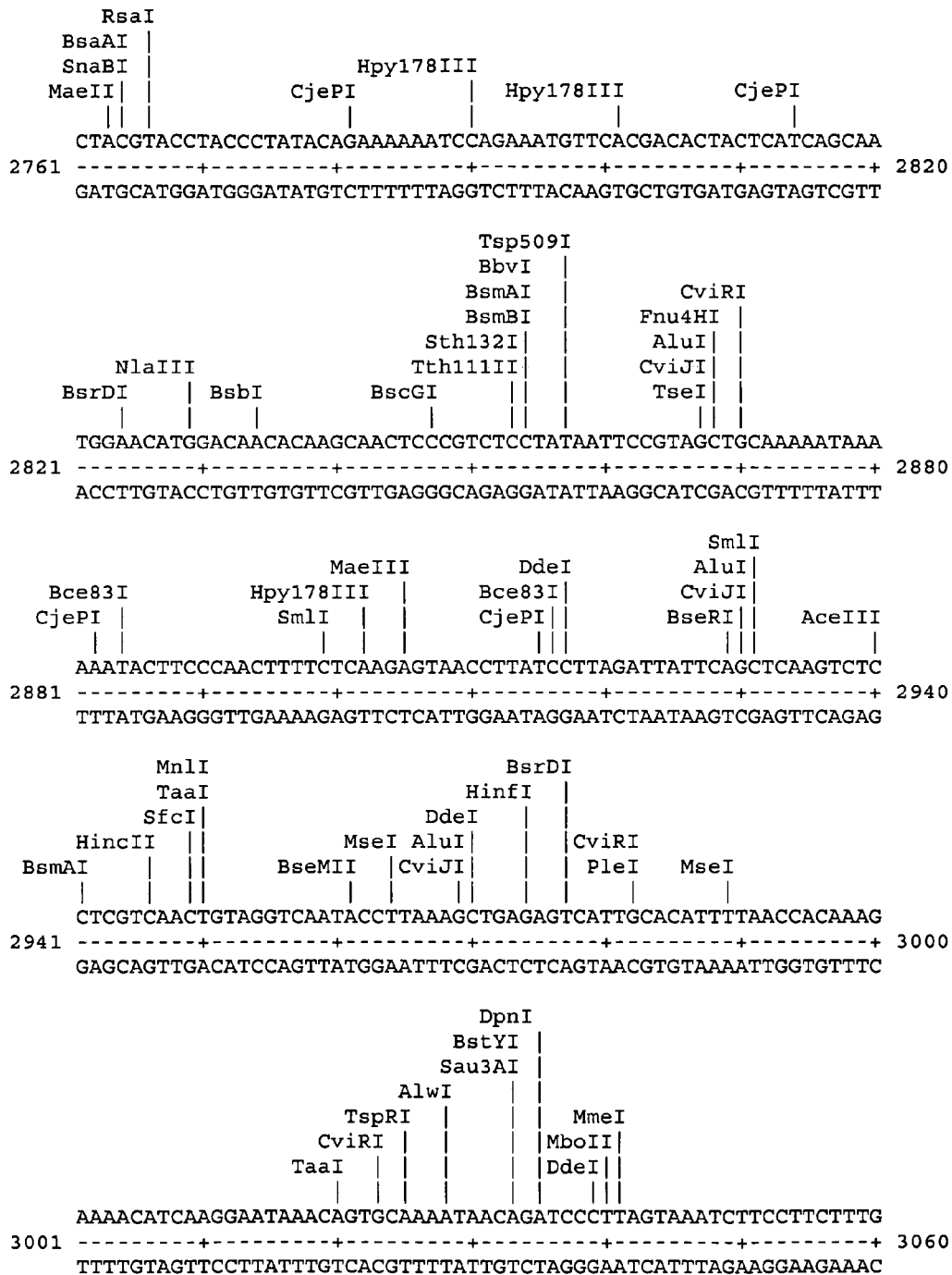
Figure 10A:
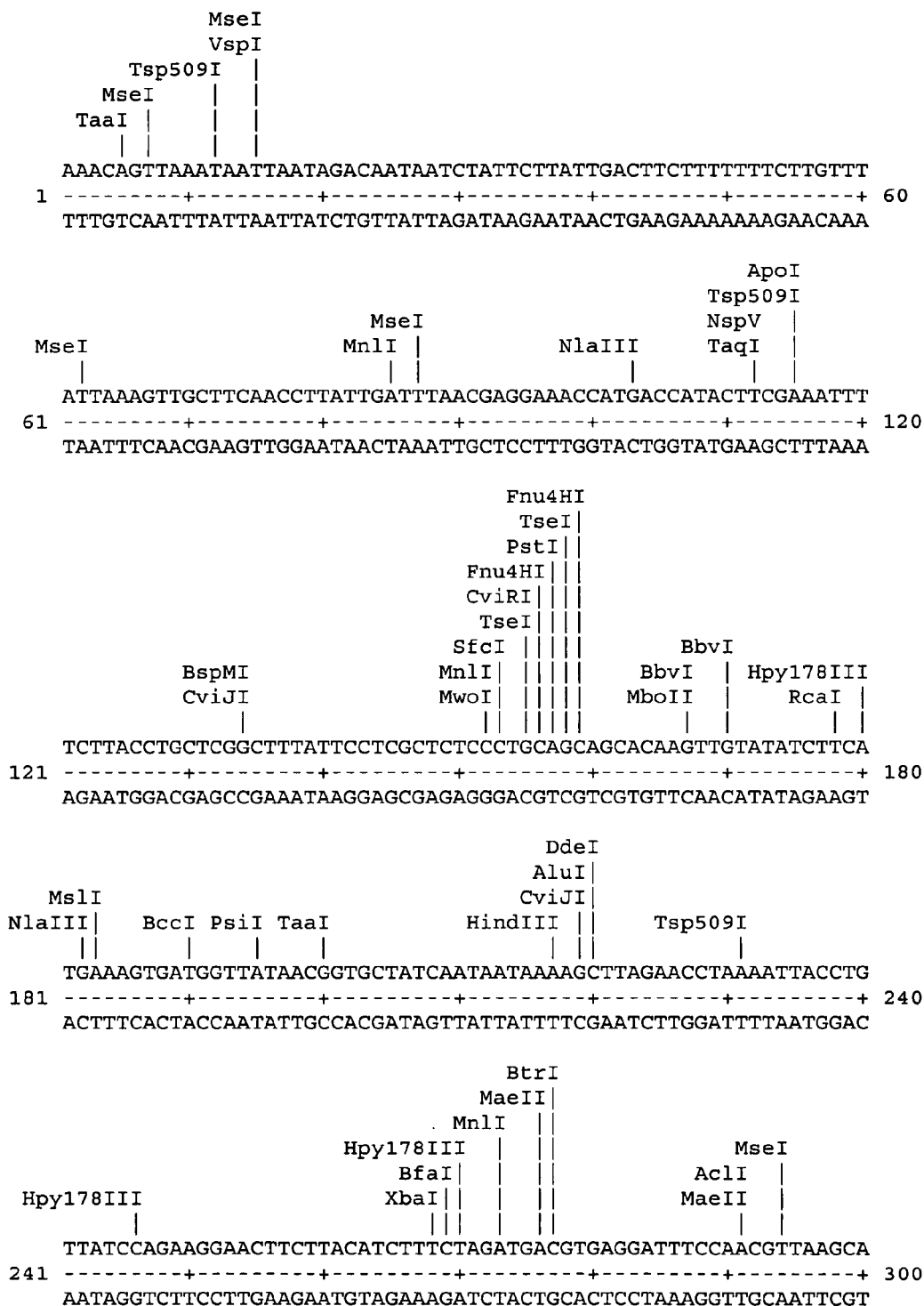
Figure 10B:
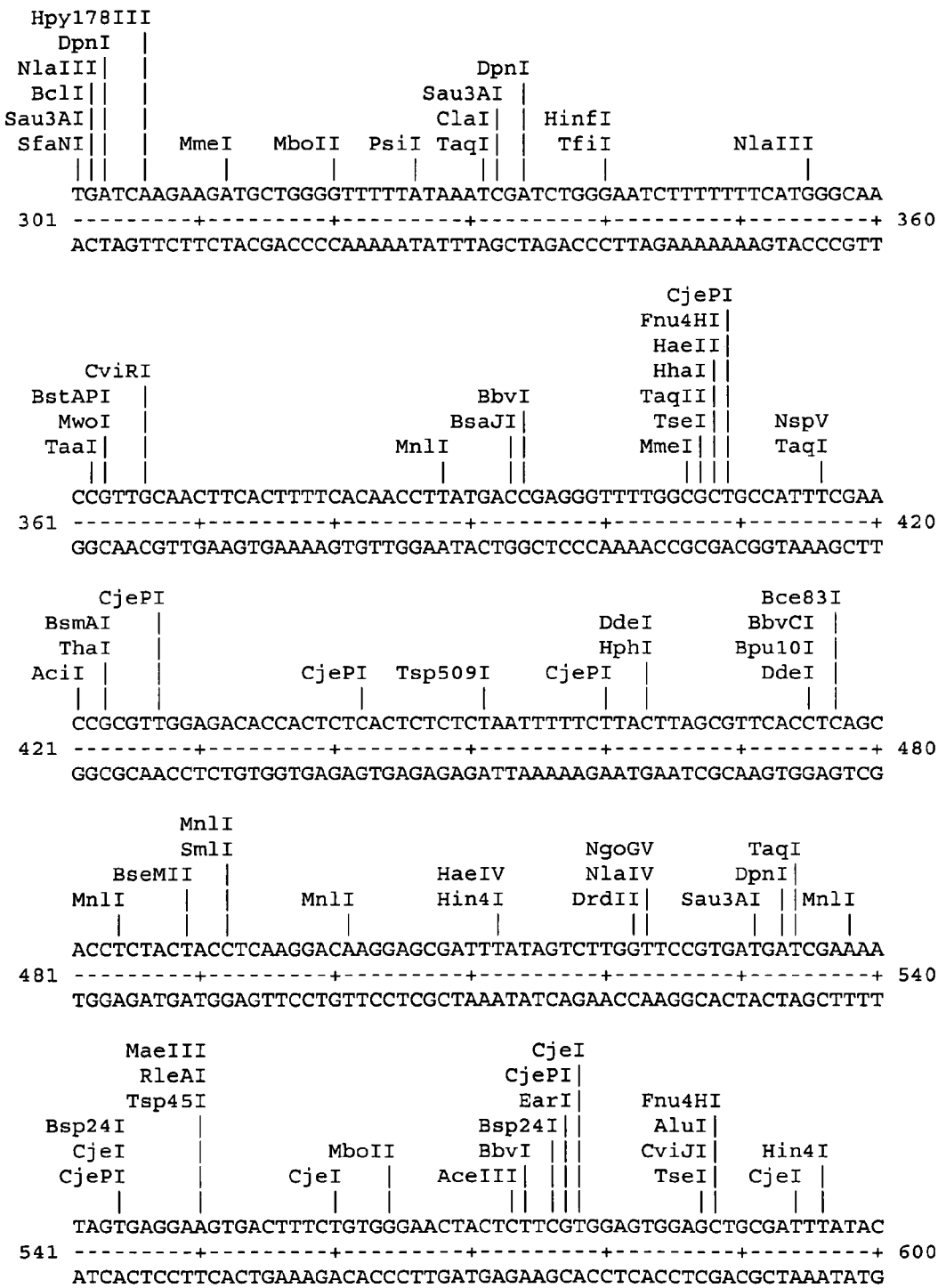
Figure 10C:
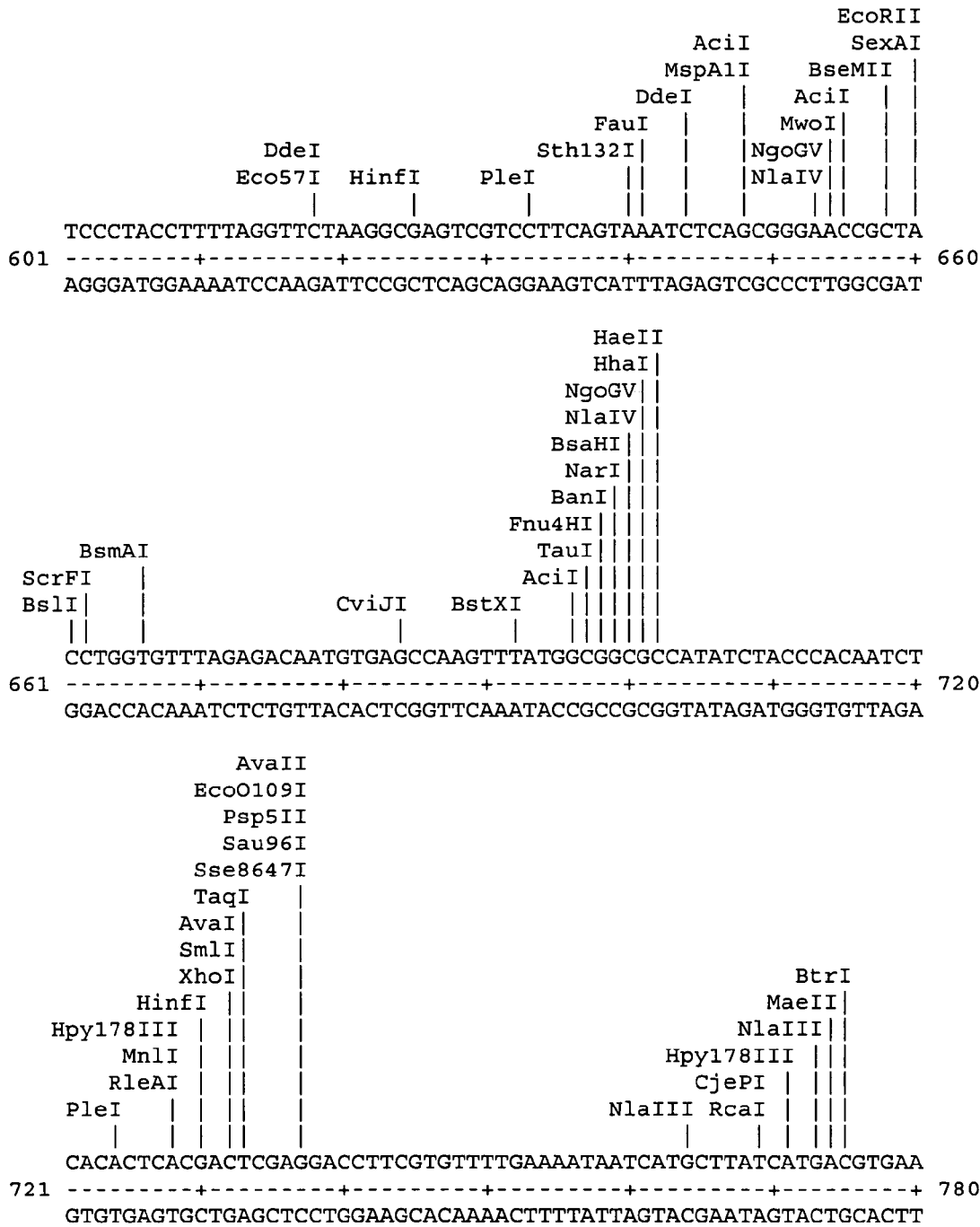
Figure 10D:
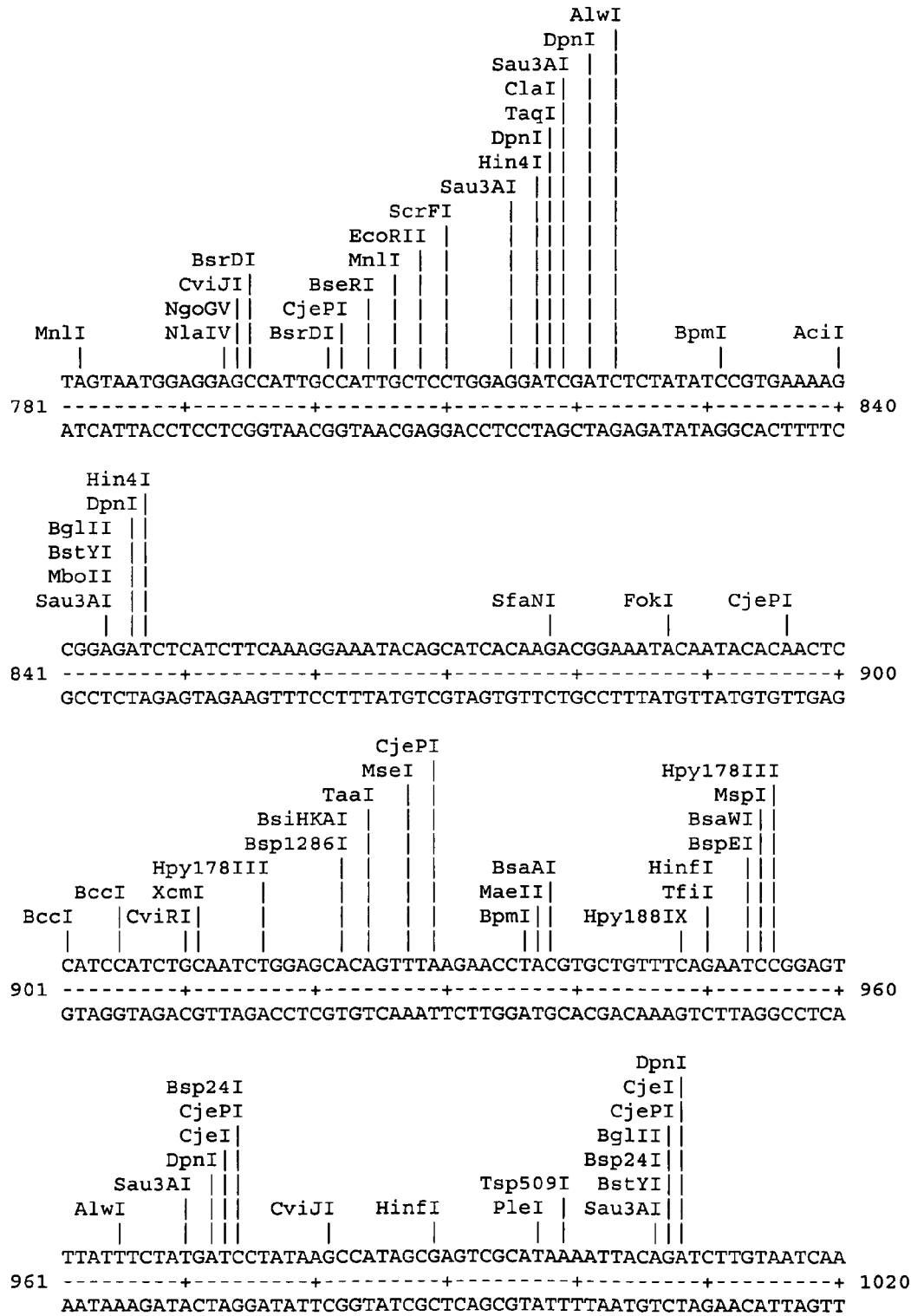
Figure 10E:
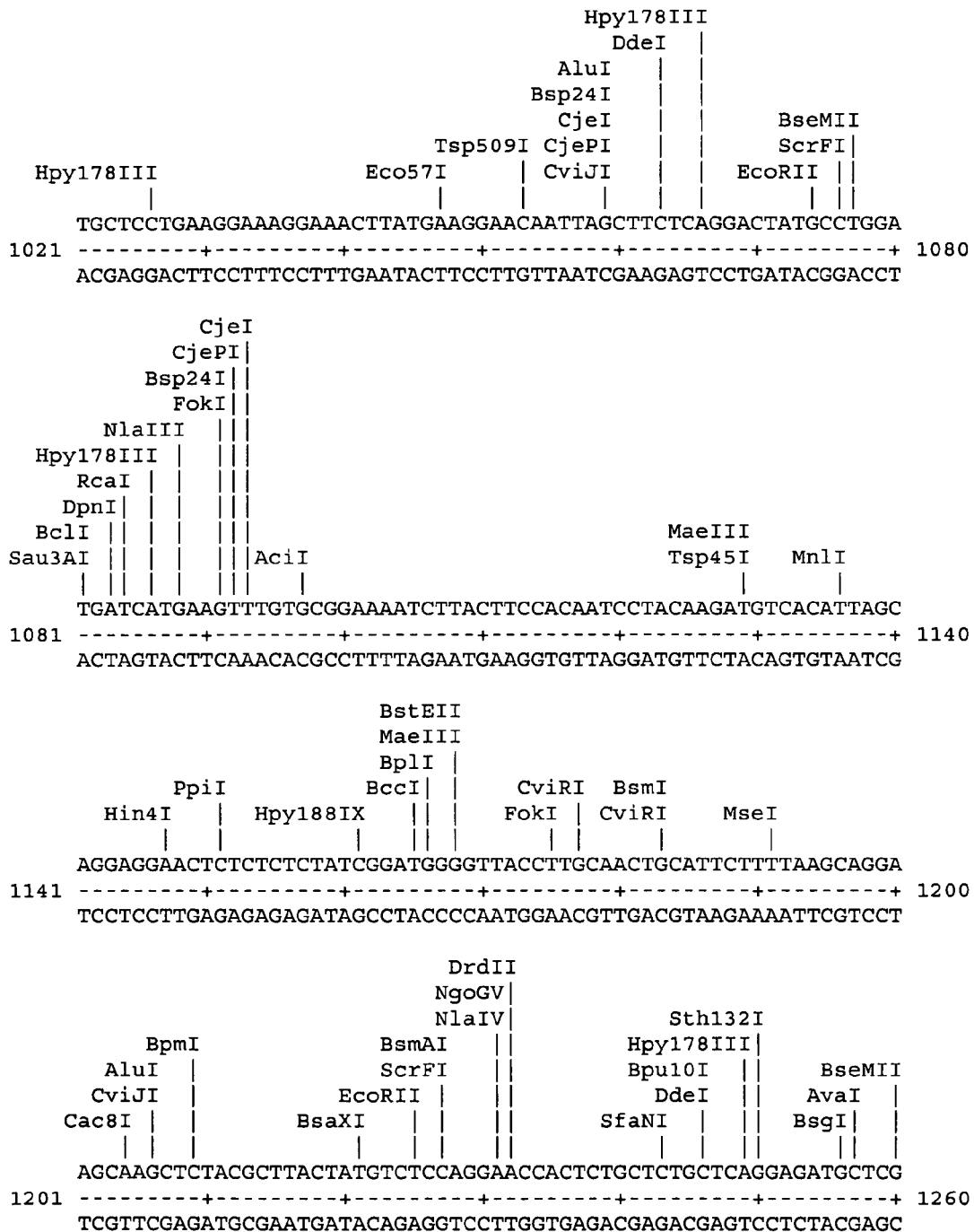
Figure 10F:
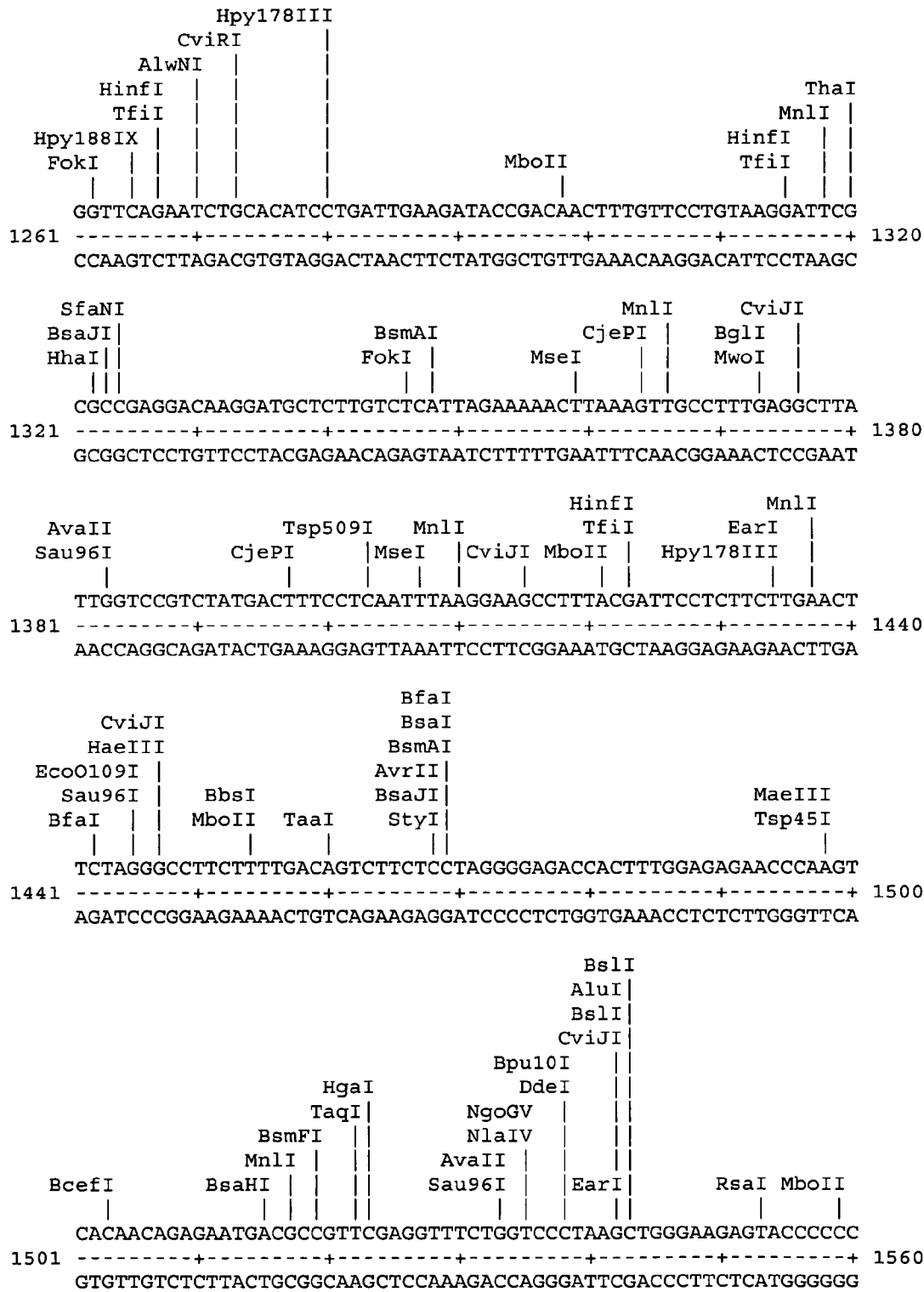
Figure 10G:
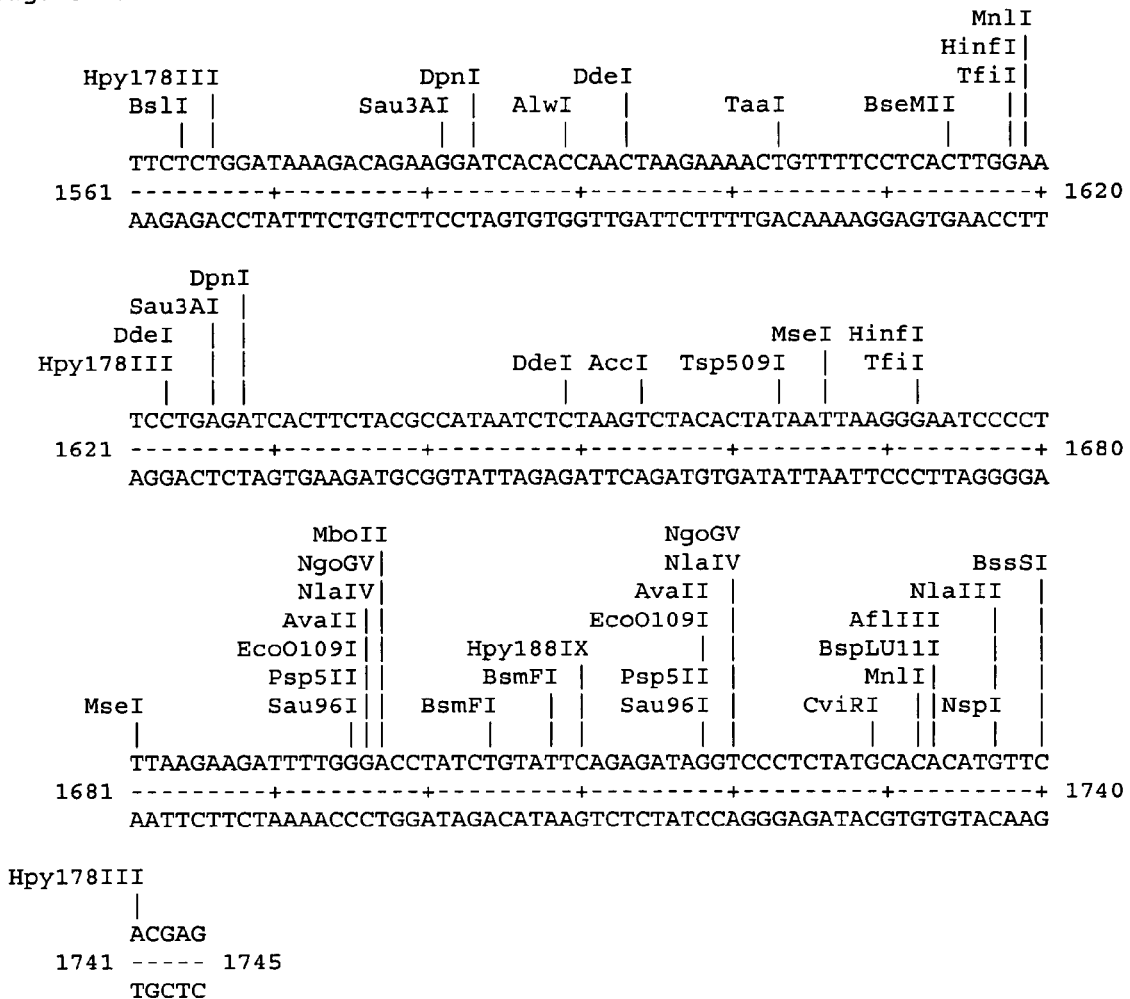
Figure 11B:
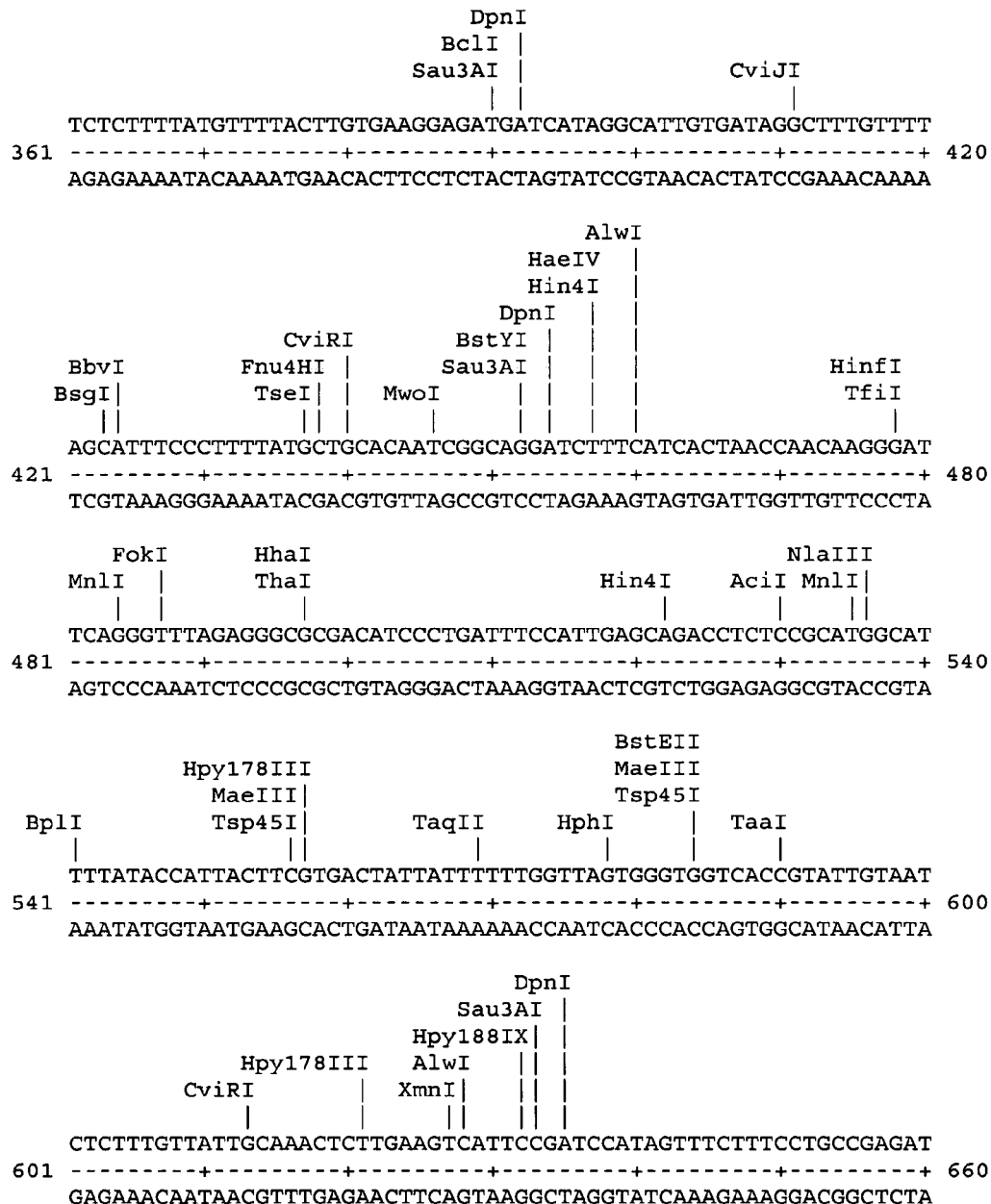
Figure 12A:
Figure 13A:
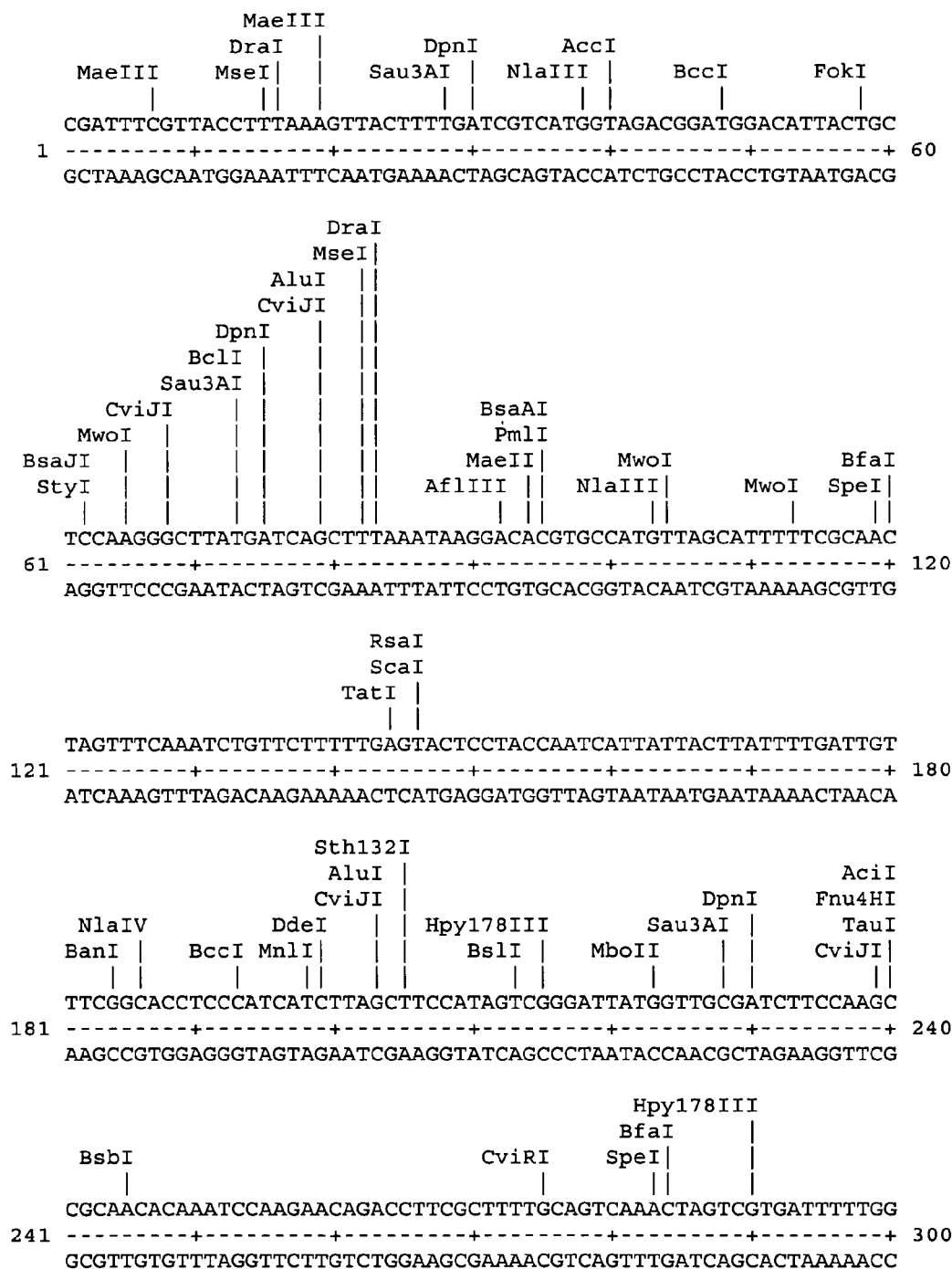

Figure 9A
Restriction enzyme analysis of CPN100624 (RY 64 - SEQ ID NO. 9)

```
                                    MseI
                                    NlaIII|
                        AflIII      ||              DraI
                        BspLU11I    ||              SwaI
                SspI            |NspI|              MseI|
                  |              |  ||                ||
       TCAAATATATGAGTTTACTAACTCTGTAATATTCAACATGTTAATAAGCATATTTAAATA
     1 ---------+---------+---------+---------+---------+---------+ 60
       AGTTTATATACTCAAATGATTGAGACATTATAAGTTGTACAATTATTCGTATAAATTTAT

Hpy178III
       ApoI         BfaI|
       Tsp509I  PsiI  XbaI||  Tsp509I
         |       |     |||      |
       TAAATTTATAAACTTCTAGACAACAAATTGATGATTTTTATGACAAACTCTATTTTCAT
    61 ---------+---------+---------+---------+---------+---------+ 120
       ATTTAAATATTTGAAGATCTGTTGTTTAACTACTAAAAAATACTGTTTGAGATAAAAGTA

HhaI
                                                        TspRI
                        FokI        BsmAI       BtsI    |
                   SimI | DrdI DdeI  |     BseMII |     |
                    |   |  |    |    |        |   |     |
       ATCAAAGTTTGGATGTTTATGCGACCCATTTGTCTCAGCATTTTATCCCACTGCGCTATG
   121 ---------+---------+---------+---------+---------+---------+ 180
       TAGTTTCAAACCTACAAATACGCTGGGTAAACAGAGTCGTAAAATAGGGTGACGCGATAC

Hpy178III
                                                MnlI      |
                  Hpy178III              Hpy188IX | BfaI|
                  BsmFI      |              MnlI  | |XbaI||
                    |        |                |   | | |||
       TTGTTCCTTATCAGGAAATGAAGTCCCTAACCTCGCCTCTTGTCAGATGTCTAGAAAAGA
   181 ---------+---------+---------+---------+---------+---------+ 240
       AACAAGGAATAGTCCTTTACTTCAGGGATTGGAGCGGAGAACAGTCTACAGATCTTTTCT
```

Figure 9B

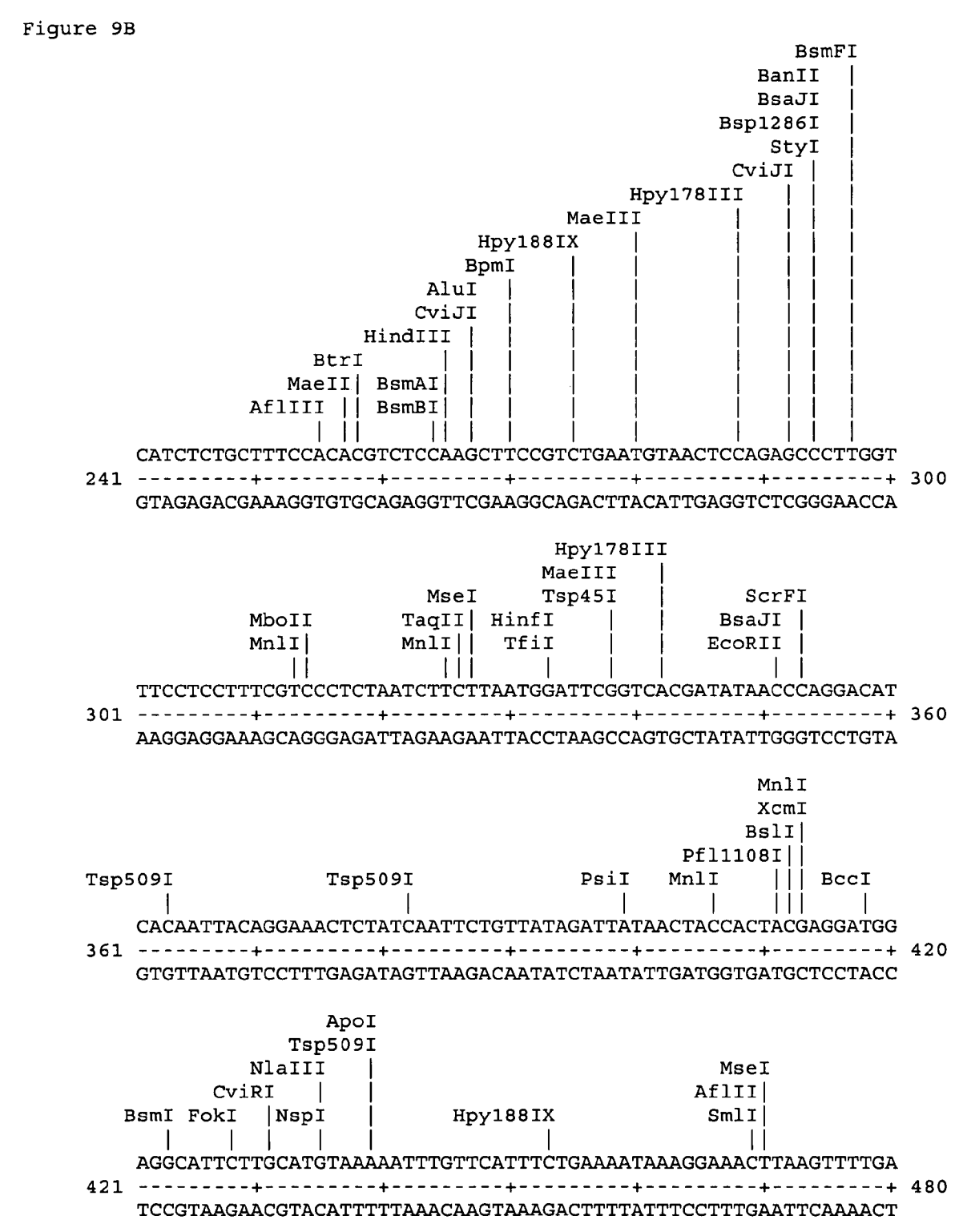

```
                                                                BsmFI
                                                          BanII  |
                                                          BsaJI  |
                                                         Bsp1286I |
                                                           StyI  |
                                                          CviJI  |  |
                                                Hpy178III   |    |  |
                                          MaeIII    |       |    |  |
                                  Hpy188IX   |      |       |    |  |
                             BpmI    |       |      |       |    |  |
                             AluI |  |       |      |       |    |  |
                            CviJI |  |       |      |       |    |  |
                          HindIII |  |       |      |       |    |  |
                     BtrI    |    |  |       |      |       |    |  |
                   MaeII| BsmAI|  |  |       |      |       |    |  |
                  AflIII ||  BsmBI|  |       |      |       |    |  |
                     |  ||   ||   |  |       |      |       |    |  |
                    CATCTCTGCTTTCCACACGTCTCCAAGCTTCCGTCTGAATGTAACTCCAGAGCCCTTGGT
              241 ---------+---------+---------+---------+---------+---------+ 300
                    GTAGAGACGAAAGGTGTGCAGAGGTTCGAAGGCAGACTTACATTGAGGTCTCGGGAACCA Hpy178III
                                                      MaeIII    |
                                          MseI       Tsp45I     |       ScrFI
                            MboII       TaqII| HinfI   |        |       BsaJI   |
                            MnlI|       MnlI|| TfiI    |        |       EcoRII  |
                               ||          |||   |     |        |         ||    |
                    TTCCTCCTTTCGTCCCTCTAATCTTCTTAATGGATTCGGTCACGATATAACCCAGGACAT
              301 ---------+---------+---------+---------+---------+---------+ 360
                    AAGGAGGAAAGCAGGGAGATTAGAAGAATTACCTAAGCCAGTGCTATATTGGGTCCTGTA MnlI
                                                                          XcmI
                                                                          BslI|
                                                                      Pfl1108I||
          Tsp509I              Tsp509I                PsiI      MnlI    |||   BccI
             |                    |                    |          |     |||    |
                    CACAATTACAGGAAACTCTATCAATTCTGTTATAGATTATAACTACCACTACGAGGATGG
              361 ---------+---------+---------+---------+---------+---------+ 420
                    GTGTTAATGTCCTTTGAGATAGTTAAGACAATATCTAATATTGATGGTGATGCTCCTACC ApoI
                            Tsp509I
                          NlaIII    |
                    CviRI    |      |                                MseI
                       |     |      |                              AflII|
              BsmI FokI |NspI |        Hpy188IX                    SmlI|
               |    |   |  |  |           |                         ||
                    AGGCATTCTTGCATGTAAAAATTTGTTCATTTCTGAAAATAAAGGAAACTTAAGTTTTGA
              421 ---------+---------+---------+---------+---------+---------+ 480
                    TCCGTAAGAACGTACATTTTTAAACAAGTAAAGACTTTTATTTCCTTTGAATTCAAAACT
```

Figure 9D

```
                AvaII
                EcoO109I
                Psp5II
                Sau96I                                    Tth111II
                Sse8647I                                  HinfI    |
      HphI      DdeI    |       Hpy178III                 TfiI    ||
       |         ||         |                              |     |||
         ATCAATCACAGACAACTTAGGTCCTATCGTTATCAAGAAAAATCAAACATTAGAAGATTC
  721  ---------+---------+---------+---------+---------+---------+ 780
         TAGTTAGTGTCTGTTGAATCCAGGATAGCAATAGTTCTTTTTAGTTTGTAATCTTCTAAG CviJI
                            PstI   |
                            BseRI  | |
      MboII                 CviRI  | |
      MnlI                  SfaNI  | |
      AluI   |    BcefI  SfcI      | |
      CviJI  |    Hin4I |BstAPI|   | |             Tsp509I
      MnlI|  |MboII |   | MwoI |   | |             FokI     |
      ||  |  | ||   |   | ||   |   | |              |      ||
         CAGCTTTGGAGGAGGCATCTTCTGCAGAGCCGTAAATATAGAAAGGAATTATCAAAACAT
  781  ---------+---------+---------+---------+---------+---------+ 840
         GTCGAAACCTCCTCCGTAGAAGACGTCTCGGCATTTATATCTTTCCTTAATAGTTTTGTA Hin4I
                                                          MboII|
                                                         HinfI ||
                                                  BfaI     |   ||
                                                  AvrII|   |   ||
                                                  BsaJI|   |   ||
                        Hpy178III                 CjeI |   |   ||
             Bsp24I       |                       StyI |   |   ||
             CjeI         |                       CjePI||   |   ||
      Eco57I  CjePI       |                       Bsp24I|||  |   ||
       |       |          |                         ||||    |   ||
         CCAAATCAATGATAATGCTTCAGGACAAGGGGTGGTATATTTTCTGCCCCTAGGAGTCAT
  841  ---------+---------+---------+---------+---------+---------+ 900
         GGTTTAGTTACTATTACGAAGTCCTGTTCCCCACCATATAAAAGACGGGGATCCTCAGTA HaeIV
                              Hin4I
                              FokI|                 MseI
                              DpnI||                SfaNI|
      PleI    EarI  Tsp509I   Sau3AI||        AciI  Tsp509I ||MnlI
       |       |      |         ||||           |     |     |||  |
         TATCTCTTCAAATAAAGAAATTATAGAGATCAGCAATCACTCCGCATCCTCAATTAACAC
  901  ---------+---------+---------+---------+---------+---------+ 960
         ATAGAGAAGTTTATTTCTTTAATATCTCTAGTCGTTAGTGAGGCGTAGGAGTTAATTGTG
```

Figure 9K

```
                              MseI    SimI      CviJI   MseI
                                |       |         |       |
         GCTTTGCCACTATACAGAAATCTTAAAAGGGTCGTCCAAAGCCTTCTTTAATAACCACAC
2461     ---------+---------+---------+---------+---------+---------+ 2520
         CGAAACGGTGATATGTCTTTAGAATTTTCCCAGCAGGTTTCGGAAGAAATTATTGGTGTG

CjePI
                                           HinfI      Hpy178III    |
                   Hpy178III                 TfiI         TaqI     |
              CviJI    |                     BfaI         FauI|    |
           BsgI  |     |         CjePI       AluI|        Sth132I| |
        BslI  |  |     | BfaI| CviRI         CviJI|       AciI  ||| |
        PflMI |  |     | XbaI| |MnlI |       HphI||     BpmI    ||| |
           |  |  |     |  |||    |  |          |||       |      ||| |
         TTTGGTAGCCTCTCTAGACTGCACATTCTTACCAGCTAGAATCACCCGCACTCTCGAACT
2521     ---------+---------+---------+---------+---------+---------+ 2580
         AAACCATCGGAGAGATCTGACGTGTAAGAATGGTCGATCTTAGTGGGCGTGAGAGCTTGA CviJI
                                         HaeI
                                         HaeIII
                                         StuI              BstXI
                                         ScrFI             BsaI  |
                        TspRI     HhaI BsaJI  |            BsmAI |
         CviJI          BsrDI|    CjeI |EcoRII|            MnlI| |
           |             ||    |  |     |   |                |  | |
         CCAGCCCTTTATCAGTGCCATTGCTCTGCGCTGTTCCCAGGCCTCGTTCCAAGAAACTGG
2581     ---------+---------+---------+---------+---------+---------+ 2640
         GGTCGGGAAATAGTCACGGTAACGAGACGCGACAAGGGTCCGGAGCAAGGTTCTTTGACC BccI              Hin4I
                          BpmI |             DpnI    |
                         FokI  |             BglII   |
           CjeI         ApoI|  |             BstYI   |             CviJI
         BsrI|FokI Tsp509I|  |  |             Sau3AI  |             MnlI  |
           ||  |      ||  |  |                 |     |               ||   |
         AGACCATATAAGAAAATTCCATCCAAAACATCCCCTTACAGATCTTTCCTCTCCCATAGG
2641     ---------+---------+---------+---------+---------+---------+ 2700
         TCTGGTATATTCTTTTAAGGTAGGTTTTGTAGGGGAATGTCTAGAAAGGAGAGGGTATCC BslI
                                         PflMI
              Hpy188IX                   NlaIII
                  |                          | |
         CTTCCGTTCTGAATGGAAAACTTCACATCATATCCCCATGCTATGGACTACGGAAATATC
2701     ---------+---------+---------+---------+---------+---------+ 2760
         GAAGGCAAGACTTACCTTTTGAAGTGTAGTATAGGGGTACGATACCTGATGCCTTTATAG
```

Figure 9M

```
            Tsp509I
              MseI|
         CviJI   ||
         NgoGV|  ||
         NlaIV|  ||
             || ||
         TTGGAGCCTTAATTTTAGGTAAAACTACAATA
   3061  ----------+---------+----------+--  3092
         AACCTCGGAATTAAAATCCATTTTGATGTTAT
```

Restriction enzyme analysis of CPN100633 (RY 65 - SEQ ID NO. 10)

Figure 11A

Restriction enzyme analysis of CPN100985 (RY 66 - SEQ ID NO. 11)

```
                       Hpy178III
                         DpnI
                         MnlI
            Sau3AI   |      Bpu1102I
          MseI  |    |        DdeI          BspMI
    NlaIV  |   |    |         CviJI|       BpmI        CviRI
      |    |   |    |          ||   |       |            |
     TTTGGAACCTTAATGATCTCTGGAGGGTGGCTTAGCAATATGATTTTACGCTTTGCAGGT
   1 ---------+---------+---------+---------+---------+---------+ 60
     AAACCTTGGAATTACTAGAGACCTCCCACCGAATCGTTATACTAAAATGCGAAACGTCCA

AluI    HinfI
 Hpy188IX                            CviJI    TfiI              CjeI
     |                                 |       |                  |
     CAGATTTTCCAAAACTTCTATAAATGGAAATAAAGAGCTTATGGGAATCTCTCTACCAGA
  61 ---------+---------+---------+---------+---------+---------+ 120
     GTCTAAAAGGTTTTGAAGATATTTACCTTTATTTCTCGAATACCCTTAGAGAGATGGTCT BfaI                                       CviJI
             AvrII|                  CjeI                HaeIII
      AluI   BsaJI|                  FokI|          MspI    |
      CviJI   StyI|            DdeI MmeI|       Tth111II |  |MnlI
       |     ||                  |   ||            |     |  | |
     GCTTTTTTCCAACCTAGGTTCTGCTTACTTAGATTATATCTTTCAACATCCTCCGGCCTA
 121 ---------+---------+---------+---------+---------+---------+ 180
     CGAAAAAAGGTTGGATCCAAGACGAATGAATCTAATATAGAAAGTTGTAGGAGGCCGGAT Sth132I             AluI
             MboII                BscGI   |                 CviJI
      BslI     |                  CviJI   |           SfcI    |
       |       |                    | |   |             |     |
     TGTTTGGTCAGTTTTTCTTCTTTTATTAGCCCGTCTGCTTCCTATTTTGCTGTAGCTCC
 181 ---------+---------+---------+---------+---------+---------+ 240
     ACAAACCAGTCAAAAAGAAGAAAATAATCGGGCAGACGAAGGATAAAAACGACATCGAGG Hpy178III
                                       MnlI
                 AluI                  MseI|                  Cac8I
       BslI      CviJI                 BplI||                 CviJI |
       DdeI|    Hin4I  |             Sth132I|||        BsmAI        | |
        ||     |    |                  ||||              |          | |
     CTTCTTAGGAGCAAAGCTCTTTCCCTCCCCTATTAAAATCGGGATTAGTCTCTCTTGGCT
 241 ---------+---------+---------+---------+---------+---------+ 300
     GAAGAATCCTCGTTTCGAGAAAGGGAGGGGATAATTTTAGCCCTAATCAGAGAGAACCGA EciI      Tsp509I
                             AciI|       DpnI              BsaBI
      CviRI         BciVI       ||      Sau3AI|       NlaIII   |
        |            |          ||        |   |         |      |
     TGCAATCATCTTTCCAAAAGTCTTGGCGGATACGCAGATCACAAATTACATGGATAACAA
 301 ---------+---------+---------+---------+---------+---------+ 360
     ACGTTAGTAGAAAGGTTTTCAGAACCGCCTATGCGTCTAGTGTTTAATGTACCTATTGTT
```

Figure 11C

```
              MseI
       AflII|                            Hpy178III                    AceIII
        SmlI|Bsp1286I                    DpnI       |      AluI       BsmAI
        AluI|| BmgI    |Sth132I          BclI       |      CviJI      Hpy178III
       CviJI|| BseSI   | BslI            Sau3AI     |      Cac8I  |   BssSI      |
         |||   ||       |  |              |         |       |  |       |  |      |
        GATGAGCTTAAGTGCCCCGATTTGGATTACTATGATCAAGATGTGCCAGCTCTGTCTCGT
   661  ---------+---------+---------+---------+---------+---------+  720
        CTACTCGAATTCACGGGGCTAAACCTAATGATACTAGTTCTACACGGTCGAGACAGAGCA

MwoI
                              AluI  |
                              CviJI |
                              PstI| |
                             Fnu4HI|| |
                              CviRI||| |
                DdeI          MwoI ||| |
                AluI|         TseI ||| |
               CviJI|         SfcI |||| |         Hpy188IX
              MspA1I| BsiHKAI      |||| |    MseI        |
       BseMII PvuII|Bsp1286I       |||| |    BbvI    |        DdeI
         |       ||       |        ||||| |     |     |         |
        GATGACCATACAGCTGAGTGCTCCTGCAGCTTTGGCGATGTTAATGTCCGACCTATTCTT
   721  ---------+---------+---------+---------+---------+---------+  780
        CTACTGGTATGTCGACTCACGAGGACGTCGAAACCGCTACAATTACAGGCTGGATAAGAA

BglI
                                                                  MwoI
                                                                  MseI   |
                 TaaI                                             AflII|  |
               MmeI  |          SmlI                               MnlI|  |
        Bce83I |    |    NlaIV   |          BseRI                  SmlI|  |
         MseI  |    |    BanI    |           MnlI                  MnlI|| |
          |    |    |      |     |            |                      |||| |
        AGGGATTATTAACCGTATGGCACCTCAAGTTCAGGTCATCTACCTCCTCTCTGCCCTTAA
   781  ---------+---------+---------+---------+---------+---------+  840
        TCCCTAATAATTGGCATACCGTGGAGTTCAAGTCCAGTAGATGGAGGAGAGACGGGAATT

SimI
            NlaIII|
         BbsI    ||        ScrFI                       MseI
         MboII   ||        BsaJI           |         Tsp509I  |
        CviJI    ||  HphI  EcoRII |BslI    DrdII        |     |
          |      ||   |      |    |         |           |     |
        GGCTTTCATGGGTCTTCTCTTTCTCACCCTGGCGTGGTGGTTCATAATTAAGCAGATAGA
   841  ---------+---------+---------+---------+---------+---------+  900
        CCGAAAGTACCCAGAAGAGAAAGAGTGGGACCGCACCACCAAGTATTAATTCGTCTATCT
```

Figure 11D

```
                                                           BfaI
                                                           AvrII|
                                                           BsaJI|
                             DrdII                         StyI|
  Tth111II      BsmFI          |                   Bce83I| |NlaIV    SmlI
     |            |            |                      ||| |          |
          TTATTTCACTCTTGCTTGGTTCAAAGAAGTCCCCATTATGCTCCTAGGTTCCAACCCTCA
  901   ---------+---------+---------+---------+---------+---------+ 960
          AATAAAGTGAGAACGAACCAAGTTTCTTCAGGGGTAATACGAGGATCCAAGGTTGGGAGT

Hpy178III
                         CviJI         SfaNI      |
                  BfaI     |    HinfI    |        |
        MnlI      MmeI    |Hpy178III|    |        |
    RsaI  |   AvrII|      | MaeIII| |    |                        BpmI
    ScaI  |   BsaJI|      | Tsp45I| |    |            HhaI        HinfI|
  TatI |  |    StyI|      | PleI ||||    |     Hin4I  |           TfiI|
    ||  |  |     ||  |    |  |   ||||    |       |    |            ||
          AGTACTCTAATCCCCTAGGCTCTTATCGTGACTCTTATCTGGAGATGCGCTCACTTACGA
  961   ---------+---------+---------+---------+---------+---------+ 1020
          TCATGAGATTAGGGGATCCGAGAATAGCACTGAGAATAGACCTCTACGCGAGTGAATGCT BplI      TspRI              CjeI
       DdeI |     TaaI  |           HinfI |
     CjeI | |HhaI |     |       DdeI  TfiI|                       DdeI
      ||| |  |    |     |         |    ||                          |
          ATCTTAGCGCACTGTTTATGGATTATCTTAGGGAATCTCTCGCATATTCTTTTGTAATCT
  1021  ---------+---------+---------+---------+---------+---------+ 1080
          TAGAATCGCGTGACAAATACCTAATAGAATCCCTTAGAGAGCGTATAAGAAAACATTAGA Hpy178III
     HinfI  ApoI    |
      TfiI Tsp509I  |
       |     |      |
          AAGAATCTATAAATTCAAGA
  1081  ---------+---------+ 1100
          TTCTTAGATATTTAAGTTCT
```

Restriction enzyme analysis of CPN100987 (RY 67 - SEQ ID NO. 12)

Figure 12B

```
                           CviJI
                           MboII
                           NlaIV|
             Hpy188IX       ||
              RleAI    |    ||
           BsiHKAI |   |    ||
           Bsp1286I|   |    ||                            DpnI
             BseSI |   |    ||   Hpy178III                BstYI |
             CviRI |   |    ||      BfaI|                 Sau3AI |
         ApaLI |   |   |    ||      XbaI||    DdeI AlwI     |   |
           |  |||  |   |    ||       |||      |    |        |   |
           CTGTGCACCTTTCGGAGCCTTCTATCTTCTAGATATGCTAAGTAAAAAGATCCGTCCTTG
       361 ---------+---------+---------+---------+---------+---------+ 420
           GACACGTGGAAAGCCTCGGAAGATAGAAGATCTATACGATTCATTTTTCTAGGCAGGAAC

SfaNI
                                              MwoI  |
                           XmnI              BbvCI| |
                         FokI |              Bpu10I| |    BseMII
           Tsp509I       MboII | |MboII CviRI DdeI| | MnlI  |
              |           |||   |   |      |   ||  |  |    |
           TGGAATTACAGAAGAAATCTTTCTTCCTGCATCCTCAGCAAATGCTATACTTTACTATAC
       421 ---------+---------+---------+---------+---------+---------+ 480
           ACCTTAATGTCTTCTTTAGAAAGAAGGACGTAGGAGTCGTTTACGATATGAAATGATATG

AlwNI
        AvaII  |
      EcoO109I |                     BfaI
        Psp5II |                    AvrII|
        Sau96I |      DpnI          BsaJI|
      Sse8647I | Sau3AI | MseI       StyI|
           |   |   ||   |   |         |||
           AGGTCCTGTAAAGATCGCTTTAATCAACTGCCTAGGTCTTTATTCTATTGCTAAAGAGTT
       481 ---------+---------+---------+---------+---------+---------+ 540
           TCCAGGACATTTCTAGCGAAATTAGTTGACGGATCCAGAAATAAGATAACGATTTCTCAA

MboII
              Hpy178III                             BsmI | SfcI
                 |                                   |   |  |
           GAAGCACATTCTGGATAAGGTTGTGATTGAACGAGTGAAGAATGCTCTCTCCCCTACAGA
       541 ---------+---------+---------+---------+---------+---------+ 600
           CTTCGTGTAAGACCTATTCCAACACTAACTTGCTCACTTCTTACGAGAGAGGGGATGTCT

MboII
                                                         ApoI  |
                                                       Tsp509I |
                   FokI       Hpy188IX               Pfl1108I| |
                    |             |                     |   ||
           GAAACTCTTTCTTACCTACTGCCAATCTCATCCGATGAAACATTTAGAAACTACGAATTT
       601 ---------+---------+---------+---------+---------+---------+ 660
           CTTTGAGAAAGAATGGATGACGGTTAGAGTAGGCTACTTTGTAAATCTTTGATGCTTAAA
```

Figure 12C

```
                  Tsp509I
        SfaNI     CviRI        TaaI
          |         | |         |
       TCTTTCTTCTTGGACTACTGATGCAGAATTACGACAGTTCGTTCATAAGCAAGGGTTAGA
  661  ---------+---------+---------+---------+---------+---------+  720
       AGAAAGAAGAACCTGATGACTACGTCTTAATGCTGTCAAGCAAGTATTCGTTCCCAATCT

TaqII
                                                              BsaAI  |
                                                              SnaBI  |
                          MseI                                MaeII| |
                            |                                   || |
       GTTTTTAGGTAAAGCATTAACAAAAGAAAACGCTTCTTTTCTATGGTATTTTCTACGTAG
  721  ---------+---------+---------+---------+---------+---------+  780
       CAAAAATCCATTTCGTAATTGTTTTCTTTTGCGAAGAAAAGATACCATAAAAGATGCATC

FokI
        BsiEI                              DraI  |                MslI
          TaqI Hin4I      TaqI             MseI| |NlaIII     BccI   |
            |   |           |                || |   |         |     |
       GTTAGATGTCGGTCGAGCATATATCGTCGAGCAGACTTTAAAAACATGGTATGACCATCC
  781  ---------+---------+---------+---------+---------+---------+  840
       CAATCTACAGCCAGCTCGTATATAGCAGCTCGTCTGAAATTTTGTACCATACTGGTAGG

FauI
                     Sth132I|       NlaIII
                       BfaI ||        NsiI  |
        BsmFI   MseI   AciI |||      CviRI | |    DdeI         HindIII
          |      |      |   |||        |   | |     |              |
       CTATGTGGATTATTTTAAGTCCCGCCTAGAACAATGCATGAAAGTCTTAGTGAAATAAAA
  841  ---------+---------+---------+---------+---------+---------+  900
       GATACACCTAATAAAATTCAGGGCGGATCTTGTTACGTACTTTCAGAATCACTTTATTTT AluI           AluI
        CviJI          CviJI
          |              |
       GCTTTATAAGTAAAGATTTAGCTTTATACAAAGTATAGAAAAATAACACG
  901  ---------+---------+---------+---------+--------+  950
       CGAAATATTCATTTCTAAATCGAAATATGTTTCATATCTTTTATTGTGC
```

Restriction enzyme analysis of CPN100988 (ry68 - SEQ ID NO. 13)

Figure 13B

```
              Hpy178III
         DpnI       |
         MnlI       |
    Sau3AI |    | Bpu1102I
    MseI   |    |   DdeI       BspMI        Hpy188IX
NlaIV |    |    |   CviJI| BpmI  |    CviRI     |
  |   |    |    |   ||     |     |      |       |
   AACCTTAATGATCTCTGGAGGGTGGCTTAGCAATATGATTTTACGCTTTGCAGGTCAGAT
301 ---------+---------+---------+---------+---------+---------+ 360
   TTGGAATTACTAGAGACCTCCCACCGAATCGTTATACTAAAATGCGAAACGTCCAGTCTA

AluI
                                        AluI   HinfI     CviJI
                                       CviJI    TfiI     CjeI|
                                         |       |         ||
   TTTCCAAAACTTCTATAAATGGAAATAAAGAGCTTATGGGAATCTCTCTACCAGAGCTTT
361 ---------+---------+---------+---------+---------+---------+ 420
   AAAGGTTTTGAAGATATTTACCTTTATTTCTCGAATACCCTTAGAGAGATGGTCTCGAAA BfaI                                 CviJI
    AvrII|              CjeI                HaeIII
    BsaJI|              FokI|       MspI  |    BslI
    StyI|        DdeI MmeI|      Tth111II |  |MnlI |
     ||           |    ||              |  |  |  |  |
   TTTCCAACCTAGGTTCTGCTTACTTAGATTATATCTTTCAACATCCTCCGGCCTATGTTT
421 ---------+---------+---------+---------+---------+---------+ 480
   AAAGGTTGGATCCAAGACGAATGAATCTAATATAGAAAGTTGTAGGAGGCCGGATACAAA MboII
    |
   GGTCAGTTTTTCTTCTTTTA
481 ---------+---------+ 500
   CCAGTCAAAAAGAAGAAAAT
```

Figure 14: Identification of T- and B-cell epitopes from the amino acid sequences SEQ ID No. 14; ORF: cpn100686

```
  1 MVSSPILNVP LKNHASVSGK FTHREVSKLA SDLKSGAMSF VPEVLSEETI
 51 SSDLGKKQCT QGIISACCGL AMLIVLMSVY YRFGGVIASG AVLLNLLLIW
101 AALQYLDAPL TLSGLAGIVL AMGMAVDANV LVFERIREEF LLSQSLKKSV
151 EKGYTKAFGA IFDSNLTTVL ASALLFFLDT GPIKGFALTL ILGIFSSMFT
201 ALFMTKFFFM LWMNKTQHTQ LHMMNKFVGI KHDFLRGCKK LWAVSGSVFL
251 LGCVALGFGA WNSVLGMDFK GGYAFTFNPK EHGISDVAQM RGKVVHKLQE
301 AGLSSRDFRI QTFGSSEKIK IYFSDKALSY TKQIRASLLK LTIMSWRYCG
351 IVVRNRPRFL YGNSKRNAKF WSKVSSKLSK KMRYQATIGL LGALAIILLY
401 VSLRFEWQYA FSAVCALIHD LLATCAVLFI AHFFLKKIQI DLQAIGALMT
451 VLGYSLNNTL IIFDRIREDR QANLFTPMHV LVNDALQKTF SRTVMTTATT
501 LSVLLMLLFI GGSSVFNFAF IMTIGILLGT LSSLYIAPPL LLFMVRKENR
551 SK
```

Possible T cell epitope:

427    VLFIAHFFL

Possible B cell epitope:

465    RIREDRQAN

Figure 15: Identification of T- and B-cell epitopes from the amino acid sequences SEQ ID No. 15; ORF: cpn100696

```
  1 MSSNLHPVGG TGTGAAAPES VLNIVEEIAA SGSVTAGLQA ITSSPGMVNL
 51 LIGWAKTKFI QPIRESKLFQ SRACQITLLV LGILLVVAGL ACMFIFHSQL
101 GANAFWLIIP AAIGLIKLLV TSLCFDEACT SEKLMVFQKW AGVLEDQLDD
151 GILNNSNKIF GHVKTEGNTS RATTPVLNDG RGTPVLSPLV SKIARV
```

Possible T cell epitope:

133    KLMVFQKWA

Possible B cell epitope:

163:   VKTEGNTSRAT

Figure 16: Identification of T- and B-cell epitopes from the amino acid sequences SEQ ID No. 16; ORF: cpn100709

```
  1 MTIRILAEGL AFRYGSKGPN IIHDVSFSVY DGDFIGIIGP NGGGKSTLTM
 51 LILGLLTPTF GSLKTFPSHS AGKQTHSMIG WVPQHFSYDP CFPISVKDVV
101 LSGRLSQLSW HGKYKKKDFE AVDHALDLVG LSDTTTTAFA HLSGGQIQRV
151 LLARALASYP EILILDEPTT NIDPDNQQRI LSILKKLNRT CTILMVTHDL
201 HHTTNYFNKV FYMNKTLHFI GRHFDLNRPI LLSSYKNQEF SCSPH
```

Possible T cell epitope:

212    YMNKTLHFI

Possible B cell epitopes:

109    SWHGKYKKKDFE

166    DEPTTNIDPDNQQR

Figure 17: Identification of T- and B-cell epitopes from the amino acid sequences SEQ ID No. 17; ORF: cpn100710

```
  1 MHKVIVFIFL TLYSLKSYGN DVIDKPHVLV SIAPYKFLVE QIAEETCFVY
 51 AIVTNHYDPH TYELPPQQIK ELRQGDLWFR IGEAFGKNLL EKPYMQQVDL
101 SQNVSLIQGK PCCNQHTTNY DTHTWLSPKN LKVQVETIVT TLSKKYPQHA
151 TLYQSNGEKL LLALDQLNEE ILTITSKAKQ RHILVSHGAF GYFCRDYNFS
201 QHTIEKSSHV EPSPKDVARV FRDIEQYKIS SVILLEYSGR RSSAMLADRF
251 HMHTVNLDPY AENVLVNLKT IATTFSSL
```

Possible T cell epitope:

125 WLSPKNLKV

Possible B cell epitope:

55 NHYDPHTYELPPQQIKELRQGD

Figure 18: Identification of T- and B-cell epitopes from the amino acid sequences SEQ ID No. 18; ORF: cpn100711

```
  1 MGPGSVLSNH SKEAGGIAIN NVIIDFSEIV PTKDNATVAP PTLKLVSRTN
 51 ADSKDKIDIT GTVTLLDPNG NLYQNSYLGE DRDITLFNID NSASGAVTAT
101 NVTLQGNLGA KKGYLGTWNL DPNSSGSKII LKWTFDKYLR WPYIPRDNHF
151 YINSIWGAQN SLVTVNQGIL GNMLNNARFE DPAFNNFWAS AIGSFLRKEV
201 SRNSDSFTYH GRGYTAAVDA KPRQEFILGA AFSQVFGHAE SEYHLDNYKH
251 KGSGHSTQAS LYAGNIFYFP AIRSRPILFQ GVATYGYMQH DTTTYYPSIE
301 EKNMANWDSI AWLFDLRFSV DLKEPQPHST ARLTFYTEAE YTRIRQEKFT
351 ELDYDPRSFS ACSYGNLAIP TGFSVDGALA WREIILYNKV SAAYLPVILR
401 NNPKATYEVL STKEKGNVVN VLPTRNAARA EVSSQIYLGS YWTLYGTYTI
451 DASMNTLVQM ANGGIRFVF
```

Possible T cell epitope:

312    WLFDLRFSV

Possible B cell epitope:

240:   ESEYHLDNYKHKGSGHST

Figure 19: Identification of T- and B-cell epitopes from the amino acid sequences SEQ ID No. 19; ORF: cpn100877

```
  1 MRFSLCGFPL VFSFTLLSVF DTSLSATTIS LTPEDSFHGD SQNAERSYNV
 51 QAGDVYSLTG DVSISNVDNS ALNKACFNVT SGSVTFAGNH HGLYFNNISS
101 GTTKEGAVLC CQDPQATARF SGFSTLSFIQ SPGDIKEQGC LYSKNALMLL
151 NNYVVRFEQN QSKTKGGAIS GANVTIVGNY DSVSFYQNAA TFGGAIHSSG
201 PLQIAVNQAE IRFAQNTAKN GSGGALYSDG DIDIDQNAYV LFRENEALTT
251 AIGKGGAVCC LPTSGSSTPV PIVTFSDNKQ LVFERNHSIM GGGAIYARKL
301 SISSGGPTLF INNISYANSQ NLGGAIAIDT GGEISLSAEK GTITFQGNRT
351 SLPFLNGIHL LQNAKFLKLQ ARNGYSIEFY DPITSEADGS TQLNINGDPK
401 NKEYTGTILF SGEKSLANDP RDFKSTIPQN VNLSAGYLVI KEGAEVTVSK
451 FTQSPGSHLV LDLGTKLIAS KEDIAITGLA IDIDSLSSSS TAAVIKANTA
501 NKQISVTDSI ELISPTGNAY EDLRMRNSQT FPLLSLEPGA GGSVTVTAGD
551 FLPVSPHYGF QGNWKLAWTG TGNKVGEFFW DKINYKPRPE KEGNLVPNIL
601 WGNAVDVRSL MQVQETHASS LQTDRGLWID GIGNFFHVSA SEDNIRYRHN
651 SGGYVLSVNN EITPKHYTSM AFSQLFSRDK DYAVSNNEYR MYLGSYLYQY
701 TTSLGNIFRY ASRNPNVNVG ILSRRFLQNP LMIFHFLCAY GHATNDMKTD
751 YANFPMVKNS WRNNCWAIEC GGSMPLLVFE NGRLFQGAIP FMKLQLVYAY
801 HGDFKETTAD GRRFSNGSLT SISVPLGIRF EKLALSQDVL YDFSFSYIPD
851 IFRKDPSCEA ALVISGDSWL VPAAHVSRHA FVGSGTGRYH FNDYTELLCR
901 GSIECRPHAR NYNINCGSKF RF
```

Possible T cell epitope:

146    ALMLLNNYV

Possible B cell epitope:

581    DKINYKPRPEKEG

Figure 20: Identification of T- and B-cell epitopes from the amino acid sequences SEQ ID No. 20; ORF: CPN100325

```
  1 MPSSWKRLLQ VLSHKIAATE SGGGIYAKDI QLQALPGSFT ITDNKVETSL
 51 TTSTNLYGGG IYSSGAVTLT NISGTFGITG NSVINTATSQ DADIQGGGIY
101 ATTSLSINQC NTPILFSNNS AATKKTSTTK QIAGGAIFSA AVTIENNSQP
151 IIFLNNSAKS EATTAATAGN KDSCGGAIAA NSVTLTNNPE ITFKGNYAET
201 GGAIGCIDLT NGSPPRKVSI ADNGSVLFQD NSALNRGGAI YGETIDISRT
251 GATFIGNSSK HDGSAICCST ALTLAPNSQL IFENNKVTET TATTKASINN
301 LGAAIYGNNE TSDVTISLSA ENGSIFFKNN LCTATNKYCS IAGNVKFTAI
351 EASAGKAISF YDAVNVPPKK QLLKS
```

Possible T cell epitope:

226    VLFQDNSAL

Possible B cell epitope:

257    NSSKHDG

Figure 21: Identification of T- and B-cell epitopes from the amino acid sequences SEQ ID No. 21; ORF: CPN100368

```
  1 MKYSLPWLLT SSALVFSLHP LMAANTDLSS SDNYENGSSG SAAFTAKETS
 51 DASGTTYTLT SDVSITNVSA ITPADKSCFT NTGGALSFVG ADHSLVLQTI
101 ALTHDGAAIN NTNTALSFSG FSSLLIDSAP ATGTSGGKGA ICVTNTEGGT
151 ATFTDNASVT LQKNTSEKDG AAVSAYSIDL AKTTTAALLD QNTSTKNGGA
201 LCSTANTTVQ GNSGTVTFSS NTATDKGGGI YSKEKDSTLD ANTGVVTFKS
251 NTAKTGGAWS SDDNLALTGN TQVLFQENKT TGSAAQANNP EGCGGAICCY
301 LATATDKTGL AISQNQEMSF TSNTTTANGG AIYATKCTLD GNTTLTFDQN
351 TATAGCGGAI YTETEDFSLK GSTGTVTFST NTAKTGGALY SKGNSSLTGN
401 TNLLFSGNKA TGPSNSSANQ EGCGGAILAF IDSGSVSDKT GLSIANNQEV
451 SLTSNAATVS GGAIYATKCT LTGNGSLTFD GNTAGTSGGA IYTETEDFTL
501 TGSTGTVTFS TNTAKTGGAL YSKGNNSLSG NTNLLFSGNK ATGPSNSSAN
551 QEGCGGAILS FLESASVSTK KGLWIEDNEN VSLSGNTATV SGGAIYATKC
601 ALHGNTTLTF DGNTAETAGG AIYTETEDFT LTGSTGTVTF STNTAKTAGA
651 LHTKGNTSFT KNKALVFSGN SATATATTTT DQEGCGGAIL CNISESDIAT
701 KSLTLTENES LSFINNTAKR SGGGIYAPKC VISGSESINF DGNTAETSGG
751 AIYSKNLSIT ANGPVSFTNN SGGKGGAIYI ADSGELSLEA IDGDITFSGN
801 RATEGTSTPN SIHLGARGKI TKLAAAPGHT IYFYDPITME APASGGTIEE
851 LVINPVVKAI VPPPQPKNGP I
```

Possible T cell epitope:

7   WLLTSSALV

Possible B cell epitopes:

162   QKNTSEKDG
538   GNKATGPSNSSANQEG

Figure 22: Identification of T- and B-cell epitopes from the amino acid sequences SEQ ID No. 22; ORF: CPN100624

```
   1 MTNSIFISKF GCLCDPFVSA FYPTALCCSL SGNEVPNLAS CQMSRKDISA
  51 FHTSPSFRLN VTPEPLVSSF RPSNLLNGFG HDITQDITIT GNSINSVIDY
 101 NYHYEDGGIL ACKNLFISEN KGNLSFERNS SHSSGGALYS VRECWISKNQ
 151 NYSFISNAAS LATTTTSGFG GAIHALDSYI TNNLGEGQFL DNVSKNRGGA
 201 IYVGVSLSIT DNLGPIVIKK NQTLEDSSFG GGIFCRAVNI ERNYQNIQIN
 251 DNASGQGVVY FLPLGVIISS NKEIIEISNH SASSINTASG KLYPGGGGIM
 301 CTSLSHENNP KGLIFNNKTA ALSGGVYTRD LSSSKITVRT AFINNSATSG
 351 GALINLSGIG STPQNFFLSA DYGDILFNNN TITSSSPQPG YRNALYAAPG
 401 INLKLGARQG YKILFYDPID HDQTTTDPIV FNYEPHHLGT VLFSGINVDS
 451 NATNPLNFLS KFSNSSRLER GVLAIEDRAA ISCKTLSQTG GILRLGNAAL
 501 IRTKGPGSSI NFNAIAINLP SILQSEASAP KFWIYPTLTG STYSEDTSST
 551 ITLSGPLTFL NDENENPYDS LDLSEPRKDI PPPLPPRCDC KKIDTSNLIV
 601 EAMNLDEHYG YQGIWSPYWM ETTTTTSSTV PEQTNTNHRQ LYVDWTPVGY
 651 RPNPERHGEF IANTLWQSAY NALLGIRILP PQNLKEHDLE ASLQGLGLLI
 701 NQHNREGRKG FRNHTTGYAA TTSAKTAARH SFSLGFAQMF SKTRERQSPS
 751 TTSSHNYFAG LRFDSLLFRD FISTGLSLGY SYGDHHMLCH YTEILKGSSK
 801 AFFNNHTLVA SLDCTFLPAR ITRTLELQPF ISAIALRCSQ ASFQETGDHI
 851 RKFHPKHPLT DLSSPIGFRS EWKTSHHIPM LWTTEISYVP TLYRKNPEMF
 901 TTLLISNGTW TTQATPVSYN SVAAKIKNTS QLFSRVTLSL DYSAQVSSST
 951 VGQYLKAESH CTF
```

Possible T cell epitope:

640     QLYVDWTPV

Possible B cell epitopes:

701     NQHNREGRKGFRNHTTG

741     SKTRERQSPSTTSSHNY

Figure 23: Identification of T- and B-cell epitopes from the amino acid sequences SEQ ID No. 23; ORF: CPN100633

```
  1 MTILRNFLTC SALFLALPAA AQVVYLHESD GYNGAINNKS LEPKITCYPE
 51 GTSYIFLDDV RISNVKHDQE DAGVFINRSG NLFFMGNRCN FTFHNLMTEG
101 FGAAISNRVG DTTLTLSNFS YLAFTSAPLL PQGQGAIYSL GSVMIENSEE
151 VTFCGNYSSW SGAAIYTPYL LGSKASRPSV NLSGNRYLVF RDNVSQVYGG
201 AISTHNLTLT TRGPSCFENN HAYHDVNSNG GAIAIAPGGS ISISVKSGDL
251 IFKGNTASQD GNTIHNSIHL QSGAQFKNLR AVSESGVYFY DPISHSESHK
301 ITDLVINAPE GKETYEGTIS FSGLCLDDHE VCAENLTSTI LQDVTLAGGT
351 LSLSDGVTLQ LHSFKQEASS TLTMSPGTTL LCSGDARVQN LHILIEDTDN
401 FVPVRIRAED KDALVSLEKL KVAFEAYWSV YDFPQFKEAF TIPLLELLGP
451 SFDSLLLGET TLERTQVTTE NDAVRGFWSL SWEEYPPSLD KDRRITPTKK
501 TVFLTWNPEI TSTP
```

Possible T cell epitope:

640    QLYVDWTPV

Possible B cell epitope:

482    WEEYPPSLDKDRRITPTKK

Figure 24: Identification of T- and B-cell epitopes from the amino acid sequences SEQ ID No. 24; ORF: cpn100985

```
  1 MGISLPELFS NLGSAYLDYI FQHPPAYVWS VFLLLLARLL PIFAVAPFLG
 51 AKLFPSPIKI GISLSWLAII FPKVLADTQI TNYMDNNLFY VLLVKEMIIG
101 IVIGFVLAFP FYAAQSAGSF ITNQQGIQGL EGATSLISIE QTSPHGILYH
151 YFVTIIFWLV GGHRIVISLL LQTLEVIPIH SFFPAEMMSL SAPIWITMIK
201 MCQLCLVMTI QLSAPAALAM LMSDLFLGII NRMAPQVQVI YLLSALKAFM
251 GLLFLTLAWW FIIKQIDYFT LAWFKEVPIM LLGSNPQVL
```

Possible T cell epitope:

83 YMDNNLFYV

Possible B cell epitope:

78 TQITNYMDNN

Figure 25: Identification of T- and B-cell epitopes from the amino acid sequences SEQ ID No. 25; ORF: cpn100987

```
  1 MKHSKEDDLS RFLPKNLLVE SPHPEEIPLK SLSFTMSWLP TIHPSWITIA
 51 MKEFPPEIQG QLLAWLPEPL VQEILPLLPG ISIAPHRCAP FGAFYLLDML
101 SKKIRPCGIT EEIFLPASSA NAILYYTGPV KIALINCLGL YSIAKELKHI
151 LDKVVIERVK NALSPTEKLF LTYCQSHPMK HLETTNFLSS WTTDAELRQF
201 VHKQGLEFLG KALTKENASF LWYFLRRLDV GRAYIVEQTL KTWYDHPYVD
251 YFKSRLEQCM KVLVK
```

Possible T cell epitope:

220 FLWYFLRRL

Possible B cell epitope:

1 MKHSKEDDLSR

Figure 26: Identification of T- and B-cell epitopes from the amino acid sequences SEQ ID No. 26; ORF: cpn100988

```
 1  MLAFFATSFK SVLFEYSYQS LLLILIVSAP PIILASIVGI MVAIFQAATQ
51  IQEQTFAFAV KLVVIFGTLM ISGGWLSNMI LRFAGQIFQN FYKWK
```

Possible T cell epitope:

21   LLLILIVSA

Possible B cell epitope:

89   QNFYKWK

CHLAMYDIA ANTIGENS AND CORRESPONDING DNA FRAGMENTS AND USES THEREOF

REFERENCE TO RELATED APPLICATIONS

This application claims the benefit of 13 U.S. provisional applications: U.S. Provisional Application Nos. 60/113,280, 60/113,281, 60/113,282, 60/113,283, 60/113,284, 60/113,285, 60/113,385, all of which were filed Dec. 23, 1998; and U.S. Provisional Application Nos. 60/114,050, 60/114,056, 60/114,057, 60/114,058, 60/114,059, 60/114,061, all of which were filed Dec. 28, 1998.

FIELD OF INVENTION

The present invention relates to *Chlamydia* antigens and corresponding DNA molecules, which can be used to prevent and treat *Chlamydia* infection in mammals, such as humans.

BACKGROUND OF THE INVENTION

Chlamydiae are prokaryotes. They exhibit morphologic and structural similarities to gram-negative bacteria including a trilaminar outer membrane, which contains lipopolysaccharide and several membrane proteins that are structurally and functionally analogous to proteins found in *E. coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other chlamydia species (*C. trachomatis, C. pecorum* and *C. psittaci*). It shows 10% or less DNA sequence homology with either of *C. trachomatis* or *C. psittaci*.

*C. pneumoniae* is a common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Opthalmology and Visual Science 36:1477). It can also cause upper respiratory tract symptoms and disease, including bronchitis and sinusitis (Grayston et al. (1995) Journal of Infectious Diseases 168:1231; Grayston et al. (1990) Journal of Infectious Diseases 161:618; Marrie (1993) Clinical Infectious Diseases. 18:501; Wang et al (1986) Chlamydial infections. Cambridge University Press, Cambridge. p. 329. The great majority of the adult population (over 60%) has antibodies to *C. pneumoniae* (Wang et al (1986) Chlamydial infections. Cambridge University-Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against chlamydial infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23-27) has reported that many children in this age group show PCR evidence of infection despite being seronegative, and estimates a prevalence of 17-19% in 2-4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al. (1988) Lancet; ii:983; Thom et al. (1992) JAMA 268:68; Linnanmaki et al. (1993), Circulation 87:1030; Saikku et al. (1992) Annals Internal Medicine 116:273; Melnick et al (1993) American Journal of Medicine 95:499). Moreover, the organisms have been detected in atheromas and fatty streaks of the coronary, carotid, peripheral arteries and aorta (Shor et al. (1992) South African. Medical Journal 82:158; Kuo et al. (1993) Journal of Infectious Diseases 167:841; Kuo et al. (1993) Arteriosclerosis and Thrombosis 13:1500; Campbell et al (1995) Journal of Infectious Diseases 172:585; Chiu et al. Circulation, 1997 (In Press)). Viable *C. pneumoniae* has been recovered from the coronary and carotid artery (Ramirez et al (1996) Annals of Internal Medicine 125:979; Jackson et al. Abst. K121, p 272, 36$^{th}$ ICAAC, 15-18 Sept. 1996, New Orleans). Furthermore, it has been shown that *C. pneumoniae* can induce changes of atherosclerosis in a rabbit model (Fong et al (1997) Journal of Clinical Microbiology 35:48). Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. 1998 January; 80(1): 45-49; Hahn D L, et al. Association of *Chlamydia pneumoniae* IgA antibodies with recently symptomatic asthma. Epidemiol Infect. 1996 December; 117(3): 513-517; Bjornsson E, et al. Serology of chlamydia in relation to asthma and bronchial hyperresponsiveness. Scand J Infect Dis. 1996; 28(1): 63-69; Hahn D L. Treatment of *Chlamydia pneumoniae* infection in adult asthma: a before-after trial. J Fam Pract. 1995 October; 41(4): 345-351; Allegra L, et al. Acute exacerbations of asthma in adults: role of *Chlamydia pneumoniae* infection. Eur Respir J. 1994 December; 7(12): 2165-2168; Hahn D L, et al. Association of *Chlamydia pneumoniae* (strain TWAR) infection with wheezing, asthmatic bronchitis, and adult-onset asthma. JAMA. 1991 Jul. 10; 266(2): 225-230).

In light of these results a protective vaccine against *C. pneumoniae* infection would be of considerable importance. There is not yet an effective vaccine for any human chlamydial infection. It is conceivable that an effective vaccine can be developed using physically or chemically inactivated *Chlamydiae*. However, such a vaccine does not have a high margin of safety. In general, safer vaccines are made by genetically manipulating the organism by attenuation or by recombinant means. Accordingly, a major obstacle in creating an effective and safe vaccine against human chlamydial infection has been the paucity of genetic information regarding *Chlamydia*, specifically *C. pneumoniae.*

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity. 64:5341). Similarly, sheep immunized with inactivated *C. psittaci* were protected from subsequent chlamydial-induced abortions and stillbirths (Jones et al. (1995) Vaccine 13:715). Protection from chlamydial infections has been associated with Th1 immune responses, particularly the induction of INFg-producing CD4+ T-cells (Igietsemes et al. (1993) Immunology 5:317). The adoptive transfer of CD4+ cell lines or clones to nude or SCID mice conferred protection from challenge or cleared chronic disease (Igietseme et al (1993) Regional Immunology 5:317; Magee et al (1993) Regional Immunology 5: 305), and in vivo depletion of CD4+ T cells exacerbated disease post-challenge (Landers et al (1991) Infection & Immunity 59:3774; Magee et al (1995) Infection & Immunity 63:516). However, the presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al (1990) Infection and Immunity 58:93; McCafferty et al (1995) Infection and Immunity 63:2387-9; Gaydos et al (1992) Infection and Immunity 60(12):5319-5323). Regions of the protein known to be conserved in other chlamydial MOMPs are conserved in *C. pneumoniae* (Campbell et al (1990) Infection and Immunity 58:93; McCafferty et al (1995) Infection and Immunity 63:2387-9). One study has described a strain of *C. pneumoniae* with a MOMP of greater that usual molecular weight, but the gene for this has not been sequenced (Grayston et al. (1995) Journal of Infectious Diseases 168: 1231). Partial sequences of outer membrane protein 2 from nine diverse isolates were also found to be invariant (Ramirez et al (1996) Annals of Internal Medicine 125:979). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes (Marrie (1993) Clinical Infectious Diseases. 18:501).

Many antigens recognised by immune sera to *C. pneumoniae* are conserved across all chlamydiae, but 98 kDa, 76 kDa and 54 kDa proteins appear to be *C. pneumoniae*-specific (Campos et al. (1995) Investigation of Opthalmology and Visual Science 36:1477; Marrie (1993) Clinical Infectious Diseases. 18:501; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4(6): 700-704). Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979). However, the results are potentially confounded by the infection status of the patients, since immunoblot profiles of a patient's sera change with time post-infection. An assessment of the number and relative frequency of any serotypes, and the defining antigens, is not yet possible.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode *Chlamydia* polypeptides which can be used in methods to prevent, treat, and diagnose *Chlamydia* infection. In one form of the invention, the polynucleotide molecules are selected from DNA that encode polypeptides CPN100686 RY 54 (SEQ ID No: 1), CPN100696 RY-55 (SEQ ID No: 2), CPN100709 RY-57 (SEQ ID No: 3), CPN100710 RY-58 (SEQ ID No:4), CPN100711 RY-59 (SEQ ID No: 5), CPN100877 RY-61 (SEQ ID No:6), CPN100325 RY-62 (SEQ ID No:7), CPN100368 RY-63 (SEQ ID No:8), CPN100624 RY-64 (SEQ ID No:9), CPN100633 RY-65 (SEQ ID No:10), CPN100985 RY-66 (SEQ ID No:11), CPN100987 RY-67 (SEQ ID No:12) and CPN100988 RY-68 (SEQ ID No:13). Another form of the invention provides polypeptides corresponding to the isolated DNA molecules. The amino acid sequences of the corresponding encoded polypeptides are shown for CPN100686 RY 54 as SEQ ID No: 14, CPN100696 RY-55 as SEQ ID No: 15, CPN100709 RY-57 as SEQ ID No: 16, CPN100710 RY-58 as SEQ ID No: 17, CPN100711 RY-59 as SEQ ID No: 18, CPN100877 RY-61 as SEQ ID No: 19, CPN100325 RY-62 as SEQ ID No: 20, CPN100368 RY-63 as SEQ ID No: 21, CPN100624 RY-64 as SEQ ID No: 22, CPN100633 RY-65 as SEQ ID No: 23, CPN100985 RY-66 as SEQ ID No: 24, CPN100987 RY-67 as SEQ ID No: 24 and CPN100988 RY-68 as SEQ ID No: 26.

Those skilled in the art will readily understand that the invention, having provided the polynucleotide sequences encoding *Chlamydia* polypeptides, also provides polynucleotides encoding fragments derived from such peptides. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium*, or *Vibrio cholerae* vector, containing a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to the drawings, in which:

FIGS. 1 through 13 show the restriction enzyme analysis of the nucleic acid sequences of the invention.

FIGS. 14 through 26 show an identification of T and B cell epitopes from the amino acid sequences SEQ ID Nos: 14 to 26.

DETAILED DESCRIPTION OF INVENTION

Open reading frames (ORFs) encoding chlamydial polypeptides have been identified from the *C. pneumoniae* genome. These polypeptides include polypeptides found permanently in the bacterial membrane structure, polypeptides present in the external vicinity of the bacterial membrane, polypeptides found permanently in the inclusion membrane structure, polypeptides present in the external vicinity of the inclusion membrane, and polypeptides released into the cytoplasm of the infected cell. These polypeptides can be used to prevent and treat *Chlamydia* infection.

The polypeptide CPN100686 RY 54 whose amino acid sequence is shown as SEQ ID No: 14 is a putative 98 kDa outer membrane protein; the polypeptide CPN100696 RY-55 (SEQ ID No: 15) is consistent with a sulfur-rich protein; the polypeptide CPN100709 RY-57 (SEQ ID No: 16) is a ABC transporter; the polypeptide CPN100710 RY-58 (SEQ ID No: 17) is an adhesion protein; the polypeptide CPN100711 RY-59 (SEQ ID No: 18) is a putative outer membrane protein; the polypeptide CPN100877 RY-61 (SEQ ID No: 19) is a putative 98 kDa outer membrane protein, and so are the polypeptides CPN100325 RY-62 (SEQ ID No: 20), CPN100368 RY-63 (SEQ ID No: 21), CPN100624 RY-64 (SEQ ID No: 22), and CPN100633 RY-65 (SEQ ID No: 23); the polypeptide CPN100985 RY-66 (SEQ ID No: 24) is yscT; and CPN100988 RY-68 (SEQ ID No: 26) is a flagellar protein.

According to a first aspect of the invention, isolated polynucleotides are provided which encode the precursor and mature forms of *Chlamydia* polypeptides, whose amino acid sequences are selected from the group consisting of SEQ ID Nos: 14 to 26.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotides of the invention are either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID Nos: 1 to 13 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to any one of SEQ ID Nos: 14 to 26. As used herein, "homologous amino acid sequence" is any polypeptide which is encoded, in whole or in part, by a nucleic acid sequence which hybridizes at 25-35° C. below critical melting temperature (Tm), to any portion of the nucleic acid sequences of SEQ ID Nos: 1 to 13. A homologous amino acid sequence is one that differs from an amino acid sequence shown in any one of SEQ ID Nos: 13 to 26 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to any one of SEQ ID Nos: 14 to 26.

Homologous amino acid sequences include sequences that are identical or substantially identical to SEQ ID Nos: 14 to 26. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 60%, and most preferably 85% identical to any one of coding sequences SEQ ID Nos: 1 to 13.

Consistent with the first aspect of the invention, polypeptides having a sequence homologous to any one of SEQ ID Nos: 14 to 26 include naturally-occurring allelic variants, as well as mutants or any other non-naturally occurring variants that retain the inherent characteristics of the polypeptide of SEQ ID Nos: 14 to 26.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae*, is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the Chlamydial MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID Nos: 1 to 13. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 MM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+0.5×(% G+C)+1.6 log (positive ion concentration)−0.6×(% formamide). Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4-16 hours at 42° C., in 6×SSC containing 50% formamide, or (ii) within 4-16 hours at 65° C. in an aqueous 6×SSC solution (1 M NaCl, 0.1 M sodium citrate (pH 7.0)).

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using the BLAST homology searching algorithm of Altschul et al., Nucleic Acids Res. 25:3389-3402 (1997). Alternatively, sequences are modified such that they become more reactive to T- and/or B-cells. (See FIGS. 11 to 15 below for identification of T- and B-epitopes). Yet another alternative is to mutate a particular amino acid residue or sequence within the polypeptide in vitro, then screen the mutant polypeptides for their ability to prevent or treat *Chlamydia* infection according to the method outlined below.

A person skilled in the art will readily understand that by following the screening process of this invention, it will be determined without undue experimentation whether a particular homolog of any of SEQ ID Nos: 14 to 26 may be useful in the prevention or treatment of *Chlamydia* infection. The screening procedure comprises the steps:
(i) immunizing an animal, preferably mouse, with the test homolog or fragment;
(ii) inoculating the immunized animal with *Chlamydia*; and,
(iii) selecting those homologs or fragments which confer protection against *Chlamydia*.

By "conferring protection" is meant that there is a reduction in severity of any of the effects of *Chlamydia* infection, in comparison with a control animal which was not immunized with the test homolog or fragment.

It has been previously demonstrated (Yang, Z. P., Chi, E. Y., Kuo, C. C. and Grayston, J. T. 1993. A mouse model of *C. pneumoniae* strain TWAR pneumonitis. *Infect. Immun.* 61(5):2037-2040) that mice are susceptible to intranasal infection with different isolates of *C. pneumoniae*. Strain AR-39 (Chi, E. Y., Kuo, C. C. and Grayston, J. T., 1987. Unique ultrastructure in the elementary body of *Chlamydia* sp. strain TWAR. *J. Bacteriol.* 169(8):3757-63) is used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (6 to 10 per group) are immunized intramuscularly (i.m.) plus intranasally (i.n.) with plasmid DNA containing the coding sequence of a *C. pneumoniae* polypeptide. Saline or the plasmid vector lacking an inserted chlamydial gene is given to groups of control animals.

For i.m. immunization alternate left and right quadriceps are injected with 100 µg of DNA in 50 µl of PBS on three occasions at 0, 3 and 6 weeks. For i.n. immunization, anaesthetized mice aspirates 50 µl of PBS containing 50 µg DNA on three occasions at 0, 3 and 6 weeks. At week 8, immunized mice are inoculated i.n. with $5\times10^5$ IFU of *C. pneumoniae*, strain AR39 in 100 µl of SPG buffer to test their ability to limit the growth of a sublethal *C. pneumoniae* challenge.

Lungs are taken from mice at day 9 post-challenge and immediately homogenised in SPG buffer (7.5% sucrose, 5 mM glutamate, 12.5 mM phosphate pH 7.5). The homogenate is stored frozen at −70° C. until assay. Dilutions of the homogenate are assayed for the presence of infectious chlamydia by inoculation onto monolayers of susceptible cells. The inoculum is centrifuged onto the cells at 3000 rpm for 1 hour, then the cells are incubated for three days at 35° C. in the presence of 1 µg/ml cycloheximide. After incubation the monolayers are fixed with formalin and methanol then immunoperoxidase stained for the presence of chlamydial inclusions using convalescent sera from rabbits infected with *C. pneumoniae* and metal-enhanced DAB as a peroxidase substrate.

Consistent with the first aspect of the invention, polypeptide derivatives are provided that are partial sequences of SEQ ID Nos: 14 to 26, partial sequences of polypeptide sequences homologous to SEQ ID Nos: 14 to 26, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than *Chlamydia* have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. *J. Gen. Virol.* 72:557-565), and two overlapping peptides of 15 residues each from canine parvovirus (Langeveld et al., *Vaccine* 12 (15):1473-1480, 1994).

Accordingly, it will be readily apparent to one skilled in the art, having read the present description, that partial sequences of SEQ ID Nos: 14 to 26 or their homologous amino acid sequences are inherent to the full-length sequences and are taught by the present invention. Such polypeptide fragments preferably are at least 12 amino acids in length. Advantageously, they are at least 20 amino acids, preferably at least 50 amino acids, more preferably at least 75 amino acids, and most preferably at least 100 amino acids in length.

Polynucleotides of 30 to 600 nucleotides encoding partial sequences of sequences homologous to SEQ ID Nos: 14 to 26 are retrieved by PCR amplification using the parameters outlined above and using primers matching the sequences upstream and downstream of the 5' and 3' ends of the fragment to be amplified. The template polynucleotide for such amplification is either the full length polynucleotide homologous to one of SEQ ID Nos: 1 to 13, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20-30 bases are to be obtained, the formula for calculating the Tm is as follows: Tm=4×(G+C)+2 (A+T). For example, an 18 nucleotide fragment of 50% G+C would have an approximate Tm of 54° C. Short peptides that are fragments of SEQ. ID Nos. 14 to 26 or their homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This identifies probable surface-exposed, antigenic regions (Hughes et al., 1992. Infect. Immun. 60(9):3497). An analysis of the 6 amino acid sequences contained in SEQ ID Nos: 14 to 26, based on the product of flexibility and hydrophobicity propensities using the program SEQSEE (Wishart D S, et al. "SEQSEE: a comprehensive program suite for protein sequence analysis." *Comput Appl Biosci.* 1994 Apr; 10(2):121-32), reveal a number of potential B- and T-cell epitopes which may be used as a basis for selecting useful immunogenic fragments and variants. The results are shown in FIGS. 11 to 15. This analysis uses a reasonable combination of external surface features that is likely to be recognized by antibodies. Probable T-cell epitopes for HLA-A0201 MHC subclass were revealed by an algorithm written at Connaught Laboratories that emulates an approach developed at the NIH (Parker K C, et al. "Peptide binding to MHC class I molecules: implications for antigenic peptide prediction." *Immunol Res* 1995; 14(1):34-57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and expose the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547-549), or one which has been identified in another polypeptide of the invention (FIGS. 11-15). Consistent with this aspect of the invention is a fusion polypeptide comprising T- or B-cell epitopes from one of SEQ ID Nos: 14 to 26 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

A polynucleotide molecule according to the invention, including RNA, DNA, or modifications or combinations thereof, has various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation-signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis*, *C. psittaci*, *C. pneumonia*, *C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof, optionally together with a cytokine such as IL-2 or IL-12.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus*, Bacille bilié de Calmette-Guérin (BCG), and *Streptococcus*.

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1\times10^5$ to about $1\times10^9$, preferably about $1\times10^6$ to about $1\times10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis, C. psittaci, C. pneumoniae*, or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Uses of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional polynucleotide encoding another *Chlamydia* antigen such as urease subunit A, B, or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utilizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis (oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N—(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 pg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in any one of SEQ ID Nos: 1 to 13.

The term "probe" as used in the present application refers to DNA (preferably single stranded) or RNA molecules (or modifications or combinations thereof) that hybridize under the stringent conditions, as defined above, to nucleic acid molecules having SEQ ID Nos: 1 to 13 or to sequences homologous to SEQ ID Nos: 1 to 13, or to their complementary or anti-sense sequences. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of any of SEQ ID Nos: 1 to 13 or that are complementary to such sequences. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID Nos: 1 to 13, their homolog, and partial sequences of either enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methyhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of any one of SEQ ID Nos: 14 to 26. The procedure is as follows: a monospecific hyperimmune antiserum is raised against a purified reference polypeptide, a fusion polypeptide (for example, an expression product of MBP, GST, or His-tag systems), or a synthetic peptide predicted to be antigenic. Where an antiserum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After a 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed.

The reaction is developed with the appropriate substrate and the reaction is measured by colorimetry (absorbance measured spectrophotometrically). Under the above experimental conditions, a positive reaction is shown by O.D. values greater than a non-immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit a protective immune response to Chlamydia; and particularly, (iv) a method for preventing and/or treating a Chlamydia (e.g., C. trachomatis, C. psittaci, C. pneumoniae, or C. pecorum) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating Chlamydia infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention.

The composition optionally contains at least one additional Chlamydia antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RPC New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (see the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 pg to about 500 mg, preferably from about 1 mg to about 200 mg. For the parenteral route of administration, the dose usually does not exceed about 1 mg, preferably about 100 µg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-Chlamydia antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680. For monoclonal antibodies, see Kohler and Milstein (1975) Nature. 256:495-497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-Chlamydia antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as a *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis, C. psittaci, C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium,* or *Shigella flexneri*; saponins, or polylactide glycolide (PLGA) microspheres, are also be used in mucosal administration.

Adjuvants useful for both mucosal and parenteral administrations include polyphosphazene (WO 95/02415), DC-chol (3 b-(N-(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

Amounts of the above-listed compounds used in the methods and compositions of the invention are readily determined by one skilled in the art. Treatment/immunization schedules are also known and readily designed by one skilled in the art. For example, the non-vaccine components can be administered on days 1-14, and the vaccine antigen+adjuvant can be administered on days 7, 14, 21, and 28.

What is claimed is:

1. An isolated nucleic acid molecule which encodes the polypeptide SEQ ID NO: 14.

2. An isolated nucleic acid molecule comprising the nucleic acid sequence SEQ ID No: 1.

3. An isolated nucleic acid molecule which is fully complementary to the nucleic acid molecule of claim 1.

4. An isolated nucleic acid molecule which encodes a fusion protein, said fusion protein comprising the polypeptide encoded by the nucleic acid molecule of claim 1 and a second polypeptide.

5. The nucleic acid molecule of claim 4 wherein the second polypeptide is a heterologous signal peptide.

6. The nucleic acid molecule of claim 4 wherein the second polypeptide has adjuvant activity.

7. The nucleic acid molecule of claim 1, operably linked to one or more expression control sequences.

8. A vaccine vector comprising the nucleic acid sequence selected from any one of
   (i) SEQ ID No: 1; or
   (ii) a nucleic acid sequence which encodes the polypeptide of SEQ ID NO:14; wherein the nucleic acid sequence is capable of being expressed.

9. The vaccine vector of claim 8 comprising a hybrid gene, wherein the hybrid gene encodes a fusion polypeptide, wherein the fusion polypeptide comprises the polypeptide of
   SEQ ID No:14; and
   a heterologous polypeptide;
   wherein the hybrid gene is capable of being expressed.

10. The vaccine vector of claim 9 wherein the second polypeptide is a heterologous signal peptide.

11. The vaccine vector of claim 9 wherein the second polypeptide has adjuvant activity.

12. The vaccine vector of claim 8 wherein the nucleic acid is operably linked to one or more expression control sequences.

13. The vaccine vector of claim 8 wherein the polypeptide-encoding nucleic acid is the first nucleic acid, and wherein the vaccine vector further comprises a second nucleic acid encoding an additional polypeptide which enhances the immune response to the polypeptide expressed by said first nucleic acid.

14. The vaccine vector of claim 13 rein the additional polypeptide is a *Chlamydia* polypeptide.

15. A pharmaceutical composition comprising the nucleic acid according to claim 1 and a pharmaceutically acceptable carrier.

16. A pharmaceutical composition comprising a pharmaceutically acceptable carrier or diluent, and a nucleic acid molecule which encodes the polypeptide of SEQ ID NO: 14; wherein the nucleic acid is capable of being expressed.

17. A unicellular host transformed with the nucleic acid molecule of claim 7.

18. A method for preventing or treating *Chlamydia pneumoniae* infection comprising administering to a patient an effective amount of:
   (a) the nucleic acid according to claim 1;
   (b) a vaccine vector wherein the vaccine vector comprises the nucleic acid according to claim 1; or
   (c) a pharmaceutical composition comprising the nucleic acid according to claim 1 and a pharmaceutically acceptable carrier.

* * * * *

UNITED STATES PATENT AND TRADEMARK OFFICE
CERTIFICATE OF CORRECTION

PATENT NO.          : 7,297,341 B1
APPLICATION NO. : 09/868987
DATED                   : November 20, 2007
INVENTOR(S)         : Andrew D. Murdin, Raymond P. Oomen and Joe Wang It is certified that error appears in the above-identified patent and that said Letters Patent is hereby corrected as shown below:

Column 114, Claim 14, line 20, "...of claim 13 rein..." should read -- of claim 13 wherein --

Signed and Sealed this

Twenty-sixth Day of August, 2008

JON W. DUDAS
*Director of the United States Patent and Trademark Office*

SEQUENCE LISTING

```
<160> NUMBER OF SEQ ID NOS: 54

<210> SEQ ID NO 1
<211> LENGTH: 1864
<212> TYPE: DNA
<213> ORGANISM: Chlamydia pneumoniae
<220> FEATURE:
<221> NAME/KEY: CDS
<222> LOCATION: (101)..(1756)

<400> SEQUENCE: 1
```

```
-continued atggacttcc gcatattgtc aggagggat cagcggcact gctaatggac aatattctgc         60
aaaccgtgga tggcgtatgg ctgtagtgat tgacggttat atg gtc agc agc cct        115
                                             Met Val Ser Ser Pro
                                              1               5 att tta aac gtc cca ttg aaa aat cat gcc agt gtc tca ggg aaa ttt        163
Ile Leu Asn Val Pro Leu Lys Asn His Ala Ser Val Ser Gly Lys Phe
             10                  15                  20 acc cac cgt gaa gtg agc aaa ctc gcc tca gat tta aaa tct gga gcg        211
Thr His Arg Glu Val Ser Lys Leu Ala Ser Asp Leu Lys Ser Gly Ala
             25                  30                  35 atg tct ttt gtt ccc gag gtt ctc agt gaa gag acg atc tct tct gat        259
Met Ser Phe Val Pro Glu Val Leu Ser Glu Glu Thr Ile Ser Ser Asp
         40                  45                  50 ctt ggg aaa aaa caa tgt aca caa ggc att atc tca gca tgc tgt ggc        307
Leu Gly Lys Lys Gln Cys Thr Gln Gly Ile Ile Ser Ala Cys Cys Gly
         55                  60                  65 ttg gca atg ctt att gtt ttg atg agc gta tat tat aga ttt gga ggc        355
Leu Ala Met Leu Ile Val Leu Met Ser Val Tyr Tyr Arg Phe Gly Gly
 70                  75                  80                  85 gtc atc gct tcg gga gct gtt ctt ctg aat ctt ttg ctt atc tgg gca        403
Val Ile Ala Ser Gly Ala Val Leu Leu Asn Leu Leu Leu Ile Trp Ala
                 90                  95                 100 gct cta cag tat ttg gat gcg cca ctc acc ttg tca gga ctc gct ggg        451
Ala Leu Gln Tyr Leu Asp Ala Pro Leu Thr Leu Ser Gly Leu Ala Gly
             105                 110                 115 att gtt ctt gct atg ggg atg gcc gta gat gca aat gtt ctt gta ttc        499
Ile Val Leu Ala Met Gly Met Ala Val Asp Ala Asn Val Leu Val Phe
         120                 125                 130 gaa aga atc cga gag gaa ttt tta ttg tct caa agt ctt aaa aaa tct        547
Glu Arg Ile Arg Glu Glu Phe Leu Leu Ser Gln Ser Leu Lys Lys Ser
         135                 140                 145 gta gaa aaa gga tat acc aag gct ttt gga gcc att ttt gat tct aac        595
Val Glu Lys Gly Tyr Thr Lys Ala Phe Gly Ala Ile Phe Asp Ser Asn
150                 155                 160                 165 ttg act aca gta ttg gcc tca gca ctt ctt ttc tta gat aca ggg            643
Leu Thr Thr Val Leu Ala Ser Ala Leu Leu Phe Phe Leu Asp Thr Gly
                 170                 175                 180 cct att aaa ggg ttt gct ttg aca ttg att tta gga att ttc tct tca        691
Pro Ile Lys Gly Phe Ala Leu Thr Leu Ile Leu Gly Ile Phe Ser Ser
             185                 190                 195 atg ttt acg gct ctt ttc atg act aaa ttt ttc ttc atg ctg tgg atg        739
Met Phe Thr Ala Leu Phe Met Thr Lys Phe Phe Phe Met Leu Trp Met
         200                 205                 210 aat aag acc caa cat aca cag ttg cat atg atg aat aag ttc gtg ggg        787
Asn Lys Thr Gln His Thr Gln Leu His Met Met Asn Lys Phe Val Gly
         215                 220                 225 ata aag cat gat ttc ttg aga gga tgc aaa aaa ctt tgg gct gtt tct        835
Ile Lys His Asp Phe Leu Arg Gly Cys Lys Lys Leu Trp Ala Val Ser
230                 235                 240                 245 gga agt gtt ttt ctt tta ggt tgc gtt gct ctc ggg ttt gga gcc tgg        883
Gly Ser Val Phe Leu Leu Gly Cys Val Ala Leu Gly Phe Gly Ala Trp
                 250                 255                 260 aat tcc gtt ttg gga atg gat ttt aaa gga ggg tat gcc ttt acc ttt        931
Asn Ser Val Leu Gly Met Asp Phe Lys Gly Gly Tyr Ala Phe Thr Phe
             265                 270                 275 aat cca aaa gag cat ggc atc agc gat gtt gct caa atg cgt ggc aaa        979
Asn Pro Lys Glu His Gly Ile Ser Asp Val Ala Gln Met Arg Gly Lys
             280                 285                 290 gtt gtg cat aaa cta cag gaa gct ggt ctt tct tct aga gac ttc cgt       1027
```

-continued

| | | |
|---|---|---|
| Val Val His Lys Leu Gln Glu Ala Gly Leu Ser Ser Arg Asp Phe Arg<br>295                     300                    305 | | |
| att caa aca ttt gga tct tca gaa aag atc aaa atc tat ttt agt gat<br>Ile Gln Thr Phe Gly Ser Ser Glu Lys Ile Lys Ile Tyr Phe Ser Asp<br>310                 315                    320                    325 | 1075 |
| aaa gct tta agc tat act aag cag ata cga gcc tct ctc cta aaa tta<br>Lys Ala Leu Ser Tyr Thr Lys Gln Ile Arg Ala Ser Leu Leu Lys Leu<br>                      330                    335                    340 | 1123 |
| acg atc atg agc tgg cgt tat tgt ggg att gtt gtc aga aac agg cct<br>Thr Ile Met Ser Trp Arg Tyr Cys Gly Ile Val Val Arg Asn Arg Pro<br>345                     350                    355 | 1171 |
| aga ttt ctc tac gga aac tct aaa cga aac gca aaa ttt tgg tca aag<br>Arg Phe Leu Tyr Gly Asn Ser Lys Arg Asn Ala Lys Phe Trp Ser Lys<br>           360                    365                    370 | 1219 |
| gta agc agc aaa cta tcg aag aaa atg cgt tat cag gcg acc atc ggg<br>Val Ser Ser Lys Leu Ser Lys Lys Met Arg Tyr Gln Ala Thr Ile Gly<br>375                     380                    385 | 1267 |
| ctt tta gga gct ttg gca atc atc ttg ctc tat gtg agt ttg cgc ttt<br>Leu Leu Gly Ala Leu Ala Ile Ile Leu Leu Tyr Val Ser Leu Arg Phe<br>390                     395                    400                    405 | 1315 |
| gaa tgg caa tat gct ttc agt gcc gta tgc gct tta att cat gac ctt<br>Glu Trp Gln Tyr Ala Phe Ser Ala Val Cys Ala Leu Ile His Asp Leu<br>                          410                    415                    420 | 1363 |
| ttg gct acc tgt gca gtc ttg ttt ata gca cat ttc ttt ttg aag aaa<br>Leu Ala Thr Cys Ala Val Leu Phe Ile Ala His Phe Phe Leu Lys Lys<br>                  425                    430                    435 | 1411 |
| att caa ata gat ttg caa gcc att ggt gct tta atg act gta ttg ggg<br>Ile Gln Ile Asp Leu Gln Ala Ile Gly Ala Leu Met Thr Val Leu Gly<br>           440                    445                    450 | 1459 |
| tat tca tta aac aat act ttg atc att ttt gat cgt att cgt gaa gat<br>Tyr Ser Leu Asn Asn Thr Leu Ile Ile Phe Asp Arg Ile Arg Glu Asp<br>455                     460                    465 | 1507 |
| cgc caa gcg aac ctg ttt acc cct atg cat gtt tta gtt aat gat gcc<br>Arg Gln Ala Asn Leu Phe Thr Pro Met His Val Leu Val Asn Asp Ala<br>470                     475                    480                    485 | 1555 |
| ctt caa aag acg ttc agc cgc acg gta atg aca aca gct aca act cta<br>Leu Gln Lys Thr Phe Ser Arg Thr Val Met Thr Thr Ala Thr Thr Leu<br>                  490                    495                    500 | 1603 |
| tca gtt ttg tta atg ctt ttg ttt ata ggc ggc tcc tct gtc ttt aat<br>Ser Val Leu Leu Met Leu Leu Phe Ile Gly Gly Ser Ser Val Phe Asn<br>505                     510                    515 | 1651 |
| ttt gca ttt att atg acc ata ggg att ctt cta gga act tta tcg tct<br>Phe Ala Phe Ile Met Thr Ile Gly Ile Leu Leu Gly Thr Leu Ser Ser<br>           520                    525                    530 | 1699 |
| ctt tat att gca cca cct ctg ttg ttt atg gtc cgt aaa gaa aat<br>Leu Tyr Ile Ala Pro Pro Leu Leu Leu Phe Met Val Arg Lys Glu Asn<br>535                     540                    545 | 1747 |
| cgc tca aaa taagtaccgt taaacttaat ctaacgtgta gcaatataaa<br>Arg Ser Lys<br>550 | 1796 |
| aatctccttt gggactttag tcccaaggcc cctgtggta ttaaatttat gacaaattca | 1856 |
| gataatgc | 1864 |

<210> SEQ ID NO 2
<211> LENGTH: 800
<212> TYPE: DNA
<213> ORGANISM: Chlamydia pneumoniae
<220> FEATURE:
<221> NAME/KEY: CDS
<222> LOCATION: (101)..(688)

-continued

```
<400> SEQUENCE: 2
ttattttaaa agcccatctt tttaggtatg taattaaaat ttttaattaa tgttttccta        60
gtgtaacctg cttctttagg aactacacta ggagaacggt atg tca tca aat cta        115
                                             Met Ser Ser Asn Leu
                                               1               5 cat ccc gta gga gga aca gga aca gga gca gct gct cct gag tct gtg        163
His Pro Val Gly Gly Thr Gly Thr Gly Ala Ala Ala Pro Glu Ser Val
             10                  15                  20 cta aac ata gta gag gaa ata gca gca tcg ggg agt gtc acc gct ggt        211
Leu Asn Ile Val Glu Glu Ile Ala Ala Ser Gly Ser Val Thr Ala Gly
         25                  30                  35 cta caa gca att acg tcc agt cca gga atg gtg aat cta ctc ata gga        259
Leu Gln Ala Ile Thr Ser Ser Pro Gly Met Val Asn Leu Leu Ile Gly
     40                  45                  50 tgg gca aag aca aaa ttt att caa cct ata cgt gaa tca aag ctc ttt        307
Trp Ala Lys Thr Lys Phe Ile Gln Pro Ile Arg Glu Ser Lys Leu Phe
 55                  60                  65 caa tcc aga gct tgc caa att acc ctg ctc gtt tta gga att ctt ttg        355
Gln Ser Arg Ala Cys Gln Ile Thr Leu Leu Val Leu Gly Ile Leu Leu
 70                  75                  80                  85 gtt gtt gct gga tta gca tgt atg ttt atc ttc cat agc cag tta ggg        403
Val Val Ala Gly Leu Ala Cys Met Phe Ile Phe His Ser Gln Leu Gly
                 90                  95                 100 gca aat gca ttt tgg ttg att att cct gct gcc ata gga ttg att aag        451
Ala Asn Ala Phe Trp Leu Ile Ile Pro Ala Ala Ile Gly Leu Ile Lys
            105                 110                 115 tta cta gtt aca tca tta tgt ttt gat gaa gct tgt aca tct gaa aaa        499
Leu Leu Val Thr Ser Leu Cys Phe Asp Glu Ala Cys Thr Ser Glu Lys
        120                 125                 130 ctc atg gtt ttc caa aaa tgg gca ggt gtt tta gaa gat cag ctc gat        547
Leu Met Val Phe Gln Lys Trp Ala Gly Val Leu Glu Asp Gln Leu Asp
    135                 140                 145 gat ggg atc ctt aat aac tca aat aag att ttt ggc cat gtg aaa aca        595
Asp Gly Ile Leu Asn Asn Ser Asn Lys Ile Phe Gly His Val Lys Thr
150                 155                 160                 165 gaa gga aat acc tct agg gct act acc cca gta ctt aat gat ggc cgc        643
Glu Gly Asn Thr Ser Arg Ala Thr Thr Pro Val Leu Asn Asp Gly Arg
                170                 175                 180 gga act cct gta ctt tca cct tta gta agt aaa ata gct cgc gtt            688
Gly Thr Pro Val Leu Ser Pro Leu Val Ser Lys Ile Ala Arg Val
            185                 190                 195 tagacgttca tctcacaagc atcctagaac ttgggatgct actttccacg tacgagatca      748
gatgtaaaga gcaacagtaa ttattttcta cactgttgta ataaaatcat gt              800

<210> SEQ ID NO 3
<211> LENGTH: 950
<212> TYPE: DNA
<213> ORGANISM: Chlamydia pneumoniae
<220> FEATURE:
<221> NAME/KEY: CDS
<222> LOCATION: (101)..(835)

<400> SEQUENCE: 3
tgctggcaga tcgtttccac atgcatactg tgaatctcga tccctatgcg gaaaatgtac       60
ttgtaaactt aaaaaccata gcgacgactt tttctagttt atg aca ata cga att       115
                                             Met Thr Ile Arg Ile
                                               1               5 ctt gct gaa ggc cta gct ttc cgt tac gga agc aag gga ccg aat atc       163
```

| | | |
|---|---|---|
| Leu Ala Glu Gly Leu Ala Phe Arg Tyr Gly Ser Lys Gly Pro Asn Ile<br>              10                  15              20 | |
| att cat gat gtt tct ttc tct gtc tat gat ggc gac ttt ata gga atc<br>Ile His Asp Val Ser Phe Ser Val Tyr Asp Gly Asp Phe Ile Gly Ile<br>              25                  30                 35 | 211 |
| ata gga cca aac gga ggg ggg aaa agc acc tta acg atg tta att ttg<br>Ile Gly Pro Asn Gly Gly Gly Lys Ser Thr Leu Thr Met Leu Ile Leu<br>      40                      45                  50 | 259 |
| ggc ttg ctt act cct aca ttc gga tcc ttg aag act ttc cct tcg cat<br>Gly Leu Leu Thr Pro Thr Phe Gly Ser Leu Lys Thr Phe Pro Ser His<br>   55                      60                  65 | 307 |
| tcc gcg ggg aaa caa acc cat tcc atg atc ggt tgg gtt ccc caa cat<br>Ser Ala Gly Lys Gln Thr His Ser Met Ile Gly Trp Val Pro Gln His<br>70                    75                  80                  85 | 355 |
| ttc tct tat gat cct tgt ttt cct atc tca gta aaa gat gtt gtc ctc<br>Phe Ser Tyr Asp Pro Cys Phe Pro Ile Ser Val Lys Asp Val Val Leu<br>              90                  95               100 | 403 |
| tca gga aga ttg tct caa ctc tcc tgg cat gga aaa tat aaa aag aaa<br>Ser Gly Arg Leu Ser Gln Leu Ser Trp His Gly Lys Tyr Lys Lys Lys<br>           105                  110               115 | 451 |
| gat ttt gaa gct gta gat cac gct ttg gat ctt gtt gga ctt tct gac<br>Asp Phe Glu Ala Val Asp His Ala Leu Asp Leu Val Gly Leu Ser Asp<br>          120                  125               130 | 499 |
| acc acc acc act gct ttc gcc cat ctc tca gga gga caa atc cag cgt<br>Thr Thr Thr Thr Ala Phe Ala His Leu Ser Gly Gly Gln Ile Gln Arg<br>135                   140                 145 | 547 |
| gta ctt ctg gca aga gcc tta gcc tcc tac cct gaa att tta att ctt<br>Val Leu Leu Ala Arg Ala Leu Ala Ser Tyr Pro Glu Ile Leu Ile Leu<br>150                   155                 160               165 | 595 |
| gat gag ccg acg aca aac att gat cct gac aat caa caa aga att tta<br>Asp Glu Pro Thr Thr Asn Ile Asp Pro Asp Asn Gln Gln Arg Ile Leu<br>               170                  175               180 | 643 |
| agt atc cta aaa aag ctc aac cgt acg tgc acc att ctt atg gta act<br>Ser Ile Leu Lys Lys Leu Asn Arg Thr Cys Thr Ile Leu Met Val Thr<br>          185                  190               195 | 691 |
| cac gat ctt cac cat acg acg aat tac ttt aat aaa gtt ttt tat atg<br>His Asp Leu His His Thr Thr Asn Tyr Phe Asn Lys Val Phe Tyr Met<br>          200                  205               210 | 739 |
| aac aaa act ttg cac ttc att ggc aga cac ttc gac ctt aac aga cca<br>Asn Lys Thr Leu His Phe Ile Gly Arg His Phe Asp Leu Asn Arg Pro<br>215                   220                 225 | 787 |
| att ttg ttg tca tcc tat aaa aat cag gaa ttt tca tgc tct cct cac<br>Ile Leu Leu Ser Ser Tyr Lys Asn Gln Glu Phe Ser Cys Ser Pro His<br>230                   235                 240               245 | 835 |
| taatccgtga ttcatttccc cttcttattt tacttccac attcctagcg gcattaggag | 895 |
| cctccgtagc tggcggcgtt atgggaacct atatcgttgt aaaacgtatt gtttc | 950 |

<210> SEQ ID NO 4
<211> LENGTH: 1050
<212> TYPE: DNA
<213> ORGANISM: Chlamydia pneumoniae
<220> FEATURE:
<221> NAME/KEY: CDS
<222> LOCATION: (101)..(934)

<400> SEQUENCE: 4

| | |
|---|---|
| gagaatttt tcctaagatc accgcttctt aggatattcg ttctttatta aaattatgcc | 60 |
| ccaatagaat aatagatcat cttatcaaac tgcttttgtc atg cat aaa gta ata<br>                                                                             Met His Lys Val Ile<br>                                                                             1                 5 | 115 |

```
gtt ttc att ttc ctt acc cta tat tcg tta aaa agt tat ggg aat gat      163
Val Phe Ile Phe Leu Thr Leu Tyr Ser Leu Lys Ser Tyr Gly Asn Asp
             10                  15                  20 gta ata gat aag ccc cat gtt ctt gtc agt atc gcc ccc tat aaa ttc      211
Val Ile Asp Lys Pro His Val Leu Val Ser Ile Ala Pro Tyr Lys Phe
         25                  30                  35 cta gtt gaa caa att gct gaa gag acc tgt ttt gtc tat gcg ata gtt      259
Leu Val Glu Gln Ile Ala Glu Glu Thr Cys Phe Val Tyr Ala Ile Val
             40                  45                  50 acg aat cac tat gat ccc cat acc tat gaa ctt cct cct cag caa atc      307
Thr Asn His Tyr Asp Pro His Thr Tyr Glu Leu Pro Pro Gln Gln Ile
         55                  60                  65 aag gag tta cga caa gga gac ctt tgg ttc cgt ata gga gag gca ttt      355
Lys Glu Leu Arg Gln Gly Asp Leu Trp Phe Arg Ile Gly Glu Ala Phe
 70                  75                  80                  85 gga aaa aac ttg tta gag aaa cct tac atg caa caa gtc gat ctt tcc      403
Gly Lys Asn Leu Leu Glu Lys Pro Tyr Met Gln Gln Val Asp Leu Ser
             90                  95                 100 caa aat gtc tcg ctg att caa gga aag cct tgc tgt aat caa cat acc      451
Gln Asn Val Ser Leu Ile Gln Gly Lys Pro Cys Cys Asn Gln His Thr
        105                 110                 115 acg aac tac gac acc cac act tgg tta agc cct aaa aac ctt aaa gtc      499
Thr Asn Tyr Asp Thr His Thr Trp Leu Ser Pro Lys Asn Leu Lys Val
        120                 125                 130 caa gtg gag act atc gtt acc act tta agt aaa aaa tat cct caa cac      547
Gln Val Glu Thr Ile Val Thr Thr Leu Ser Lys Lys Tyr Pro Gln His
        135                 140                 145 gcg act cta tat caa agc aat gga gag aaa ctt ctg tta gct ttg gac      595
Ala Thr Leu Tyr Gln Ser Asn Gly Glu Lys Leu Leu Leu Ala Leu Asp
150                 155                 160                 165 caa ctc aat gag gaa att ctt acg att acc tcc aaa gcg aaa caa cgc      643
Gln Leu Asn Glu Glu Ile Leu Thr Ile Thr Ser Lys Ala Lys Gln Arg
                170                 175                 180 cat att tta gtt tcc cat gga gcc ttt ggg tat ttt tgc cgt gat tac      691
His Ile Leu Val Ser His Gly Ala Phe Gly Tyr Phe Cys Arg Asp Tyr
            185                 190                 195 aat ttc tct cag cac act ata gag aaa agc agt cat gtt gag cct tct      739
Asn Phe Ser Gln His Thr Ile Glu Lys Ser Ser His Val Glu Pro Ser
        200                 205                 210 cct aaa gat gtg gct cgc gta ttt cgt gac att gaa cag tac aaa att      787
Pro Lys Asp Val Ala Arg Val Phe Arg Asp Ile Glu Gln Tyr Lys Ile
        215                 220                 225 tct tct gtg att ctt ctc gaa tac tct gga aga cga agt agt gct atg      835
Ser Ser Val Ile Leu Leu Glu Tyr Ser Gly Arg Arg Ser Ser Ala Met
230                 235                 240                 245 ctg gca gat cgt ttc cac atg cat act gtg aat ctc gat ccc tat gcg      883
Leu Ala Asp Arg Phe His Met His Thr Val Asn Leu Asp Pro Tyr Ala
                250                 255                 260 gaa aat gta ctt gta aac tta aaa acc ata gcg acg act ttt tct agt      931
Glu Asn Val Leu Val Asn Leu Lys Thr Ile Ala Thr Thr Phe Ser Ser
            265                 270                 275 tta tgacaatacg aattcttgct gaaggcctag ctttccgtta cggaagcaag           984
Leu ggaccgaata tcattcatga tgtttctttc tctgtctatg atggcgactt tataggaatc   1044
atagga                                                              1050

<210> SEQ ID NO 5
<211> LENGTH: 1550
```

```
<212> TYPE: DNA
<213> ORGANISM: Chlamydia pneumoniae
<220> FEATURE:
<221> NAME/KEY: CDS
<222> LOCATION: (10)..(1416)

<400> SEQUENCE: 5 acaatcact atg ggc cca gga tcg gtt ctt tcc aac cat agc aaa gaa gca       51
          Met Gly Pro Gly Ser Val Leu Ser Asn His Ser Lys Glu Ala
          1               5                  10 gga gga atc gct ata aac aat gtc atc att gat ttt agt gaa atc gtt        99
Gly Gly Ile Ala Ile Asn Asn Val Ile Ile Asp Phe Ser Glu Ile Val
 15              20                  25                  30 cct act aaa gat aat gca aca gta gct cca ccc act ctt aaa tta gta       147
Pro Thr Lys Asp Asn Ala Thr Val Ala Pro Pro Thr Leu Lys Leu Val
             35                  40                  45 tcg aga act aat gca gat agt aaa gat aag att gat att aca gga act       195
Ser Arg Thr Asn Ala Asp Ser Lys Asp Lys Ile Asp Ile Thr Gly Thr
             50                  55                  60 gtg act ctt cta gat cct aat ggc aac tta tat caa aat tct tat ctt       243
Val Thr Leu Leu Asp Pro Asn Gly Asn Leu Tyr Gln Asn Ser Tyr Leu
         65                  70                  75 ggt gaa gac cgc gat atc act ctt ttc aat ata gac aat tct gca agt       291
Gly Glu Asp Arg Asp Ile Thr Leu Phe Asn Ile Asp Asn Ser Ala Ser
 80                  85                  90 ggg gca gtt aca gcc acg aat gtc acc ctt caa ggg aat tta gga gct       339
Gly Ala Val Thr Ala Thr Asn Val Thr Leu Gln Gly Asn Leu Gly Ala
 95                 100                 105                 110 aaa aaa gga tat tta gga acc tgg aat ttg gat cca aat tcc tcg ggt       387
Lys Lys Gly Tyr Leu Gly Thr Trp Asn Leu Asp Pro Asn Ser Ser Gly
                115                 120                 125 tca aaa att att cta aaa tgg acc ttt gac aaa tac ctg cgc tgg ccc       435
Ser Lys Ile Ile Leu Lys Trp Thr Phe Asp Lys Tyr Leu Arg Trp Pro
            130                 135                 140 tac atc cct aga gac aac cac ttc tac atc aac tct att tgg gga gca       483
Tyr Ile Pro Arg Asp Asn His Phe Tyr Ile Asn Ser Ile Trp Gly Ala
            145                 150                 155 caa aac tct tta gtg act gtg aac caa ggg atc tta ggg aac atg ttg       531
Gln Asn Ser Leu Val Thr Val Asn Gln Gly Ile Leu Gly Asn Met Leu
        160                 165                 170 aac aat gca agg ttt gaa gat cct gct ttc aac aac ttc tgg gct tcg       579
Asn Asn Ala Arg Phe Glu Asp Pro Ala Phe Asn Asn Phe Trp Ala Ser
175                 180                 185                 190 gct ata gga tct ttc ctt agg aaa gaa gta tct cga aat tct gac tca       627
Ala Ile Gly Ser Phe Leu Arg Lys Glu Val Ser Arg Asn Ser Asp Ser
                195                 200                 205 ttc acc tat cat ggc aga ggc tat acc gct gct gtg gat gcc aaa cct       675
Phe Thr Tyr His Gly Arg Gly Tyr Thr Ala Ala Val Asp Ala Lys Pro
            210                 215                 220 cgc caa gaa ttt att tta gga gct gcc ttc agt cag gtt ttt ggt cac       723
Arg Gln Glu Phe Ile Leu Gly Ala Ala Phe Ser Gln Val Phe Gly His
            225                 230                 235 gcc gag tct gaa tat cac ctt gac aac tat aag cat aaa ggc tca ggt       771
Ala Glu Ser Glu Tyr His Leu Asp Asn Tyr Lys His Lys Gly Ser Gly
        240                 245                 250 cac tct aca caa gca tct ctt tat gct ggc aat atc ttc tat ttt cct       819
His Ser Thr Gln Ala Ser Leu Tyr Ala Gly Asn Ile Phe Tyr Phe Pro
255                 260                 265                 270 gcg ata cgg tct cgg cct att cta ttc caa ggt gtg gcg acc tat ggt       867
Ala Ile Arg Ser Arg Pro Ile Leu Phe Gln Gly Val Ala Thr Tyr Gly
                275                 280                 285
```

-continued

```
tat atg caa cat gac acc aca acc tac tat cct tct att gaa gaa aaa        915
Tyr Met Gln His Asp Thr Thr Thr Tyr Tyr Pro Ser Ile Glu Glu Lys
        290                 295                 300 aat atg gca aac tgg gat agc att gct tgg tta ttt gat ctg cgt ttc        963
Asn Met Ala Asn Trp Asp Ser Ile Ala Trp Leu Phe Asp Leu Arg Phe
            305                 310                 315 agt gtg gat ctt aaa gaa cct caa cct cac tct aca gca agg ctt acc       1011
Ser Val Asp Leu Lys Glu Pro Gln Pro His Ser Thr Ala Arg Leu Thr
        320                 325                 330 ttc tat aca gaa gct gag tat acc aga att cgc cag gag aaa ttc aca       1059
Phe Tyr Thr Glu Ala Glu Tyr Thr Arg Ile Arg Gln Glu Lys Phe Thr
335                 340                 345                 350 gag cta gac tat gat cct aga tct ttc tct gca tgc tct tat gga aac       1107
Glu Leu Asp Tyr Asp Pro Arg Ser Phe Ser Ala Cys Ser Tyr Gly Asn
                355                 360                 365 tta gca att cct act gga ttc tct gta gac gga gca tta gct tgg cgt       1155
Leu Ala Ile Pro Thr Gly Phe Ser Val Asp Gly Ala Leu Ala Trp Arg
            370                 375                 380 gag att att cta tat aat aaa gta tca gct gcg tac ctc cct gtg att       1203
Glu Ile Ile Leu Tyr Asn Lys Val Ser Ala Ala Tyr Leu Pro Val Ile
        385                 390                 395 ctc agg aat aat cca aaa gcg acc tat gaa gtt ctc tct aca aaa gaa       1251
Leu Arg Asn Asn Pro Lys Ala Thr Tyr Glu Val Leu Ser Thr Lys Glu
    400                 405                 410 aag ggc aac gta gtc aac gtt ctc cct aca aga aac gca gct cgt gca       1299
Lys Gly Asn Val Val Asn Val Leu Pro Thr Arg Asn Ala Ala Arg Ala
415                 420                 425                 430 gag gtg agc tct caa att tat ctt gga agt tac tgg aca ctc tac ggc       1347
Glu Val Ser Ser Gln Ile Tyr Leu Gly Ser Tyr Trp Thr Leu Tyr Gly
                435                 440                 445 acg tat act att gat gct tca atg aat act tta gtg caa atg gcc aac       1395
Thr Tyr Thr Ile Asp Ala Ser Met Asn Thr Leu Val Gln Met Ala Asn
            450                 455                 460 gga ggg atc cgg ttt gta ttc tagggtatac aattaaagat tttatgaaat          1446
Gly Gly Ile Arg Phe Val Phe
        465 tgaggatacg gagagagtgg gattcgaacc cacggtacgc gttaacgcac acacgctttc     1506 caagcgtgct ccttaagcca ctcggacatc tctccatatt tata                     1550

<210> SEQ ID NO 6
<211> LENGTH: 2950
<212> TYPE: DNA
<213> ORGANISM: Chlamydia pneumoniae
<220> FEATURE:
<221> NAME/KEY: CDS
<222> LOCATION: (101)..(2866)

<400> SEQUENCE: 6
aattcttttt aagtgacaag aaattcttgt gctcggcttg ctttcttatt cttattgacg      60
tattgcttga tcagatattc attttgattt aggtactaaa atg cga ttt tcg ctc       115
                                              Met Arg Phe Ser Leu
                                                1               5 tgc gga ttt cct cta gtt ttt tct ttt aca ttg ctc tca gtc ttc gac       163
Cys Gly Phe Pro Leu Val Phe Ser Phe Thr Leu Leu Ser Val Phe Asp
            10                  15                  20 act tct ttg agt gct act acg att tct tta acc cca gaa gat agt ttt       211
Thr Ser Leu Ser Ala Thr Thr Ile Ser Leu Thr Pro Glu Asp Ser Phe
        25                  30                  35 cat gga gat agt cag aat gca gaa cgt tct tat aat gtt caa gct ggg       259
```

```
His Gly Asp Ser Gln Asn Ala Glu Arg Ser Tyr Asn Val Gln Ala Gly
         40                  45                  50 gat gtc tat agc ctt act ggt gat gtc tca ata tct aac gtc gat aac      307
Asp Val Tyr Ser Leu Thr Gly Asp Val Ser Ile Ser Asn Val Asp Asn
     55                  60                  65 tct gca tta aat aaa gcc tgc ttc aat gtg acc tca gga agt gtg acg      355
Ser Ala Leu Asn Lys Ala Cys Phe Asn Val Thr Ser Gly Ser Val Thr
 70                  75                  80                  85 ttc gca gga aat cat cat ggg tta tat ttt aat aat att tcc tca gga      403
Phe Ala Gly Asn His His Gly Leu Tyr Phe Asn Asn Ile Ser Ser Gly
                     90                  95                 100 act aca aag gaa ggg gct gta ctt tgt tgc caa gat cct caa gca acg      451
Thr Thr Lys Glu Gly Ala Val Leu Cys Cys Gln Asp Pro Gln Ala Thr
                105                 110                 115 gca cgt ttt tct ggg ttc tcc acg ctc tct ttt att cag agc ccc gga      499
Ala Arg Phe Ser Gly Phe Ser Thr Leu Ser Phe Ile Gln Ser Pro Gly
            120                 125                 130 gat att aaa gaa cag gga tgt ctc tat tca aaa aat gca ctt atg ctc      547
Asp Ile Lys Glu Gln Gly Cys Leu Tyr Ser Lys Asn Ala Leu Met Leu
        135                 140                 145 tta aac aat tat gta gtg cgt ttt gaa caa aac caa agt aag act aaa      595
Leu Asn Asn Tyr Val Val Arg Phe Glu Gln Asn Gln Ser Lys Thr Lys
150                 155                 160                 165 ggc gga gct att agt ggg gcg aat gtt act ata gta ggc aac tac gat      643
Gly Gly Ala Ile Ser Gly Ala Asn Val Thr Ile Val Gly Asn Tyr Asp
                170                 175                 180 tcc gtc tct ttc tat cag aat gca gcc act ttt gga ggt gct atc cat      691
Ser Val Ser Phe Tyr Gln Asn Ala Ala Thr Phe Gly Gly Ala Ile His
            185                 190                 195 tct tca ggt ccc cta cag att gca gta aat cag gca gag ata aga ttt      739
Ser Ser Gly Pro Leu Gln Ile Ala Val Asn Gln Ala Glu Ile Arg Phe
        200                 205                 210 gca caa aat act gcc aag aat ggt tct gga ggg gct ttg tac tcc gat      787
Ala Gln Asn Thr Ala Lys Asn Gly Ser Gly Gly Ala Leu Tyr Ser Asp
    215                 220                 225 ggt gat att gat att gat cag aat gct tat gtt cta ttt cga gaa aat      835
Gly Asp Ile Asp Ile Asp Gln Asn Ala Tyr Val Leu Phe Arg Glu Asn
230                 235                 240                 245 gag gca ttg act act gct ata ggt aag gga ggg gct gtc tgt tgt ctt      883
Glu Ala Leu Thr Thr Ala Ile Gly Lys Gly Gly Ala Val Cys Cys Leu
                250                 255                 260 ccc act tca gga agt agt act cca gtt cct att gtg act ttc tct gac      931
Pro Thr Ser Gly Ser Ser Thr Pro Val Pro Ile Val Thr Phe Ser Asp
            265                 270                 275 aat aaa cag tta gtc ttt gaa aga aac cat tcc ata atg ggt ggc gga      979
Asn Lys Gln Leu Val Phe Glu Arg Asn His Ser Ile Met Gly Gly Gly
        280                 285                 290 gcc att tat gct agg aaa ctt agc atc tct tca gga ggt cct act cta     1027
Ala Ile Tyr Ala Arg Lys Leu Ser Ile Ser Ser Gly Gly Pro Thr Leu
    295                 300                 305 ttt atc aat aat ata tca tat gca aat tcg caa aat tta ggt gga gct     1075
Phe Ile Asn Asn Ile Ser Tyr Ala Asn Ser Gln Asn Leu Gly Gly Ala
310                 315                 320                 325 att gcc att gat act gga ggg gag atc agt tta tca gca gag aaa gga     1123
Ile Ala Ile Asp Thr Gly Gly Glu Ile Ser Leu Ser Ala Glu Lys Gly
                330                 335                 340 aca att aca ttc caa gga aac cgg acg agc tta ccg ttt ttg aat ggc     1171
Thr Ile Thr Phe Gln Gly Asn Arg Thr Ser Leu Pro Phe Leu Asn Gly
            345                 350                 355
```

```
atc cat ctt tta caa aat gct aaa ttc ctg aaa tta cag gcg aga aat    1219
Ile His Leu Leu Gln Asn Ala Lys Phe Leu Lys Leu Gln Ala Arg Asn
        360                 365                 370 gga tac tct ata gaa ttt tat gat cct att act tct gaa gca gat ggg    1267
Gly Tyr Ser Ile Glu Phe Tyr Asp Pro Ile Thr Ser Glu Ala Asp Gly
    375                 380                 385 tct acc caa ttg aat atc aac gga gat cct aaa aat aaa gag tac aca    1315
Ser Thr Gln Leu Asn Ile Asn Gly Asp Pro Lys Asn Lys Glu Tyr Thr
390                 395                 400                 405 ggg acc ata ctc ttt tct gga gaa aag agt cta gca aac gat cct agg    1363
Gly Thr Ile Leu Phe Ser Gly Glu Lys Ser Leu Ala Asn Asp Pro Arg
            410                 415                 420 gat ttt aaa tct aca atc cct cag aac gtc aac ctg tct gca gga tac    1411
Asp Phe Lys Ser Thr Ile Pro Gln Asn Val Asn Leu Ser Ala Gly Tyr
                425                 430                 435 tta gtt att aaa gag ggg gcc gaa gtc aca gtt tca aaa ttc acg cag    1459
Leu Val Ile Lys Glu Gly Ala Glu Val Thr Val Ser Lys Phe Thr Gln
        440                 445                 450 tct cca gga tcg cat tta gtt tta gat tta gga acc aaa ctg ata gcc    1507
Ser Pro Gly Ser His Leu Val Leu Asp Leu Gly Thr Lys Leu Ile Ala
455                 460                 465 tct aag gaa gac att gcc atc aca ggc ctc gcg ata gat ata gat agc    1555
Ser Lys Glu Asp Ile Ala Ile Thr Gly Leu Ala Ile Asp Ile Asp Ser
470                 475                 480                 485 tta agc tca tcc tca aca gca gct gtt att aaa gca aac acc gca aat    1603
Leu Ser Ser Ser Ser Thr Ala Ala Val Ile Lys Ala Asn Thr Ala Asn
            490                 495                 500 aaa cag ata tcc gtg acg gac tct ata gaa ctt atc tcg cct act ggc    1651
Lys Gln Ile Ser Val Thr Asp Ser Ile Glu Leu Ile Ser Pro Thr Gly
                505                 510                 515 aat gcc tat gaa gat ctc aga atg aga aat tca cag acg ttc cct ctg    1699
Asn Ala Tyr Glu Asp Leu Arg Met Arg Asn Ser Gln Thr Phe Pro Leu
        520                 525                 530 ctc tct tta gag cct gga gcc ggg ggt agt gtg act gta act gct gga    1747
Leu Ser Leu Glu Pro Gly Ala Gly Gly Ser Val Thr Val Thr Ala Gly
535                 540                 545 gat ttc cta ccg gta agt ccc cat tat ggt ttt caa ggc aat tgg aaa    1795
Asp Phe Leu Pro Val Ser Pro His Tyr Gly Phe Gln Gly Asn Trp Lys
550                 555                 560                 565 tta gct tgg aca gga act gga aac aaa gtt gga gaa ttc ttc tgg gat    1843
Leu Ala Trp Thr Gly Thr Gly Asn Lys Val Gly Glu Phe Phe Trp Asp
            570                 575                 580 aaa ata aat tat aag cct aga cct gaa aaa gaa gga aat tta gtt cct    1891
Lys Ile Asn Tyr Lys Pro Arg Pro Glu Lys Glu Gly Asn Leu Val Pro
                585                 590                 595 aat atc ttg tgg ggg aat gct gta gat gtc aga tcc tta atg cag gtt    1939
Asn Ile Leu Trp Gly Asn Ala Val Asp Val Arg Ser Leu Met Gln Val
        600                 605                 610 caa gag acc cat gca tcg agc tta cag aca gat cga ggg ctg tgg atc    1987
Gln Glu Thr His Ala Ser Ser Leu Gln Thr Asp Arg Gly Leu Trp Ile
615                 620                 625 gat gga att ggg aat ttc ttc cat gta tct gcc tcc gaa gac aat ata    2035
Asp Gly Ile Gly Asn Phe Phe His Val Ser Ala Ser Glu Asp Asn Ile
630                 635                 640                 645 agg tac cgt cat aac agc ggt gga tat gtt cta tct gta aat aat gag    2083
Arg Tyr Arg His Asn Ser Gly Gly Tyr Val Leu Ser Val Asn Asn Glu
            650                 655                 660 atc aca cct aag cac tat act tcg atg gca ttt tcc caa ctc ttt agt    2131
Ile Thr Pro Lys His Tyr Thr Ser Met Ala Phe Ser Gln Leu Phe Ser
                665                 670                 675
```

-continued

```
aga gac aag gac tat gcg gtt tcc aac aac gaa tac aga atg tat tta      2179
Arg Asp Lys Asp Tyr Ala Val Ser Asn Asn Glu Tyr Arg Met Tyr Leu
        680                 685                 690 gga tcg tat ctc tat caa tat aca acc tcc cta ggg aat att ttc cgt      2227
Gly Ser Tyr Leu Tyr Gln Tyr Thr Thr Ser Leu Gly Asn Ile Phe Arg
    695                 700                 705 tat gct tcg cgt aac cct aat gta aac gtc ggg att ctc tca aga agg      2275
Tyr Ala Ser Arg Asn Pro Asn Val Asn Val Gly Ile Leu Ser Arg Arg
710                 715                 720                 725 ttt ctt caa aat cct ctt atg att ttt cat ttt ttg tgt gct tat ggt      2323
Phe Leu Gln Asn Pro Leu Met Ile Phe His Phe Leu Cys Ala Tyr Gly
                730                 735                 740 cat gcc acc aat gat atg aaa aca gac tac gca aat ttc cct atg gtg      2371
His Ala Thr Asn Asp Met Lys Thr Asp Tyr Ala Asn Phe Pro Met Val
            745                 750                 755 aaa aac agc tgg aga aac aat tgt tgg gct ata gag tgc gga ggg agc      2419
Lys Asn Ser Trp Arg Asn Asn Cys Trp Ala Ile Glu Cys Gly Gly Ser
        760                 765                 770 atg cct cta ttg gta ttt gag aac gga aga ctt ttc caa ggt gcc atc      2467
Met Pro Leu Leu Val Phe Glu Asn Gly Arg Leu Phe Gln Gly Ala Ile
    775                 780                 785 cca ttt atg aaa cta caa tta gtt tat gct tat cat gga gat ttc aaa      2515
Pro Phe Met Lys Leu Gln Leu Val Tyr Ala Tyr His Gly Asp Phe Lys
790                 795                 800                 805 gag acg act gca gat ggc cgt aga ttt agt aat ggg agt tta aca tcg      2563
Glu Thr Thr Ala Asp Gly Arg Arg Phe Ser Asn Gly Ser Leu Thr Ser
                810                 815                 820 att tct gta cct cta ggc ata cgc ttt gag aag ctg gca ctt tct cag      2611
Ile Ser Val Pro Leu Gly Ile Arg Phe Glu Lys Leu Ala Leu Ser Gln
            825                 830                 835 gat gta ctc tat gac ttt agt ttc tcc tat att cct gat att ttc cgt      2659
Asp Val Leu Tyr Asp Phe Ser Phe Ser Tyr Ile Pro Asp Ile Phe Arg
        840                 845                 850 aag gat ccc tca tgt gaa gct gct ctg gtg att agc gga gac tcc tgg      2707
Lys Asp Pro Ser Cys Glu Ala Ala Leu Val Ile Ser Gly Asp Ser Trp
    855                 860                 865 ctt gtt ccg gca gca cac gta tca aga cat gct ttt gta ggg agt gga      2755
Leu Val Pro Ala Ala His Val Ser Arg His Ala Phe Val Gly Ser Gly
870                 875                 880                 885 acg ggt cgg tat cac ttt aac gac tat act gag ctc tta tgt cga gga      2803
Thr Gly Arg Tyr His Phe Asn Asp Tyr Thr Glu Leu Leu Cys Arg Gly
                890                 895                 900 agt ata gaa tgc cgc ccc cat gct agg aat tat aat ata aac tgt gga      2851
Ser Ile Glu Cys Arg Pro His Ala Arg Asn Tyr Asn Ile Asn Cys Gly
            905                 910                 915 agc aaa ttt cgt ttt tagaaggttt ccattgcctg tgtggttccg gatcttaact      2906
Ser Lys Phe Arg Phe
        920 ataaatcctg gactatggat cataggcatt gggtttctcg aact                     2950

<210> SEQ ID NO 7
<211> LENGTH: 1328
<212> TYPE: DNA
<213> ORGANISM: Chlamydia pneumoniae
<220> FEATURE:
<221> NAME/KEY: CDS
<222> LOCATION: (101)..(1225)
<220> FEATURE:
<221> NAME/KEY: unsure
<222> LOCATION: (1254)...(1323)
<223> OTHER INFORMATION: n is a or g or c or t/u, unknown, or other
```

-continued

```
<400> SEQUENCE: 7
gtgggggcat tgctggggga aaagcacatt tcgatcgcat tgataatctt atcagtccaa      60
agcaaccaag caaagaaagg tggtggggtt tatcttgaag atg ccc tca tcc tgg      115
                                             Met Pro Ser Ser Trp
                                               1               5 aaa agg tta tta cag gtt ctg tct cac aaa ata gca gct aca gaa agt      163
Lys Arg Leu Leu Gln Val Leu Ser His Lys Ile Ala Ala Thr Glu Ser
             10                  15                  20 ggt ggg ggt atc tac gct aag gat att caa cta caa gct cta cct gga      211
Gly Gly Gly Ile Tyr Ala Lys Asp Ile Gln Leu Gln Ala Leu Pro Gly
         25                  30                  35 agc ttc aca att acc gat aat aaa gtc gaa act agt ctt act act agc      259
Ser Phe Thr Ile Thr Asp Asn Lys Val Glu Thr Ser Leu Thr Thr Ser
     40                  45                  50 act aat tta tat ggt ggg ggc atc tat tcc agt gga gct gtc acg cta      307
Thr Asn Leu Tyr Gly Gly Gly Ile Tyr Ser Ser Gly Ala Val Thr Leu
 55                  60                  65 acc aat ata tct gga acc ttt ggc att aca gga aac tct gtt atc aat      355
Thr Asn Ile Ser Gly Thr Phe Gly Ile Thr Gly Asn Ser Val Ile Asn
 70                  75                  80                  85 aca gcg aca tcc cag gat gca gat ata caa ggt ggg ggc att tat gca      403
Thr Ala Thr Ser Gln Asp Ala Asp Ile Gln Gly Gly Gly Ile Tyr Ala
             90                  95                 100 acc acg tct ctc tca ata aat caa tgt aat aca ccc att cta ttt agc      451
Thr Thr Ser Leu Ser Ile Asn Gln Cys Asn Thr Pro Ile Leu Phe Ser
        105                 110                 115 aac aac tct gct gcc act aaa aaa aca tca aca aca aag caa att gct      499
Asn Asn Ser Ala Ala Thr Lys Lys Thr Ser Thr Thr Lys Gln Ile Ala
    120                 125                 130 ggt ggg gct atc ttc tcc gct gca gta act atc gag aat aac tct cag      547
Gly Gly Ala Ile Phe Ser Ala Ala Val Thr Ile Glu Asn Asn Ser Gln
135                 140                 145 ccc att att ttc tta aat aat tcc gca aag tcg gaa gca act aca gca      595
Pro Ile Ile Phe Leu Asn Asn Ser Ala Lys Ser Glu Ala Thr Thr Ala
150                 155                 160                 165 gca act gca gga aat aaa gat agc tgt gga gga gcc att gca gct aac      643
Ala Thr Ala Gly Asn Lys Asp Ser Cys Gly Gly Ala Ile Ala Ala Asn
                170                 175                 180 tct gtt act tta aca aat aac cct gaa ata acc ttt aaa gga aat tat      691
Ser Val Thr Leu Thr Asn Asn Pro Glu Ile Thr Phe Lys Gly Asn Tyr
            185                 190                 195 gca gaa act gga gga gcg att ggc tgt att gat ctt act aat ggc tca      739
Ala Glu Thr Gly Gly Ala Ile Gly Cys Ile Asp Leu Thr Asn Gly Ser
        200                 205                 210 cct ccc cgt aaa gtc tct att gca gac aac ggt tct gtc ctt ttt caa      787
Pro Pro Arg Lys Val Ser Ile Ala Asp Asn Gly Ser Val Leu Phe Gln
215                 220                 225 gac aac tct gcg tta aat cgc gga ggc gct atc tat gga gag act atc      835
Asp Asn Ser Ala Leu Asn Arg Gly Gly Ala Ile Tyr Gly Glu Thr Ile
230                 235                 240                 245 gat atc tcc agg aca ggt gcg act ttc atc ggt aac tct tca aaa cat      883
Asp Ile Ser Arg Thr Gly Ala Thr Phe Ile Gly Asn Ser Ser Lys His
                250                 255                 260 gat gga agt gca att tgc tgt tca aca gcc cta act ctt gcg cca aac      931
Asp Gly Ser Ala Ile Cys Cys Ser Thr Ala Leu Thr Leu Ala Pro Asn
            265                 270                 275 tcc caa ctt atc ttt gaa aac aat aag gtt acg gaa acc aca gcc act      979
Ser Gln Leu Ile Phe Glu Asn Asn Lys Val Thr Glu Thr Thr Ala Thr
```

-continued

```
           280             285             290
aca aaa gct tcc ata aat aat tta gga gct gca att tat gga aat aat    1027
Thr Lys Ala Ser Ile Asn Asn Leu Gly Ala Ala Ile Tyr Gly Asn Asn
    295             300             305 gag act agt gac gtc act atc tct tta tca gct gag aat gga agt att    1075
Glu Thr Ser Asp Val Thr Ile Ser Leu Ser Ala Glu Asn Gly Ser Ile
310             315             320             325 ttc ttt aaa aac aat cta tgc aca gca aca aac aaa tac tgc agt att    1123
Phe Phe Lys Asn Asn Leu Cys Thr Ala Thr Asn Lys Tyr Cys Ser Ile
                330             335             340 gct gga aac gta aaa ttt aca gca ata gaa gct tca gca ggg aaa gct    1171
Ala Gly Asn Val Lys Phe Thr Ala Ile Glu Ala Ser Ala Gly Lys Ala
            345             350             355 ata tct ttc tat gat gca gtt aac gtt cca cca aag aaa caa ttg ctc    1219
Ile Ser Phe Tyr Asp Ala Val Asn Val Pro Pro Lys Lys Gln Leu Leu
        360             365             370 aag agc taaattaaat gaaaaagcga caagtacang gacgtttcta ntttctgggg    1275
Lys Ser
    375 gacttcacgg aaataaatcc ctattccaca gaaagtcact tcgccctngg gat         1328

<210> SEQ ID NO 8
<211> LENGTH: 2816
<212> TYPE: DNA
<213> ORGANISM: Chlamydia pneumoniae
<220> FEATURE:
<221> NAME/KEY: CDS
<222> LOCATION: (101)..(2713)

<400> SEQUENCE: 8
ttacttgatt tatttaactg tattctctat tggtgcacca tgctcctaaa gccacatgct      60
atgggagtat ttttgataaa aagcttttcc ccaaagacac atg aaa tat tct tta     115
                                              Met Lys Tyr Ser Leu
                                                1               5 cct tgg cta ctt acc tct tcg gct tta gtt ttc tcc cta cat cca cta    163
Pro Trp Leu Leu Thr Ser Ser Ala Leu Val Phe Ser Leu His Pro Leu
        10              15              20 atg gct gct aac acg gat ctc tca tca tcc gat aac tat gaa aat ggt    211
Met Ala Ala Asn Thr Asp Leu Ser Ser Ser Asp Asn Tyr Glu Asn Gly
25              30              35 agt agt ggt agc gca gca ttc act gcc aag gaa act tcg gat gct tca    259
Ser Ser Gly Ser Ala Ala Phe Thr Ala Lys Glu Thr Ser Asp Ala Ser
    40              45              50 gga act acc tac act ctc act agc gat gtt tct att acg aat gta tct    307
Gly Thr Thr Tyr Thr Leu Thr Ser Asp Val Ser Ile Thr Asn Val Ser
55              60              65 gca att act cct gca gat aaa agc tgt ttt aca aac aca gga gga gca    355
Ala Ile Thr Pro Ala Asp Lys Ser Cys Phe Thr Asn Thr Gly Gly Ala
70              75              80              85 ttg agt ttt gtt gga gct gat cac tca ttg gtt ctg caa acc ata gcg    403
Leu Ser Phe Val Gly Ala Asp His Ser Leu Val Leu Gln Thr Ile Ala
            90              95              100 ctt acg cat gat ggt gct gca att aac aat acc aac aca gct ctt tct    451
Leu Thr His Asp Gly Ala Ala Ile Asn Asn Thr Asn Thr Ala Leu Ser
        105             110             115 ttc tca gga ttc tcg tca ctc tta atc gac tca gct cca gca aca gga    499
Phe Ser Gly Phe Ser Ser Leu Leu Ile Asp Ser Ala Pro Ala Thr Gly
    120             125             130 act tcg ggc ggc aag ggt gct att tgt gtg aca aat aca gag gga ggt    547
Thr Ser Gly Gly Lys Gly Ala Ile Cys Val Thr Asn Thr Glu Gly Gly
```

-continued

|  |  |
|---|---|
| act gcg act ttt act gac aat gcc agt gtc acc ctc caa aaa aat act<br>Thr Ala Thr Phe Thr Asp Asn Ala Ser Val Thr Leu Gln Lys Asn Thr<br>150               155               160               165 | 595 |
| tca gaa aaa gat gga gct gca gtt tct gcc tac agc atc gat ctt gct<br>Ser Glu Lys Asp Gly Ala Ala Val Ser Ala Tyr Ser Ile Asp Leu Ala<br>               170               175               180 | 643 |
| aag act acg aca gca gct ctc tta gat caa aat act agc aca aaa aat<br>Lys Thr Thr Thr Ala Ala Leu Leu Asp Gln Asn Thr Ser Thr Lys Asn<br>               185               190               195 | 691 |
| ggc ggg gcc ctc tgt agt aca gca aac act aca gtc caa gga aac tca<br>Gly Gly Ala Leu Cys Ser Thr Ala Asn Thr Thr Val Gln Gly Asn Ser<br>          200               205               210 | 739 |
| gga acg gtg acc ttc tcc tca aat act gct aca gat aaa ggt ggg ggg<br>Gly Thr Val Thr Phe Ser Ser Asn Thr Ala Thr Asp Lys Gly Gly Gly<br>215               220               225 | 787 |
| atc tac tca aaa gaa aag gat agc acg cta gat gcc aat aca gga gtc<br>Ile Tyr Ser Lys Glu Lys Asp Ser Thr Leu Asp Ala Asn Thr Gly Val<br>230               235               240               245 | 835 |
| gtt acc ttc aaa tct aat act gca aag acg ggg ggt gct tgg agc tct<br>Val Thr Phe Lys Ser Asn Thr Ala Lys Thr Gly Gly Ala Trp Ser Ser<br>               250               255               260 | 883 |
| gat gac aat ctt gct ctt acc ggc aac act caa gta ctt ttt cag gaa<br>Asp Asp Asn Leu Ala Leu Thr Gly Asn Thr Gln Val Leu Phe Gln Glu<br>          265               270               275 | 931 |
| aat aaa aca acc ggc tca gca gca cag gca aat aac ccg gaa ggt tgt<br>Asn Lys Thr Thr Gly Ser Ala Ala Gln Ala Asn Asn Pro Glu Gly Cys<br>          280               285               290 | 979 |
| ggt ggg gca atc tgt tgt tat ctt gct aca gca aca gac aaa act gga<br>Gly Gly Ala Ile Cys Cys Tyr Leu Ala Thr Ala Thr Asp Lys Thr Gly<br>295               300               305 | 1027 |
| tta gcc att tct cag aat caa gaa atg agc ttc act agt aat aca aca<br>Leu Ala Ile Ser Gln Asn Gln Glu Met Ser Phe Thr Ser Asn Thr Thr<br>310               315               320               325 | 1075 |
| act gcg aat ggt gga gcg atc tac gct act aaa tgt act ctg gat gga<br>Thr Ala Asn Gly Gly Ala Ile Tyr Ala Thr Lys Cys Thr Leu Asp Gly<br>               330               335               340 | 1123 |
| aac aca act ctt acc ttc gat cag aat act gcg aca gca gga tgt ggc<br>Asn Thr Thr Leu Thr Phe Asp Gln Asn Thr Ala Thr Ala Gly Cys Gly<br>          345               350               355 | 1171 |
| gga gct atc tat aca gaa act gaa gat ttt tct ctt aag gga agt acg<br>Gly Ala Ile Tyr Thr Glu Thr Glu Asp Phe Ser Leu Lys Gly Ser Thr<br>          360               365               370 | 1219 |
| gga acc gtg acc ttc agc aca aat aca gca aag aca ggc ggc gcc tta<br>Gly Thr Val Thr Phe Ser Thr Asn Thr Ala Lys Thr Gly Gly Ala Leu<br>375               380               385 | 1267 |
| tat tct aaa gga aac agc tcg ctg act gga aat acc aac ctg ctc ttt<br>Tyr Ser Lys Gly Asn Ser Ser Leu Thr Gly Asn Thr Asn Leu Leu Phe<br>390               395               400               405 | 1315 |
| tca ggg aac aaa gct acg ggc ccg agt aat tct tca gca aat caa gag<br>Ser Gly Asn Lys Ala Thr Gly Pro Ser Asn Ser Ser Ala Asn Gln Glu<br>               410               415               420 | 1363 |
| ggt tgc ggt ggg gca atc cta gcc ttt att gat tca gga tcc gta agc<br>Gly Cys Gly Gly Ala Ile Leu Ala Phe Ile Asp Ser Gly Ser Val Ser<br>          425               430               435 | 1411 |
| gat aaa aca gga cta tcg att gca aac aac caa gaa gtc agc ctc act<br>Asp Lys Thr Gly Leu Ser Ile Ala Asn Asn Gln Glu Val Ser Leu Thr<br>          440               445               450 | 1459 |
| agt aat gct gca aca gta agt ggt ggt gcg atc tat gct acc aaa tgt | 1507 |

```
                                   -continued

Ser Asn Ala Ala Thr Val Ser Gly Gly Ala Ile Tyr Ala Thr Lys Cys
    455                 460                 465 act cta act gga aac ggc tcc ctg acc ttt gac ggc aat act gct gga    1555
Thr Leu Thr Gly Asn Gly Ser Leu Thr Phe Asp Gly Asn Thr Ala Gly
470                 475                 480                 485 act tca gga ggg gcg atc tat aca gaa act gaa gat ttt act ctt aca    1603
Thr Ser Gly Gly Ala Ile Tyr Thr Glu Thr Glu Asp Phe Thr Leu Thr
                    490                 495                 500 gga agt aca gga acc gtg acc ttc agc aca aat aca gca aag aca ggc    1651
Gly Ser Thr Gly Thr Val Thr Phe Ser Thr Asn Thr Ala Lys Thr Gly
                505                 510                 515 ggc gcc tta tat tct aaa ggc aac aac tct ctg tct ggt aat acc aac    1699
Gly Ala Leu Tyr Ser Lys Gly Asn Asn Ser Leu Ser Gly Asn Thr Asn
            520                 525                 530 ctg ctc ttt tca ggg aac aaa gct acg ggc ccg agt aat tct tca gca    1747
Leu Leu Phe Ser Gly Asn Lys Ala Thr Gly Pro Ser Asn Ser Ser Ala
        535                 540                 545 aat caa gag ggt tgc ggt ggg gca atc cta tcg ttt ctt gag tca gca    1795
Asn Gln Glu Gly Cys Gly Gly Ala Ile Leu Ser Phe Leu Glu Ser Ala
550                 555                 560                 565 tct gta agt act aaa aaa gga ctc tgg att gaa gat aac gaa aac gtg    1843
Ser Val Ser Thr Lys Lys Gly Leu Trp Ile Glu Asp Asn Glu Asn Val
                570                 575                 580 agt ctc tct ggt aat act gca aca gta agt ggc ggt gcg atc tat gcg    1891
Ser Leu Ser Gly Asn Thr Ala Thr Val Ser Gly Gly Ala Ile Tyr Ala
                    585                 590                 595 acc aag tgt gct ctg cat gga aac acg act ctt acc ttt gat ggc aat    1939
Thr Lys Cys Ala Leu His Gly Asn Thr Thr Leu Thr Phe Asp Gly Asn
                600                 605                 610 act gcc gaa act gca gga gga gcg atc tat aca gaa acc gaa gat ttt    1987
Thr Ala Glu Thr Ala Gly Gly Ala Ile Tyr Thr Glu Thr Glu Asp Phe
615                 620                 625 act ctt acg gga agt acg gga acc gtg acc ttc agc aca aat aca gca    2035
Thr Leu Thr Gly Ser Thr Gly Thr Val Thr Phe Ser Thr Asn Thr Ala
            630                 635                 640                 645 aag aca gca ggg gct cta cat act aaa gga aat act tcc ttt acc aaa    2083
Lys Thr Ala Gly Ala Leu His Thr Lys Gly Asn Thr Ser Phe Thr Lys
                    650                 655                 660 aat aag gct ctt gta ttt tct gga aat tca gca aca gca aca gca aca    2131
Asn Lys Ala Leu Val Phe Ser Gly Asn Ser Ala Thr Ala Thr Ala Thr
                665                 670                 675 aca act aca gat caa gaa ggt tgt ggt gga gcg atc ctc tgt aat atc    2179
Thr Thr Thr Asp Gln Glu Gly Cys Gly Gly Ala Ile Leu Cys Asn Ile
            680                 685                 690 tca gag tct gac ata gct aca aaa agc tta act ctt act gaa aat gag    2227
Ser Glu Ser Asp Ile Ala Thr Lys Ser Leu Thr Leu Thr Glu Asn Glu
        695                 700                 705 agt tta agt ttc att aac aat acg gca aaa aga agt ggt ggt ggt att    2275
Ser Leu Ser Phe Ile Asn Asn Thr Ala Lys Arg Ser Gly Gly Gly Ile
710                 715                 720                 725 tat gct cct aag tgt gta atc tca ggc agt gaa tcc ata aac ttt gat    2323
Tyr Ala Pro Lys Cys Val Ile Ser Gly Ser Glu Ser Ile Asn Phe Asp
                730                 735                 740 ggc aat act gct gaa act tcg gga gga gcg att tat tcg aaa aac ctt    2371
Gly Asn Thr Ala Glu Thr Ser Gly Gly Ala Ile Tyr Ser Lys Asn Leu
                    745                 750                 755 tcg att aca gct aac ggt cct gtc tcc ttt acc aat aat tct gga ggc    2419
Ser Ile Thr Ala Asn Gly Pro Val Ser Phe Thr Asn Asn Ser Gly Gly
                760                 765                 770
```

-continued

```
aag gga ggc gcc att tat ata gcc gat agc gga gaa ctt tcc tta gag      2467
Lys Gly Gly Ala Ile Tyr Ile Ala Asp Ser Gly Glu Leu Ser Leu Glu
        775                 780                 785 gct att gat ggg gat att act ttc tca ggg aac cga gcg act gag gga      2515
Ala Ile Asp Gly Asp Ile Thr Phe Ser Gly Asn Arg Ala Thr Glu Gly
790                 795                 800                 805 act tca act ccc aac tcg atc cat tta ggt gcc agg ggc aag atc act      2563
Thr Ser Thr Pro Asn Ser Ile His Leu Gly Ala Arg Gly Lys Ile Thr
                810                 815                 820 aag ctt gca gca gct cct ggt cat acg att tat ttt tat gat cct att      2611
Lys Leu Ala Ala Ala Pro Gly His Thr Ile Tyr Phe Tyr Asp Pro Ile
            825                 830                 835 acg atg gaa gct cct gca tct gga gga aca ata gag gag tta gtc atc      2659
Thr Met Glu Ala Pro Ala Ser Gly Gly Thr Ile Glu Glu Leu Val Ile
        840                 845                 850 aat cct gtt gtc aaa gct att gtt cct cct ccc caa cca aaa aat ggt      2707
Asn Pro Val Val Lys Ala Ile Val Pro Pro Pro Gln Pro Lys Asn Gly
    855                 860                 865 cct ata tagaagaaaa acgaatgctc tttgtaaggc tcaagagtaa aaaattctaa      2763
Pro Ile
870 aggtattctc tcaataggtt ctgaagtgct gccgtagaat tcataaatat ctc           2816

<210> SEQ ID NO 9
<211> LENGTH: 3092
<212> TYPE: DNA
<213> ORGANISM: Chlamydia pneumoniae
<220> FEATURE:
<221> NAME/KEY: CDS
<222> LOCATION: (101)..(2989)

<400> SEQUENCE: 9
tcaaatatat gagtttacta actctgtaat attcaacatg ttaataagca tatttaaata     60
taaatttata aacttctaga caacaaattg atgattttt atg aca aac tct att       115
                                              Met Thr Asn Ser Ile
                                                1               5 ttc ata tca aag ttt gga tgt tta tgc gac cca ttt gtc tca gca ttt      163
Phe Ile Ser Lys Phe Gly Cys Leu Cys Asp Pro Phe Val Ser Ala Phe
                10                  15                  20 tat ccc act gcg cta tgt tgt tcc tta tca gga aat gaa gtc cct aac      211
Tyr Pro Thr Ala Leu Cys Cys Ser Leu Ser Gly Asn Glu Val Pro Asn
            25                  30                  35 ctc gcc tct tgt cag atg tct aga aaa gac atc tct gct ttc cac acg      259
Leu Ala Ser Cys Gln Met Ser Arg Lys Asp Ile Ser Ala Phe His Thr
        40                  45                  50 tct cca agc ttc cgt ctg aat gta act cca gag ccc ttg gtt tcc tcc      307
Ser Pro Ser Phe Arg Leu Asn Val Thr Pro Glu Pro Leu Val Ser Ser
    55                  60                  65 ttt cgt ccc tct aat ctt ctt aat gga ttc ggt cac gat ata acc cag      355
Phe Arg Pro Ser Asn Leu Leu Asn Gly Phe Gly His Asp Ile Thr Gln
70                  75                  80                  85 gac atc aca att aca gga aac tct atc aat tct gtt ata gat tat aac      403
Asp Ile Thr Ile Thr Gly Asn Ser Ile Asn Ser Val Ile Asp Tyr Asn
                90                  95                 100 tac cac tac gag gat gga ggc att ctt gca tgt aaa aat ttg ttc att      451
Tyr His Tyr Glu Asp Gly Gly Ile Leu Ala Cys Lys Asn Leu Phe Ile
            105                 110                 115 tct gaa aat aaa gga aac tta agt ttt gaa agg aat agc tcc cac agt      499
Ser Glu Asn Lys Gly Asn Leu Ser Phe Glu Arg Asn Ser Ser His Ser
        120                 125                 130
```

|     |     |     |     |     |     |     |     |     |     |     |     |     |     |     |     | |
|---|---|---|---|---|---|---|---|---|---|---|---|---|---|---|---|---|
| tct | gga | ggg | gct | ctc | tac | agt | gtt | cgg | gaa | tgc | tgg | att | tct | aag | aat | 547 |
| Ser | Gly | Gly | Ala | Leu | Tyr | Ser | Val | Arg | Glu | Cys | Trp | Ile | Ser | Lys | Asn | |
| | 135 | | | | 140 | | | | | 145 | | | | | | |
| cag | aac | tac | tcg | ttt | att | tca | aat | gcg | gct | tcc | tta | gct | act | act | aca | 595 |
| Gln | Asn | Tyr | Ser | Phe | Ile | Ser | Asn | Ala | Ala | Ser | Leu | Ala | Thr | Thr | Thr | |
| 150 | | | | | 155 | | | | | 160 | | | | | 165 | |
| act | tca | gga | ttt | ggt | ggg | gct | ata | cat | gca | cta | gat | agc | tat | att | aca | 643 |
| Thr | Ser | Gly | Phe | Gly | Gly | Ala | Ile | His | Ala | Leu | Asp | Ser | Tyr | Ile | Thr | |
| | | | | 170 | | | | | 175 | | | | | 180 | | |
| aat | aac | tta | gga | gaa | gga | caa | ttc | tta | gat | aat | gtc | tct | aaa | aat | aga | 691 |
| Asn | Asn | Leu | Gly | Glu | Gly | Gln | Phe | Leu | Asp | Asn | Val | Ser | Lys | Asn | Arg | |
| | | | | 185 | | | | | 190 | | | | | 195 | | |
| gga | gga | gct | atc | tat | gtt | ggg | gtg | agt | tta | tca | atc | aca | gac | aac | tta | 739 |
| Gly | Gly | Ala | Ile | Tyr | Val | Gly | Val | Ser | Leu | Ser | Ile | Thr | Asp | Asn | Leu | |
| | | | | 200 | | | | | 205 | | | | | 210 | | |
| ggt | cct | atc | gtt | atc | aag | aaa | aat | caa | aca | tta | gaa | gat | tcc | agc | ttt | 787 |
| Gly | Pro | Ile | Val | Ile | Lys | Lys | Asn | Gln | Thr | Leu | Glu | Asp | Ser | Ser | Phe | |
| | | 215 | | | | | 220 | | | | | 225 | | | | |
| gga | gga | ggc | atc | ttc | tgc | aga | gcc | gta | aat | ata | gaa | agg | aat | tat | caa | 835 |
| Gly | Gly | Gly | Ile | Phe | Cys | Arg | Ala | Val | Asn | Ile | Glu | Arg | Asn | Tyr | Gln | |
| 230 | | | | | 235 | | | | | 240 | | | | | 245 | |
| aac | atc | caa | atc | aat | gat | aat | gct | tca | gga | caa | ggg | gtg | gta | tat | ttt | 883 |
| Asn | Ile | Gln | Ile | Asn | Asp | Asn | Ala | Ser | Gly | Gln | Gly | Val | Val | Tyr | Phe | |
| | | | | 250 | | | | | 255 | | | | | 260 | | |
| ctg | ccc | cta | gga | gtc | att | atc | tct | tca | aat | aaa | gaa | att | ata | gag | atc | 931 |
| Leu | Pro | Leu | Gly | Val | Ile | Ile | Ser | Ser | Asn | Lys | Glu | Ile | Ile | Glu | Ile | |
| | | | 265 | | | | | 270 | | | | | 275 | | | |
| agc | aat | cac | tcc | gca | tcc | tca | att | aac | aca | gca | tca | gga | aaa | cta | tat | 979 |
| Ser | Asn | His | Ser | Ala | Ser | Ser | Ile | Asn | Thr | Ala | Ser | Gly | Lys | Leu | Tyr | |
| | | | 280 | | | | | 285 | | | | | 290 | | | |
| ccc | ggt | ggt | ggc | ggt | atc | atg | tgt | acc | tcc | ctt | agt | cat | gag | aac | aat | 1027 |
| Pro | Gly | Gly | Gly | Gly | Ile | Met | Cys | Thr | Ser | Leu | Ser | His | Glu | Asn | Asn | |
| | 295 | | | | | 300 | | | | | 305 | | | | | |
| ccc | aaa | ggt | ctt | atc | ttt | aac | aat | aaa | acg | gca | gca | ctt | agc | ggc | gga | 1075 |
| Pro | Lys | Gly | Leu | Ile | Phe | Asn | Asn | Lys | Thr | Ala | Ala | Leu | Ser | Gly | Gly | |
| 310 | | | | | 315 | | | | | 320 | | | | | 325 | |
| gta | tac | aca | cga | gat | ctt | tca | tct | tcc | aaa | ata | acg | gtc | cgc | aca | gca | 1123 |
| Val | Tyr | Thr | Arg | Asp | Leu | Ser | Ser | Ser | Lys | Ile | Thr | Val | Arg | Thr | Ala | |
| | | | | 330 | | | | | 335 | | | | | 340 | | |
| ttt | att | aat | aac | tct | gcg | act | tca | gga | ggg | gct | ctc | atc | aat | ctt | tct | 1171 |
| Phe | Ile | Asn | Asn | Ser | Ala | Thr | Ser | Gly | Gly | Ala | Leu | Ile | Asn | Leu | Ser | |
| | | | 345 | | | | | 350 | | | | | 355 | | | |
| ggt | ata | gga | agt | act | cct | caa | aat | ttc | ttc | ctc | tct | gca | gac | tac | ggc | 1219 |
| Gly | Ile | Gly | Ser | Thr | Pro | Gln | Asn | Phe | Phe | Leu | Ser | Ala | Asp | Tyr | Gly | |
| | | 360 | | | | | 365 | | | | | 370 | | | | |
| gat | att | cta | ttt | aac | aat | aat | aca | atc | aca | tct | tct | tct | cct | caa | ccc | 1267 |
| Asp | Ile | Leu | Phe | Asn | Asn | Asn | Thr | Ile | Thr | Ser | Ser | Ser | Pro | Gln | Pro | |
| 375 | | | | | 380 | | | | | 385 | | | | | | |
| gga | tat | aga | aat | gca | ctc | tat | gct | gct | ccg | ggg | att | aac | tta | aaa | cta | 1315 |
| Gly | Tyr | Arg | Asn | Ala | Leu | Tyr | Ala | Ala | Pro | Gly | Ile | Asn | Leu | Lys | Leu | |
| 390 | | | | | 395 | | | | | 400 | | | | | 405 | |
| gga | gca | aga | cag | ggt | tat | aaa | att | ctc | ttt | tat | gat | cct | ata | gat | cac | 1363 |
| Gly | Ala | Arg | Gln | Gly | Tyr | Lys | Ile | Leu | Phe | Tyr | Asp | Pro | Ile | Asp | His | |
| | | | 410 | | | | | 415 | | | | | 420 | | | |
| gat | cag | acg | aca | aca | gat | cct | ata | gta | ttt | aat | tat | gaa | ccc | cat | cac | 1411 |
| Asp | Gln | Thr | Thr | Thr | Asp | Pro | Ile | Val | Phe | Asn | Tyr | Glu | Pro | His | His | |
| | | | 425 | | | | | 430 | | | | | 435 | | | |
| ctt | ggc | acc | gtg | ttg | ttt | tcc | gga | atc | aat | gta | gat | tct | aac | gca | aca | 1459 |
| Leu | Gly | Thr | Val | Leu | Phe | Ser | Gly | Ile | Asn | Val | Asp | Ser | Asn | Ala | Thr | |
| | | 440 | | | | | 445 | | | | | 450 | | | | |

-continued

```
aat cca ttg aac ttc cta tca aaa ttt tct aac tct tca cga ctt gaa      1507
Asn Pro Leu Asn Phe Leu Ser Lys Phe Ser Asn Ser Ser Arg Leu Glu
455                 460                 465 agg ggt gtg ctc gct att gaa gat cgg gct gct att tct tgc aaa acc      1555
Arg Gly Val Leu Ala Ile Glu Asp Arg Ala Ala Ile Ser Cys Lys Thr
470                 475                 480                 485 cta tcg caa act ggg ggc att cta cgt tta gga aac gca gca tta atc      1603
Leu Ser Gln Thr Gly Gly Ile Leu Arg Leu Gly Asn Ala Ala Leu Ile
                490                 495                 500 agg acg aaa ggc ccg gga agc tcc ata aat ttt aat gca atc gcg atc      1651
Arg Thr Lys Gly Pro Gly Ser Ser Ile Asn Phe Asn Ala Ile Ala Ile
505                 510                 515 aat ctt cct tct att tta caa tca gaa gcc tca gct cca aag ttc tgg      1699
Asn Leu Pro Ser Ile Leu Gln Ser Glu Ala Ser Ala Pro Lys Phe Trp
520                 525                 530 att tat cct aca tta aca gga tcc acc tat tct gaa gac act tct tct      1747
Ile Tyr Pro Thr Leu Thr Gly Ser Thr Tyr Ser Glu Asp Thr Ser Ser
535                 540                 545 act atc act ctc tca gga ccc ttg act ttt cta aac gat gaa aat gaa      1795
Thr Ile Thr Leu Ser Gly Pro Leu Thr Phe Leu Asn Asp Glu Asn Glu
550                 555                 560                 565 aac ccc tat gat agc tta gat ctc tct gaa cct cga aag gat atc ccc      1843
Asn Pro Tyr Asp Ser Leu Asp Leu Ser Glu Pro Arg Lys Asp Ile Pro
                570                 575                 580 cct cct cta cct cct cga tgt gac tgc aaa aaa atc gat act tcg aat      1891
Pro Pro Leu Pro Pro Arg Cys Asp Cys Lys Lys Ile Asp Thr Ser Asn
585                 590                 595 ctc att gta gaa gcc atg aac tta gat gag cac tat gga tat cag gga      1939
Leu Ile Val Glu Ala Met Asn Leu Asp Glu His Tyr Gly Tyr Gln Gly
600                 605                 610 atc tgg tct ccc tat tgg atg gaa act acg act aca aca agc tct aca      1987
Ile Trp Ser Pro Tyr Trp Met Glu Thr Thr Thr Thr Thr Ser Ser Thr
615                 620                 625 gta ccg gaa cag acc aat aca aac cac agg cag ctc tac gta gac tgg      2035
Val Pro Glu Gln Thr Asn Thr Asn His Arg Gln Leu Tyr Val Asp Trp
630                 635                 640                 645 act cct gta gga tac cgc cct aac ccg gaa cgt cac gga gaa ttt att      2083
Thr Pro Val Gly Tyr Arg Pro Asn Pro Glu Arg His Gly Glu Phe Ile
                650                 655                 660 gct aat acc tta tgg cag tct gcc tat aac gct ctg tta gga atc cgc      2131
Ala Asn Thr Leu Trp Gln Ser Ala Tyr Asn Ala Leu Leu Gly Ile Arg
665                 670                 675 atc tta cct cca caa aac ctc aaa gag cat gac ctt gaa gcc tct ctg      2179
Ile Leu Pro Pro Gln Asn Leu Lys Glu His Asp Leu Glu Ala Ser Leu
680                 685                 690 caa gga ctc ggg ctt cta att aac caa cat aat cgc gag gga cgc aaa      2227
Gln Gly Leu Gly Leu Leu Ile Asn Gln His Asn Arg Glu Gly Arg Lys
695                 700                 705 ggc ttc cga aac cat act acg ggc tat gca gca aca acc tca gca aaa      2275
Gly Phe Arg Asn His Thr Thr Gly Tyr Ala Ala Thr Thr Ser Ala Lys
710                 715                 720                 725 act gca gca cga cat agt ttc tct tta gga ttc gca caa atg ttc tcc      2323
Thr Ala Ala Arg His Ser Phe Ser Leu Gly Phe Ala Gln Met Phe Ser
                730                 735                 740 aaa act aga gaa cgt caa tct cca agt acg act tcc tcc cac aac tac      2371
Lys Thr Arg Glu Arg Gln Ser Pro Ser Thr Thr Ser Ser His Asn Tyr
745                 750                 755 ttt gca gga ctc cgc ttc gac agt ctc ctc ttc agg gac ttc atc tct      2419
Phe Ala Gly Leu Arg Phe Asp Ser Leu Leu Phe Arg Asp Phe Ile Ser
```

-continued

```
                760               765                 770
aca ggg cta tcc cta ggt tat agc tac gga gat cac cat atg ctt tgc    2467
Thr Gly Leu Ser Leu Gly Tyr Ser Tyr Gly Asp His His Met Leu Cys
        775                 780                 785 cac tat aca gaa atc tta aaa ggg tcg tcc aaa gcc ttc ttt aat aac    2515
His Tyr Thr Glu Ile Leu Lys Gly Ser Ser Lys Ala Phe Phe Asn Asn
790                 795                 800                 805 cac act ttg gta gcc tct cta gac tgc aca ttc tta cca gct aga atc    2563
His Thr Leu Val Ala Ser Leu Asp Cys Thr Phe Leu Pro Ala Arg Ile
                810                 815                 820 acc cgc act ctc gaa ctc cag ccc ttt atc agt gcc att gct ctg cgc    2611
Thr Arg Thr Leu Glu Leu Gln Pro Phe Ile Ser Ala Ile Ala Leu Arg
            825                 830                 835 tgt tcc cag gcc tcg ttc caa gaa act gga gac cat ata aga aaa ttc    2659
Cys Ser Gln Ala Ser Phe Gln Glu Thr Gly Asp His Ile Arg Lys Phe
        840                 845                 850 cat cca aaa cat ccc ctt aca gat ctt tcc tct ccc ata ggc ttc cgt    2707
His Pro Lys His Pro Leu Thr Asp Leu Ser Ser Pro Ile Gly Phe Arg
855                 860                 865 tct gaa tgg aaa act tca cat cat atc ccc atg cta tgg act acg gaa    2755
Ser Glu Trp Lys Thr Ser His His Ile Pro Met Leu Trp Thr Thr Glu
870                 875                 880                 885 ata tcc tac gta cct acc cta tac aga aaa aat cca gaa atg ttc acg    2803
Ile Ser Tyr Val Pro Thr Leu Tyr Arg Lys Asn Pro Glu Met Phe Thr
                890                 895                 900 aca cta ctc atc agc aat gga aca tgg aca aca caa gca act ccc gtc    2851
Thr Leu Leu Ile Ser Asn Gly Thr Trp Thr Thr Gln Ala Thr Pro Val
            905                 910                 915 tcc tat aat tcc gta gct gca aaa ata aaa aat act tcc caa ctt ttc    2899
Ser Tyr Asn Ser Val Ala Ala Lys Ile Lys Asn Thr Ser Gln Leu Phe
        920                 925                 930 tca aga gta acc tta tcc tta gat tat tca gct caa gtc tcc tcg tca    2947
Ser Arg Val Thr Leu Ser Leu Asp Tyr Ser Ala Gln Val Ser Ser Ser
935                 940                 945 act gta ggt caa tac ctt aaa gct gag agt cat tgc aca ttt              2989
Thr Val Gly Gln Tyr Leu Lys Ala Glu Ser His Cys Thr Phe
950                 955                 960 taaccacaaa gaaacatca aggaataaac agtgcaaaat aacagatccc ttagtaaatc    3049
ttccttcttt gttggagcct taattttagg taaaactaca ata                      3092

<210> SEQ ID NO 10
<211> LENGTH: 1745
<212> TYPE: DNA
<213> ORGANISM: Chlamydia pneumoniae
<220> FEATURE:
<221> NAME/KEY: CDS
<222> LOCATION: (101)..(1642)

<400> SEQUENCE: 10
aaacagttaa ataattaata gacaataatc tattcttatt gacttctttt tttcttgttt    60
attaaagttg cttcaacctt attgatttaa cgaggaaacc atg acc ata ctt cga    115
                                              Met Thr Ile Leu Arg
                                                1               5 aat ttt ctt acc tgc tcg gct tta ttc ctc gct ctc cct gca gca gca    163
Asn Phe Leu Thr Cys Ser Ala Leu Phe Leu Ala Leu Pro Ala Ala Ala
                10                  15                  20 caa gtt gta tat ctt cat gaa agt gat ggt tat aac ggt gct atc aat    211
Gln Val Val Tyr Leu His Glu Ser Asp Gly Tyr Asn Gly Ala Ile Asn
            25                  30                  35
```

-continued

```
aat aaa agc tta gaa cct aaa att acc tgt tat cca gaa gga act tct    259
Asn Lys Ser Leu Glu Pro Lys Ile Thr Cys Tyr Pro Glu Gly Thr Ser
         40                  45                  50 tac atc ttt cta gat gac gtg agg att tcc aac gtt aag cat gat caa    307
Tyr Ile Phe Leu Asp Asp Val Arg Ile Ser Asn Val Lys His Asp Gln
 55                  60                  65 gaa gat gct ggg gtt ttt ata aat cga tct ggg aat ctt ttt ttc atg    355
Glu Asp Ala Gly Val Phe Ile Asn Arg Ser Gly Asn Leu Phe Phe Met
 70                  75                  80                  85 ggc aac cgt tgc aac ttc act ttt cac aac ctt atg acc gag ggt ttt    403
Gly Asn Arg Cys Asn Phe Thr Phe His Asn Leu Met Thr Glu Gly Phe
                 90                  95                 100 ggc gct gcc att tcg aac cgc gtt gga gac acc act ctc act ctc tct    451
Gly Ala Ala Ile Ser Asn Arg Val Gly Asp Thr Thr Leu Thr Leu Ser
                105                 110                 115 aat ttt tct tac tta gcg ttc acc tca gca cct cta cta cct caa gga    499
Asn Phe Ser Tyr Leu Ala Phe Thr Ser Ala Pro Leu Leu Pro Gln Gly
                120                 125                 130 caa gga gcg att tat agt ctt ggt tcc gtg atg atc gaa aat agt gag    547
Gln Gly Ala Ile Tyr Ser Leu Gly Ser Val Met Ile Glu Asn Ser Glu
135                 140                 145 gaa gtg act ttc tgt ggg aac tac tct tcg tgg agt gga gct gcg att    595
Glu Val Thr Phe Cys Gly Asn Tyr Ser Ser Trp Ser Gly Ala Ala Ile
150                 155                 160                 165 tat act ccc tac ctt tta ggt tct aag gcg agt cgt cct tca gta aat    643
Tyr Thr Pro Tyr Leu Leu Gly Ser Lys Ala Ser Arg Pro Ser Val Asn
                170                 175                 180 ctc agc ggg aac cgc tac ctg gtg ttt aga gac aat gtg agc caa gtt    691
Leu Ser Gly Asn Arg Tyr Leu Val Phe Arg Asp Asn Val Ser Gln Val
                185                 190                 195 tat ggc ggc gcc ata tct acc cac aat ctc aca ctc acg act cga gga    739
Tyr Gly Gly Ala Ile Ser Thr His Asn Leu Thr Leu Thr Thr Arg Gly
200                 205                 210 cct tcg tgt ttt gaa aat aat cat gct tat cat gac gtg aat agt aat    787
Pro Ser Cys Phe Glu Asn Asn His Ala Tyr His Asp Val Asn Ser Asn
                215                 220                 225 gga gga gcc att gcc att gct cct gga gga tcg atc tct ata tcc gtg    835
Gly Gly Ala Ile Ala Ile Ala Pro Gly Gly Ser Ile Ser Ile Ser Val
230                 235                 240                 245 aaa agc gga gat ctc atc ttc aaa gga aat aca gca tca caa gac gga    883
Lys Ser Gly Asp Leu Ile Phe Lys Gly Asn Thr Ala Ser Gln Asp Gly
                250                 255                 260 aat aca ata cac aac tcc atc cat ctg caa tct gga gca cag ttt aag    931
Asn Thr Ile His Asn Ser Ile His Leu Gln Ser Gly Ala Gln Phe Lys
                265                 270                 275 aac cta cgt gct gtt tca gaa tcc gga gtt tat ttc tat gat cct ata    979
Asn Leu Arg Ala Val Ser Glu Ser Gly Val Tyr Phe Tyr Asp Pro Ile
                280                 285                 290 agc cat agc gag tcg cat aaa att aca gat ctt gta atc aat gct cct   1027
Ser His Ser Glu Ser His Lys Ile Thr Asp Leu Val Ile Asn Ala Pro
            295                 300                 305 gaa gga aag gaa act tat gaa gga aca att agc ttc tca gga cta tgc   1075
Glu Gly Lys Glu Thr Tyr Glu Gly Thr Ile Ser Phe Ser Gly Leu Cys
310                 315                 320                 325 ctg gat gat cat gaa gtt tgt gcg gaa aat ctt act tcc aca atc cta   1123
Leu Asp Asp His Glu Val Cys Ala Glu Asn Leu Thr Ser Thr Ile Leu
                330                 335                 340 caa gat gtc aca tta gca gga gga act ctc tct cta tcg gat ggg gtt   1171
Gln Asp Val Thr Leu Ala Gly Gly Thr Leu Ser Leu Ser Asp Gly Val
                345                 350                 355
```

```
acc ttg caa ctg cat tct ttt aag cag gaa gca agc tct acg ctt act      1219
Thr Leu Gln Leu His Ser Phe Lys Gln Glu Ala Ser Ser Thr Leu Thr
        360                 365                 370 atg tct cca gga acc act ctg ctc tgc tca gga gat gct cgg gtt cag      1267
Met Ser Pro Gly Thr Thr Leu Leu Cys Ser Gly Asp Ala Arg Val Gln
375                 380                 385 aat ctg cac atc ctg att gaa gat acc gac aac ttt gtt cct gta agg      1315
Asn Leu His Ile Leu Ile Glu Asp Thr Asp Asn Phe Val Pro Val Arg
390                 395                 400                 405 att cgc gcc gag gac aag gat gct ctt gtc tca tta gaa aaa ctt aaa      1363
Ile Arg Ala Glu Asp Lys Asp Ala Leu Val Ser Leu Glu Lys Leu Lys
                410                 415                 420 gtt gcc ttt gag gct tat tgg tcc gtc tat gac ttt cct caa ttt aag      1411
Val Ala Phe Glu Ala Tyr Trp Ser Val Tyr Asp Phe Pro Gln Phe Lys
            425                 430                 435 gaa gcc ttt acg att cct ctt ctt gaa ctt cta ggg cct tct ttt gac      1459
Glu Ala Phe Thr Ile Pro Leu Leu Glu Leu Leu Gly Pro Ser Phe Asp
        440                 445                 450 agt ctt ctc cta ggg gag acc act ttg gag aga acc caa gtc aca aca      1507
Ser Leu Leu Leu Gly Glu Thr Thr Leu Glu Arg Thr Gln Val Thr Thr
455                 460                 465 gag aat gac gcc gtt cga ggt ttc tgg tcc cta agc tgg gaa gag tac      1555
Glu Asn Asp Ala Val Arg Gly Phe Trp Ser Leu Ser Trp Glu Glu Tyr
470                 475                 480                 485 ccc cct tct ctg gat aaa gac aga agg atc aca cca act aag aaa act      1603
Pro Pro Ser Leu Asp Lys Asp Arg Arg Ile Thr Pro Thr Lys Lys Thr
                490                 495                 500 gtt ttc ctc act tgg aat cct gag atc act tct acg cca taatctctaa      1652
Val Phe Leu Thr Trp Asn Pro Glu Ile Thr Ser Thr Pro
            505                 510 gtctacacta taattaaggg aatccccttt aagaagattt tgggacctat ctgtattcag    1712
agataggtcc ctctatgcac acatgttcac gag                                 1745

<210> SEQ ID NO 11
<211> LENGTH: 1100
<212> TYPE: DNA
<213> ORGANISM: Chlamydia pneumoniae
<220> FEATURE:
<221> NAME/KEY: CDS
<222> LOCATION: (101)..(967)

<400> SEQUENCE: 11
tttggaacct taatgatctc tggagggtgg cttagcaata tgattttacg ctttgcaggt     60
cagattttcc aaaacttcta taatggaaa taagagctt atg gga atc tct cta        115
                                            Met Gly Ile Ser Leu
                                              1               5 cca gag ctt ttt tcc aac cta ggt tct gct tac tta gat tat atc ttt      163
Pro Glu Leu Phe Ser Asn Leu Gly Ser Ala Tyr Leu Asp Tyr Ile Phe
                10                  15                  20 caa cat cct ccg gcc tat gtt tgg tca gtt ttt ctt ctt tta tta gcc      211
Gln His Pro Pro Ala Tyr Val Trp Ser Val Phe Leu Leu Leu Leu Ala
            25                  30                  35 cgt ctg ctt cct att ttt gct gta gct ccc ttc tta gga gca aag ctc      259
Arg Leu Leu Pro Ile Phe Ala Val Ala Pro Phe Leu Gly Ala Lys Leu
        40                  45                  50 ttt ccc tcc cct att aaa atc ggg att agt ctc tct tgg ctt gca atc      307
Phe Pro Ser Pro Ile Lys Ile Gly Ile Ser Leu Ser Trp Leu Ala Ile
55                  60                  65 atc ttt cca aaa gtc ttg gcg gat acg cag atc aca aat tac atg gat      355
```

```
                                                                -continued

Ile Phe Pro Lys Val Leu Ala Asp Thr Gln Ile Thr Asn Tyr Met Asp
 70              75                  80                  85 aac aat ctc ttt tat gtt tta ctt gtg aag gag atg atc ata ggc att        403
Asn Asn Leu Phe Tyr Val Leu Leu Val Lys Glu Met Ile Ile Gly Ile
                 90                  95                 100 gtg ata ggc ttt gtt tta gca ttt ccc ttt tat gct gca caa tcg gca        451
Val Ile Gly Phe Val Leu Ala Phe Pro Phe Tyr Ala Ala Gln Ser Ala
            105                 110                 115 gga tct ttc atc act aac caa caa ggg att cag ggt tta gag ggc gcg        499
Gly Ser Phe Ile Thr Asn Gln Gln Gly Ile Gln Gly Leu Glu Gly Ala
        120                 125                 130 aca tcc ctg att tcc att gag cag acc tct ccg cat ggc att tta tac        547
Thr Ser Leu Ile Ser Ile Glu Gln Thr Ser Pro His Gly Ile Leu Tyr
    135                 140                 145 cat tac ttc gtg act att att ttt tgg tta gtg ggt ggt cac cgt att        595
His Tyr Phe Val Thr Ile Ile Phe Trp Leu Val Gly Gly His Arg Ile
150                 155                 160                 165 gta atc tct ttg tta ttg caa act ctt gaa gtc att ccg atc cat agt        643
Val Ile Ser Leu Leu Leu Gln Thr Leu Glu Val Ile Pro Ile His Ser
                170                 175                 180 ttc ttt cct gcc gag atg atg agc tta agt gcc ccg att tgg att act        691
Phe Phe Pro Ala Glu Met Met Ser Leu Ser Ala Pro Ile Trp Ile Thr
            185                 190                 195 atg atc aag atg tgc cag ctc tgt ctc gtg atg acc ata cag ctg agt        739
Met Ile Lys Met Cys Gln Leu Cys Leu Val Met Thr Ile Gln Leu Ser
        200                 205                 210 gct cct gca gct ttg gcg atg tta atg tcc gac cta ttc tta ggg att        787
Ala Pro Ala Ala Leu Ala Met Leu Met Ser Asp Leu Phe Leu Gly Ile
    215                 220                 225 att aac cgt atg gca cct caa gtt cag gtc atc tac ctc ctc tct gcc        835
Ile Asn Arg Met Ala Pro Gln Val Gln Val Ile Tyr Leu Leu Ser Ala
230                 235                 240                 245 ctt aag gct ttc atg ggt ctt ctc ttt ctc acc ctg gcg tgg tgg ttc        883
Leu Lys Ala Phe Met Gly Leu Leu Phe Leu Thr Leu Ala Trp Trp Phe
                250                 255                 260 ata att aag cag ata gat tat ttc act ctt gct tgg ttc aaa gaa gtc        931
Ile Ile Lys Gln Ile Asp Tyr Phe Thr Leu Ala Trp Phe Lys Glu Val
            265                 270                 275 ccc att atg ctc cta ggt tcc aac cct caa gta ctc taatccccta            977
Pro Ile Met Leu Leu Gly Ser Asn Pro Gln Val Leu
        280                 285 ggctcttatc gtgactctta tctggagatg cgctcactta cgaatcttag cgcactgttt    1037
atggattatc ttagggaatc tctcgcatat tcttttgtaa tctaagaatc tataaattca    1097
aga                                                                  1100

<210> SEQ ID NO 12
<211> LENGTH: 950
<212> TYPE: DNA
<213> ORGANISM: Chlamydia pneumoniae
<220> FEATURE:
<221> NAME/KEY: CDS
<222> LOCATION: (101)..(895)

<400> SEQUENCE: 12
ccagtgataa agactctagt gataaagatg ctccagaagg aagcaatgaa attgagggtg     60
cttagtgact gccaacactt ttggaactct agacatcttg atg aag cac tcc aag      115
                                            Met Lys His Ser Lys
                                              1               5 gaa gat gac ctc tcc agg ttt ctt cct aaa aat ctt ctt gtt gaa tct      163
```

-continued

```
                Glu Asp Asp Leu Ser Arg Phe Leu Pro Lys Asn Leu Leu Val Glu Ser
                             10                  15                  20 cct cat ccc gaa gaa atc cct tta aaa tct tta tct ttt acg atg agt           211
Pro His Pro Glu Glu Ile Pro Leu Lys Ser Leu Ser Phe Thr Met Ser
             25                  30                  35 tgg cta cct aca att cat cct tca tgg att acc att gcc atg aaa gag           259
Trp Leu Pro Thr Ile His Pro Ser Trp Ile Thr Ile Ala Met Lys Glu
         40                  45                  50 ttc cct cct gaa atc caa ggt caa tta tta gcg tgg ttg cca gag cct           307
Phe Pro Pro Glu Ile Gln Gly Gln Leu Leu Ala Trp Leu Pro Glu Pro
     55                  60                  65 tta gtt caa gaa att cta ccc tta ctg cct ggc atc tct ata gcc cca           355
Leu Val Gln Glu Ile Leu Pro Leu Leu Pro Gly Ile Ser Ile Ala Pro
 70                  75                  80                  85 cat cgc tgt gca cct ttc gga gcc ttc tat ctt cta gat atg cta agt           403
His Arg Cys Ala Pro Phe Gly Ala Phe Tyr Leu Leu Asp Met Leu Ser
                 90                  95                 100 aaa aag atc cgt cct tgt gga att aca gaa gaa atc ttt ctt cct gca           451
Lys Lys Ile Arg Pro Cys Gly Ile Thr Glu Glu Ile Phe Leu Pro Ala
            105                 110                 115 tcc tca gca aat gct ata ctt tac tat aca ggt cct gta aag atc gct           499
Ser Ser Ala Asn Ala Ile Leu Tyr Tyr Thr Gly Pro Val Lys Ile Ala
        120                 125                 130 tta atc aac tgc cta ggt ctt tat tct att gct aaa gag ttg aag cac           547
Leu Ile Asn Cys Leu Gly Leu Tyr Ser Ile Ala Lys Glu Leu Lys His
    135                 140                 145 att ctg gat aag gtt gtg att gaa cga gtg aag aat gct ctc tcc cct           595
Ile Leu Asp Lys Val Val Ile Glu Arg Val Lys Asn Ala Leu Ser Pro
150                 155                 160                 165 aca gag aaa ctc ttt ctt acc tac tgc caa tct cat ccg atg aaa cat           643
Thr Glu Lys Leu Phe Leu Thr Tyr Cys Gln Ser His Pro Met Lys His
                170                 175                 180 tta gaa act acg aat ttt ctt tct tct tgg act act gat gca gaa tta           691
Leu Glu Thr Thr Asn Phe Leu Ser Ser Trp Thr Thr Asp Ala Glu Leu
            185                 190                 195 cga cag ttc gtt cat aag caa ggg tta gag ttt tta ggt aaa gca tta           739
Arg Gln Phe Val His Lys Gln Gly Leu Glu Phe Leu Gly Lys Ala Leu
        200                 205                 210 aca aaa gaa aac gct tct ttt cta tgg tat ttt cta cgt agg tta gat           787
Thr Lys Glu Asn Ala Ser Phe Leu Trp Tyr Phe Leu Arg Arg Leu Asp
    215                 220                 225 gtc ggt cga gca tat atc gtc gag cag act tta aaa aca tgg tat gac           835
Val Gly Arg Ala Tyr Ile Val Glu Gln Thr Leu Lys Thr Trp Tyr Asp
230                 235                 240                 245 cat ccc tat gtg gat tat ttt aag tcc cgc cta gaa caa tgc atg aaa           883
His Pro Tyr Val Asp Tyr Phe Lys Ser Arg Leu Glu Gln Cys Met Lys
                250                 255                 260 gtc tta gtg aaa taaagcttt ataagtaaag atttagcttt atacaaagta                935
Val Leu Val Lys
            265 tagaaaaata acacg                                                          950
```

<210> SEQ ID NO 13
<211> LENGTH: 500
<212> TYPE: DNA
<213> ORGANISM: Chlamydia pneumoniae
<220> FEATURE:
<221> NAME/KEY: CDS
<222> LOCATION: (101)..(385)

<400> SEQUENCE: 13

| | |
|---|---|
| cgatttcgtt acctttaaag ttactttga tcgtcatggt agacggatgg acattactgc | 60 |
| tccaagggct tatgatcagc tttaaataag gacacgtgcc atg tta gca ttt ttc<br>　　　　　　　　　　　　　　　　　　　　　　Met Leu Ala Phe Phe<br>　　　　　　　　　　　　　　　　　　　　　　1　　　　　　　　5 | 115 |
| gca act agt ttc aaa tct gtt ctt ttt gag tac tcc tac caa tca tta<br>Ala Thr Ser Phe Lys Ser Val Leu Phe Glu Tyr Ser Tyr Gln Ser Leu<br>　　　　　　　　10　　　　　　　　　　　15　　　　　　　　　　　20 | 163 |
| tta ctt att ttg att gtt tcg gca cct ccc atc atc tta gct tcc ata<br>Leu Leu Ile Leu Ile Val Ser Ala Pro Pro Ile Ile Leu Ala Ser Ile<br>　　　　　25　　　　　　　　　　　30　　　　　　　　　　　35 | 211 |
| gtc ggg att atg gtt gcg atc ttc caa gcc gca aca caa atc caa gaa<br>Val Gly Ile Met Val Ala Ile Phe Gln Ala Ala Thr Gln Ile Gln Glu<br>　　40　　　　　　　　　　　45　　　　　　　　　　　50 | 259 |
| cag acc ttc gct ttt gca gtc aaa cta gtc gtg att ttt gga acc tta<br>Gln Thr Phe Ala Phe Ala Val Lys Leu Val Val Ile Phe Gly Thr Leu<br>55　　　　　　　　　　　60　　　　　　　　　　　65 | 307 |
| atg atc tct gga ggg tgg ctt agc aat atg att tta cgc ttt gca ggt<br>Met Ile Ser Gly Gly Trp Leu Ser Asn Met Ile Leu Arg Phe Ala Gly<br>70　　　　　　　　　　75　　　　　　　　　　　80　　　　　　　　　85 | 355 |
| cag att ttc caa aac ttc tat aaa tgg aaa taaagagctt atgggaatct<br>Gln Ile Phe Gln Asn Phe Tyr Lys Trp Lys<br>　　　　　　　　90　　　　　　　　　　95 | 405 |
| ctctaccaga gcttttttcc aacctaggtt ctgcttactt agattatatc tttcaacatc | 465 |
| ctccggccta tgtttggtca gttttcttc tttta | 500 |

<210> SEQ ID NO 14
<211> LENGTH: 552
<212> TYPE: PRT
<213> ORGANISM: Chlamydia pneumoniae

<400> SEQUENCE: 14

Met Val Ser Ser Pro Ile Leu Asn Val Pro Leu Lys Asn His Ala Ser
1               5                   10                  15

Val Ser Gly Lys Phe Thr His Arg Glu Val Ser Lys Leu Ala Ser Asp
            20                  25                  30

Leu Lys Ser Gly Ala Met Ser Phe Val Pro Glu Val Leu Ser Glu Glu
        35                  40                  45

Thr Ile Ser Ser Asp Leu Gly Lys Lys Gln Cys Thr Gln Gly Ile Ile
    50                  55                  60

Ser Ala Cys Cys Gly Leu Ala Met Leu Ile Val Leu Met Ser Val Tyr
65                  70                  75                  80

Tyr Arg Phe Gly Gly Val Ile Ala Ser Gly Ala Val Leu Leu Asn Leu
                85                  90                  95

Leu Leu Ile Trp Ala Ala Leu Gln Tyr Leu Asp Ala Pro Leu Thr Leu
            100                 105                 110

Ser Gly Leu Ala Gly Ile Val Leu Ala Met Gly Met Ala Val Asp Ala
        115                 120                 125

Asn Val Leu Val Phe Glu Arg Ile Arg Glu Glu Phe Leu Leu Ser Gln
    130                 135                 140

Ser Leu Lys Lys Ser Val Glu Lys Gly Tyr Thr Lys Ala Phe Gly Ala
145                 150                 155                 160

Ile Phe Asp Ser Asn Leu Thr Thr Val Leu Ala Ser Ala Leu Leu Phe
                165                 170                 175

Phe Leu Asp Thr Gly Pro Ile Lys Gly Phe Ala Leu Thr Leu Ile Leu
            180                 185                 190

-continued

```
Gly Ile Phe Ser Ser Met Phe Thr Ala Leu Phe Met Thr Lys Phe Phe
            195                 200                 205

Phe Met Leu Trp Met Asn Lys Thr Gln His Thr Gln Leu His Met Met
        210                 215                 220

Asn Lys Phe Val Gly Ile Lys His Asp Phe Leu Arg Gly Cys Lys Lys
225                 230                 235                 240

Leu Trp Ala Val Ser Gly Ser Val Phe Leu Gly Cys Val Ala Leu
                245                 250                 255

Gly Phe Gly Ala Trp Asn Ser Val Leu Gly Met Asp Phe Lys Gly Gly
                260                 265                 270

Tyr Ala Phe Thr Phe Asn Pro Lys Glu His Gly Ile Ser Asp Val Ala
                275                 280                 285

Gln Met Arg Gly Lys Val Val His Lys Leu Gln Glu Ala Gly Leu Ser
            290                 295                 300

Ser Arg Asp Phe Arg Ile Gln Thr Phe Gly Ser Ser Glu Lys Ile Lys
305                 310                 315                 320

Ile Tyr Phe Ser Asp Lys Ala Leu Ser Tyr Thr Lys Gln Ile Arg Ala
                325                 330                 335

Ser Leu Leu Lys Leu Thr Ile Met Ser Trp Arg Tyr Cys Gly Ile Val
            340                 345                 350

Val Arg Asn Arg Pro Arg Phe Leu Tyr Gly Asn Ser Lys Arg Asn Ala
            355                 360                 365

Lys Phe Trp Ser Lys Val Ser Ser Lys Leu Ser Lys Lys Met Arg Tyr
        370                 375                 380

Gln Ala Thr Ile Gly Leu Leu Gly Ala Leu Ala Ile Ile Leu Leu Tyr
385                 390                 395                 400

Val Ser Leu Arg Phe Glu Trp Gln Tyr Ala Phe Ser Ala Val Cys Ala
                405                 410                 415

Leu Ile His Asp Leu Leu Ala Thr Cys Ala Val Leu Phe Ile Ala His
                420                 425                 430

Phe Phe Leu Lys Lys Ile Gln Ile Asp Leu Gln Ala Ile Gly Ala Leu
            435                 440                 445

Met Thr Val Leu Gly Tyr Ser Leu Asn Asn Thr Leu Ile Ile Phe Asp
        450                 455                 460

Arg Ile Arg Glu Asp Arg Gln Ala Asn Leu Phe Thr Pro Met His Val
465                 470                 475                 480

Leu Val Asn Asp Ala Leu Gln Lys Thr Phe Ser Arg Thr Val Met Thr
                485                 490                 495

Thr Ala Thr Thr Leu Ser Val Leu Leu Met Leu Leu Phe Ile Gly Gly
            500                 505                 510

Ser Ser Val Phe Asn Phe Ala Phe Ile Met Thr Ile Gly Ile Leu Leu
            515                 520                 525

Gly Thr Leu Ser Ser Leu Tyr Ile Ala Pro Pro Leu Leu Leu Phe Met
        530                 535                 540

Val Arg Lys Glu Asn Arg Ser Lys
545                 550
```

<210> SEQ ID NO 15
<211> LENGTH: 196
<212> TYPE: PRT
<213> ORGANISM: Chlamydia pneumoniae

<400> SEQUENCE: 15

```
Met Ser Ser Asn Leu His Pro Val Gly Gly Thr Gly Thr Gly Ala Ala
  1               5                  10                  15
```

-continued

```
Ala Pro Glu Ser Val Leu Asn Ile Val Glu Ile Ala Ala Ser Gly
             20                  25                  30

Ser Val Thr Ala Gly Leu Gln Ala Ile Thr Ser Ser Pro Gly Met Val
         35                  40                  45

Asn Leu Leu Ile Gly Trp Ala Lys Thr Lys Phe Ile Gln Pro Ile Arg
     50                  55                  60

Glu Ser Lys Leu Phe Gln Ser Arg Ala Cys Gln Ile Thr Leu Leu Val
 65                  70                  75                  80

Leu Gly Ile Leu Leu Val Val Ala Gly Leu Ala Cys Met Phe Ile Phe
                 85                  90                  95

His Ser Gln Leu Gly Ala Asn Ala Phe Trp Leu Ile Ile Pro Ala Ala
             100                 105                 110

Ile Gly Leu Ile Lys Leu Leu Val Thr Ser Leu Cys Phe Asp Glu Ala
         115                 120                 125

Cys Thr Ser Glu Lys Leu Met Val Phe Gln Lys Trp Ala Gly Val Leu
    130                 135                 140

Glu Asp Gln Leu Asp Asp Gly Ile Leu Asn Asn Ser Asn Lys Ile Phe
145                 150                 155                 160

Gly His Val Lys Thr Glu Gly Asn Thr Ser Arg Ala Thr Thr Pro Val
                165                 170                 175

Leu Asn Asp Gly Arg Gly Thr Pro Val Leu Ser Pro Leu Val Ser Lys
            180                 185                 190

Ile Ala Arg Val
        195

<210> SEQ ID NO 16
<211> LENGTH: 245
<212> TYPE: PRT
<213> ORGANISM: Chlamydia pneumoniae

<400> SEQUENCE: 16

Met Thr Ile Arg Ile Leu Ala Glu Gly Leu Ala Phe Arg Tyr Gly Ser
  1               5                  10                  15

Lys Gly Pro Asn Ile Ile His Asp Val Ser Phe Ser Val Tyr Asp Gly
             20                  25                  30

Asp Phe Ile Gly Ile Ile Gly Pro Asn Gly Gly Lys Ser Thr Leu
         35                  40                  45

Thr Met Leu Ile Leu Gly Leu Leu Thr Pro Thr Phe Gly Ser Leu Lys
     50                  55                  60

Thr Phe Pro Ser His Ser Ala Gly Lys Gln Thr His Ser Met Ile Gly
 65                  70                  75                  80

Trp Val Pro Gln His Phe Ser Tyr Asp Pro Cys Phe Pro Ile Ser Val
                 85                  90                  95

Lys Asp Val Val Leu Ser Gly Arg Leu Ser Gln Leu Ser Trp His Gly
             100                 105                 110

Lys Tyr Lys Lys Lys Asp Phe Glu Ala Val Asp His Ala Leu Asp Leu
         115                 120                 125

Val Gly Leu Ser Asp Thr Thr Thr Ala Phe Ala His Leu Ser Gly
    130                 135                 140

Gly Gln Ile Gln Arg Val Leu Ala Arg Ala Leu Ala Ser Tyr Pro
145                 150                 155                 160

Glu Ile Leu Ile Leu Asp Glu Pro Thr Asn Ile Asp Pro Asp Asn
                165                 170                 175

Gln Gln Arg Ile Leu Ser Ile Leu Lys Lys Leu Asn Arg Thr Cys Thr
```

```
                  180                 185                 190
Ile Leu Met Val Thr His Asp Leu His His Thr Thr Asn Tyr Phe Asn
            195                 200                 205

Lys Val Phe Tyr Met Asn Lys Thr Leu His Phe Ile Gly Arg His Phe
210                 215                 220

Asp Leu Asn Arg Pro Ile Leu Leu Ser Ser Tyr Lys Asn Gln Glu Phe
225                 230                 235                 240

Ser Cys Ser Pro His
                245

<210> SEQ ID NO 17
<211> LENGTH: 278
<212> TYPE: PRT
<213> ORGANISM: Chlamydia pneumoniae

<400> SEQUENCE: 17

Met His Lys Val Ile Val Phe Ile Phe Leu Thr Leu Tyr Ser Leu Lys
  1               5                  10                  15

Ser Tyr Gly Asn Asp Val Ile Asp Lys Pro His Val Leu Val Ser Ile
             20                  25                  30

Ala Pro Tyr Lys Phe Leu Val Glu Gln Ile Ala Glu Thr Cys Phe
         35                  40                  45

Val Tyr Ala Ile Val Thr Asn His Tyr Asp Pro His Thr Tyr Glu Leu
     50                  55                  60

Pro Pro Gln Gln Ile Lys Glu Leu Arg Gln Gly Asp Leu Trp Phe Arg
 65                  70                  75                  80

Ile Gly Glu Ala Phe Gly Lys Asn Leu Leu Glu Lys Pro Tyr Met Gln
                 85                  90                  95

Gln Val Asp Leu Ser Gln Asn Val Ser Leu Ile Gln Gly Lys Pro Cys
            100                 105                 110

Cys Asn Gln His Thr Thr Asn Tyr Asp Thr His Thr Trp Leu Ser Pro
        115                 120                 125

Lys Asn Leu Lys Val Gln Val Glu Thr Ile Val Thr Thr Leu Ser Lys
    130                 135                 140

Lys Tyr Pro Gln His Ala Thr Leu Tyr Gln Ser Asn Gly Glu Lys Leu
145                 150                 155                 160

Leu Leu Ala Leu Asp Gln Leu Asn Glu Glu Ile Leu Thr Ile Thr Ser
                165                 170                 175

Lys Ala Lys Gln Arg His Ile Leu Val Ser His Gly Ala Phe Gly Tyr
            180                 185                 190

Phe Cys Arg Asp Tyr Asn Phe Ser Gln His Thr Ile Glu Lys Ser Ser
        195                 200                 205

His Val Glu Pro Ser Pro Lys Asp Val Ala Arg Val Phe Arg Asp Ile
    210                 215                 220

Glu Gln Tyr Lys Ile Ser Ser Val Ile Leu Leu Glu Tyr Ser Gly Arg
225                 230                 235                 240

Arg Ser Ser Ala Met Leu Ala Asp Arg Phe His Met His Thr Val Asn
                245                 250                 255

Leu Asp Pro Tyr Ala Glu Asn Val Leu Val Asn Leu Lys Thr Ile Ala
            260                 265                 270

Thr Thr Phe Ser Ser Leu
        275

<210> SEQ ID NO 18
<211> LENGTH: 469
```

<212> TYPE: PRT
<213> ORGANISM: Chlamydia pneumoniae

<400> SEQUENCE: 18

```
Met Gly Pro Gly Ser Val Leu Ser Asn His Ser Lys Glu Ala Gly Gly
 1               5                  10                  15

Ile Ala Ile Asn Asn Val Ile Ile Asp Phe Ser Glu Ile Val Pro Thr
            20                  25                  30

Lys Asp Asn Ala Thr Val Ala Pro Thr Leu Lys Leu Val Ser Arg
        35                  40                  45

Thr Asn Ala Asp Ser Lys Asp Lys Ile Asp Ile Thr Gly Thr Val Thr
    50                  55                  60

Leu Leu Asp Pro Asn Gly Asn Leu Tyr Gln Asn Ser Tyr Leu Gly Glu
65                  70                  75                  80

Asp Arg Asp Ile Thr Leu Phe Asn Ile Asp Asn Ser Ala Ser Gly Ala
                85                  90                  95

Val Thr Ala Thr Asn Val Thr Leu Gln Gly Asn Leu Ala Lys Lys
            100                 105                 110

Gly Tyr Leu Gly Thr Trp Asn Leu Asp Pro Asn Ser Ser Gly Ser Lys
        115                 120                 125

Ile Ile Leu Lys Trp Thr Phe Asp Lys Tyr Leu Arg Trp Pro Tyr Ile
130                 135                 140

Pro Arg Asp Asn His Phe Tyr Ile Asn Ser Ile Trp Gly Ala Gln Asn
145                 150                 155                 160

Ser Leu Val Thr Val Asn Gln Gly Ile Leu Gly Asn Met Leu Asn Asn
                165                 170                 175

Ala Arg Phe Glu Asp Pro Ala Phe Asn Asn Phe Trp Ala Ser Ala Ile
            180                 185                 190

Gly Ser Phe Leu Arg Lys Glu Val Ser Arg Asn Ser Asp Ser Phe Thr
        195                 200                 205

Tyr His Gly Arg Gly Tyr Thr Ala Ala Val Asp Ala Lys Pro Arg Gln
    210                 215                 220

Glu Phe Ile Leu Gly Ala Ala Phe Ser Gln Val Phe Gly His Ala Glu
225                 230                 235                 240

Ser Glu Tyr His Leu Asp Asn Tyr Lys His Lys Gly Ser Gly His Ser
                245                 250                 255

Thr Gln Ala Ser Leu Tyr Ala Gly Asn Ile Phe Tyr Phe Pro Ala Ile
            260                 265                 270

Arg Ser Arg Pro Ile Leu Phe Gln Gly Val Ala Thr Tyr Gly Tyr Met
        275                 280                 285

Gln His Asp Thr Thr Thr Tyr Tyr Pro Ser Ile Glu Glu Lys Asn Met
    290                 295                 300

Ala Asn Trp Asp Ser Ile Ala Trp Leu Phe Asp Leu Arg Phe Ser Val
305                 310                 315                 320

Asp Leu Lys Glu Pro Gln Pro His Ser Thr Ala Arg Leu Thr Phe Tyr
                325                 330                 335

Thr Glu Ala Glu Tyr Thr Arg Ile Arg Gln Glu Lys Phe Thr Glu Leu
            340                 345                 350

Asp Tyr Asp Pro Arg Ser Phe Ser Ala Cys Ser Tyr Gly Asn Leu Ala
        355                 360                 365

Ile Pro Thr Gly Phe Ser Val Asp Gly Ala Leu Ala Trp Arg Glu Ile
    370                 375                 380

Ile Leu Tyr Asn Lys Val Ser Ala Ala Tyr Leu Pro Val Ile Leu Arg
385                 390                 395                 400
```

```
Asn Asn Pro Lys Ala Thr Tyr Glu Val Leu Ser Thr Lys Lys Gly
            405                 410                 415

Asn Val Val Asn Val Leu Pro Thr Arg Asn Ala Ala Arg Ala Glu Val
            420                 425                 430

Ser Ser Gln Ile Tyr Leu Gly Ser Tyr Trp Thr Leu Tyr Gly Thr Tyr
            435                 440                 445

Thr Ile Asp Ala Ser Met Asn Thr Leu Val Gln Met Ala Asn Gly Gly
            450                 455                 460

Ile Arg Phe Val Phe
465

<210> SEQ ID NO 19
<211> LENGTH: 922
<212> TYPE: PRT
<213> ORGANISM: Chlamydia pneumoniae

<400> SEQUENCE: 19

Met Arg Phe Ser Leu Cys Gly Phe Pro Leu Val Ser Phe Thr Leu
  1               5                  10                  15

Leu Ser Val Phe Asp Thr Ser Leu Ser Ala Thr Thr Ile Ser Leu Thr
             20                  25                  30

Pro Glu Asp Ser Phe His Gly Asp Ser Gln Asn Ala Glu Arg Ser Tyr
             35                  40                  45

Asn Val Gln Ala Gly Asp Val Tyr Ser Leu Thr Gly Asp Val Ser Ile
 50                  55                  60

Ser Asn Val Asp Asn Ser Ala Leu Asn Lys Ala Cys Phe Asn Val Thr
 65                  70                  75                  80

Ser Gly Ser Val Thr Phe Ala Gly Asn His His Gly Leu Tyr Phe Asn
             85                  90                  95

Asn Ile Ser Ser Gly Thr Thr Lys Glu Gly Ala Val Leu Cys Cys Gln
            100                 105                 110

Asp Pro Gln Ala Thr Ala Arg Phe Ser Gly Phe Ser Thr Leu Ser Phe
            115                 120                 125

Ile Gln Ser Pro Gly Asp Ile Lys Glu Gln Gly Cys Leu Tyr Ser Lys
            130                 135                 140

Asn Ala Leu Met Leu Leu Asn Asn Tyr Val Val Arg Phe Glu Gln Asn
145                 150                 155                 160

Gln Ser Lys Thr Lys Gly Gly Ala Ile Ser Gly Ala Asn Val Thr Ile
            165                 170                 175

Val Gly Asn Tyr Asp Ser Val Ser Phe Tyr Gln Asn Ala Ala Thr Phe
            180                 185                 190

Gly Gly Ala Ile His Ser Ser Gly Pro Leu Gln Ile Ala Val Asn Gln
            195                 200                 205

Ala Glu Ile Arg Phe Ala Gln Asn Thr Ala Lys Asn Gly Ser Gly Gly
            210                 215                 220

Ala Leu Tyr Ser Asp Gly Asp Ile Asp Ile Asp Gln Asn Ala Tyr Val
225                 230                 235                 240

Leu Phe Arg Glu Asn Glu Ala Leu Thr Thr Ala Ile Gly Lys Gly Gly
            245                 250                 255

Ala Val Cys Cys Leu Pro Thr Ser Gly Ser Thr Pro Val Pro Ile
            260                 265                 270

Val Thr Phe Ser Asp Asn Lys Gln Leu Val Phe Glu Arg Asn His Ser
            275                 280                 285

Ile Met Gly Gly Gly Ala Ile Tyr Ala Arg Lys Leu Ser Ile Ser Ser
```

-continued

```
                290                 295                 300
Gly Gly Pro Thr Leu Phe Ile Asn Asn Ile Ser Tyr Ala Asn Ser Gln
305                 310                 315                 320

Asn Leu Gly Gly Ala Ile Ala Ile Asp Thr Gly Gly Glu Ile Ser Leu
                325                 330                 335

Ser Ala Glu Lys Gly Thr Ile Thr Phe Gln Gly Asn Arg Thr Ser Leu
                340                 345                 350

Pro Phe Leu Asn Gly Ile His Leu Leu Gln Asn Ala Lys Phe Leu Lys
                355                 360                 365

Leu Gln Ala Arg Asn Gly Tyr Ser Ile Glu Phe Tyr Asp Pro Ile Thr
370                 375                 380

Ser Glu Ala Asp Gly Ser Thr Gln Leu Asn Ile Asn Gly Asp Pro Lys
385                 390                 395                 400

Asn Lys Glu Tyr Thr Gly Thr Ile Leu Phe Ser Gly Glu Lys Ser Leu
                405                 410                 415

Ala Asn Asp Pro Arg Asp Phe Lys Ser Thr Ile Pro Gln Asn Val Asn
                420                 425                 430

Leu Ser Ala Gly Tyr Leu Val Ile Lys Glu Gly Ala Glu Val Thr Val
                435                 440                 445

Ser Lys Phe Thr Gln Ser Pro Gly Ser His Leu Val Leu Asp Leu Gly
                450                 455                 460

Thr Lys Leu Ile Ala Ser Lys Glu Asp Ile Ala Ile Thr Gly Leu Ala
465                 470                 475                 480

Ile Asp Ile Asp Ser Leu Ser Ser Ser Thr Ala Ala Val Ile Lys
                485                 490                 495

Ala Asn Thr Ala Asn Lys Gln Ile Ser Val Thr Asp Ser Ile Glu Leu
                500                 505                 510

Ile Ser Pro Thr Gly Asn Ala Tyr Glu Asp Leu Arg Met Arg Asn Ser
                515                 520                 525

Gln Thr Phe Pro Leu Leu Ser Leu Glu Pro Gly Ala Gly Gly Ser Val
                530                 535                 540

Thr Val Thr Ala Gly Asp Phe Leu Pro Val Ser Pro His Tyr Gly Phe
545                 550                 555                 560

Gln Gly Asn Trp Lys Leu Ala Trp Thr Gly Thr Gly Asn Lys Val Gly
                565                 570                 575

Glu Phe Phe Trp Asp Lys Ile Asn Tyr Lys Pro Arg Pro Glu Lys Glu
                580                 585                 590

Gly Asn Leu Val Pro Asn Ile Leu Trp Gly Asn Ala Val Asp Val Arg
                595                 600                 605

Ser Leu Met Gln Val Gln Glu Thr His Ala Ser Ser Leu Gln Thr Asp
610                 615                 620

Arg Gly Leu Trp Ile Asp Gly Ile Gly Asn Phe Phe His Val Ser Ala
625                 630                 635                 640

Ser Glu Asp Asn Ile Arg Tyr Arg His Asn Ser Gly Gly Tyr Val Leu
                645                 650                 655

Ser Val Asn Asn Glu Ile Thr Pro Lys His Tyr Thr Ser Met Ala Phe
                660                 665                 670

Ser Gln Leu Phe Ser Arg Asp Lys Asp Tyr Ala Val Ser Asn Asn Glu
                675                 680                 685

Tyr Arg Met Tyr Leu Gly Ser Tyr Leu Tyr Gln Tyr Thr Thr Ser Leu
                690                 695                 700

Gly Asn Ile Phe Arg Tyr Ala Ser Arg Asn Pro Asn Val Asn Val Gly
705                 710                 715                 720
```

```
Ile Leu Ser Arg Arg Phe Leu Gln Asn Pro Leu Met Ile Phe His Phe
                725                 730                 735

Leu Cys Ala Tyr Gly His Ala Thr Asn Asp Met Lys Thr Asp Tyr Ala
            740                 745                 750

Asn Phe Pro Met Val Lys Asn Ser Trp Arg Asn Asn Cys Trp Ala Ile
        755                 760                 765

Glu Cys Gly Gly Ser Met Pro Leu Leu Val Phe Glu Asn Gly Arg Leu
    770                 775                 780

Phe Gln Gly Ala Ile Pro Phe Met Lys Leu Gln Leu Val Tyr Ala Tyr
785                 790                 795                 800

His Gly Asp Phe Lys Glu Thr Thr Ala Asp Gly Arg Arg Phe Ser Asn
                805                 810                 815

Gly Ser Leu Thr Ser Ile Ser Val Pro Leu Gly Ile Arg Phe Glu Lys
            820                 825                 830

Leu Ala Leu Ser Gln Asp Val Leu Tyr Asp Phe Ser Phe Ser Tyr Ile
        835                 840                 845

Pro Asp Ile Phe Arg Lys Asp Pro Ser Cys Glu Ala Ala Leu Val Ile
    850                 855                 860

Ser Gly Asp Ser Trp Leu Val Pro Ala Ala His Val Ser Arg His Ala
865                 870                 875                 880

Phe Val Gly Ser Gly Thr Gly Arg Tyr His Phe Asn Asp Tyr Thr Glu
                885                 890                 895

Leu Leu Cys Arg Gly Ser Ile Glu Cys Arg Pro His Ala Arg Asn Tyr
            900                 905                 910

Asn Ile Asn Cys Gly Ser Lys Phe Arg Phe
        915                 920

<210> SEQ ID NO 20
<211> LENGTH: 375
<212> TYPE: PRT
<213> ORGANISM: Chlamydia pneumoniae

<400> SEQUENCE: 20

Met Pro Ser Ser Trp Lys Arg Leu Leu Gln Val Leu Ser His Lys Ile
1               5                   10                  15

Ala Ala Thr Glu Ser Gly Gly Ile Tyr Ala Lys Asp Ile Gln Leu
            20                  25                  30

Gln Ala Leu Pro Gly Ser Phe Thr Ile Thr Asp Asn Lys Val Glu Thr
        35                  40                  45

Ser Leu Thr Thr Ser Thr Asn Leu Tyr Gly Gly Ile Tyr Ser Ser
    50                  55                  60

Gly Ala Val Thr Leu Thr Asn Ile Ser Gly Thr Phe Gly Ile Thr Gly
65                  70                  75                  80

Asn Ser Val Ile Asn Thr Ala Thr Ser Gln Asp Ala Asp Ile Gln Gly
                85                  90                  95

Gly Gly Ile Tyr Ala Thr Thr Ser Leu Ser Ile Asn Gln Cys Asn Thr
            100                 105                 110

Pro Ile Leu Phe Ser Asn Asn Ser Ala Ala Thr Lys Lys Thr Ser Thr
        115                 120                 125

Thr Lys Gln Ile Ala Gly Gly Ala Ile Phe Ser Ala Ala Val Thr Ile
    130                 135                 140

Glu Asn Asn Ser Gln Pro Ile Ile Phe Leu Asn Asn Ser Ala Lys Ser
145                 150                 155                 160

Glu Ala Thr Thr Ala Ala Thr Ala Gly Asn Lys Asp Ser Cys Gly Gly
```

-continued

```
                    165                 170                 175
Ala Ile Ala Ala Asn Ser Val Thr Leu Thr Asn Asn Pro Glu Ile Thr
            180                 185                 190

Phe Lys Gly Asn Tyr Ala Glu Thr Gly Gly Ala Ile Gly Cys Ile Asp
        195                 200                 205

Leu Thr Asn Gly Ser Pro Pro Arg Lys Val Ser Ile Ala Asp Asn Gly
    210                 215                 220

Ser Val Leu Phe Gln Asp Asn Ser Ala Leu Asn Arg Gly Gly Ala Ile
225                 230                 235                 240

Tyr Gly Glu Thr Ile Asp Ile Ser Arg Thr Gly Ala Thr Phe Ile Gly
                245                 250                 255

Asn Ser Ser Lys His Asp Gly Ser Ala Ile Cys Cys Ser Thr Ala Leu
            260                 265                 270

Thr Leu Ala Pro Asn Ser Gln Leu Ile Phe Glu Asn Asn Lys Val Thr
        275                 280                 285

Glu Thr Thr Ala Thr Thr Lys Ala Ser Ile Asn Asn Leu Gly Ala Ala
    290                 295                 300

Ile Tyr Gly Asn Asn Glu Thr Ser Asp Val Thr Ile Ser Leu Ser Ala
305                 310                 315                 320

Glu Asn Gly Ser Ile Phe Phe Lys Asn Asn Leu Cys Thr Ala Thr Asn
                325                 330                 335

Lys Tyr Cys Ser Ile Ala Gly Asn Val Lys Phe Thr Ala Ile Glu Ala
            340                 345                 350

Ser Ala Gly Lys Ala Ile Ser Phe Tyr Asp Ala Val Asn Val Pro Pro
        355                 360                 365

Lys Lys Gln Leu Leu Lys Ser
    370                 375

<210> SEQ ID NO 21
<211> LENGTH: 871
<212> TYPE: PRT
<213> ORGANISM: Chlamydia pneumoniae

<400> SEQUENCE: 21

Met Lys Tyr Ser Leu Pro Trp Leu Leu Thr Ser Ser Ala Leu Val Phe
1               5                   10                  15

Ser Leu His Pro Leu Met Ala Ala Asn Thr Asp Leu Ser Ser Ser Asp
            20                  25                  30

Asn Tyr Glu Asn Gly Ser Ser Gly Ser Ala Ala Phe Thr Ala Lys Glu
        35                  40                  45

Thr Ser Asp Ala Ser Gly Thr Thr Tyr Thr Leu Thr Ser Asp Val Ser
    50                  55                  60

Ile Thr Asn Val Ser Ala Ile Thr Pro Ala Asp Lys Ser Cys Phe Thr
65                  70                  75                  80

Asn Thr Gly Gly Ala Leu Ser Phe Val Gly Ala Asp His Ser Leu Val
                85                  90                  95

Leu Gln Thr Ile Ala Leu Thr His Asp Gly Ala Ala Ile Asn Asn Thr
            100                 105                 110

Asn Thr Ala Leu Ser Phe Ser Gly Phe Ser Ser Leu Leu Ile Asp Ser
        115                 120                 125

Ala Pro Ala Thr Gly Thr Ser Gly Gly Lys Gly Ala Ile Cys Val Thr
    130                 135                 140

Asn Thr Glu Gly Gly Thr Ala Thr Phe Thr Asp Asn Ala Ser Val Thr
145                 150                 155                 160
```

-continued

```
Leu Gln Lys Asn Thr Ser Glu Lys Asp Gly Ala Ala Val Ser Ala Tyr
                165                 170                 175

Ser Ile Asp Leu Ala Lys Thr Thr Ala Ala Leu Leu Asp Gln Asn
            180                 185                 190

Thr Ser Thr Lys Asn Gly Gly Ala Leu Cys Ser Thr Ala Asn Thr Thr
        195                 200                 205

Val Gln Gly Asn Ser Gly Thr Val Thr Phe Ser Ser Asn Thr Ala Thr
    210                 215                 220

Asp Lys Gly Gly Gly Ile Tyr Ser Lys Glu Lys Asp Ser Thr Leu Asp
225                 230                 235                 240

Ala Asn Thr Gly Val Val Thr Phe Lys Ser Asn Thr Ala Lys Thr Gly
                245                 250                 255

Gly Ala Trp Ser Ser Asp Asp Asn Leu Ala Leu Thr Gly Asn Thr Gln
            260                 265                 270

Val Leu Phe Gln Glu Asn Lys Thr Thr Gly Ser Ala Ala Gln Ala Asn
        275                 280                 285

Asn Pro Glu Gly Cys Gly Gly Ala Ile Cys Cys Tyr Leu Ala Thr Ala
    290                 295                 300

Thr Asp Lys Thr Gly Leu Ala Ile Ser Gln Asn Gln Glu Met Ser Phe
305                 310                 315                 320

Thr Ser Asn Thr Thr Thr Ala Asn Gly Gly Ala Ile Tyr Ala Thr Lys
                325                 330                 335

Cys Thr Leu Asp Gly Asn Thr Thr Leu Thr Phe Asp Gln Asn Thr Ala
            340                 345                 350

Thr Ala Gly Cys Gly Gly Ala Ile Tyr Thr Glu Thr Glu Asp Phe Ser
        355                 360                 365

Leu Lys Gly Ser Thr Gly Thr Val Thr Phe Ser Thr Asn Thr Ala Lys
    370                 375                 380

Thr Gly Gly Ala Leu Tyr Ser Lys Gly Asn Ser Ser Leu Thr Gly Asn
385                 390                 395                 400

Thr Asn Leu Leu Phe Ser Gly Asn Lys Ala Thr Gly Pro Ser Asn Ser
                405                 410                 415

Ser Ala Asn Gln Glu Gly Cys Gly Gly Ala Ile Leu Ala Phe Ile Asp
            420                 425                 430

Ser Gly Ser Val Ser Asp Lys Thr Gly Leu Ser Ile Ala Asn Asn Gln
        435                 440                 445

Glu Val Ser Leu Thr Ser Asn Ala Ala Thr Val Ser Gly Gly Ala Ile
    450                 455                 460

Tyr Ala Thr Lys Cys Thr Leu Thr Gly Asn Gly Ser Leu Thr Phe Asp
465                 470                 475                 480

Gly Asn Thr Ala Gly Thr Ser Gly Gly Ala Ile Tyr Thr Glu Thr Glu
                485                 490                 495

Asp Phe Thr Leu Thr Gly Ser Thr Gly Thr Val Thr Phe Ser Thr Asn
            500                 505                 510

Thr Ala Lys Thr Gly Gly Ala Leu Tyr Ser Lys Gly Asn Asn Ser Leu
        515                 520                 525

Ser Gly Asn Thr Asn Leu Leu Phe Ser Gly Asn Lys Ala Thr Gly Pro
    530                 535                 540

Ser Asn Ser Ser Ala Asn Gln Glu Gly Cys Gly Gly Ala Ile Leu Ser
545                 550                 555                 560

Phe Leu Glu Ser Ala Ser Val Ser Thr Lys Lys Gly Leu Trp Ile Glu
                565                 570                 575

Asp Asn Glu Asn Val Ser Leu Ser Gly Asn Thr Ala Thr Val Ser Gly
```

```
                    580             585                 590
Gly Ala Ile Tyr Ala Thr Lys Cys Ala Leu His Gly Asn Thr Thr Leu
            595                 600             605

Thr Phe Asp Gly Asn Thr Ala Glu Thr Ala Gly Gly Ala Ile Tyr Thr
            610                 615             620

Glu Thr Glu Asp Phe Thr Leu Thr Gly Ser Thr Gly Thr Val Thr Phe
625             630                 635                 640

Ser Thr Asn Thr Ala Lys Thr Ala Gly Ala Leu His Thr Lys Gly Asn
            645                 650             655

Thr Ser Phe Thr Lys Asn Lys Ala Leu Val Phe Ser Gly Asn Ser Ala
            660                 665             670

Thr Ala Thr Ala Thr Thr Thr Asp Gln Glu Gly Cys Gly Gly Ala
            675                 680             685

Ile Leu Cys Asn Ile Ser Glu Ser Asp Ile Ala Thr Lys Ser Leu Thr
            690                 695             700

Leu Thr Glu Asn Glu Ser Leu Ser Phe Ile Asn Asn Thr Ala Lys Arg
705             710                 715                 720

Ser Gly Gly Gly Ile Tyr Ala Pro Lys Cys Val Ile Ser Gly Ser Glu
            725                 730             735

Ser Ile Asn Phe Asp Gly Asn Thr Ala Glu Thr Ser Gly Gly Ala Ile
            740                 745             750

Tyr Ser Lys Asn Leu Ser Ile Thr Ala Asn Gly Pro Val Ser Phe Thr
            755                 760             765

Asn Asn Ser Gly Gly Lys Gly Gly Ala Ile Tyr Ile Ala Asp Ser Gly
            770                 775             780

Glu Leu Ser Leu Glu Ala Ile Asp Gly Asp Ile Thr Phe Ser Gly Asn
785             790                 795                 800

Arg Ala Thr Glu Gly Thr Ser Thr Pro Asn Ser Ile His Leu Gly Ala
            805                 810             815

Arg Gly Lys Ile Thr Lys Leu Ala Ala Ala Pro Gly His Thr Ile Tyr
            820                 825             830

Phe Tyr Asp Pro Ile Thr Met Glu Ala Pro Ala Ser Gly Gly Thr Ile
            835                 840             845

Glu Glu Leu Val Ile Asn Pro Val Val Lys Ala Ile Val Pro Pro Pro
850             855                 860

Gln Pro Lys Asn Gly Pro Ile
865             870
```

<210> SEQ ID NO 22
<211> LENGTH: 963
<212> TYPE: PRT
<213> ORGANISM: Chlamydia pneumoniae

<400> SEQUENCE: 22

```
Met Thr Asn Ser Ile Phe Ile Ser Lys Phe Gly Cys Leu Cys Asp Pro
  1               5                  10                  15

Phe Val Ser Ala Phe Tyr Pro Thr Ala Leu Cys Cys Ser Leu Ser Gly
             20                  25                  30

Asn Glu Val Pro Asn Leu Ala Ser Cys Gln Met Ser Arg Lys Asp Ile
         35                  40                  45

Ser Ala Phe His Thr Ser Pro Ser Phe Arg Leu Asn Val Thr Pro Glu
     50                  55                  60

Pro Leu Val Ser Ser Phe Arg Pro Ser Asn Leu Leu Asn Gly Phe Gly
 65                  70                  75                  80
```

-continued

```
His Asp Ile Thr Gln Asp Ile Thr Ile Thr Gly Asn Ser Ile Asn Ser
                85                  90                  95

Val Ile Asp Tyr Asn Tyr His Tyr Glu Asp Gly Ile Leu Ala Cys
            100                 105                 110

Lys Asn Leu Phe Ile Ser Glu Asn Lys Gly Asn Leu Ser Phe Glu Arg
                115                 120                 125

Asn Ser Ser His Ser Ser Gly Gly Ala Leu Tyr Ser Val Arg Glu Cys
130                 135                 140

Trp Ile Ser Lys Asn Gln Asn Tyr Ser Phe Ile Ser Asn Ala Ala Ser
145                 150                 155                 160

Leu Ala Thr Thr Thr Ser Gly Phe Gly Ala Ile His Ala Leu
                165                 170                 175

Asp Ser Tyr Ile Thr Asn Asn Leu Gly Glu Gly Gln Phe Leu Asp Asn
            180                 185                 190

Val Ser Lys Asn Arg Gly Gly Ala Ile Tyr Val Gly Val Ser Leu Ser
            195                 200                 205

Ile Thr Asp Asn Leu Gly Pro Ile Val Ile Lys Lys Asn Gln Thr Leu
            210                 215                 220

Glu Asp Ser Ser Phe Gly Gly Gly Ile Phe Cys Arg Ala Val Asn Ile
225                 230                 235                 240

Glu Arg Asn Tyr Gln Asn Ile Gln Ile Asn Asp Asn Ala Ser Gly Gln
                245                 250                 255

Gly Val Val Tyr Phe Leu Pro Leu Gly Val Ile Ile Ser Ser Asn Lys
            260                 265                 270

Glu Ile Ile Glu Ile Ser Asn His Ser Ala Ser Ile Asn Thr Ala
            275                 280                 285

Ser Gly Lys Leu Tyr Pro Gly Gly Gly Ile Met Cys Thr Ser Leu
290                 295                 300

Ser His Glu Asn Asn Pro Lys Gly Leu Ile Phe Asn Asn Lys Thr Ala
305                 310                 315                 320

Ala Leu Ser Gly Gly Val Tyr Thr Arg Asp Leu Ser Ser Lys Ile
            325                 330                 335

Thr Val Arg Thr Ala Phe Ile Asn Asn Ser Ala Thr Ser Gly Gly Ala
            340                 345                 350

Leu Ile Asn Leu Ser Gly Ile Gly Ser Thr Pro Gln Asn Phe Phe Leu
            355                 360                 365

Ser Ala Asp Tyr Gly Asp Ile Leu Phe Asn Asn Thr Ile Thr Ser
370                 375                 380

Ser Ser Pro Gln Pro Gly Tyr Arg Asn Ala Leu Tyr Ala Ala Pro Gly
385                 390                 395                 400

Ile Asn Leu Lys Leu Gly Ala Arg Gln Gly Tyr Lys Ile Leu Phe Tyr
                405                 410                 415

Asp Pro Ile Asp His Asp Gln Thr Thr Thr Asp Pro Ile Val Phe Asn
            420                 425                 430

Tyr Glu Pro His His Leu Gly Thr Val Leu Phe Ser Gly Ile Asn Val
            435                 440                 445

Asp Ser Asn Ala Thr Asn Pro Leu Asn Phe Leu Ser Lys Phe Ser Asn
            450                 455                 460

Ser Ser Arg Leu Glu Arg Gly Val Leu Ala Ile Glu Asp Arg Ala Ala
465                 470                 475                 480

Ile Ser Cys Lys Thr Leu Ser Gln Gly Gly Ile Leu Arg Leu Gly
            485                 490                 495

Asn Ala Ala Leu Ile Arg Thr Lys Gly Pro Gly Ser Ser Ile Asn Phe
```

```
                500             505             510
Asn Ala Ile Ala Ile Asn Leu Pro Ser Ile Leu Gln Ser Glu Ala Ser
            515                 520                 525
Ala Pro Lys Phe Trp Ile Tyr Pro Thr Leu Thr Gly Ser Thr Tyr Ser
        530                 535                 540
Glu Asp Thr Ser Ser Thr Ile Thr Leu Ser Gly Pro Leu Thr Phe Leu
545                 550                 555                 560
Asn Asp Glu Asn Glu Asn Pro Tyr Asp Ser Leu Asp Leu Ser Glu Pro
                565                 570                 575
Arg Lys Asp Ile Pro Pro Leu Pro Pro Arg Cys Asp Cys Lys Lys
            580                 585                 590
Ile Asp Thr Ser Asn Leu Ile Val Glu Ala Met Asn Leu Asp Glu His
        595                 600                 605
Tyr Gly Tyr Gln Gly Ile Trp Ser Pro Tyr Trp Met Glu Thr Thr Thr
    610                 615                 620
Thr Thr Ser Ser Thr Val Pro Glu Gln Thr Thr Asn His Arg Gln
625                 630                 635                 640
Leu Tyr Val Asp Trp Thr Pro Val Gly Tyr Arg Pro Asn Pro Glu Arg
                645                 650                 655
His Gly Glu Phe Ile Ala Asn Thr Leu Trp Gln Ser Ala Tyr Asn Ala
            660                 665                 670
Leu Leu Gly Ile Arg Ile Leu Pro Pro Gln Asn Leu Lys Glu His Asp
        675                 680                 685
Leu Glu Ala Ser Leu Gln Gly Leu Gly Leu Leu Ile Asn Gln His Asn
    690                 695                 700
Arg Glu Gly Arg Lys Gly Phe Arg Asn His Thr Thr Gly Tyr Ala Ala
705                 710                 715                 720
Thr Thr Ser Ala Lys Thr Ala Ala Arg His Ser Phe Ser Leu Gly Phe
                725                 730                 735
Ala Gln Met Phe Ser Lys Thr Arg Glu Arg Gln Ser Pro Ser Thr Thr
            740                 745                 750
Ser Ser His Asn Tyr Phe Ala Gly Leu Arg Phe Asp Ser Leu Leu Phe
        755                 760                 765
Arg Asp Phe Ile Ser Thr Gly Leu Ser Leu Gly Tyr Ser Tyr Gly Asp
    770                 775                 780
His His Met Leu Cys His Tyr Thr Glu Ile Leu Lys Gly Ser Ser Lys
785                 790                 795                 800
Ala Phe Phe Asn Asn His Thr Leu Val Ala Ser Leu Asp Cys Thr Phe
                805                 810                 815
Leu Pro Ala Arg Ile Thr Arg Thr Leu Glu Leu Gln Pro Phe Ile Ser
            820                 825                 830
Ala Ile Ala Leu Arg Cys Ser Gln Ala Ser Phe Gln Glu Thr Gly Asp
        835                 840                 845
His Ile Arg Lys Phe His Pro Lys His Pro Leu Thr Asp Leu Ser Ser
    850                 855                 860
Pro Ile Gly Phe Arg Ser Glu Trp Lys Thr Ser His His Ile Pro Met
865                 870                 875                 880
Leu Trp Thr Thr Glu Ile Ser Tyr Val Pro Thr Leu Tyr Arg Lys Asn
                885                 890                 895
Pro Glu Met Phe Thr Thr Leu Leu Ile Ser Asn Gly Thr Trp Thr Thr
            900                 905                 910
Gln Ala Thr Pro Val Ser Tyr Asn Ser Val Ala Ala Lys Ile Lys Asn
        915                 920                 925
```

```
Thr Ser Gln Leu Phe Ser Arg Val Thr Leu Ser Leu Asp Tyr Ser Ala
    930                 935                 940

Gln Val Ser Ser Thr Val Gly Gln Tyr Leu Lys Ala Glu Ser His
945                 950                 955                 960

Cys Thr Phe

<210> SEQ ID NO 23
<211> LENGTH: 514
<212> TYPE: PRT
<213> ORGANISM: Chlamydia pneumoniae

<400> SEQUENCE: 23

Met Thr Ile Leu Arg Asn Phe Leu Thr Cys Ser Ala Leu Phe Leu Ala
  1               5                  10                  15

Leu Pro Ala Ala Ala Gln Val Val Tyr Leu His Glu Ser Asp Gly Tyr
                 20                  25                  30

Asn Gly Ala Ile Asn Asn Lys Ser Leu Glu Pro Lys Ile Thr Cys Tyr
             35                  40                  45

Pro Glu Gly Thr Ser Tyr Ile Phe Leu Asp Asp Val Arg Ile Ser Asn
 50                  55                  60

Val Lys His Asp Gln Glu Asp Ala Gly Val Phe Ile Asn Arg Ser Gly
 65                  70                  75                  80

Asn Leu Phe Phe Met Gly Asn Arg Cys Asn Phe Thr Phe His Asn Leu
                 85                  90                  95

Met Thr Glu Gly Phe Gly Ala Ala Ile Ser Asn Arg Val Gly Asp Thr
            100                 105                 110

Thr Leu Thr Leu Ser Asn Phe Ser Tyr Leu Ala Phe Thr Ser Ala Pro
        115                 120                 125

Leu Leu Pro Gln Gly Gln Gly Ala Ile Tyr Ser Leu Gly Ser Val Met
130                 135                 140

Ile Glu Asn Ser Glu Glu Val Thr Phe Cys Gly Asn Tyr Ser Ser Trp
145                 150                 155                 160

Ser Gly Ala Ala Ile Tyr Thr Pro Tyr Leu Leu Gly Ser Lys Ala Ser
                165                 170                 175

Arg Pro Ser Val Asn Leu Ser Gly Asn Arg Tyr Leu Val Phe Arg Asp
            180                 185                 190

Asn Val Ser Gln Val Tyr Gly Gly Ala Ile Ser Thr His Asn Leu Thr
        195                 200                 205

Leu Thr Thr Arg Gly Pro Ser Cys Phe Glu Asn Asn His Ala Tyr His
    210                 215                 220

Asp Val Asn Ser Asn Gly Gly Ala Ile Ala Ile Ala Pro Gly Gly Ser
225                 230                 235                 240

Ile Ser Ile Ser Val Lys Ser Gly Asp Leu Ile Phe Lys Gly Asn Thr
                245                 250                 255

Ala Ser Gln Asp Gly Asn Thr Ile His Asn Ser Ile His Leu Gln Ser
            260                 265                 270

Gly Ala Gln Phe Lys Asn Leu Arg Ala Val Ser Glu Ser Gly Val Tyr
        275                 280                 285

Phe Tyr Asp Pro Ile Ser His Ser Glu Ser His Lys Ile Thr Asp Leu
    290                 295                 300

Val Ile Asn Ala Pro Glu Gly Lys Glu Thr Tyr Glu Gly Thr Ile Ser
305                 310                 315                 320

Phe Ser Gly Leu Cys Leu Asp Asp His Glu Val Cys Ala Glu Asn Leu
                325                 330                 335
```

-continued

```
Thr Ser Thr Ile Leu Gln Asp Val Thr Leu Ala Gly Gly Thr Leu Ser
            340                 345                 350

Leu Ser Asp Gly Val Thr Leu Gln Leu His Ser Phe Lys Gln Glu Ala
            355                 360                 365

Ser Ser Thr Leu Thr Met Ser Pro Gly Thr Thr Leu Leu Cys Ser Gly
            370                 375                 380

Asp Ala Arg Val Gln Asn Leu His Ile Leu Ile Glu Asp Thr Asp Asn
385                 390                 395                 400

Phe Val Pro Val Arg Ile Arg Ala Glu Asp Lys Asp Ala Leu Val Ser
                405                 410                 415

Leu Glu Lys Leu Lys Val Ala Phe Glu Ala Tyr Trp Ser Val Tyr Asp
            420                 425                 430

Phe Pro Gln Phe Lys Glu Ala Phe Thr Ile Pro Leu Leu Glu Leu Leu
            435                 440                 445

Gly Pro Ser Phe Asp Ser Leu Leu Leu Gly Glu Thr Thr Leu Glu Arg
            450                 455                 460

Thr Gln Val Thr Thr Glu Asn Asp Ala Val Arg Gly Phe Trp Ser Leu
465                 470                 475                 480

Ser Trp Glu Glu Tyr Pro Pro Ser Leu Asp Lys Asp Arg Arg Ile Thr
                485                 490                 495

Pro Thr Lys Thr Val Phe Leu Thr Trp Asn Pro Glu Ile Thr Ser
            500                 505                 510

Thr Pro

<210> SEQ ID NO 24
<211> LENGTH: 289
<212> TYPE: PRT
<213> ORGANISM: Chlamydia pneumoniae

<400> SEQUENCE: 24

Met Gly Ile Ser Leu Pro Glu Leu Phe Ser Asn Leu Gly Ser Ala Tyr
1               5                   10                  15

Leu Asp Tyr Ile Phe Gln His Pro Pro Ala Tyr Val Trp Ser Val Phe
            20                  25                  30

Leu Leu Leu Leu Ala Arg Leu Leu Pro Ile Phe Ala Val Ala Pro Phe
            35                  40                  45

Leu Gly Ala Lys Leu Phe Pro Ser Pro Ile Lys Ile Gly Ile Ser Leu
        50                  55                  60

Ser Trp Leu Ala Ile Ile Phe Pro Lys Val Leu Ala Asp Thr Gln Ile
65                  70                  75                  80

Thr Asn Tyr Met Asp Asn Asn Leu Phe Tyr Val Leu Val Lys Glu
                85                  90                  95

Met Ile Gly Ile Val Ile Gly Phe Val Leu Ala Phe Pro Phe Tyr
            100                 105                 110

Ala Ala Gln Ser Ala Gly Ser Phe Ile Thr Asn Gln Gln Gly Ile Gln
            115                 120                 125

Gly Leu Glu Gly Ala Thr Ser Leu Ile Ser Ile Glu Gln Thr Ser Pro
        130                 135                 140

His Gly Ile Leu Tyr His Tyr Phe Val Thr Ile Ile Phe Trp Leu Val
145                 150                 155                 160

Gly Gly His Arg Ile Val Ile Ser Leu Leu Leu Gln Thr Leu Glu Val
                165                 170                 175

Ile Pro Ile His Ser Phe Phe Pro Ala Glu Met Met Ser Leu Ser Ala
            180                 185                 190
```

```
Pro Ile Trp Ile Thr Met Ile Lys Met Cys Gln Leu Cys Leu Val Met
        195                 200                 205

Thr Ile Gln Leu Ser Ala Pro Ala Ala Leu Ala Met Leu Met Ser Asp
    210                 215                 220

Leu Phe Leu Gly Ile Ile Asn Arg Met Ala Pro Gln Val Gln Val Ile
225                 230                 235                 240

Tyr Leu Leu Ser Ala Leu Lys Ala Phe Met Gly Leu Leu Phe Leu Thr
                245                 250                 255

Leu Ala Trp Trp Phe Ile Ile Lys Gln Ile Asp Tyr Phe Thr Leu Ala
            260                 265                 270

Trp Phe Lys Glu Val Pro Ile Met Leu Leu Gly Ser Asn Pro Gln Val
        275                 280                 285

Leu

<210> SEQ ID NO 25
<211> LENGTH: 265
<212> TYPE: PRT
<213> ORGANISM: Chlamydia pneumoniae

<400> SEQUENCE: 25

Met Lys His Ser Lys Glu Asp Asp Leu Ser Arg Phe Leu Pro Lys Asn
 1               5                  10                  15

Leu Leu Val Glu Ser Pro His Pro Glu Ile Pro Leu Lys Ser Leu
                20                  25                  30

Ser Phe Thr Met Ser Trp Leu Pro Thr Ile His Pro Ser Trp Ile Thr
            35                  40                  45

Ile Ala Met Lys Glu Phe Pro Pro Glu Ile Gln Gly Gln Leu Leu Ala
        50                  55                  60

Trp Leu Pro Glu Pro Leu Val Gln Glu Ile Leu Pro Leu Leu Pro Gly
65                  70                  75                  80

Ile Ser Ile Ala Pro His Arg Cys Ala Pro Phe Gly Ala Phe Tyr Leu
                85                  90                  95

Leu Asp Met Leu Ser Lys Lys Ile Arg Pro Cys Gly Ile Thr Glu Glu
                100                 105                 110

Ile Phe Leu Pro Ala Ser Ser Ala Asn Ala Ile Leu Tyr Tyr Thr Gly
            115                 120                 125

Pro Val Lys Ile Ala Leu Ile Asn Cys Leu Gly Leu Tyr Ser Ile Ala
        130                 135                 140

Lys Glu Leu Lys His Ile Leu Asp Lys Val Val Ile Glu Arg Val Lys
145                 150                 155                 160

Asn Ala Leu Ser Pro Thr Glu Lys Leu Phe Leu Thr Tyr Cys Gln Ser
                165                 170                 175

His Pro Met Lys His Leu Glu Thr Thr Asn Phe Leu Ser Ser Trp Thr
            180                 185                 190

Thr Asp Ala Glu Leu Arg Gln Phe Val His Lys Gln Gly Leu Glu Phe
        195                 200                 205

Leu Gly Lys Ala Leu Thr Lys Glu Asn Ala Ser Phe Leu Trp Tyr Phe
    210                 215                 220

Leu Arg Arg Leu Asp Val Gly Arg Ala Tyr Ile Val Glu Gln Thr Leu
225                 230                 235                 240

Lys Thr Trp Tyr Asp His Pro Tyr Val Asp Tyr Phe Lys Ser Arg Leu
                245                 250                 255

Glu Gln Cys Met Lys Val Leu Val Lys
                260                 265
```

```
<210> SEQ ID NO 26
<211> LENGTH: 95
<212> TYPE: PRT
<213> ORGANISM: Chlamydia pneumoniae

<400> SEQUENCE: 26

Met Leu Ala Phe Phe Ala Thr Ser Phe Lys Ser Val Leu Phe Glu Tyr
 1               5                  10                  15

Ser Tyr Gln Ser Leu Leu Ile Leu Ile Val Ser Ala Pro Pro Ile
            20                  25                  30

Ile Leu Ala Ser Ile Val Gly Ile Met Val Ala Ile Phe Gln Ala Ala
        35                  40                  45

Thr Gln Ile Gln Glu Gln Thr Phe Ala Phe Ala Val Lys Leu Val Val
    50                  55                  60

Ile Phe Gly Thr Leu Met Ile Ser Gly Gly Trp Leu Ser Asn Met Ile
65                  70                  75                  80

Leu Arg Phe Ala Gly Gln Ile Phe Gln Asn Phe Tyr Lys Trp Lys
                85                  90                  95

<210> SEQ ID NO 27
<211> LENGTH: 9
<212> TYPE: PRT
<213> ORGANISM: Artificial Sequence
<220> FEATURE:
<223> OTHER INFORMATION: T-cell epitope from SEQ ID NO:14

<400> SEQUENCE: 27

Val Leu Phe Ile Ala His Phe Phe Leu
                5

<210> SEQ ID NO 28
<211> LENGTH: 9
<212> TYPE: PRT
<213> ORGANISM: Artificial Sequence
<220> FEATURE:
<223> OTHER INFORMATION: B-cell epitope from SEQ ID NO:14

<400> SEQUENCE: 28

Arg Ile Arg Glu Asp Arg Gln Ala Asn
                5

<210> SEQ ID NO 29
<211> LENGTH: 9
<212> TYPE: PRT
<213> ORGANISM: Artificial Sequence
<220> FEATURE:
<223> OTHER INFORMATION: T-cell epitope from SEQ ID NO:15

<400> SEQUENCE: 29

Lys Leu Met Val Phe Gln Lys Trp Ala
                5

<210> SEQ ID NO 30
<211> LENGTH: 11
<212> TYPE: PRT
<213> ORGANISM: Artificial Sequence
<220> FEATURE:
<223> OTHER INFORMATION: B-cell epitope from SEQ ID NO:15

<400> SEQUENCE: 30

Val Lys Thr Glu Gly Asn Thr Ser Arg Ala Thr
                5                  10
```

```
<210> SEQ ID NO 31
<211> LENGTH: 9
<212> TYPE: PRT
<213> ORGANISM: Artificial Sequence
<220> FEATURE:
<223> OTHER INFORMATION: T-cell epitope from SEQ ID NO:16

<400> SEQUENCE: 31

Tyr Met Asn Lys Thr Leu His Phe Ile
                5

<210> SEQ ID NO 32
<211> LENGTH: 12
<212> TYPE: PRT
<213> ORGANISM: Artificial Sequence
<220> FEATURE:
<223> OTHER INFORMATION: B-cell epitope from SEQ ID NO:16

<400> SEQUENCE: 32

Ser Trp His Gly Lys Tyr Lys Lys Lys Asp Phe Glu
                5                   10

<210> SEQ ID NO 33
<211> LENGTH: 14
<212> TYPE: PRT
<213> ORGANISM: Artificial Sequence
<220> FEATURE:
<223> OTHER INFORMATION: B-cell epitope from SEQ ID NO:16

<400> SEQUENCE: 33

Asp Glu Pro Thr Thr Asn Ile Asp Pro Asp Asn Gln Gln Arg
                5                   10

<210> SEQ ID NO 34
<211> LENGTH: 9
<212> TYPE: PRT
<213> ORGANISM: Artificial Sequence
<220> FEATURE:
<223> OTHER INFORMATION: T-cell epitope from SEQ ID NO:17

<400> SEQUENCE: 34

Trp Leu Ser Pro Lys Asn Leu Lys Val
                5

<210> SEQ ID NO 35
<211> LENGTH: 22
<212> TYPE: PRT
<213> ORGANISM: Artificial Sequence
<220> FEATURE:
<223> OTHER INFORMATION: B-cell epitope from SEQ ID NO:17

<400> SEQUENCE: 35

Asn His Tyr Asp Pro His Thr Tyr Glu Leu Pro Pro Gln Gln Ile Lys
                5                   10                  15

Glu Leu Arg Gln Gly Asp
            20

<210> SEQ ID NO 36
<211> LENGTH: 9
<212> TYPE: PRT
<213> ORGANISM: Artificial Sequence
<220> FEATURE:
<223> OTHER INFORMATION: T-cell epitope from SEQ ID NO:18

<400> SEQUENCE: 36

Trp Leu Phe Asp Leu Arg Phe Ser Val
```

```
<210> SEQ ID NO 37
<211> LENGTH: 18
<212> TYPE: PRT
<213> ORGANISM: Artificial Sequence
<220> FEATURE:
<223> OTHER INFORMATION: B-cell epitope from SEQ ID NO:18

<400> SEQUENCE: 37

Glu Ser Glu Tyr His Leu Asp Asn Tyr Lys His Lys Gly Ser Gly His
                 5                  10                  15

Ser Thr

<210> SEQ ID NO 38
<211> LENGTH: 9
<212> TYPE: PRT
<213> ORGANISM: Artificial Sequence
<220> FEATURE:
<223> OTHER INFORMATION: T-cell epitope from SEQ ID NO:19

<400> SEQUENCE: 38

Ala Leu Met Leu Leu Asn Asn Tyr Val
                 5

<210> SEQ ID NO 39
<211> LENGTH: 13
<212> TYPE: PRT
<213> ORGANISM: Artificial Sequence
<220> FEATURE:
<223> OTHER INFORMATION: B-cell epitope from SEQ ID NO:19

<400> SEQUENCE: 39

Asp Lys Ile Asn Tyr Lys Pro Arg Pro Glu Lys Glu Gly
                 5                  10

<210> SEQ ID NO 40
<211> LENGTH: 9
<212> TYPE: PRT
<213> ORGANISM: Artificial Sequence
<220> FEATURE:
<223> OTHER INFORMATION: T-cell epitope from SEQ ID NO:20

<400> SEQUENCE: 40

Val Leu Phe Gln Asp Asn Ser Ala Leu
                 5

<210> SEQ ID NO 41
<211> LENGTH: 7
<212> TYPE: PRT
<213> ORGANISM: Artificial Sequence
<220> FEATURE:
<223> OTHER INFORMATION: B-cell epitope from SEQ ID NO:20

<400> SEQUENCE: 41

Asn Ser Ser Lys His Asp Gly
                 5

<210> SEQ ID NO 42
<211> LENGTH: 9
<212> TYPE: PRT
<213> ORGANISM: Artificial Sequence
<220> FEATURE:
<223> OTHER INFORMATION: T-cell epitope from SEQ ID NO:21

<400> SEQUENCE: 42
```

```
Trp Leu Leu Thr Ser Ser Ala Leu Val
                5

<210> SEQ ID NO 43
<211> LENGTH: 9
<212> TYPE: PRT
<213> ORGANISM: Artificial Sequence
<220> FEATURE:
<223> OTHER INFORMATION: B-cell epitope from SEQ ID NO:21

<400> SEQUENCE: 43

Gln Lys Asn Thr Ser Glu Lys Asp Gly
                5

<210> SEQ ID NO 44
<211> LENGTH: 16
<212> TYPE: PRT
<213> ORGANISM: Artificial Sequence
<220> FEATURE:
<223> OTHER INFORMATION: B-cell epitope from SEQ ID NO:21

<400> SEQUENCE: 44

Gly Asn Lys Ala Thr Gly Pro Ser Asn Ser Ser Ala Asn Gln Glu Gly
                5                   10                  15

<210> SEQ ID NO 45
<211> LENGTH: 9
<212> TYPE: PRT
<213> ORGANISM: Artificial Sequence
<220> FEATURE:
<223> OTHER INFORMATION: T-cell epitope from SEQ ID NO:22

<400> SEQUENCE: 45

Gln Leu Tyr Val Asp Trp Thr Pro Val
                5

<210> SEQ ID NO 46
<211> LENGTH: 17
<212> TYPE: PRT
<213> ORGANISM: Artificial Sequence
<220> FEATURE:
<223> OTHER INFORMATION: B-cell epitope from SEQ ID NO:22

<400> SEQUENCE: 46

Asn Gln His Asn Arg Glu Gly Arg Lys Gly Phe Arg Asn His Thr Thr
                5                   10                  15
Gly

<210> SEQ ID NO 47
<211> LENGTH: 17
<212> TYPE: PRT
<213> ORGANISM: Artificial Sequence
<220> FEATURE:
<223> OTHER INFORMATION: B-cell epitope from SEQ ID NO:22

<400> SEQUENCE: 47

Ser Lys Thr Arg Glu Arg Gln Ser Pro Ser Thr Thr Ser Ser His Asn
                5                   10                  15
Tyr

<210> SEQ ID NO 48
<211> LENGTH: 19
<212> TYPE: PRT
<213> ORGANISM: Artificial Sequence
<220> FEATURE:
<223> OTHER INFORMATION: B-cell epitope from SEQ ID NO:23
```

```
<400> SEQUENCE: 48

Trp Glu Glu Tyr Pro Pro Ser Leu Asp Lys Asp Arg Arg Ile Thr Pro
                 5                  10                  15
Thr Lys Lys

<210> SEQ ID NO 49
<211> LENGTH: 9
<212> TYPE: PRT
<213> ORGANISM: Artificial Sequence
<220> FEATURE:
<223> OTHER INFORMATION: T-cell epitope from SEQ ID NO:24

<400> SEQUENCE: 49

Tyr Met Asp Asn Asn Leu Phe Tyr Val
                 5

<210> SEQ ID NO 50
<211> LENGTH: 10
<212> TYPE: PRT
<213> ORGANISM: Artificial Sequence
<220> FEATURE:
<223> OTHER INFORMATION: B-cell epitope from SEQ ID NO:24

<400> SEQUENCE: 50

Thr Gln Ile Thr Asn Tyr Met Asp Asn Asn
                 5                  10

<210> SEQ ID NO 51
<211> LENGTH: 9
<212> TYPE: PRT
<213> ORGANISM: Artificial Sequence
<220> FEATURE:
<223> OTHER INFORMATION: T-cell epitope from SEQ ID NO:25

<400> SEQUENCE: 51

Phe Leu Trp Tyr Phe Leu Arg Arg Leu
                 5

<210> SEQ ID NO 52
<211> LENGTH: 11
<212> TYPE: PRT
<213> ORGANISM: Artificial Sequence
<220> FEATURE:
<223> OTHER INFORMATION: B-cell epitope from SEQ ID NO:25

<400> SEQUENCE: 52

Met Lys His Ser Lys Glu Asp Asp Leu Ser Arg
                 5                  10

<210> SEQ ID NO 53
<211> LENGTH: 9
<212> TYPE: PRT
<213> ORGANISM: Artificial Sequence
<220> FEATURE:
<223> OTHER INFORMATION: T-cell epitope from SEQ ID NO:26

<400> SEQUENCE: 53

Leu Leu Leu Ile Leu Ile Val Ser Ala
                 5

<210> SEQ ID NO 54
<211> LENGTH: 7
<212> TYPE: PRT
<213> ORGANISM: Artificial Sequence
<220> FEATURE:
```

-continued

```
<223> OTHER INFORMATION: B-cell epitope from SEQ ID NO:26

<400> SEQUENCE: 54

Gln Asn Phe Tyr Lys Trp Lys
                5
```